United States Patent
Mailliet et al.

(10) Patent No.: US 7,674,795 B2
(45) Date of Patent: Mar. 9, 2010

(54) FLUORENE DERIVATIVES, COMPOSITION CONTAINING SAID DERIVATIVES AND THE USE THEREOF

(75) Inventors: Patrick Mailliet, Fontenay sous Bois (FR); Luc Bertin, Crosnes (FR); Fabienne Thompson, Paris (FR); Jean-Marie Ruxer, Issy les Moulineaux (FR); Fabienne Pilorge, Tournan en Brie (FR); Didier Benard, Montsoult (FR); Hervé Minoux, Thiais (FR); Chantal Carrez, Thiais (FR); Hélène Goulaouic, Paris (FR); Thierry Gouyon, Vigneux sur Seine (FR)

(73) Assignee: Aventis Pharma SA, Antony (FR)

( * ) Notice: Subject to any disclaimer, the term of this patent is extended or adjusted under 35 U.S.C. 154(b) by 282 days.

(21) Appl. No.: 11/939,735

(22) Filed: Nov. 14, 2007

(65) Prior Publication Data

US 2008/0153837 A1    Jun. 26, 2008

Related U.S. Application Data

(63) Continuation of application No. PCT/FR2006/001137, filed on May 19, 2006.

(30) Foreign Application Priority Data

May 19, 2005   (FR) .................................. 05 05037

(51) Int. Cl.
*A61K 31/497*  (2006.01)
*C07D 471/04*  (2006.01)
*C07D 401/10*  (2006.01)
*A61K 31/501*  (2006.01)
*A61P 3/10*  (2006.01)
*A61P 35/00*  (2006.01)
*C07D 239/02*  (2006.01)
*A61K 31/437*  (2006.01)

(52) U.S. Cl. ............... 514/252.04; 514/274; 514/303; 546/118; 544/238; 544/316

(58) Field of Classification Search ............ 514/252.04, 514/274, 303; 546/118; 544/238, 316
See application file for complete search history.

(56) References Cited

U.S. PATENT DOCUMENTS

2003/0078419 A1 * 4/2003 Butler et al. ................. 544/60
2007/0032532 A1   2/2007 Nara et al.

FOREIGN PATENT DOCUMENTS

| WO | WO 2004/050087 A1 | 6/2004 |
| WO | WO 2004/056782 A1 | 7/2004 |
| WO | WO 2004/072051 A1 | 8/2004 |
| WO | WO 2004/072080 A1 | 8/2004 |
| WO | WO 2004/096212 A1 | 11/2004 |
| WO | WO 2005/000300 A1 | 1/2005 |
| WO | WO 2005/000778 A1 | 1/2005 |
| WO | WO 2005/021552 A1 | 3/2005 |
| WO | WO 2005/034950 A1 | 4/2005 |

OTHER PUBLICATIONS

Bovy et al, Synthesis and Aldose Reductase Inhibition Activity of spiro[9H-fluoren-9,4'-imidazolidine]2',5'-dione Derivatives, Eur. J. Med. Chem. (1988) 23(2) 165-172.
Janin, Heat Shock Protein 90 Inhibitors. A Text Book Example of Medicinal Chemistry?, J. Med. Chem. (2005) 48(24) 7503-7512.
Walter et al, Molecular Chaperones—Cellular Machines for Protein Folding, Angew. Chem. Int. Ed. (2002) 41, 1098-1113.

* cited by examiner

*Primary Examiner*—D. Margaret Seaman
*Assistant Examiner*—Niloofar Rahmani
(74) *Attorney, Agent, or Firm*—Jiang Lin

(57) ABSTRACT

This invention relates to derivatives of 4-(benzimidazol-2-yl)fluorene and 4-(azabenzimidazol-2-yl)fluorene, to pharmaceutical compositions comprising such derivatives, and to methods of treatment of disorders related to Hsp90 protein activity, comprising administering such derivatives.

19 Claims, No Drawings

FLUORENE DERIVATIVES, COMPOSITION CONTAINING SAID DERIVATIVES AND THE USE THEREOF

The present invention relates to novel chemical compounds, which are derivatives of fluorene, and more particularly to novel derivatives of 4-(benzimidazol-2-yl)fluorene or of 4-(azabenzimidazol-2-yl)fluorene, compositions containing them, and their use as medicinal products.

More particularly, according to a first aspect, the invention relates to novel derivatives of 4-(benzimidazol-2-yl)fluorene or of 4-(azabenzimidazol-2-yl)fluorene displaying anticancer activity, and in particular Hsp90 chaperone protein-inhibiting activity, and more particularly via inhibition of the ATPase-type catalytic activity of the Hsp90 chaperone protein.

Chaperone Proteins:

The molecular chaperones of the "Heat Shock Proteins" family (HSPs), which are classified according to their molecular weight (Hsp27, Hsp70, Hsp90, etc.), are key elements in the equilibrium between the synthesis and the degradation of cellular proteins, which are responsible for correct protein folding. They play a vital role in response to cellular stress. The HSPs, and especially Hsp90, are also involved in the regulation of various very important functions of the cell, via their association with various client proteins involved in cellular proliferation or in apoptosis (Jolly C. and Morimoto R. I., J. N. Cancer Inst. (2000), 92, 1564-72; Smith D. F. et al., Pharmacological Rev. (1998), 50, 493-513; Smith D. F., Molecular Chaperones in the Cell, 165-178, Oxford University Press 2001).

Various human pathologies are a consequence of incorrect folding of key proteins, leading notably to neurodegenerative diseases as a result of aggregation of certain proteins as in Alzheimer's disease and Huntington's disease, or diseases associated with prions (Tytell M. and Hooper P. L., Emerging Ther. Targets (2001), 5, 3788-3796). In these pathologies, approaches that aim to inhibit Hsp90 with the aim of activating stress pathways (Hsp70, for example) might be beneficial.

Hsp90 Chaperones and Hsp90 Inhibitors in Cancer Treatment:

The Hsp90 chaperone, which represents 1 to 2% of the protein content of the cell, has recently been demonstrated as a particularly promising target in anticancer therapy (for review, see: Moloney A. and Workman P., Expert Opin. Biol. Ther. (2002), 2(1), 3-24; Chiosis et al., Drug Discovery Today (2004), 9, 881-888). This interest relates in particular to the cytoplasmic interactions of Hsp90 with the main client proteins of Hsp90, proteins which are involved in the six mechanisms of progression of tumors, as defined by Hanahan D. and Weinberg R. A. (Cell (2002), 100, 57-70), namely:

ability to proliferate in the absence of growth factors: EGFR-R/HER2, Src, Akt, Raf, MEK, Bcr-Abl, Flt-3 etc.
ability to evade apoptosis: mutated form of p53, Akt, survivin
insensitivity to signals to halt proliferation: Cdk4, Plk, Wee1, etc.
ability to activate angiogenesis: VEGF-R, FAK, HIF-1, Akt, etc.
ability to proliferate without replicative limit: hTert, etc.
ability to invade new tissues and metastasize: c-Met Among the other client proteins of Hsp90, steroid hormone receptors, such as the estrogen receptor or the androgen receptor, are also of considerable interest within the scope of anticancer therapies.

It was shown recently that the alpha form of Hsp90 also has an extracellular role via its interaction with the metalloprotease MMP-2, which is itself involved in tumoral invasion (Eustace B. K. et al., Nature Cell Biology (2004), 6, 507-514.

Hsp90 is made up of two N- and C-terminal domains separated by a highly charged region. Dynamic interaction between these two domains, coordinated by the fixation of nucleotides and of co-chaperones, determines the conformation of the chaperone and its state of activation. Association of the client proteins depends mainly on the nature of the co-chaperones Hsp70/Hsp40, Hop60, etc., and on the nature of the ADP or ATP nucleotide bound to the N-terminal domain of Hsp90. Thus, hydrolysis of ATP to ADP and the ADP/ATP exchange factor control all of the chaperone "machinery", and it was shown that it is sufficient to prevent hydrolysis of ATP to ADP—ATPase activity of Hsp90—to release client proteins in the cytoplasm, and these will then be degraded to proteasome (Neckers L and Neckers K, Expert Opin. Emerging Drugs (2002), 7, 277-288; Neckers L, Current Medicinal Chemistry, (2003), 10, 733-739; Piper P. W., Current Opin. Invest. New Drugs (2001), 2, 1606-1610).

Role of Hsp90 and of Inhibitors Thereof in Pathologies Other than Cancer:

i) Huntington's disease: This neurodegenerative disease is due to an extension of CAG triplets in exon 1 of the gene encoding the huntingtin protein. It has been demonstrated that geldanamycin inhibits the aggregation of this protein due to the overexpression of the Hsp70 and Hsp40 chaperones (Human Molecular Genetics 10: 1307, 2001).

ii) Parkinson's disease: This disease is due to the progressive loss of dopaminergic neurones and is characterized by aggregation of the alpha-synuclein protein. It has been shown that geldanamycin is capable of protecting drosophilar against the toxicity of alpha-synuclein on dopaminergic neurones.

iii) Focal cerebral ischemia: It has been shown, in a rat animal model, that geldanamycin protects the brain against cerebral ischemia, due to the effect of stimulation of the transcription of genes encoding the heat-shock proteins by an Hsp90 inhibitor.

iv) Alzheimer's disease and multiple sclerosis: These diseases are due in part to the expression of pro-inflammatory cytokines and of the inducible form of NOS (nitric oxide synthase) in the brain, and this harmful expression is suppressed by the response to stress. In particular, the Hsp90 inhibitors are capable of garnering this response to stress, and it has been shown, in vitro, that geldanamycin and 17-AAG exhibit anti-inflammatory activity in brain glial cells (J. Neuroscience Res. 67: 461, 2002).

v) Amyotrophic lateral sclerosis: This neurodegenerative disease is due to the progressive loss of motor neurones. It has been shown that arimoclomol, an inducer of heat-shock proteins, delays the evolution of the disease in an animal model (Nature Medicine 10: 402, 2004). Given that an Hsp90 inhibitor is also an inducer of heat-shock proteins (Mol. Cell. Biol. 19: 8033, 1999; Mol. Cell. Biol. 18: 4949, 1998), it is probable that a beneficial effect might also be obtained in this pathology for inhibitors of this type.

Furthermore, an inhibitor of the Hsp90 protein might be potentially useful in various diseases, other than cancer mentioned above, such as parasitic, viral or fungal infections or neurodegenerative diseases, via a direct action on Hsp90 and specific client proteins. Some examples are presented below:

vi) Malaria: The Hsp90 protein of *Plasmodium falciparum* exhibits 59% identity and 69% similarity with the human Hsp90 protein, and it has been shown that geldanamycin inhibits growth of the parasite in vitro (Malaria Journal 2: 30, 2003; J. Biol. Chem. 278: 18336, 2003; J. Biol. Chem. 279: 46692, 2004).

vii) Brugia filariasis and Bancroft's filariasis: These lymphatic filarial parasites possess an Hsp90 protein which can potentially be inhibited by inhibitors of the human protein. In fact, it has been shown, for another similar parasite, *Brugia pahangi*, that the latter is sensitive to inhibition by geldanamycin. The *B. pahangi* and human sequences are 80% identical and 87% similar (Int. J. for Parasitology 35: 627, 2005).

viii) Toxoplasmosis: *Toxoplasma gondii*, the parasite responsible for toxoplasmosis, has an Hsp90 chaperone protein, for which induction has been shown during tachyzoite-bradyzoite conversion, corresponding to passage of the chronic infection towards active toxoplasmosis. Furthermore, geldanamycin blocks this tachyzoite-bradyzoite conversion in vitro (J. Mol. Biol. 350: 723, 2005).

ix) Treatment-resistant mycoses: It is possible for the Hsp90 protein to potentiate the evolution of drug resistance by allowing new mutations to develop. Consequently, an Hsp90 inhibitor, alone or in combination with another antifungal treatment, might prove to be useful in the treatment of certain resistant strains (Science 309: 2185, 2005). Furthermore, the anti-Hsp90 antibody developed by NeuTec Pharma demonstrates an activity against *C. albicans*, sensitive and resistant to fluconazole, *C. krusei, C. tropicalis, C. glabrata, C. lusitaniae* and *C. parapsilosis* in vivo (Current Molecular Medicine 5: 403, 2005).

x) Hepatitis B: Hsp90 is one of the host proteins which interacts with the reverse transcriptase of the hepatitis B virus during the replication cycle of the virus. It has been shown that geldanamycin inhibits replication of the viral DNA and encapsulation of the viral RNA (Proc. Natl. Acad. Sci. USA 93: 1060, 1996).

xi) Hepatitis C: The human Hsp90 protein participates in the step consisting of cleavage between the NS2 and NS3 proteins by the viral protease. Geldanamycin and radicicol are capable of inhibiting this NS2/3 cleavage in vitro (Proc. Natl. Acad. Sci. USA 98: 13931, 2001).

xii) The herpes virus: Geldanamycin has demonstrated inhibitory activities on HSV-1 virus replication in vitro, with a good therapeutic index (Antimicrobial Agents and Chemotherapy 48: 867, 2004). The authors have also found geldanamycin activity on the other viruses HSV-2, VSV, Cox B3, HIV-1 and the coronavirus SARS (data not shown).

xiii) Dengue (or tropical flu): It has been shown that the human Hsp90 protein participates in the step of viral entry, by forming a complex also containing Hsp70 which serves as a receptor for the virus; an anti-Hsp90 antibody decreases the infectious capacity of the virus in vitro (J. of Virology 79: 4557, 2005).

xiv) Spinal and bulbar muscular atrophy (SBMA): A hereditary neurodegenerative disease characterized by an extension of CAG triplets in the androgen receptor gene. It has been shown that 17-AAG, a geldanamycin derivative, exhibits activity in vivo on transgenic animals used as experimental models for this disease (Nature Medicine 11: 1088, 2005).

Hsp90 Inhibitors:

The first known Hsp90 inhibitors are compounds of the ansamycin group, in particular geldanamycin (1) and herbimycin A. X-ray studies showed that geldanamycin binds to the ATP site of the N-terminal domain of Hsp90 where it inhibits the ATPase activity of the chaperone (Prodromou C. et al., Cell (1997), 90, 65-75)

At present the NIH and Kosan BioSciences are providing clinical development of 17AAG (2), which is an Hsp90 inhibitor derived from geldanamycin (1), which blocks the ATPase activity of Hsp90 by binding to the N-terminal recognition site of ATP. The results of phase I clinical trials of 17AAG (1) have now led to phase II trials being started, but research is also being directed towards more-soluble derivatives, such as analogue (3) (17DMAG of Kosan BioSciences), which carries a dimethylamine chain instead of the methoxy residue, and towards optimized formulations of 17AAG (CNF1010 of Conforma Therapeutics):

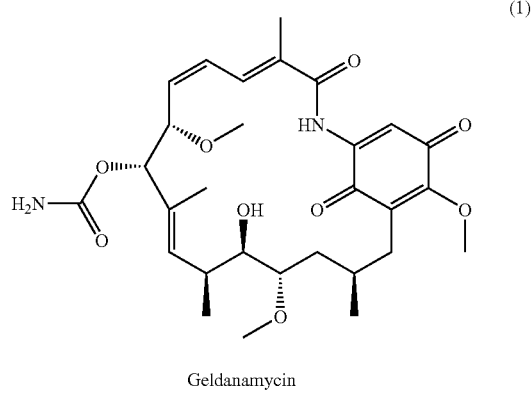

Geldanamycin (1)

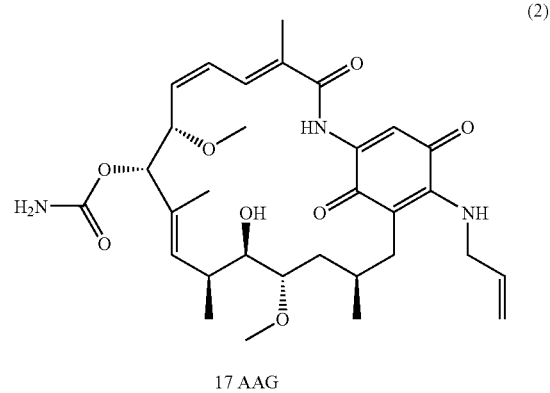

17 AAG (2)

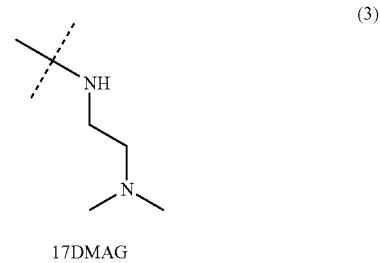

17DMAG (3)

Radicicol (4) is also an Hsp90 inhibitor of natural origin (Roe S. M. et al., J. Med. Chem. (1999), 42, 260-66). However, although the latter is by far the best inhibitor of Hsp90 in vitro, its metabolic instability with respect to sulphur-containing nucleophiles makes it difficult to use in vivo. Oxime derivatives that are much more stable, such as KF 55823 (5) or KF 25706, have been developed by the company Kyowa Hakko Kogyo (Soga et al., Cancer Research (1999), 59, 2931-2938)

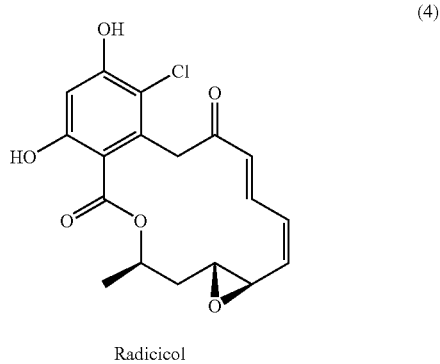

Radicicol (4)

-continued (5)

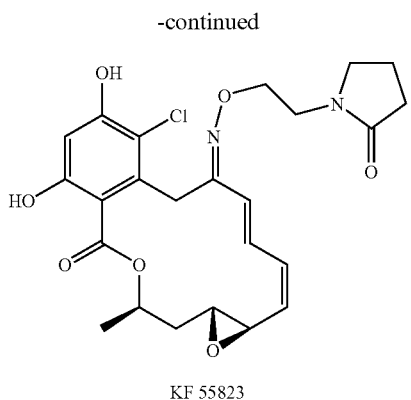

KF 55823

Structures of natural origin related to radicicol have also been described recently, such as zearalenone (6) by the company Conforma Therapeutics (WO 03041643) or compounds (7-9).

(6)

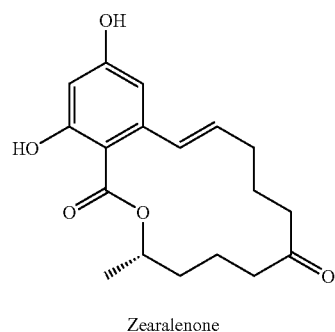

Zearalenone (7)

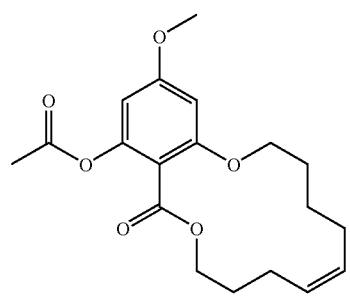

(8)

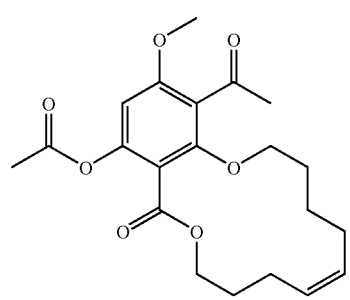

-continued (9)

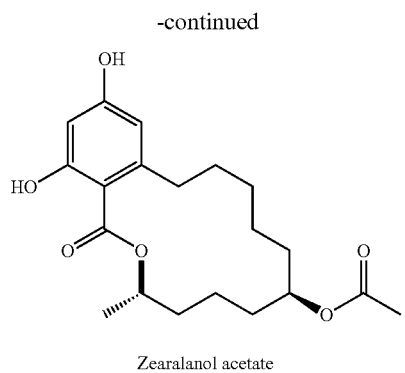

Zearalanol acetate

An Hsp90 inhibitor of natural origin, novobiocin (10), binds to a different ATP site located in the C-terminal domain of the protein (Itoh H. et al., Biochem J. (1999), 343, 697-703.

A depsipeptide, called Pipalamycin or ICI101, was recently described as a (10)

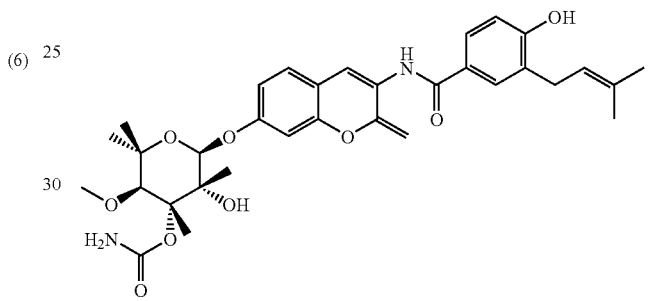

non-competitive inhibitor of the ATP site of Hsp90 (J. Pharmacol. Exp. Ther. (2004), 310, 1288-1295).

Purines, such as the compounds PU3 (11) (Chiosis et al., Chem. Biol. (2001), 8, 289-299) and PU24FCl (12) (Chiosis et al., Curr. Canc. Drug Targets (2003), 3, 371-376) have also been described as Hsp90 inhibitors:

(11)

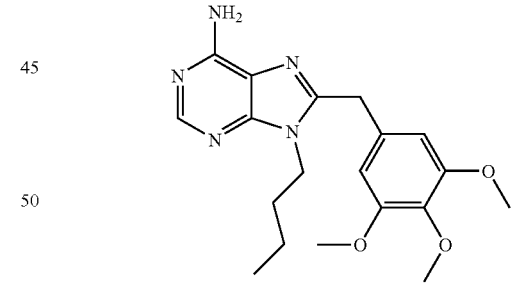

(12)

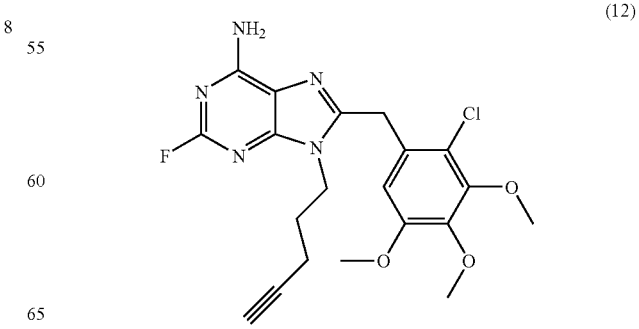

Patent application WO2004/072080 (Cellular Genomics) claims a group of 8-heteroaryl-6-phenyl-imidazo[1,2-a]pyrazines as modulators of Hsp90 activity.

Patent application WO2004/050087 (Ribotarget/Vernalis) claims a group of pyrazoles that can be used for treating pathologies associated with inhibition of heat-shock proteins such as the Hsp90 chaperone.

Patent application WO2004/056782 (Vernalis) claims a novel group of pyrazoles that can be used for treating pathologies associated with inhibition of heat-shock proteins such as the Hsp90 chaperone.

Patent application WO2004/072051 (Vernalis) claims derivatives of arylisoxazoles that can be used for treating pathologies associated with inhibition of heat-shock proteins such as the Hsp90 chaperone.

Patent application WO2004/096212 (Vernalis) claims a third group of pyrazoles that can be used for treating pathologies associated with inhibition of heat-shock proteins such as the Hsp90 chaperone.

Patent application WO2005/000300 (Vernalis) claims, more generally, 5-membered heterocycles, substituted by aryl radicals, that can be used for treating pathologies associated with inhibition of heat-shock proteins such as the Hsp90 chaperone.

Patent application WO2005/000778 (Kyowa Hakko Kogyo) claims a group of derivatives of benzophenone as Hsp90 inhibitors, which can be used for treating tumors.

Patent application WO2005/021552 (Vernalis) claims a group of derivatives of pyrimidothiophene that can be used for treating pathologies associated with inhibition of heat-shock proteins such as the Hsp90 chaperone.

European Journal of Medicinal Chemistry 1988, 23(2), 165-172 describes the preparation and the aldol reductase-inhibiting activity of the compound CAS 116792-62-2 below:

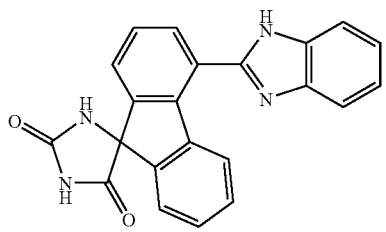

The present invention relates to products of formula (I):

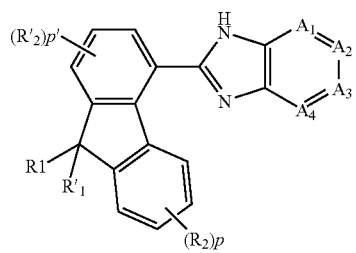

in which:

$A_1$, $A_2$, $A_3$ and $A_4$, which may be identical or different, represent CRa or N or NRb;

with Rb represents alkyl, alkoxy or OH, $R_1$ and $R_1'$ are such that: either $R_1$ and $R_1'$, which may be identical or different, are such that one of $R_1$ and $R_1'$ represents a hydrogen or halogen atom or a radical selected from $C_1C_3$-alkyl, $C_1C_3$-alkoxy, alkyl-OH, $CF_3$, cyano, carboxy and carboxamido;

and the other one of $R_1$ and $R_1'$ is selected from the group comprising H; halogen; $CF_3$; hydroxyl; mercapto; nitro; amino; NH—OH; NH—CO—H; NH—CO—OH, NH—CO-Oalkyl, NH—CO—NH$_2$; carboxy; CN; CO—NH$_2$; X—(CH$_2$)$_m$-alkyl; X—(CH$_2$)$_m$-cycloalkyl; X—(CH$_2$)$_m$-heterocycloalkyl; X—(CH$_2$)$_m$-aryl or X—(CH$_2$)$_m$-heteroaryl with X=single bond, CH$_2$, CH═CH, CH$_2$—O, CH$_2$—NH, CH$_2$—C(O), CH$_2$—C(O)—O, CH$_2$—C(O)—NH, CH$_2$—NH—(CO), CH$_2$—NH—S(O), CH$_2$—NH—S(O)$_2$, O, S, NH, O—C(O), C(O)—NH, —NH—C(O), —NH—C(O)—C(O)—, —NH—C(O)—NH—; NH—CS, NH—S(O) or NH—S(O)$_2$, —NH—CO—CH$_2$—O—; —NH—CO—CH$_2$—S—CH$_2$—CO—NH—; —NH—CO—(CH$_2$)$_2$—SO$_2$—; —NH—CO—CH$_2$—N(CH$_3$)—CO—; with m=0, 1 or 2, all the alkyl, cycloalkyl, heterocycloalkyl, aryl and heteroaryl radicals being optionally substituted, the cycloalkyl radical containing from 3 to 10 ring members, the aryl radical containing from 6 to 10 ring members, and the heterocycloalkyl and heteroaryl radicals, optionally substituted, containing from 4 to 10 ring members including 1 to 4 heteroatoms selected from O, S, N or NR$_3$ where R$_3$ represents H or alkyl, itself optionally substituted, or $R_1$ and $R_1'$ form, together with the carbon atom to which they are bound, an ═O; ═S; ═N—OH; ═N—NH$_2$; ═N—NH—CO—NH$_2$, ═CH—OH; ═Y$_1$—(CH$_2$)$_m$-aryl or ═Y$_1$—(CH$_2$)$_m$-heteroaryl radical, in which Y$_1$ represents CH, CH—CO—, CH—CO—NH, N, N—O or N—NH—, with m=0, 1 or 2 and in which aryl and heteroaryl are as defined above and optionally substituted, or $R_1$ and $R_1'$ form, together with the carbon atom to which they are bound, a partially saturated ring made up of 4 to 6 ring members and optionally containing from 1 to 3 heteroatoms selected from O, S, N or NR$_4$ where R$_4$ represents H or alkyl, itself optionally substituted, $R_2$ and $R_2'$, which may be identical or different, are selected independently from the group comprising H, halogen, $CF_3$, nitro, cyano, alkyl, hydroxy, mercapto, amino, alkylamino, dialkylamino, alkoxy, alkylthio(methylthio), free carboxy or carboxy esterified with an alkyl radical, carboxamide, CO—NH(alkyl) and CON(alkyl)$_2$, all the alkyl, alkoxy and alkylthio radicals being optionally substituted, p and p', which may be identical or different, represent the integers 1 to 4 and 1 to 3, respectively;

Ra is selected from the group comprising H; halogen; $CF_3$; hydroxy; $OCF_3$; $SO_2$—NH$_2$; $SO_2$—NH(alk), $SO_2$—N(alk)$_2$; mercapto; nitro; amino; NH(alk); N(alk)$_2$; NH—OH; NH—CO—H; NH—CO—NH$_2$; free carboxy or carboxy esterified with an alkyl radical, itself optionally substituted; CN; CO—NH$_2$; Y—(CH$_2$)n-alkyl; Y—(CH$_2$)$_n$-cycloalkyl, Y—(CH$_2$)$_n$-heterocycloalkyl, Y—(CH$_2$)$_n$-aryl or Y—(CH$_2$)$_n$-heteroaryl, where Y represents a single bond or else ═O, S, NH, O—C(O), C(O)—NH, —C(O)N(CH$_3$)—; CO; NH—C(O), NH—S(O) or NH—S(O)$_2$, with n=0, 1, 2 or 3, and in said radicals the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or NR$_3$ where R$_3$ represents H or alkyl, itself optionally substituted, all the alkyl, alkoxy, alkylthio, cycloalkyl, heterocycloalkyl, aryl and heteroaryl radicals of the substituents of the products of formula (I) being optionally substituted, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention thus relates to products of formula (I) in which:

$A_1$, $A_2$, $A_3$ and A4, which may be identical or different, represent CRa or N or NRb, where Rb represents $CH_3$ or OH;

Ra is selected from the group comprising H; halogen; $CF_3$; hydroxy; $OCF_3$; $SO_2$—$NH_2$; $SO_2$—$NHCH_3$, $SO_2$—$N(CH_3)_2$; mercapto; nitro; amino; $NH(CH_3)$; $N(CH_3)_2$; NH—OH; NH—CO—H; NH—CO—$NH_2$; free carboxy or carboxy esterified with an alkyl radical, itself optionally substituted; $CO_2$—$CH_3$; $CO_2$—$(CH_2)_3$—$N(CH_3)_2$; CN; CO—$NH_2$; Y—$(CH_2)_n$-alkyl; Y—$(CH_2)_n$-cycloalkyl, Y—$(CH_2)_n$-heterocycloalkyl, Y—$(CH_2)_n$-aryl or Y—$(CH_2)_n$-heteroaryl, where Y represents a single bond or else =O, —C(O)—NH—, —C(O)N($CH_3$)—; CO, with n=0, 1, 2, or 3, and in said radicals the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or $NR_3$ where $R_3$ represents H or alkyl, itself optionally substituted, the other substituents $R_1$, $R_1'$, $R_2$, $R_2'$ also products of formula (I) being selected from any one of the above definitions, all the alkyl, alkoxy, alkylthio, cycloalkyl, heterocycloalkyl, aryl and heteroaryl radicals of the substituents of the products of formula (I) being optionally substituted, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention relates to products of formula (I) as defined above in which:

$A_1$, $A_2$, $A_3$ and A4, which may be identical or different, represent CRa or N;

$R_1$ and $R_1'$ are such that:

either $R_1$ and $R_1'$, which may be identical or different, are such that one of $R_1$ and $R_1'$ represents a hydrogen or halogen atom or a radical selected from $C_1C_3$-alkyl, $C_1C_3$-alkoxy, alkyl-OH, $CF_3$, cyano, carboxy and carboxamido; and the other one of $R_1$ and $R_1'$ is selected from the group comprising H; halogen; $CF_3$; hydroxyl; mercapto; nitro; amino; NH—OH; NH—CO—H; NH—CO—OH, NH—CO-Oalkyl, NH—CO—$NH_2$; carboxy; CN; CO—$NH_2$; X—$(CH_2)_m$-alkyl; X—$(CH_2)_m$-cycloalkyl; X—$(CH_2)_m$-heterocycloalkyl; X—$(CH_2)_m$-aryl or X—$(CH_2)_m$-heteroaryl with X=single bond, $CH_2$, CH═CH, $CH_2$—O, $CH_2$—NH, $CH_2$—C(O), $CH_2$—C(O)—O, $CH_2$—C(O)—NH, $CH_2$—NH—(CO), $CH_2$—NH—S(O), $CH_2$—NH—$S(O)_2$, O, S, NH, O—C(O), C(O)—NH, —NH—C(O), —NH—C(O)—C(O)—, —NH—C(O)—NH—; NH—CS, NH—S(O) or NH—$S(O)_2$, with m=0, 1 or 2, all the alkyl, cycloalkyl, heterocycloalkyl, aryl and heteroaryl radicals being optionally substituted, the cycloalkyl radical containing from 3 to 10 ring members, the aryl radical containing from 6 to 10 ring members, and the heterocycloalkyl and heteroaryl radicals, optionally substituted, containing from 4 to 10 ring members including 1 to 4 heteroatoms selected from O, S, N or $NR_3$ where $R_3$ represents H or alkyl, itself optionally substituted, or $R_1$ and $R_1'$ form, together with the carbon atom to which they are bound, an =O; =S; =N—OH; =N—$NH_2$; =N—NH—CO—$NH_2$, =CH—OH; =$Y_1$—$(CH_2)_m$-aryl or =$Y_1$—$(CH_2)_m$-heteroaryl radical, in which $Y_1$ represents CH, CH—CO—, CH—CO—NH, N, N—O or N—NH—, with m=0, 1 or 2 and in which aryl and heteroaryl are as defined above and optionally substituted, or $R_1$ and $R_1'$ form, together with the carbon atom to which they are bound, a partially saturated ring made up of 4 to 6 ring members and optionally containing from 1 to 3 heteroatoms selected from O, S, N or $R_4$ where $R_4$ represents H or alkyl, itself optionally substituted, $R_2$ and $R_2'$, which may be identical or different, are selected independently from the group comprising H, halogen, $CF_3$, nitro, cyano, alkyl, hydroxy, mercapto, amino, alkylamino, dialkylamino, alkoxy, alkylthio, free or esterified carboxy, carboxamide, CO—NH(alkyl) and CON(alkyl)$_2$, p and p', which may be identical or different, represent the integers 1 to 4 and 1 to 3, respectively;

Ra is selected from the group comprising H; halogen; $CF_3$; hydroxy; mercapto; nitro; amino; NH—OH; NH—CO—H; NH—CO—$NH_2$; carboxy; CN; CO—$NH_2$; Y—$(CH_2)_n$-alkyl; Y—$(CH_2)_n$-cycloalkyl, Y—$(CH_2)_n$-heterocycloalkyl, Y—$(CH_2)_n$-aryl or Y—$(CH_2)_n$-heteroaryl, with Y=O, S, NH, O—C(O), C(O)—NH, NH—C(O), NH—S(O) or NH—$S(O)_2$, with n=0, 1, 2, or 3, and in said radicals the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or $NR_3$ where $R_3$ represents H or alkyl, itself optionally substituted, all the alkyl, alkoxy, alkylthio, cycloalkyl, heterocycloalkyl, aryl and heteroaryl radicals of the substituents of the products of formula (I) being optionally substituted, said products of formula (I) being in all possible tautomeric and isomeric forms: racemates, enantiomers and diastereoisomers, as well as salts of addition with inorganic and organic acids or with inorganic and organic bases of said products of formula (I).

In the products of formula (I) and hereinafter, the terms used have the following meanings:

the term halogen denotes the atoms of fluorine, of chlorine, of bromine or of iodine and preferably of fluorine, chlorine or bromine.

the term alkyl radical denotes a linear or branched radical containing at most 12 carbon atoms selected from the methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl and also heptyl, octyl, nonyl, decyl, undecyl and dodecyl radicals, as well as their linear or branched positional isomers. We may mention more particularly the alkyl radicals having at most 6 carbon atoms and notably the following radicals: methyl, ethyl, propyl, isopropyl, n-butyl, isobutyl, terbutyl, pentyl linear or branched, hexyl linear or branched.

the term alkenyl radical denotes a linear or branched radical containing at most 12 carbon atoms and preferably 4 carbon atoms selected for example from the following values: ethenyl or vinyl, propenyl or allyl, 1-propenyl, n-butenyl, i-butenyl, 3-methylbut-2-enyl, n-pentenyl, hexenyl, heptenyl, octenyl, cyclohexylbutenyl and decenyl as well as their linear or branched positional isomers. Among the alkenyl values, we may mention more particularly the allyl or butenyl values.

the term alkynyl radical denotes a linear or branched radical containing at most 12 carbon atoms and preferably 4 carbon atoms selected for example from the following values: ethynyl, propynyl or propargyl, butynyl, n-butynyl, i-butynyl, 3-methylbut-2-ynyl, pentynyl or hexynyl as well as their linear or branched positional isomers. Among the alkynyl values, we may mention more particularly the propargyl value.

the term alkoxy radical denotes a linear or branched radical containing at most 12 carbon atoms and preferably 6 carbon atoms selected for example from the methoxy, ethoxy, propoxy, isopropoxy, linear, secondary or tertiary butoxy, pentoxy, hexoxy and heptoxy radicals as well as their linear or branched positional isomers, the term alkylthio or alkyl-S— denotes a linear or branched radical containing at most 12 carbon atoms and represents notably the methylthio, ethylthio, isopropylthio and heptylthio radicals. In the radicals containing a sulphur atom, the sulphur atom may be oxidized to SO or $S(O)_2$ radical.

the term acyl radical or r-CO— denotes a linear or branched radical containing at most 12 carbon atoms in which the radical r represents a hydrogen atom, an alkyl, cycloalkyl, cycloalkenyl, cycloalkyl, heterocycloalkyl or aryl radical, said radicals having the values stated above and being optionally substituted as stated: we may mention for example the formyl, acetyl, propionyl, butyryl or benzoyl radicals, or the valeryl, hexanoyl, acryloyl, crotonoyl or carbamoyl radicals.

the term cycloalkyl radical denotes a monocyclic or bicyclic carbocyclic radical containing from 3 to 10 ring members and notably denotes the cyclopropyl, cyclobutyl, cyclopentyl and cyclohexyl radicals, the term cycloalkylalkyl radical denotes a radical in which cycloalkyl and alkyl are selected from the values stated above: said radical thus denotes for example the cyclopropylmethyl, cyclopentylmethyl, cyclohexylmethyl and cycloheptylmethyl radicals.

by acyloxy radical, we mean the acyl-O— radicals in which acyl has the meaning stated above: we may mention for example the acetoxy or propionyloxy radicals.

by acylamino radical, we mean the acyl-N— radicals in which acyl has the meaning stated above.

the term aryl radical denotes the unsaturated radicals, monocyclic or made up of condensed rings, carbocyclic. As examples of said aryl radical, we may mention the phenyl or naphthyl radicals.

by aralkyl we mean the radicals resulting from combining the alkyl radicals mentioned previously, optionally substituted, and the aryl radicals also mentioned above, optionally substituted: we may mention for example the benzyl, phenylethyl, 2-phenethyl, triphenylmethyl or naphthalenemethyl radicals.

the term heterocyclic radical denotes a monocyclic or bicyclic carbocyclic radical, saturated (heterocycloalkyl) or partially or fully unsaturated (heteroaryl) made up of 4 to 10 ring members interrupted by one or more heteroatoms, which may be identical or different, selected from atoms of oxygen, of nitrogen or of sulphur.

As heterocycloalkyl radicals, we may mention notably the dioxolane, dioxan, dithiolane, thiooxolane, thiooxane, oxirannyl, oxolannyl, dioxolannyl, piperazinyl, piperidyl, pyrrolidinyl, imidazolidinyl, diazepinyl, imidazolidine-2,4-dione, pyrazolidinyl and morpholinyl radicals or the tetrahydrofuryl, hexahydropyranne, tetrahydrothienyl, chromanyl, dihydrobenzofuranyl, indolinyl, perhydropyranyl, pyrindolinyl, tetrahydroquinolinyl, tetrahydroisoquinolinyl or thioazolidinyl radicals, all said radicals being optionally substituted.

Among the heterocycloalkyl radicals, we may mention notably the following radicals: piperazinyl optionally substituted, N-methylpiperazinyl, piperidyl, optionally substituted, pyrrolidinyl optionally substituted, imidazolidinyl, pyrazolidinyl, morpholinyl, hexahydropyranne or thioazolidinyl.

By heterocycloalkylalkyl radical, we mean the radicals in which the heterocycloalkyl and alkyl residues have the meanings given above among the 5-membered heteroaryl radicals we may mention the 2-furyl, 3-furyl, 2-pyrrolyl, 3-pyrrolyl, tetrazolyl, thiazolyl, isothiazolyl, diazolyl, thiadiazolyl, 1,3,4-thiadiazolyl, thiatriazolyl, oxazolyl, oxadiazolyl, isoxazolyl, 3-isoxazolyl, 4-isoxazolyl, imidazolyl, pyrazolyl, thienyl, 2-thienyl and 3-thienyl radicals, and triazolyl groups:

Among the 6-membered heteroaryl radicals we may mention notably the pyridyl radicals such as 2-pyridyl, 3-pyridyl and 4-pyridyl, pyrimidyl such as, for example, 2-pyrimidyl, pyrimidinyl such as, for example, 4-pyrimidinyl, 5-pyrimidinyl, pyridazinyl, pyrazinyl such as, for example 3-pyrazinyl, 4-pyrazinyl.

As condensed heteroaryl radicals containing at least one heteroatom selected from sulphur, nitrogen and oxygen, we may mention for example benzothienyl such as 3-benzothienyl, benzofuryl, benzofurannyl, benzopyrrolyl, benzimidazolyl, benzoxazolyl, thionaphthyl, indolyl, purinyl, quinolyl, isoquinolyl, azaindolyl and naphthyridinyl.

Among the condensed heteroaryl radicals, we may mention more particularly the radicals benzothienyl, benzofurannyl, indolyl, benzimidazolyl, benzothiazolyl, naphthyridinyl, indazolyl, quinolyl such as 4-quinolyl, 5-quinolyl, isoquinolyl, azaindolyl such as 4-azaindolyl, 3-azaindolyl, imidazo(4,5)pyridine, chromenyl, indolizinyl, quinazolinyl, etc., said radicals being optionally substituted as stated for the heteroaryl radicals.

By alkylamino radical, we mean radicals in which the alkyl radical is selected from the alkyl radicals mentioned above. The alkyl radicals having at most 4 carbon atoms are preferred, and we may mention for example the radicals: methylamino, ethylamino, propylamino or butylamino, linear or branched.

By dialkylamino radical, we mean radicals in which the alkyl radicals, which may be identical or different, are selected from the alkyl radicals mentioned above. As previously, the alkyl radicals having at most 4 carbon atoms are preferred, and we may mention for example the radicals dimethylamino, diethylamino, methylethylamino linear or branched.

The term cyclic amine denotes a monocyclic or bicyclic radical containing from 3 to 10 ring members in which at least one carbon atom is replaced by a nitrogen atom, and said cyclic radical may also contain one or more other heteroatoms selected from O, S, $SO_2$, N or $NR_3$ with $R_3$ as defined above: as examples of said cyclic amines, we may mention for example the pyrrolyl, imidazolyl, indolyl, piperidyl, morpholinyl, piperazinyl, pyrrolidinyl, indolinyl, pyrindolinyl or tetrahydroquinolyl radicals. The piperidinyl, morpholinyl or piperazinyl radicals are preferred.

The term patient denotes not only human beings, but other mammals as well. The term "Prodrug" denotes a product that can be converted in vivo by metabolic mechanisms (such as hydrolysis) to a product of formula (I). For example, an ester of a product of formula (I) containing a hydroxyl group can be converted by hydrolysis in vivo to its parent molecule. Or an ester of a product of formula (I) containing a carboxy group can be converted by hydrolysis in vivo to its respective parent molecule.

We may mention, as examples, esters of products of formula (I) containing a hydroxyl group such as the acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methanesulphonates, ethanesulphonates, benzene-sulphonates, p-toluenesulphonates, cyclohexylsulphamates and quinates.

Particularly useful esters of products of formula (I) containing a hydroxyl group can be prepared from acid residues such as those described by Bundgaard et al., J. Med. Chem., 1989, 32, page 2503-2507: these esters notably include substituted (aminomethyl)-benzoates, dialkylamino-methylbenzoates in which the two alkyl groups can be joined together or can be interrupted by an oxygen atom or by a nitrogen atom optionally substituted i.e. an alkylated nitrogen atom or alternatively (morpholino-methyl)benzoates, e.g. 3- or 4-(morpholinomethyl)-benzoates, and (4-alkylpiperazin-1-yl)-benzoates, e.g. 3- or 4-(4-alkylpiperazin-1-yl)benzoates.

The carboxy radical or radicals of the products of formula (I) can be salified or esterified by the various groups known to a person skilled in the art, among which we may mention, as non-limiting examples, the following compounds.

among the salification compounds, inorganic bases such as, for example, an equivalent of sodium, of potassium, of lithium, of calcium, of magnesium or of ammonium or of the organic bases such as, for example, methylamine, propylamine, trimethylamine, diethylamine, triethylamine, N,N-dimethyl-ethanolamine, tris(hydroxymethyl)aminomethane, ethanolamine, pyridine, picoline, dicyclohexylamine, morpholine, benzylamine, procaine, lysine, arginine, histidine, N-methylglucamine, among the esterification compounds, alkyl radicals for forming alkoxycarbonyl groups such as, for example, methoxycarbonyl, ethoxycarbonyl, tert-butoxy-carbonyl or benzyloxycarbonyl, and said alkyl radicals can be substituted by radicals selected for example from halogen atoms, the hydroxyl, alkoxy, acyl, acyloxy, alkylthio, amino or aryl radicals, for example, as in the chloromethyl, hydroxypropyl, methoxy-methyl, propionyloxymethyl, methylthiomethyl, dimethyl-aminoethyl, benzyl or phenethyl groups.

By esterified carboxy we mean for example radicals such as the alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

We may also mention radicals formed with the readily cleavable ester residues such as the methoxymethyl and ethoxymethyl radicals; the acyloxyalkyl radicals such as pivaloyloxymethyl, pivaloyloxyethyl, acetoxy-methyl or acetoxyethyl; the alkyloxycarbonyloxy alkyl radicals such as the methoxycarbonyloxy methyl or ethyl radicals, and the isopropyloxycarbonyloxy methyl or ethyl radicals.

A list of said ester radicals will be found for example in European patent EP 0 034 536.

By amidated carboxy, we mean radicals of the type —$CONH_2$ in which the hydrogen atoms are optionally substituted by one or two alkyl radicals to form alkylamino or dialkylamino radicals which are themselves optionally substituted as stated above or hereunder, and said radicals can also form, with the nitrogen atom to which they are bound, a cyclic amine as defined above.

By salified carboxy we mean the salts formed for example with an equivalent of sodium, of potassium, of lithium, of calcium, of magnesium or of ammonium. We may also mention the salts formed with organic bases such as methylamine, propylamine, trimethylamine, diethylamine, triethylamine. The sodium salt is preferred.

When the products of formula (I) contain an amino radical that is salifiable by an acid, said salts of acids are also part of the invention. We may mention the salts formed with hydrochloric acid or methanesulphonic acid for example.

The salts of addition with inorganic or organic acids of the products of formula (I) can be, for example, salts formed with hydrochloric, hydrobromic, hydriodic, nitric, sulphuric, phosphoric, propionic, acetic, trifluoroacetic, formic, benzoic, maleic, fumaric, succinic, tartaric, citric, oxalic, glyoxylic, aspartic, ascorbic acids, the alkylmonosulphonic acids such as methanesulphonic acid, ethanesulphonic acid, propanesulphonic acid, the alkyldisulphonic acids such as methanedisulphonic acid, alpha,beta-ethanedisulphonic acid, the arylmonosulphonic acids such as benzenesulphonic acid and the aryldisulphonic acids.

It may be recalled that stereoisomerism can be defined broadly as the isomerism of compounds having the same structural formulae, but with the various groups arranged differently in space, such as notably in the monosubstituted cyclohexanes where the substituent can be in the axial or equatorial position, and the various possible rotational conformations of the derivatives of ethane. However, there is another type of stereoisomerism, due to different spatial arrangements of fixed substituents, either on double bonds, or on rings, which is often called geometric isomerism or cis-trans isomerism. The term stereoisomer is used in the present application in its broadest sense and therefore relates to all of the compounds mentioned above.

The present invention notably relates to the above products of formula (I) in which $A_1$, $A_2$, $A_3$ and A4, which may be identical or different, represent CRa or N;

Ra is selected from the group comprising H; halogen; hydroxy; mercapto; amino; Y—$(CH_2)_n$-alkyl; Y—$(CH_2)_n$-cycloalkyl, Y—$(CH_2)_n$-heterocycloalkyl, Y—$(CH_2)_n$-aryl or Y—$(CH_2)_n$-heteroaryl, with Y=O, with n=0, 1, 2, or 3, radicals in which all the alkyl, cycloalkyl, heterocycloalkyl, aryl and heteroaryl radicals are optionally substituted and the heterocycloalkyl and heteroaryl radicals contain from 4 to 10 ring members including 1 to 4 heteroatoms selected from O, S, N or $NR_3$ where $R_3$ represents H or alkyl, itself optionally substituted, the other substituents $R_1$, $R_1'$, $R_2$, $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) in which $A_1$, $A_2$, $A_3$ and A4, which may be identical or different, represent CRa or N;

Ra is selected from the group comprising H; halogen; hydroxy; Y—$(CH_2)_n$-alkyl; Y—$(CH_2)_n$-cycloalkyl, Y—$(CH_2)_n$-heterocycloalkyl, Y—$(CH_2)_n$-aryl or Y—$(CH_2)_n$-heteroaryl, with Y=O, and with n=2 or 3, all the alkyl, cycloalkyl, heterocycloalkyl, aryl and heteroaryl radicals being optionally substituted, and the heterocycloalkyl and heteroaryl radicals, containing from 4 to 10 ring members including 1 to 4 heteroatoms selected from O, S, N or $NR_3$ where $R_3$ represents H or alkyl, itself optionally substituted, the other substituents $R_1$, $R_1'$, $R_2$, $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) in which $A_1$, $A_2$, $A_3$ and $A_4$ are such that all 4 represent CRa or one of them represents CRa and the other three, which may be identical or different, represent N or CRa, where Ra represents H; halogen; hydroxy or alkoxy;

the other substituents $R_1$, $R_1'$, $R_2$, $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

When Ra represents alkoxy, Ra notably represents methoxy.

More particularly the present invention relates to the above products of formula (I) in which one of $A_2$ or $A_3$ represents N and the other one of $A_2$ or $A_3$ as well as $A_1$ and A4 represents CH, the other substituents $R_1$, $R_1'$, $R_2$, $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention relates in particular to the products of formula (I) as above in which $R_2$ and $R_2'$, which may be identical or different, are selected independently from the group comprising H, halogen, methyl, ethyl, amino, methoxy, $CH_2$—$NH_2$, $CH_2$—NHalk, $CH_2$—N(alk)$_2$, $CH_2$—OH, $CH_2$—Oalk, p and p', which may be identical or different, represent the integers 1 to 4 and 1 to 3, respectively;

the other substituents $A_1$, $A_2$, $A_3$, A4, $R_1$ and $R_1'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) in which $R_2$ and $R_2'$, which may be identical or different, are selected independently from the group comprising H, halogen, methyl, ethyl, amino, methoxy, etc.

p and p', which may be identical or different, represent the integers 1 to 4 and 1 to 3, respectively;

the other substituents $A_1$, $A_2$, $A_3$, A4, $R_1$ and $R_1'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) in which $R_2$ and $R_2'$, which may be identical or different, are selected independently from the group comprising H, methyl, p and p', which may be identical or different, represent the integers 1 to 4 and 1 to 3, respectively;

the other substituents $A_1$, $A_2$, $A_3$, A4, $R_1$ and $R_1'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

Notably in the products of formula (I) of the present invention, $R_2$ and $R_2'$ can be such that $R_2'$ represents hydrogen and $R_2$ is selected from all the values stated above for $R_2$ and $R_2'$.

Notably $R_2$ and $R_2'$ both represent hydrogen.

The present invention notably relates to the above products of formula (I) in which $R_1$ and $R_1'$ are such that:

either $R_1$ and $R_1'$, which may be identical or different, are such that one of $R_1$ and $R_1'$ represents a hydrogen atom, and the other one of $R_1$ and $R_1'$ is selected from the group comprising H; halogen; hydroxyl; amino; NH—CO—H; NH—CO—OH, NH—CO-Oalkyl, NH—CO—$NH_2$; carboxy; CO—$NH_2$; X—$(CH_2)_m$-alkyl; X—$(CH_2)_m$-cycloalkyl; X—$(CH_2)_m$-heterocycloalkyl; X—$(CH_2)_m$-aryl and X—$(CH_2)_m$-heteroaryl, with X=single bond, $CH_2$, CH=CH, $CH_2$—C(O), NH, O—C(O), C(O)—NH, —NH—C(O), —NH—C(O)—C(O)—, —NH—C(O)—NH—; NH—CS, NH—S(O) or NH—S(O)$_2$, with m=0, all the alkyl, cycloalkyl, heterocycloalkyl, aryl and heteroaryl radicals being optionally substituted, the cycloalkyl radical containing from 3 to 10 ring members, the aryl radical containing from 6 to 10 ring members, and the heterocycloalkyl and heteroaryl radicals, optionally substituted containing from 4 to 10 ring members including 1 to 4 heteroatoms selected from O, S, N or $NR_3$ where $R_3$ represents H or alkyl, itself optionally substituted, or $R_1$ and $R_1'$ form, together with the carbon atom to which they are bound, an =O; =S; =N—OH; =N—$NH_2$; =N—NH—CO—$NH_2$, =CH—OH; =$Y_1$—$(CH_2)_m$-aryl or =$Y_1$—$(CH_2)_m$-heteroaryl radical, in which $Y_1$ represents CH, CH—CO—, CH—CO—NH, N, N—O or N—NH—, with m=0, 1 or 2 and in which aryl and heteroaryl are as defined above and optionally substituted, or $R_1$ and $R_1'$ form, together with the carbon atom to which they are bound, a partially saturated heterocycle made up of 5 to 6 ring members and containing from 1 to 3 heteroatoms selected from O, S, N or $NR_4$ where $R_4$ represents H or alkyl, itself optionally substituted, the other substituents $A_1$, $A_2$, $A_3$, A4, $R_2$ and $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

Notably in the products of formula (I) as defined above, when $R_1$ and $R_1'$ are such that one of $R_1$ and $R_1'$ represents a hydrogen atom and the other one of $R_1$ and $R_1'$ represents X—$(CH_2)_m$-cycloalkyl; X—$(CH_2)_m$-heterocycloalkyl; X—$(CH_2)_m$-aryl or X—$(CH_2)_m$-heteroaryl then X represents notably a single bond NH, O—C(O), C(O)—NH, —NH—C(O), —NH—C(O)—C(O)—, —NH—C(O)—NH—;

NH—CS or NH—S(O)$_2$, with m=0, all the alkyl, cycloalkyl, heterocycloalkyl, aryl and heteroaryl radicals being optionally substituted.

The present invention relates more particularly to the above products of formula (I) in which $A_1$, $A_2$, $A_3$ and A4, which may be identical or different, represent CRa or N or NRb where Rb represents $CH_3$ or OH;

Ra is selected from the group comprising H; $CH_3$; $CH_2$—$NH_2$; halogen; $CF_3$; hydroxy; $OCF_3$; $SO_2$—$NH_2$; $SO_2$—N($CH_3$)$_2$; mercapto; nitro; amino; NH($CH_3$); N($CH_3$)$_2$; NH—OH; NH—CO—H; NH—CO—$NH_2$; free carboxy or carboxy esterified with an alkyl radical, itself optionally substituted; $CO_2$—$CH_3$; $CO_2$—$(CH_2)_3$—N($CH_3$)$_2$; CN; CO—$NH_2$; CO—N($CH_3$)$_2$; CO—$CH_3$, CO—$(CH_2)_3$—O—$CH_3$); morpholinyl; piperazinyl-$CH_3$; imidazolinyl-$CH_3$; diazepin-$CH_3$; —CO-piperazinyl-$CH_3$; —CO-pyrrolidinyl; Y—$(CH_2)_n$-alkyl; Y—$(CH_2)_n$-cycloalkyl, Y—$(CH_2)_n$-heterocycloalkyl, Y—$(CH_2)_n$-aryl or Y—$(CH_2)_n$-heteroaryl, where Y represents a single bond or else =O, —C(O)—NH—, —C(O)N($CH_3$)—; CO, with n=0, 1, 2 or 3, and in said radicals the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or $NR_3$ where $R_3$ represents H or alkyl, itself optionally substituted, $R_1$ and $R_1'$ are such that: either one of $R_1$ and $R_1'$ represents a hydrogen atom, and the other one of $R_1$ and $R_1'$ is selected from the group comprising X—$(CH_2)_m$-heterocycloalkyl, X—$(CH_2)_m$-aryl and X—$(CH_2)_m$-heteroaryl, and in particular X—$(CH_2)_m$-heteroaryl, where X represents —O—C(O), —NH—C(O), NH—CS, —NH—CO—$CH_2$—O—; —NH—CO—$CH_2$—S—$CH_2$—CO—NH—; —NH—CO—$(CH_2)_2$—$SO_2$—; —NH—CO—$CH_2$—N($CH_3$)—CO—; and m=0, or $R_1$ and $R_1'$ form, together with the carbon atom to which they are bound an =N—OH or =N—$NH_2$ radical, $R_2$ and $R_2'$, which may be identical or different, are selected independently from the group comprising H, halogen, methyl, ethyl, amino, methoxy, $CH_2$—$NH_2$, $CH_2$—NHalk, $CH_2$—N(alk)$_2$, $CH_2$—OH and $CH_2$—Oalk, p and p', which may be identical or different, represent the integers 1 to 4 and 1 to 3, respectively;

all the alkyl, alkoxy, alkylthio, cycloalkyl, heterocycloalkyl, aryl and heteroaryl radicals of the substituents of the products of formula (I) being optionally substituted, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention relates more particularly to the above products of formula (I) in which $R_1$ and $R_1'$ are such that: either one of $R_1$ and $R_1'$ represents a hydrogen atom and the other one of $R_1$ and $R_1'$ is selected from the group comprising X—$(CH_2)_m$-heterocycloalkyl, X—$(CH_2)_m$-aryl and X—$(CH_2)_m$-heteroaryl, and notably X—$(CH_2)_m$-heteroaryl, where X represents —O—C(O), —NH—C(O) or NH—CS and m=0, or $R_1$ and $R_1'$ form, together with the carbon atom to which they are bound, a radical =N—OH or =N—$NH_2$, all the heterocycloalkyl, aryl and heteroaryl radicals being optionally substituted, the other substituents $A_1$, $A_2$, $A_3$, A4, $R_2$ and $R_2'$ of said products of formula (I) being selected from any one of the above definitions, said products of formula (I) being in all the possible tautomeric and isomeric forms: racemic, enantiomeric and diastereoisomeric, as well as the salts of addition with inorganic and organic acids or with inorganic and organic bases of said products of formula (I).

In the products of formula (I) as defined above and hereunder, all the alkyl, alkoxy, alkylthio, cycloalkyl, heterocycloalkyl, aryl and heteroaryl radicals are optionally substituted by one or more radicals, which may be identical or different, selected from the halogen atoms; the following radicals: hydroxyl; cyano; mercapto, nitro; carboxy—free, salified or esterified; tetrazolyl; —$NH_2$, —NH(alk), —N(alk)(alk); —$SO_2$—NH—CO—NH-alkyl; —$SO_2$—NH—CO—NH-phenyl; —C(O)—$NH_2$; CO-alkyl, $CONH_2$, —C(O)—NH(alk); —C(O)—N(alk)(alk), CO—NH-alk-O-alk, —NH—C(O)-(alk), —N(alk)-C(O)-(alk); —NH—COO-alkyl, NH—CO—$NH_2$, alkyl, acyl; alkylthio, cycloalkyl, heterocycloalkyl, aryl, heteroaryl, alkoxy and phenoxy, themselves optionally substituted by one or more radicals selected from the halogen atoms and the hydroxyl, alkoxy, alkyl, —$NH_2$, —NH(alk) and —N(alk)(alk) radicals.

Notably all the alkyl, alkoxy, alkylthio, cycloalkyl, heterocycloalkyl, aryl and heteroaryl radicals defined above can be optionally substituted by one or more substituents, identical or different, selected from halogen, OH, CN, SH, $NH_2$, NHalk, N(alk)$_2$, COOH, COOalk, $CONH_2$, CO—NH-alkyl, CO—NH-alk-O-alk, COalkyl, NH—COOalkyl, NH—CO—$NH_2$, NHCOalk, alkyl, hydroxyalkyl, alkoxy, cycloalkyl, heterocycloalkyl, aryl and heteroaryl.

Notably alkyl is optionally substituted by one or more substituents, identical or different, selected from $NH_2$, COOH, COOalk, $CONH_2$, COalkyl, NH—COOalkyl, NH—CO—$NH_2$, aryl, heteroaryl.

Notably heteroaryl is optionally substituted by one or more substituents, identical or different, selected from halogen, OH, CN, SH, $NH_2$, NHCOalk, NHalk, N(alk)$_2$, alkyl, hydroxyalkyl($CH_2OH$), alkoxy, COOH, COOalk, $CONH_2$, CO—NH-alkyl, CO—NH-Alk-O-Alk, COalkyl, NH—COOalkyl, NH—CO—$NH_2$, cycloalkyl, heterocycloalkyl, aryl, heteroaryl.

Notably heteroaryl is optionally substituted by one or more substituents, identical or different, selected from F, Cl, Br, OH, $NH_2$, NHCOalk such as $NHCOCH_3$, NHalk, N(alk)$_2$, alkyl, hydroxyalkyl such as $CH_2OH$ or COOalk.

In the above products of formula (I), in particular the alkyl, alkoxy, alkylthio, cycloalkyl, heterocycloalkyl, aryl and heteroaryl radicals of the substituents of the products of formula (I) are optionally substituted with one or more substituents, which may be identical or different, selected from halogen atoms and alkyl, OH, Oalkyl, $NH_2$, NH(alk) and N(alk)$_2$ radicals, and phenyl, piperazinyl and pyrrolidinyl radicals, themselves optionally substituted with one or more substituents selected from halogen atoms and alk, OH, Oalkyl, $NH_2$, NH(alk) and N(alk)$_2$ radicals.

In the above products of formula (I), in particular the alkyl, alkoxy, alkylthio, cycloalkyl, heterocycloalkyl, aryl and heteroaryl radicals of the substituents of the products of formula (I) are optionally substituted with one or more substituents, which may be identical or different, selected from halogen atoms and $CH_3$, OH, $OCH_3$, $NH_2$, NH($CH_3$) and N($CH_3$)$_2$ radicals, and phenyl, piperazinyl and pyrrolidinyl radicals, themselves optionally substituted with one or more substituents selected from halogen atoms and $CH_3$, OH, $OCH_3$, $NH_2$, NH($CH_3$) and N($CH_3$)$_2$ radicals.

The present invention relates in particular to the compounds in which $R_1$ and $R_1'$ are such that one of $R_1$ and $R_1'$ represents a hydrogen atom and the other one represents the —X—$(CH_2)_m$-heteroaryl radical, in which X represents —CO—NH— and m and heteroaryl have the meanings indicated above; by way of examples, the X—$(CH_2)_m$-heteroaryl radicals hereinafter are indicated:

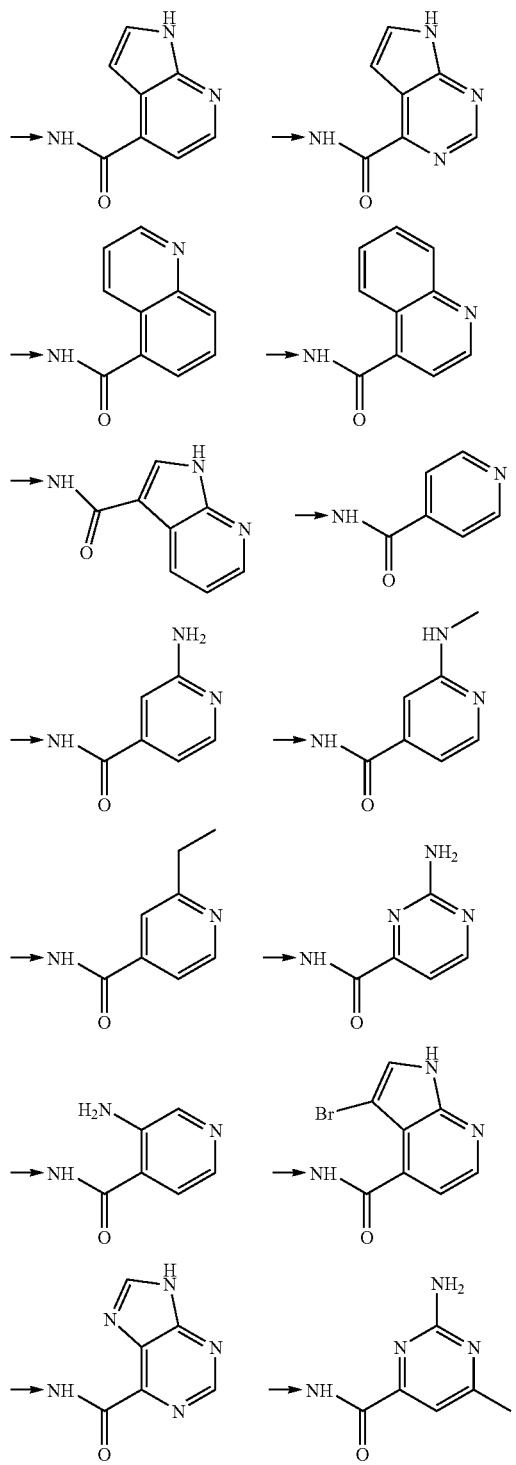

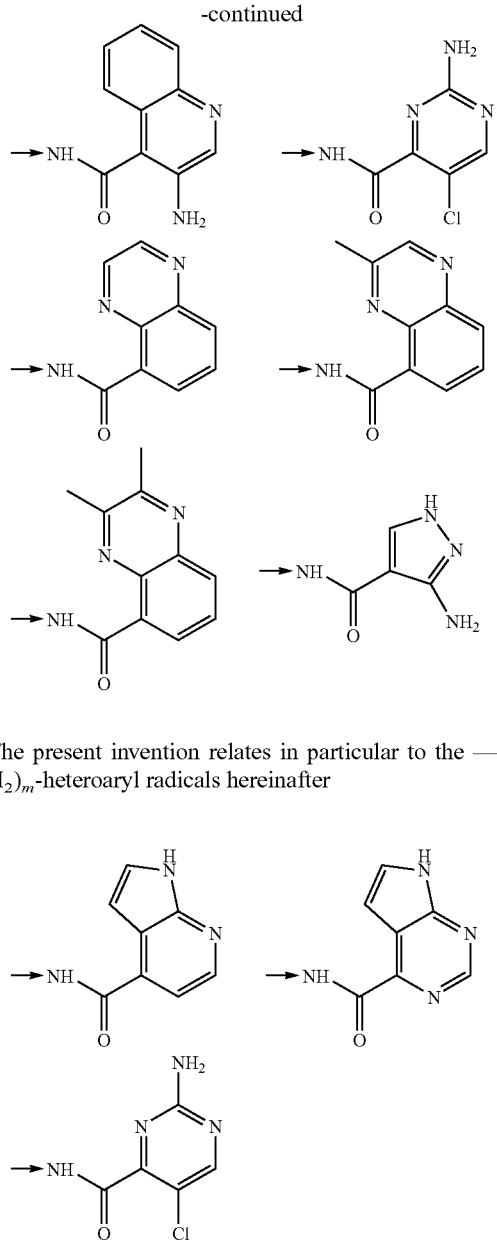

The present invention relates in particular to the —X—$(CH_2)_m$-heteroaryl radicals hereinafter In another aspect, the present invention also relates particularly to the compounds in which the radical

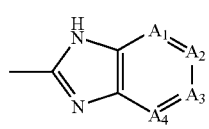

represents either a benzimidazole radical in which $A_1$, $A_2$, $A_3$ and A4, which may be identical or different, are selected from the values of CRa as defined above, or an aza-benzimidazole radical in which one or two of $A_1$, $A_2$, $A_3$ and A4 represent(s) N and the other three or the other two, which may be identical or different, are selected from the values of CRa as defined above.

Thus, by way of examples, the radicals of benzimidazole or aza-benzimidazole type hereinafter are indicated:
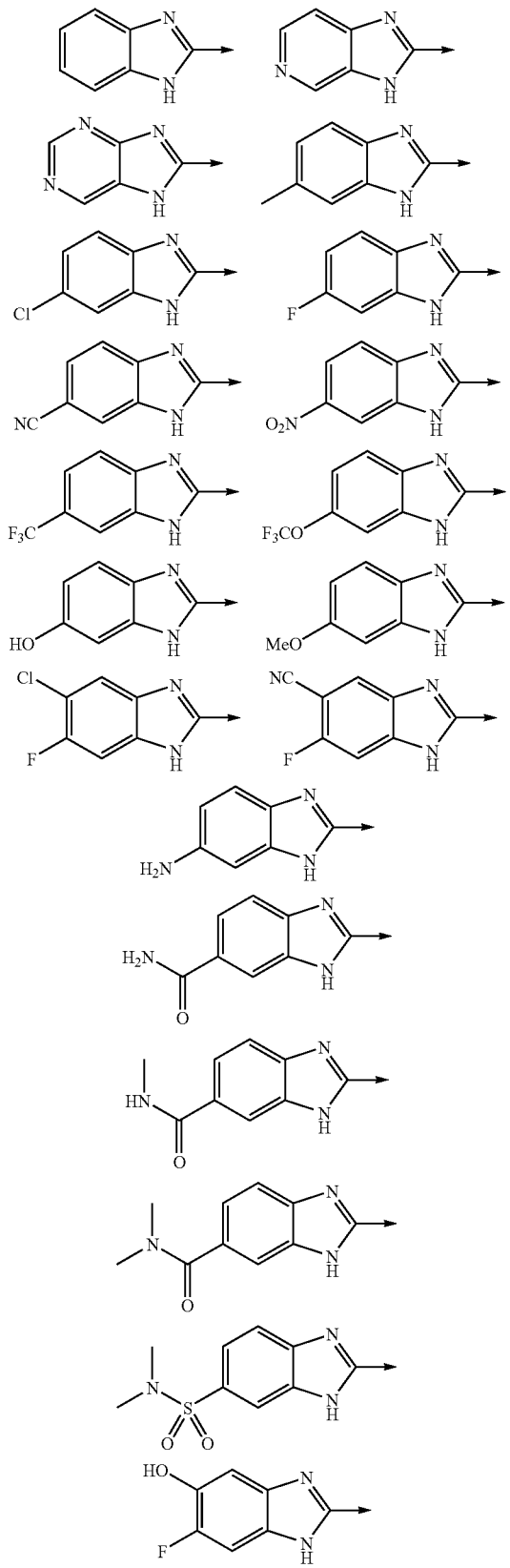
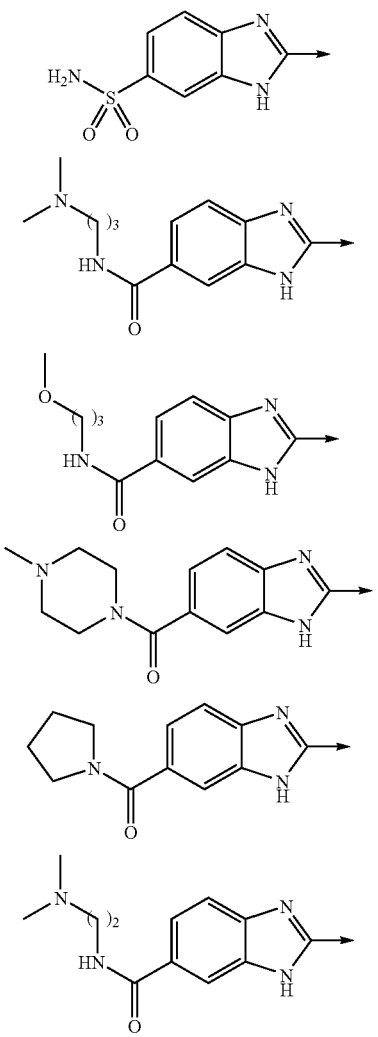
The radicals of benzimidazole or aza-benzimidazole type hereinafter are more particularly indicated by way of examples:
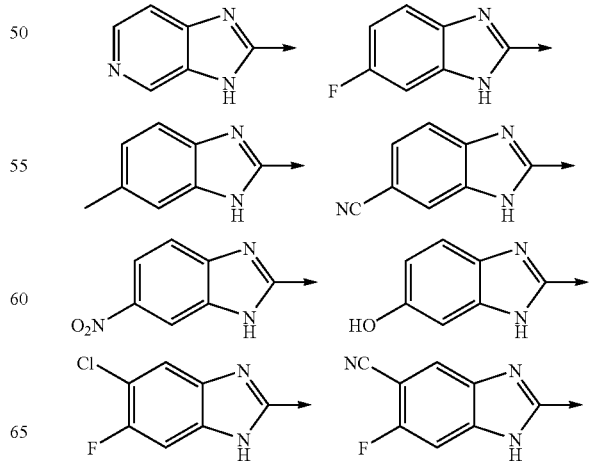

-continued

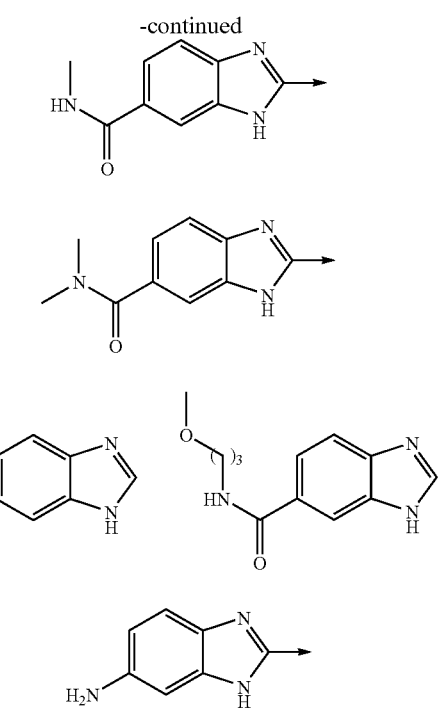

The present invention relates in particular to the products of general formula (I) as defined above, in which R$_2$' represents a hydrogen atom, where p' is equal to 3, and R$_2$ represents a hydrogen atom or an amino radical, it being understood that positions 5, 6 and 8 of the fluorene ring are preferentially substituted with a hydrogen atom and that position 7 of the fluorene ring is preferentially substituted with a hydrogen atom or an amino radical.

The present invention relates in particular to the products of general formula (I) as defined above, in which:

R$_2$' represents a hydrogen atom, with p' equal to 3, and R$_2$ represents a hydrogen atom or an amino radical, it being understood that positions 5, 6 and 8 of the fluorene ring are preferentially substituted with a hydrogen atom and that position 7 of the fluorene ring is preferentially substituted with a hydrogen atom or an amino radical, R$_1$ and R$_1$' are such that one of R$_1$ and R$_1$' represents a hydrogen atom and the other one is selected from the group comprising:

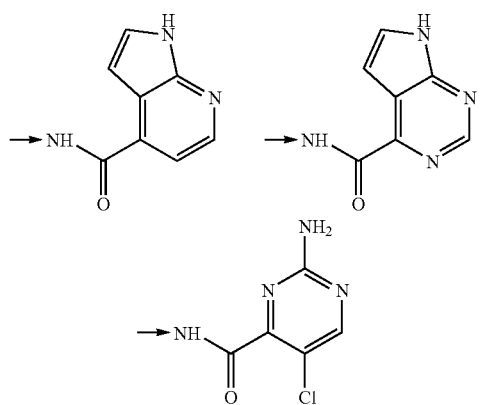

and the radical:

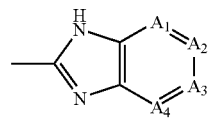

represents in particular the benzimidazole and aza-benzimidazole radicals below:

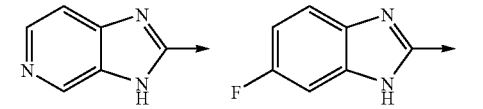

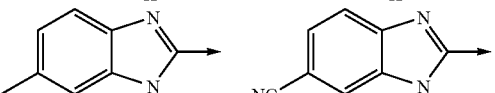

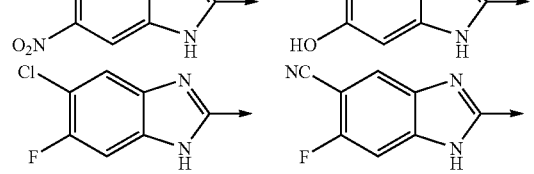

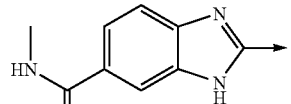

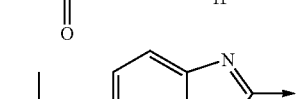

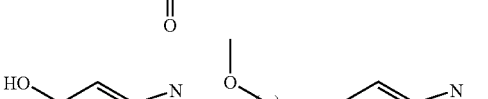

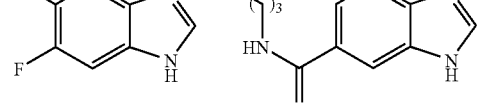

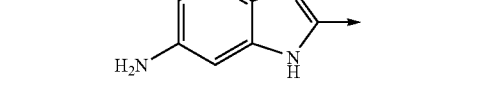

The present invention relates in particular to the dextrorotatory enantiomers of the above compounds.

The present invention notably relates to the above products of formula (I) with the following names:

4-(3H-imidazo[4,5-c]pyridin-2-yl)-fluoren-9-one oxime (Z, E).

N-[4-(1H-imidazo[4,5-c]pyridin-2-yl)-fluoren-9-ylidene]-hydrazine, 60/40 mixture of E and Z isomers

[4-(3H-imidazo[4,5-c]pyridin-2-yl)-9H-fluoren-9(R,S)-yl] amide of quinoline-5-carboxylic acid dextrorotatory enantiomer of [4-(3H-imidazo[4,5-c]pyridin-2-yl)-9H-fluoren-9(R,S)-yl]amide of quinoline-5-carboxylic acid 4-(3H-imidazo[4,5-c]pyridin-2-yl)-fluoren-9-one oxime (E).

trifluoroacetate of [4-(3H-imidazo[4,5-c]pyridin-2-yl)-9H-fluoren-9(R,S)-yl]amide of 1H-pyrazole-4-carboxylic acid trifluoroacetate of N-[4-(3H-imidazo[4,5-c]pyridin-2-yl)-9H-fluoren-9(R,S)-yl]-succinamide.

trifluoroacetate of [4-(3H-imidazo[4,5-c]pyridin-2-yl)-9H-fluoren-9(R,S)-yl]amide of 1H-benzotriazole-5-carboxylic acid

[4-(3H-imidazo[4,5-c]pyridin-2-yl)-9H-fluoren-9(R,S)-yl]amide of 1H-indazole-5-carboxylic acid

[4-(3H-imidazo[4,5-c]pyridin-2-yl)-9H-fluoren-9(R,S)-yl]amide of 1H-indole-6-carboxylic acid N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl]amide of 1H-indole-4-carboxylic acid trifluoroacetate of [4-(3H-imidazo[4,5-c]pyridin-2-yl)-9H-fluoren-9(R,S)-yl]amide of quinoline-5-carbothioic acid 2-acetylamino-N-[4-(3H-imidazo[4,5-c]pyridin-2-yl)-9H-fluoren-9(R,S)-yl]-iso-nicotinamide

[4-(3H-imidazo[4,5-c]pyridin-2-yl)-9H-fluoren-9(R,S)-yl]amide of quinoline-4-carboxylic acid 2-amino-N-[4-(3H-imidazo[4,5-c]pyridin-2-yl)-9H-fluoren-9(R,S)-yl]-iso-nicotinamide.

2-ethyl-N-[4-(3H-imidazo[4,5-c]pyridin-2-yl)-9H-fluoren-9(R,S)-yl]-iso-nicotinamide

[4-(6-fluoro-1H-benzimidazol-2-yl)-9H-fluoren-9(R,S)-yl]amide of quinoline-5-carboxylic acid 2-chloro-N-[4-(3H-imidazo[4,5-c]pyridin-2-yl)-9H-fluoren-9(R,S)-yl]-iso-nicotinamide

[4-(3H-imidazo[4,5-c]pyridin-2-yl)-9H-fluoren-9(R,S)-yl]amide of 2-amino-pyrimidine-4-carboxylic acid

[4-(3H-imidazo[4,5-c]pyridin-2-yl)-9H-fluoren-9(R,S)-yl]amide of 1H-pyrrolo[2,3-b]pyridine-4-carboxylic acid 2-hydroxymethyl-N-[4-(3H-imidazo[4,5-c]pyridin-2-yl)-9H-fluoren-9(R,S)-yl]-isonicotinamide N-[4-(3H-imidazo[4,5-c]pyridin-2-yl)-9H-fluoren-9(R,S)-yl]-3-methyl-iso-nicotinamide hydrochloride of [4-(3H-imidazo[4,5-c]pyridin-2-yl)-9H-fluoren-9(R,S)-yl]amide of 1,8-naphthyridine-4-carboxylic acid

[4-(3H-imidazo[4,5-c]pyridin-2-yl)-9H-fluoren-9(R,S)-yl]amide of 1H-pyrrolo[2,3-b]pyridine-3-carboxylic acid 5-[4-(3H-imidazo[4,5-c]pyridin-2-yl)-9H-fluoren-9(R,S)-yl]amide of 1-methyl-1H-pyrrolo[2,3-b]pyridine-3-carboxylic acid 2-bromo-N-[4-(3H-imidazo[4,5-c]pyridin-2-yl)-9H-fluoren-9(R,S)-yl]-iso-nicotinamide 3-hydroxy-N-[4-(3H-imidazo[4,5-c]pyridin-2-yl)-9H-fluoren-9(R,S)-yl]-isonicotinamide 3-amino-N-[4-(3H-imidazo[4,5-c]pyridin-2-yl)-9H-fluoren-9(R,S)-yl]-iso-nicotinamide methyl ester of 4-[4-(3H-imidazo[4,5-c]pyridin-2-yl)-9H-fluoren-9(R,S)-ylcarbamoyl]-pyridine-2-carboxylic acid

[4-(3H-imidazo[4,5-c]pyridin-2-yl)-9H-fluoren-9(R,S)-yl]amide of 1H-indazole-4-carboxylic acid N-[4-(3H-imidazo[4,5-c]pyridin-2-yl)-9H-fluoren-9(R,S)-yl]-2-methylamino-isonicotinamide N-[4-(6-hydroxy-1H-benzimidazol-2-yl)-9H-fluoren-9(R,S)-yl]-isonicotinamide

[4-(3H-imidazo[4,5-c]pyridin-2-yl)-9H-fluoren-9(R,S)-yl]amide of 6-bromo-3H-imidazo[4,5-b]pyridine-7-carboxylic acid 4-(3H-imidazo[4,5-c]pyridin-2-yl)-9H-fluoren-9-yl ester of isonicotinic acid, N-[4-(3H-imidazo[4,5-c]pyridin-2-yl)-9H-fluoren-9(R,S)-yl]amide of 2-tert-butoxycarbonylamino-isonicotinic acid N-[4-(3H-imidazo[4,5-c]pyridin-2-yl)-9H-fluoren-9(R,S)-yl]amide of 3-chloro-6-methoxy-quinoline-4-carboxylic acid N-[4-(3H-imidazo[4,5-c]pyridin-2-yl)-9H-fluoren-9(R,S)-yl]amide of 3-hydroxy-quinoline-4-carboxylic acid N-[4-(3H-imidazo[4,5-c]pyridin-2-yl)-9H-fluoren-9(R,S)-yl]amide of 2-amino-5-chloro-pyrimidine-4-carboxylic acid

[4-(3H-imidazo[4,5-c]pyridin-2-yl)-9H-fluoren-9(R,S)-yl] amide of 3-bromo-1H-pyrrolo[2,3-b]pyridine-4-carboxylic acid dextrorotatory enantiomer of [4-(3H-imidazo[4,5-c]pyridin-2-yl)-9H-fluoren-9(R,S)-yl]amide of 1H-pyrrolo[2,3-b]pyridine-4-carboxylic acid N-[4-(3H-imidazo[4,5-c]pyridin-2-yl)-9H-fluoren-9(R,S)-yl]amide of 9H-purine-6-carboxylic acid N-[4-(3H-imidazo[4,5-c]pyridin-2-yl)-9H-fluoren-9(R,S)-yl]amide of 2-amino-6-methyl-pyrimidine-4-carboxylic acid

[4-(3H-imidazo[4,5-c]pyridin-2-yl)-9H-fluoren-9(R,S)-yl] amide of 5-amino-3H-1,2,3-triazole-4-carboxylic acid N-[4-(3H-imidazo[4,5-c]pyridin-2-yl)-9H-fluoren-9(R,S)-yl]amide of 6-methyl-2-methylamino-pyrimidine-4-carboxylic acid N-[4-(3H-imidazo[4,5-c]pyridin-2-yl)-9H-fluoren-9(R,S)-yl]amide of 6-methoxy-quinoline-4-carboxylic acid 3,5-dihydroxy-N-[4-(3H-imidazo[4,5-c]pyridin-2-yl)-9H-fluoren-9(R,S)-yl]-benzamide N-[4-(3H-imidazo[4,5-c]pyridin-2-yl)-9H-fluoren-9(R,S)-yl]amide of pyrimidine-4-carboxylic acid 4-hydroxy-N-[4-(3H-imidazo[4,5-c]pyridin-2-yl)-9H-fluoren-9(R,S)-yl]-benzamide 2,4-dihydroxy-N-[4-(3H-imidazo[4,5-c]pyridin-2-yl)-9H-fluoren-9(R,S)-yl]-benzamide

[4-(5-cyano-6-fluoro-1H-benzimidazol-2-yl)-9H-fluoren-9(R,S)-yl]amide of 1H-pyrrolo[2,3-b]pyridine-4-carboxylic acid 4-(1H-benzimidazol-2-yl)-9H-fluoren-9(R,S)-yl]amide of 2-amino-5-chloro-pyrimidine-4-carboxylic acid

[4-(5-fluoro-1H-benzimidazol-2-yl)-9H-fluoren-9(R,S)-yl] amide of 2-amino-5-chloro-pyrimidine-4-carboxylic acid

[4-(5-fluoro-1H-benzimidazol-2-yl)-9H-fluoren-9(R,S)-yl] amide of 1H-pyrrolo[2,3-b]pyridine-4-carboxylic acid

[4-(3H-imidazo[4,5-c]pyridin-2-yl)-9H-fluoren-9(R,S)-yl] amide of 2,3-dimethyl-quinoxaline-5-carboxylic acid

[4-(3H-imidazo[4,5-c]pyridin-2-yl)-9H-fluoren-9(R,S)-yl] amide of 3-amino-1H-pyrazole-4-carboxylic acid dextrorotatory enantiomer of N-[4-(3H-imidazo[4,5-c]pyridin-2-yl)-9H-fluoren-9(R,S)-yl]amide of 2-amino-5-chloro-pyrimidine-4-carboxylic acid levorotatory enantiomer of N-[4-(3H-imidazo[4,5-c]pyridin-2-yl)-9H-fluoren-9(R,S)-yl]amide of 2-amino-5-chloro-pyrimidine-4-carboxylic acid

[4-(3H-imidazo[4,5-c]pyridin-2-yl)-9H-fluoren-9(R,S)-yl] amide of 3-methyl-quinoxaline-5-carboxylic acid

[4-(3H-imidazo[4,5-c]pyridin-2-yl)-9H-fluoren-9(R,S)-yl] amide of quinoxaline-5-carboxylic acid

[4-(9H-purine-8-yl)-9H-fluoren-9(R,S)-yl]amide of 1H-pyrrolo[2,3-b]pyridine-4-carboxylic acid

[4-(1H-benzimidazol-2-yl)-9H-fluoren-9(R,S)-yl]amide of 1H-pyrrolo[2,3-b]-pyridine-4-carboxylic acid

[4-(5-trifluoromethyl-1H-benzimidazol-2-yl)-9H-fluoren-9(R,S)-yl]amide of 1H-pyrrolo[2,3-b]pyridine-4-carboxylic acid

[4-(5-methoxycarbonyl-1H-benzimidazol-2-yl)-9H-fluoren-9(R,S)-yl]amide of 1H-pyrrolo[2,3-b]pyridine-4-carboxylic acid

[4-(5-carboxy-1H-benzimidazol-2-yl)-9H-fluoren-9(R,S)-yl]amide of 1H-pyrrolo[2,3-b]pyridine-4-carboxylic acid

[4-(4-methyl-1H-benzimidazol-2-yl)-9H-fluoren-9(R,S)-yl]amide of 1H-pyrrolo[2,3-b]pyridine-4-carboxylic acid

[4-(5-carboxamido-1H-benzimidazol-2-yl)-9H-fluoren-9(R,S)-yl]amide of 1H-pyrrolo[2,3-b]pyridine-4-carboxylic acid

[4-(6-sulphamoyl-1H-benzimidazol-2-yl)-9H-fluoren-9(R,S)-yl]amide of 1H-pyrrolo[2,3-b]pyridine-4-carboxylic acid

[4-(5-trifluoromethoxy-1H-benzimidazol-2-yl)-9H-fluoren-9(R,S)-yl]amide of 1H-pyrrolo[2,3-b]pyridine-4-carboxylic acid

[4-(5-cyano-1H-benzimidazol-2-yl)-9H-fluoren-9(R,S)-yl]amide of 1H-pyrrolo[2,3-b]pyridine-4-carboxylic acid D diastereoisomer of [4-(3H-imidazo[4,5-c]pyridin-2-yl)-9H-fluoren-9(R,S)-yl]amide of 2-(3-acetyl-2,2-dimethyl-cyclobutan-1-yl)acetic acid

[4-(6-chloro-1H-benzimidazol-2-yl)-9H-fluoren-9(R,S)-yl]amide of 1H-pyrrolo[2,3-b]pyridine-4-carboxylic acid

[4-(5-fluoro-6-morpholino-1H-benzimidazole-2-yl)-9H-fluoren-9(R,S)-yl]amide of 1H-pyrrolo[2,3-b]pyridine-4-carboxylic acid

[4-(6-chloro-5-fluoro-1H-benzimidazole-2-yl)-9H-fluoren-9(R,S)-yl]amide of 1H-pyrrolo[2,3-b]pyridine-4-carboxylic acid

[4-(4,5,6,7-tetrahydro-1H-benzimidazol-2-yl)-9H-fluoren-9(R,S)-yl]amide of 1H-pyrrolo[2,3-b]pyridine-4-carboxylic acid

[2-amino-5-(1H-benzimidazol-2-yl)-9H-fluoren-9(R,S)-yl]amide of 1H-pyrrolo[2,3-b]pyridine-4-carboxylic acid

[4-(5-hydroxy-5H-imidazo[4,5-c]pyridin-2-yl)-9H-fluoren-9(R,S)-yl]amide of 1H-pyrrolo[2,3-b]pyridine-4-carboxylic acid

[4-(5-hydroxy-1H-benzimidazole-2-yl)-9H-fluoren-9(R,S)-yl]amide of 1H-pyrrolo[2,3-b]pyridine-4-carboxylic acid

[4-(5-methylaminocarbonyl-1H-benzimidazol-2-yl)-9H-fluoren-9(R,S)-yl]amide of 1H-pyrrolo[2,3-b]pyridine-4-carboxylic acid

[4-(5-dimethylaminocarbonyl-1H-benzimidazol-2-yl)-9H-fluoren-9(R,S)-yl]amide of 1H-pyrrolo[2,3-b]pyridine-4-carboxylic acid

[4-5-(2-dimethylamino-ethyl)aminocarbonyl-1H-benzimidazol-2-yl)-9H-fluoren-9(R,S)-yl]amide of 1H-pyrrolo[2,3-b]pyridine-4-carboxylic acid

[4-(4,5,6,7-tetrafluoro-1H-benzimidazol-2-yl)-9H-fluoren-9(R,S)-yl]amide of 1H-pyrrolo[2,3-b]pyridine-4-carboxylic acid 4-[5-(3-methoxypropyl)aminocarbonyl-1H-benzimidazol-2-yl)-9H-fluoren-9(R,S)-yl]amide of 1H-pyrrolo[2,3-b]pyridine-4-carboxylic acid 4-[5-(4-methyl-piperazine-1-yl)carbonyl-1H-benzimidazol-2-yl)-9H-fluoren-9(R,S)-yl]amide of 1H-pyrrolo[2,3-b]pyridine-4-carboxylic acid

[4-(6-dimethylsulphamoyl-1H-benzimidazol-2-yl)-9H-fluoren-9(R,S)-yl]amide of 1H-pyrrolo[2,3-b]pyridine-4-carboxylic acid

[4-(5-(pyrrolidin-1-yl)carbonyl-1H-benzimidazol-2-yl)-9H-fluoren-9(R,S)-yl]amide of 1H-pyrrolo[2,3-b]pyridine-4-carboxylic acid dextrorotatory enantiomer of {4-{9(R,S)-[(1H-pyrrolo[2,3-b]pyridine-4-carbonyl)-amino]-9H-fluoren-4-yl}-1H-benzimidazole-5-carboxylic acid {{4-{5-[2-(pyrrolidin-1-yl)ethylaminocarbonyl]-1H-benzimidazole-2-yl}-9H-fluoren-9(R,S)-yl}}amide of 1H-pyrrolo[2,3-b]pyridine-4-carboxylic acid

[4-(6-dimethylamino-1H-benzimidazol-2-yl)-9H-fluoren-9(R,S)-yl]amide of 1H-pyrrolo[2,3-b]pyridine-4-carboxylic acid {4-[6-(4-methyl-piperazin-1-yl)-1H-benzimidazol-2-yl]-9H-fluoren-9(R,S)-yl}-amide of 1H-pyrrolo[2,3-b]pyridine-4-carboxylic acid

[4-[6-(methyl-4(5)-imidazolin-2-yl)-1H-benzimidazol-2-yl]-9H-fluoren-9(R,S)-yl]amide of 1H-pyrrolo[2,3-b]pyridine-4-carboxylic acid {{4-{5-[(3-dimethylamino-propyl)aminocarbonyl]-1H-benzimidazol-2-yl}-9H-fluoren-9(R,S)-yl}}-amide of 1H-pyrrolo[2,3-b]pyridine-4-carboxylic acid {4-[5-fluoro-6-(4-methyl-piperazin-1-yl)-1H-benzimidazol-2-yl]-9H-fluoren-9(R,S)-yl}-amide of 1H-pyrrolo[2,3-b]pyridine-4-carboxylic acid {{4-{5-[(3-dimethylamino-propyl)carbonyloxy]-1H-benzimidazol-2-yl}-9H-fluoren-9(R,S)-yl}}-amide of 1H-pyrrolo[2,3-b]pyridine-4-carboxylic acid

[4-(6-amino-1H-benzimidazol-2-yl)-9H-fluoren-9-(R,S)yl]amide of 1H-pyrrolo[2,3-b]pyridine-4-carboxylic acid

[4-(6-methyl-1H-benzimidazol-2-yl)-9H-fluoren-9(R,S)-yl]amide of 1H-pyrrolo[2,3-b]pyridine-4-carboxylic acid {{4-{5-[(3-hydroxy-propyl)aminocarbonyl]-1H-benzimidazole-2-yl}-9H-fluoren-9(R,S)-yl}}-amide of 1H-pyrrolo[2,3-b]pyridine-4-carboxylic acid dextrorotatory enantiomer of {4-[5-cyano-1H-benzimidazol-2-yl]-9H-fluoren-9(R,S)-yl}-amide of 1H-pyrrolo[2,3-b]pyridine-4-carboxylic acid

[4-(3H-imidazo[4,5-c]pyridin-2-yl)-9H-fluoren-9(R,S)-yl]amide of 7H-pyrrolo[2,3-d]pyrimidine-4-carboxylic acid

[4-(6-amino-1H-benzimidazol-2-yl)-9H-fluoren-9(R,S)-yl]amide of 1H-pyrrolo[2,3-b]pyridine-4-carboxylic acid dextrorotatory enantiomer of {4-[5-fluoro-1H-benzimidazol-2-yl]-9H-fluoren-9(R,S)-yl}-amide of 1H-pyrrolo[2,3-b]pyridine-4-carboxylic acid methyl ester of 2-{9(R,S)-[(1H-pyrrolo[2,3-b]pyridine-4-carbonyl)-amino]-9H-fluoren-4-yl}-1H-imidazo[4,5-c]pyridine-6-carboxylic acid

[4-(6-fluoro-5-methoxy-1H-benzimidazol-2-yl)-9H-fluoren-9(R,S)-yl]amide of 1H-pyrrolo[2,3-b]pyridine-4-carboxylic acid

[4-(6-fluoro-5-hydroxy-1H-benzimidazol-2-yl)-9H-fluoren-9(R,S)-yl]amide of 1H-pyrrolo[2,3-b]pyridine-4-carboxylic acid {4-[5-fluoro-6-(3-methoxy-propoxy)-1H-benzimidazol-2-yl]-9H-fluoren-9(R,S)-yl}-amide of 1H-pyrrolo[2,3-b]pyridine-4-carboxylic acid {4-[6-(3-dimethylamino-propoxy)-5-fluoro-1H-benzimidazol-2-yl]-9H-fluoren-9(R,S)-yl}-amide of 1H-pyrrolo[2,3-b]pyridine-4-carboxylic acid said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) with the following names:

4-(3H-imidazo[4,5-c]pyridin-2-yl)-fluoren-9-one oxime (Z, E).

N-[4-(1H-imidazo[4,5-c]pyridin-2-yl)-fluoren-9-ylidene]-hydrazine, 60/40 mixture of E and Z isomers

[4-(3H-imidazo[4,5-c]pyridin-2-yl)-9H-fluoren-9(R,S)-yl]amide of quinoline-5-carboxylic acid dextrorotatory enantiomer of [4-(3H-imidazo[4,5-c]pyridin-2-yl)-9H-fluoren-9(R,S)-yl]amide of quinoline-5-carboxylic acid 4-(3H-imidazo[4,5-c]pyridin-2-yl)-9H-fluoren-9-one oxime (E).

trifluoroacetate of [4-(3H-imidazo[4,5-c]pyridin-2-yl)-9H-fluoren-9(R,S)-yl]amide of 1H-pyrazole-4-carboxylic acid trifluoroacetate of N-[4-(3H-imidazo[4,5-c]pyridin-2-yl)-9H-fluoren-9(R,S)-yl]-succinamide.

trifluoroacetate of [4-(3H-imidazo[4,5-c]pyridin-2-yl)-9H-fluoren-9(R,S)-yl]amide of 1H-benzotriazole-5-carboxylic acid

[4-(3H-imidazo[4,5-c]pyridin-2-yl)-9H-fluoren-9(R,S)-yl] amide of 1H-indazole-5-carboxylic acid

[4-(3H-imidazo[4,5-c]pyridin-2-yl)-9H-fluoren-9(R,S)-yl] amide of 1H-indole-6-carboxylic acid N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 1H-indole-4-carboxylic acid trifluoroacetate of [4-(3H-imidazo[4,5-c]pyridin-2-yl)-9H-fluoren-9(R,S)-yl]amide of quinoline-5-carbothioic acid 2-acetylamino-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of quinoline-4-carboxylic acid 2-amino-N-[4-(3H-imidazo[4,5-c]pyridin-2-yl)-9H-fluoren-9(R,S)-yl]-isonicotinamide.

2-ethyl-N-[4-(3H-imidazo[4,5-c]pyridin-2-yl)-9H-fluoren-9(R,S)-yl]-isonicotinamide

[4-(6-fluoro-1H-benzimidazol-2-yl)-9H-fluoren-9(R,S)-yl] amide of quinoline-5-carboxylic acid 2-chloro-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 2-amino-pyrimidine-4-carboxylic acid

[4-(3H-imidazo[4,5-c]pyridin-2-yl)-9H-fluoren-9(R,S)-yl] amide of 1H-pyrrolo[2,3-b]pyridine-4-carboxylic acid 2-hydroxymethyl-N-[4-(3H-imidazo[4,5-c]pyridin-2-yl)-9H-fluoren-9(R,S)-yl]-isonicotinamide N-[4-(3H-imidazo[4,5-c]pyridin-2-yl)-9H-fluoren-9(R,S)-yl]-3-methyl-isonicotinamide hydrochloride of [4-(3H-imidazo[4,5-c]pyridin-2-yl)-9H-fluoren-9(R,S)-yl]amide of 1,8-naphthyridine-4-carboxylic acid

[4-(3H-imidazo[4,5-c]pyridin-2-yl)-9H-fluoren-9(R,S)-yl] amide of 1H-pyrrolo[2,3-b]pyridine-3-carboxylic acid

[4-(3H-imidazo[4,5-c]pyridin-2-yl)-9H-fluoren-9(R,S)-yl] amide of 1-methyl-1H-pyrrolo[2,3-b]pyridine-3-carboxylic acid 2-bromo-N-[4-(3H-imidazo[4,5-c]pyridin-2-yl)-9H-fluoren-9(R,S)-yl]-isonicotinamide 3-hydroxy-N-[4-(3H-imidazo[4,5-c]pyridin-2-yl)-9H-fluoren-9(R,S)-yl]-isonicotinamide 3-amino-N-[4-(3H-imidazo[4,5-c]pyridin-2-yl)-9H-fluoren-9(R,S)-yl]-isonicotinamide methyl ester of 4-[4-(3H-imidazo[4,5-c]pyridin-2-yl)-9H-fluoren-9(R,S)-ylcarbamoyl]-pyridine-2-carboxylic acid

[4-(3H-imidazo[4,5-c]pyridin-2-yl)-9H-fluoren-9(R,S)-yl] amide of 1H-indazole-4-carboxylic acid N-[4-(3H-imidazo[4,5-c]pyridin-2-yl)-9H-fluoren-9(R,S)-yl]-2-methylamino-isonicotinamide N-[4-(6-hydroxy-1H-benzimidazol-2-yl)-9H-fluoren-9(R,S)-yl]-isonicotinamide

[4-(3H-imidazo[4,5-c]pyridin-2-yl)-9H-fluoren-9(R,S)-yl] amide of 6-bromo-3H-imidazo[4,5-b]pyridine-7-carboxylic acid 4-(3H-imidazo[4,5-c]pyridin-2-yl)-9H-fluoren-9-yl ester of isonicotinic acid, said products of formula (I) being in all the possible tautomeric and isomeric forms: racemic, enantiomeric and diastereoisomeric, as well as the salts of addition with inorganic and organic acids or with inorganic and organic bases of said products of formula (I)

The present invention notably relates to the above products of formula (I) with the following names:

[4-(3H-imidazo[4,5-c]pyridin-2-yl)-9H-fluoren-9(R,S)-yl] amide of quinoline-5-carboxylic acid the dextrorotatory enantiomer of [4-(3H-imidazo[4,5-c]pyridin-2-yl)-9H-fluoren-9(R,S)-yl]amide of quinoline-5-carboxylic acid 4-(3H-imidazo[4,5-c]pyridin-2-yl)-fluoren-9-one oxime (E).

trifluoroacetate of [4-(3H-imidazo[4,5-c]pyridin-2-yl)-9H-fluoren-9(R,S)-yl]amide of 1H-benzotriazole-5-carboxylic acid N-[4-(3H-imidazo[4,5-c]pyridin-2-yl)-9H-fluoren-9(R,S)-yl]-isonicotinamide trifluoroacetate of [4-(3H-imidazo[4,5-c]pyridin-2-yl)-9H-fluoren-9(R,S)-yl]amide of quinoline-5-carbothioic acid 2-acetylamino-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of quinoline-4-carboxylic acid 2-amino-N-[4-(3H-imidazo[4,5-c]pyridin-2-yl)-9H-fluoren-9(R,S)-yl]-isonicotinamide.

2-ethyl-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 2-amino-pyrimidine-4-carboxylic acid

[4-(3H-imidazo[4,5-c]pyridin-2-yl)-9H-fluoren-9(R,S)-yl] amide of 1H-pyrrolo[2,3-b]pyridine-4-carboxylic acid

[4-(3H-imidazo[4,5-c]pyridin-2-yl)-9H-fluoren-9(R,S)-yl] amide of 1H-pyrrolo[2,3-b]pyridine-3-carboxylic acid 2-bromo-N-[4-(3H-imidazo[4,5-c]pyridin-2-yl)-9H-fluoren-9(R,S)-yl]-isonicotinamide 3-hydroxy-N-[4-(3H-imidazo[4,5-c]pyridin-2-yl)-9H-fluoren-9(R,S)-yl]-isonicotinamide 3-amino-N-[4-(3H-imidazo[4,5-c]pyridin-2-yl)-9H-fluoren-9(R,S)-yl]-isonicotinamide methyl ester of 4-[4-(3H-imidazo[4,5-c]pyridin-2-yl)-9H-fluoren-9(R,S)-ylcarbamoyl]-pyridine-2-carboxylic acid

[4-(3H-imidazo[4,5-c]pyridin-2-yl)-9H-fluoren-9(R,S)-yl] amide of 1H-indazole-4-carboxylic acid

[4-(3H-imidazo[4,5-c]pyridin-2-yl)-9H-fluoren-9(R,S)-yl] amide of 6-bromo-3H-imidazo[4,5-b]pyridine-7-carboxylic acid 4-(3H-imidazo[4,5-c]pyridin-2-yl)-9H-fluoren-9-yl ester of isonicotinic acid, said products of formula (I) being in all the possible tautomeric and isomeric forms: racemic, enantiomeric and diastereoisomeric, as well as the salts of addition with inorganic and organic acids or with inorganic and organic bases of said products of formula (I).

The present invention notably relates to the above products of formula (I) with the following names:

[4-(3H-imidazo[4,5-c]pyridin-2-yl)-9H-fluoren-9(R,S)-yl] amide of quinoline-5-carboxylic acid N-[4-(3H-imidazo[4,5-c]pyridin-2-yl)-9H-fluoren-9(R,S)-yl]-isonicotinamide 2-amino-N-[4-(3H-imidazo[4,5-c]pyridin-2-yl)-9H-fluoren-9(R,S)-yl]-isonicotinamide.

2-ethyl-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 2-amino-pyrimidine-4-carboxylic acid

[4-(3H-imidazo[4,5-c]pyridin-2-yl)-9H-fluoren-9(R,S)-yl] amide of 1H-pyrrolo[2,3-b]pyridine-4-carboxylic acid

[4-(3H-imidazo[4,5-c]pyridin-2-yl)-9H-fluoren-9(R,S)-yl] amide of 1H-pyrrolo[2,3-b]pyridine-3-carboxylic acid 3-amino-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 6-bromo-3H-imidazo[4,5-b]pyridine-7-carboxylic acid said products of formula (I) being in all the possible tautomeric and isomeric forms: racemic, enantiomeric and diastereoisomeric, as well as the salts of addition with inorganic and organic acids or with inorganic and organic bases of said products of formula (I).

The invention also relates to the methods of preparation of products of formula (I) as defined above.

Generally, products of general formula (I) according to the invention can be prepared by the various methods described by K. H. Wünsch and A. J. Boulton in Advances in Heterocyclic Chemistry Vol. 8, 277-302.

Generally, products of general formula (I) according to the invention can be prepared advantageously by at least one of the four general methods of synthesis indicated below.

General Methods of Synthesis:

A first general method of synthesis was developed starting from a 9-H-fluoren-9-one-4-carboxylic acid or its chloride—such as the chloride of commercial 9-H-fluoren-9-one-4-carboxylic acid—by forming a ring of the benzimidazole type. It was found to be particularly advantageous, within the scope of the present invention, to work in two successive stages according to scheme 1:

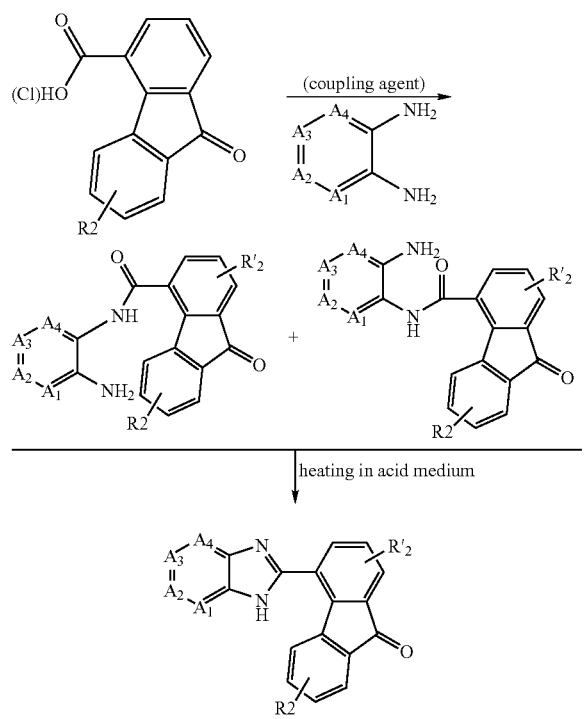

When using a fluoren-9-one-4-carboxylic acid, it is particularly advantageous to activate said acid using a coupling agent known to a person skilled in the art, such as hydrochloride of 1-(3-dimethylaminopropyl)-3-ethylcarbodiimide (EDCI), in the presence of 1-hydroxybenzotriazole (HOBT).

Various conditions of cyclization of the mixture of intermediate amides can be used within the scope of the invention, such as acetic acid or a mixture of trifluoroacetic acid and anhydride. It is also particularly advantageous within the scope of the invention to carry out this type of thermal cyclization in an acid environment by heating in a microwave reactor.

The reaction can also be carried out in a single stage by heating in an agent such as polyphosphoric acid or in phosphorus trichloride.

A second general method of synthesis that is advantageous within the scope of the invention comprises starting from a 9-H-fluoren-9-one-4-carboxaldehyde—such as 9-H-fluoren-9-one-4-carboxaldehyde, which can be obtained according to Helv. Chim. Acta 1972, 55, 1973-8—by formation of the ring of the benzimidazole or aza-benzimidazole type according to scheme 2:

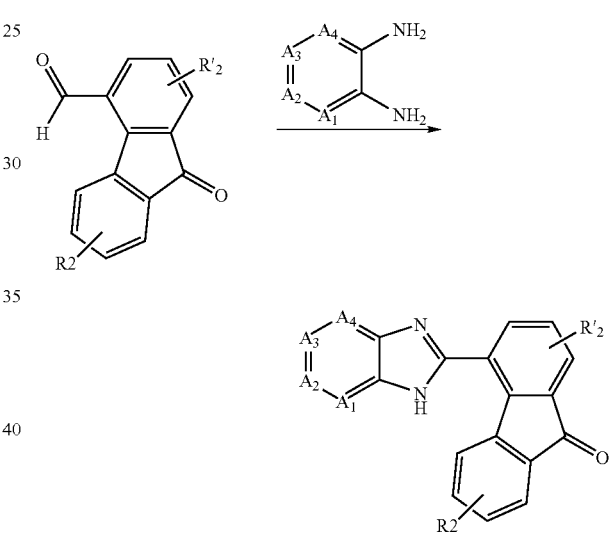

In this case, it is particularly advantageous within the scope of the invention, to work:

either with microwave heating in the presence of silica, according to Tetrahedron Lett. 1998, 39, 4481-84;

or in the presence of dichloro-dicyano-benzoquinone (DDQ), according to Tetrahedron 1995, 51, 5813-18;

or in the presence of a mixture of thionyl chloride and pyridine, according to E.P. 511187;

In this case, it is more particularly advantageous within the scope of the invention, to work in the presence of ferric chloride, according to Eur. J. Med. Chem. 2006, 31, 635-42.

A third general method of synthesis comprises coupling a 9H-4-halo-fluoren-9-one—such as 9H-4-bromo-fluoren-9-one, which can be obtained according to J. Amer. Chem. Soc. 1935, 2443-6 or 9H-4-iodo-fluoren-9-one, which can be obtained according to Helv. Chim. Acta 1973, 3044-9—with an organometallic derivative of a benzimidazole—or of an aza-benzimidazole—the NH function of which is protected, according to scheme 3:

Scheme 3

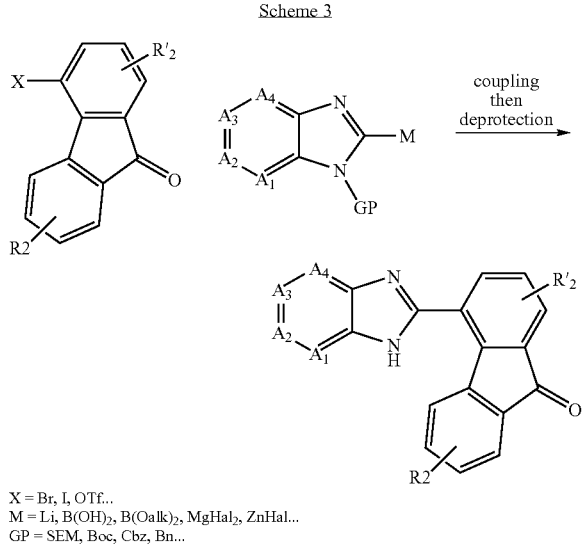

X = Br, I, OTf...
M = Li, B(OH)$_2$, B(Oalk)$_2$, MgHal$_2$, ZnHal...
GP = SEM, Boc, Cbz, Bn...

Within the scope of the invention, it is particularly advantageous to use a benzyl (Bn) or (trimethylsilylethyl)oxymethyl (SEM) group for protecting the benzimidazole derivative.

Within the scope of the invention, it is particularly advantageous to use either a lithium alcoholate or a boronic acid as the organometallic derivative of benzimidazole.

Within the scope of the invention, it is particularly advantageous to carry out coupling in the presence of a catalyst derived from palladium (0), in the conditions of a reaction of the Suzuki type.

Inverse coupling can also be envisaged, in particular using derivatives of 2-iodo-benzimidazole—or an aza-analogue of benzimidazoles—the NH function of which is protected, with organometallic derivatives of fluoren-9-ones—the carbonyl function of which is protected according to scheme 3':

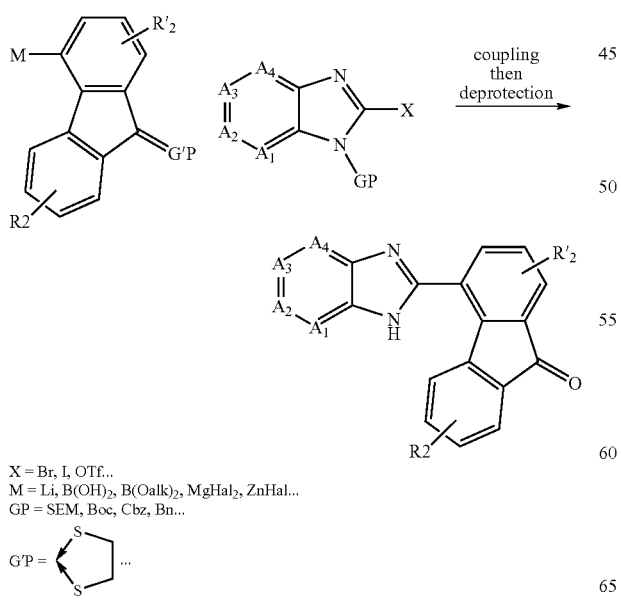

X = Br, I, OTf...
M = Li, B(OH)$_2$, B(Oalk)$_2$, MgHal$_2$, ZnHal...
GP = SEM, Boc, Cbz, Bn...

G'P = [dithiolane structure] ...

Conversion of the C=O radical to CR$_1$R$_1$' radicals as defined in general formula (I) can be carried out according to the general methods familiar to a person skilled in the art, in particular those described in:

Comprehensive Organic Chemistry, by D. Barton et al. (Pergamon Press); Advanced Organic Chemistry, by J. Marsh (Wiley Interscience).

A fourth general method of synthesis comprises first converting the C=O radical of an ester of 9-oxo-fluorene-4-carboxylic acid to CR$_1$R$_1$' radicals, as defined in general formula (I), and then forming the radical of the benzimidazole or aza-benzimidazole type according to the scheme below:

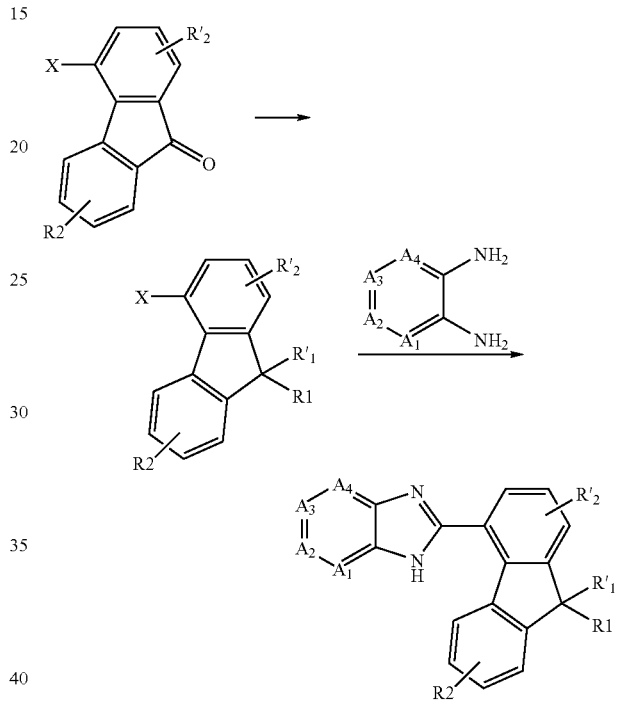

Within the scope of the invention, it is particularly advantageous to form the radical of the benzimidazole or aza-benzimidazole type by reaction:

either directly using the ester (X=CO$_2$Me or CO$_2$Et), working at the reflux of a solvent, such as toluene, in the presence of trimethylaluminium;

or to convert the ester to acid (X=CO$_2$H) or to acid chloride (X=COCl) and to work under the conditions described in general method 1;

or to convert the ester to aldehyde (X=CHO) and to operate under the conditions described in general method 2.

In the latter case, it is particularly advantageous within the scope of the invention to work in two stages: first reducing the ester to primary alcohol (X=CH$_2$OH), in particular using diisopropylaluminum hydride; and then reoxidizing the primary alcohol formed to aldehyde (X=CHO), in particular using 2,2,6,6-tetramethylpiperidine N-oxide.

The products covered by the present invention have interesting pharmacological properties: notably they were found to possess inhibiting properties on the ATPase activity of chaperone proteins.

Among these chaperone proteins, notably we may mention HSP90.

Thus, the products corresponding to general formula (I) as defined above display considerable inhibitory activity of the Hsp90 chaperone.

Tests given below in the experimental section illustrate the inhibitory activity of products of the present invention with respect to said proteins.

These properties therefore mean that the products of general formula (I) of the present invention can be used as medicinal products for the treatment of malignant tumors.

The products of formula (I) can also be used in the veterinary field.

The invention therefore relates to the application, as medicinal products, of the pharmaceutically acceptable products of general formula (I).

The invention relates in particular to the application, as medicinal products, of the products with the following names 4-(3H-imidazo[4,5-c]pyridin-2-yl)-fluoren-9-one oxime (Z, E).
N-[4-(1H-imidazo[4,5-c]pyridin-2-yl)-fluoren-9-ylidene]-hydrazine, 60/40 mixture of E and Z isomers
[4-(3H-imidazo[4,5-c]pyridin-2-yl)-9H-fluoren-9(R,S)-yl] amide of quinoline-5-carboxylic acid
the dextrorotatory enantiomer of [4-(3H-imidazo[4,5-c]pyridin-2-yl)-9H-fluoren-9(R,S)-yl]amide of quinoline-5-carboxylic acid
4-(3H-imidazo[4,5-c]pyridin-2-yl)-fluoren-9-one oxime (E).
trifluoroacetate of [4-(3H-imidazo[4,5-c]pyridin-2-yl)-9H-fluoren-9(R,S)-yl]amide of 1H-pyrazole-4-carboxylic acid
trifluoroacetate of N-[4-(3H-imidazo[4,5-c]pyridin-2-yl)-9H-fluoren-9(R,S)-yl]-succinamide.
trifluoroacetate of [4-(3H-imidazo[4,5-c]pyridin-2-yl)-9H-fluoren-9(R,S)-yl]amide of 1H-benzotriazole-5-carboxylic acid
[4-(3H-imidazo[4,5-c]pyridin-2-yl)-9H-fluoren-9(R,S)-yl] amide of 1H-indazole-5-carboxylic acid
[4-(3H-imidazo[4,5-c]pyridin-2-yl)-9H-fluoren-9(R,S)-yl] amide of 1H-indole-6-carboxylic acid
N-[4-(3H-imidazo[4,5-c]pyridin-2-yl)-9H-fluoren-9(R,S)-yl]-isonicotinamide
[4-(3H-imidazo[4,5-c]pyridin-2-yl)-9H-fluoren-9(R,S)-yl] amide of 1H-indole-4-carboxylic acid
trifluoroacetate of [4-(3H-imidazo[4,5-c]pyridin-2-yl)-9H-fluoren-9(R,S)-yl]amide of quinoline-5-carbothioic acid
2-acetylamino-N-[4-(3H-imidazo[4,5-c]pyridin-2-yl)-9H-fluoren-9(R,S)-yl]-isonicotinamide
[4-(3H-imidazo[4,5-c]pyridin-2-yl)-9H-fluoren-9(R,S)-yl] amide of quinoline-4-carboxylic acid
2-amino-N-[4-(3H-imidazo[4,5-c]pyridin-2-yl)-9H-fluoren-9(R,S)-yl]-isonicotinamide.
2-ethyl-N-[4-(3H-imidazo[4,5-c]pyridin-2-yl)-9H-fluoren-9(R,S)-yl]-isonicotinamide
[4-(6-fluoro-1H-benzimidazol-2-yl)-9H-fluoren-9(R,S)-yl] amide of quinoline-5-carboxylic acid
2-chloro-N-[4-(3H-imidazo[4,5-c]pyridin-2-yl)-9H-fluoren-9(R,S)-yl]-isonicotinamide
[4-(3H-imidazo[4,5-c]pyridin-2-yl)-9H-fluoren-9(R,S)-yl] amide of 2-amino-pyrimidine-4-carboxylic acid
[4-(3H-imidazo[4,5-c]pyridin-2-yl)-9H-fluoren-9(R,S)-yl] amide of 1H-pyrrolo[2,3-b]pyridine-4-carboxylic acid
2-hydroxymethyl-N-[4-(3H-imidazo[4,5-c]pyridin-2-yl)-9H-fluoren-9(R,S)-yl]-isonicotinamide
N-[4-(3H-imidazo[4,5-c]pyridin-2-yl)-9H-fluoren-9(R,S)-yl]-3-methyl-isonicotinamide
hydrochloride of [4-(3H-imidazo[4,5-c]pyridin-2-yl)-9H-fluoren-9(R,S)-yl]amide of 1,8-naphthyridine-4-carboxylic acid
[4-(3H-imidazo[4,5-c]pyridin-2-yl)-9H-fluoren-9(R,S)-yl] amide of 1H-pyrrolo[2,3-b]pyridine-3-carboxylic acid
[4-(3H-imidazo[4,5-c]pyridin-2-yl)-9H-fluoren-9(R,S)-yl] amide of 1-methyl-1H-pyrrolo[2,3-b]pyridine-3-carboxylic acid
2-bromo-N-[4-(3H-imidazo[4,5-c]pyridin-2-yl)-9H-fluoren-9(R,S)-yl]-isonicotinamide
3-hydroxy-N-[4-(3H-imidazo[4,5-c]pyridin-2-yl)-9H-fluoren-9(R,S)-yl]-isonicotinamide
3-amino-N-[4-(3H-imidazo[4,5-c]pyridin-2-yl)-9H-fluoren-9(R,S)-yl]-isonicotinamide
methyl ester of 4-[4-(3H-imidazo[4,5-c]pyridin-2-yl)-9H-fluoren-9(R,S)-ylcarbamoyl]-pyridine-2-carboxylic acid
[4-(3H-imidazo[4,5-c]pyridin-2-yl)-9H-fluoren-9(R,S)-yl] amide of 1H-indazole-4-carboxylic acid
N-[4-(3H-imidazo[4,5-c]pyridin-2-yl)-9H-fluoren-9(R,S)-yl]-2-methylamino-isonicotinamide
N-[4-(6-hydroxy-1H-benzimidazol-2-yl)-9H-fluoren-9(R,S)-yl]-isonicotinamide
[4-(3H-imidazo[4,5-c]pyridin-2-yl)-9H-fluoren-9(R,S)-yl] amide of 6-bromo-3H-imidazo[4,5-b]pyridine-7-carboxylic acid
4-(3H-imidazo[4,5-c]pyridin-2-yl)-9H-fluoren-9(R,S)-yl ester of isonicotinic acid,
N-[4-(3H-imidazo[4,5-c]pyridin-2-yl)-9H-fluoren-9(R,S)-yl]amide of 2-tert-butoxycarbonylamino-isonicotinic acid
N-[4-(3H-imidazo[4,5-c]pyridin-2-yl)-9H-fluoren-9(R,S)-yl]amide of 3-chloro-6-methoxy-quinoline-4-carboxylic acid
N-[4-(3H-imidazo[4,5-c]pyridin-2-yl)-9H-fluoren-9(R,S)-yl]amide of 3-hydroxy-quinoline-4-carboxylic acid
N-[4-(3H-imidazo[4,5-c]pyridin-2-yl)-9H-fluoren-9(R,S)-yl]amide of 2-amino-5-chloro-pyrimidine-4-carboxylic acid
[4-(3H-imidazo[4,5-c]pyridin-2-yl)-9H-fluoren-9(R,S)-yl] amide of 3-bromo-1H-pyrrolo[2,3-b]pyridine-4-carboxylic acid
dextrorotatory enantiomer of [4-(3H-imidazo[4,5-c]pyridin-2-yl)-9H-fluoren-9(R,S)-yl]amide of 1H-pyrrolo[2,3-b]pyridine-4-carboxylic acid
N-[4-(3H-imidazo[4,5-c]pyridin-2-yl)-9H-fluoren-9(R,S)-yl]amide of 9H-purine-6-carboxylic acid
N-[4-(3H-imidazo[4,5-c]pyridin-2-yl)-9H-fluoren-9(R,S)-yl]amide of 2-amino-6-methyl-pyrimidine-4-carboxylic acid
[4-(3H-imidazo[4,5-c]pyridin-2-yl)-9H-fluoren-9(R,S)-yl] amide of 5-amino-3H-1,2,3-triazole-4-carboxylic acid
N-[4-(3H-imidazo[4,5-c]pyridin-2-yl)-9H-fluoren-9(R,S)-yl]amide of 6-methyl-2-methylamino-pyrimidine-4-carboxylic acid
N-[4-(3H-imidazo[4,5-c]pyridin-2-yl)-9H-fluoren-9(R,S)-yl]amide of 6-methoxy-quinoline-4-carboxylic acid
3,5-dihydroxy-N-[4-(3H-imidazo[4,5-c]pyridin-2-yl)-9H-fluoren-9(R,S)-yl]-benzamide.
N-[4-(3H-imidazo[4,5-c]pyridin-2-yl)-9H-fluoren-9(R,S)-yl]amide of pyrimidine-4-carboxylic acid
4-hydroxy-N-[4-(3H-imidazo[4,5-c]pyridin-2-yl)-9H-fluoren-9(R,S)-yl]-benzamide.
2,4-dihydroxy-N-[4-(3H-imidazo[4,5-c]pyridine-2-yl)-9H-fluoren-9(R,S)-yl]-benzamide.
[4-(5-cyano-6-fluoro-1H-benzimidazol-2-yl)-9H-fluoren-9 (R,S)-yl]amide of 1H-pyrrolo[2,3-b]pyridine-4-carboxylic acid
4-(1H-benzimidazol-2-yl)-9H-fluoren-9(R,S)-yl]amide of 2-amino-5-chloro-pyrimidine-4-carboxylic acid
[4-(5-fluoro-1H-benzimidazol-2-yl)-9H-fluoren-9(R,S)-yl] amide of 2-amino-5-chloro-pyrimidine-4-carboxylic acid

[4-(5-fluoro-1H-benzimidazol-2-yl)-9H-fluoren-9(R,S)-yl]amide of 1H-pyrrolo[2,3-b]pyridine-4-carboxylic acid

[4-(3H-imidazo[4,5-c]pyridin-2-yl)-9H-fluoren-9(R,S)-yl]amide of 2,3-dimethyl-quinoxaline-5-carboxylic acid

[4-(3H-imidazo[4,5-c]pyridin-2-yl)-9H-fluoren-9(R,S)-yl]amide of 3-amino-1H-pyrazole-4-carboxylic acid dextrorotatory enantiomer of N-[4-(3H-imidazo[4,5-c]pyridin-2-yl)-9H-fluoren-9(R,S)-yl]amide of 2-amino-5-chloro-pyrimidine-4-carboxylic acid levorotatory enantiomer of N-[4-(3H-imidazo[4,5-c]pyridin-2-yl)-9H-fluoren-9(R,S)-yl]amide of 2-amino-5-chloro-pyrimidine-4-carboxylic acid

[4-(3H-imidazo[4,5-c]pyridin-2-yl)-9H-fluoren-9(R,S)-yl]amide of 3-methyl-quinoxaline-5-carboxylic acid

[4-(3H-imidazo[4,5-c]pyridin-2-yl)-9H-fluoren-9(R,S)-yl]amide of quinoxaline-5-carboxylic acid

[4-(9H-purine-8-yl)-9H-fluoren-9(R,S)-yl]amide of 1H-pyrrolo[2,3-b]pyridine-4-carboxylic acid

[4-(1H-benzimidazol-2-yl)-9H-fluoren-9(R,S)-yl]amide of 1H-pyrrolo[2,3-b]-pyridine-4-carboxylic acid

[4-(5-trifluoromethyl-1H-benzimidazol-2-yl)-9H-fluoren-9(R,S)-yl]amide of 1H-pyrrolo[2,3-b]pyridine-4-carboxylic acid

[4-(5-methoxycarbonyl-1H-benzimidazol-2-yl)-9H-fluoren-9(R,S)-yl]amide of 1H-pyrrolo[2,3-b]pyridine-4-carboxylic acid

[4-(5-carboxy-1H-benzimidazol-2-yl)-9H-fluoren-9(R,S)-yl]amide of 1H-pyrrolo[2,3-b]pyridine-4-carboxylic acid

[4-(4-methyl-1H-benzimidazol-2-yl)-9H-fluoren-9(R,S)-yl]amide of 1H-pyrrolo[2,3-b]pyridine-4-carboxylic acid

[4-(5-carboxamido-1H-benzimidazol-2-yl)-9H-fluoren-9(R,S)-yl]amide of 1H-pyrrolo[2,3-b]pyridine-4-carboxylic acid

[4-(6-sulphamoyl-1H-benzimidazol-2-yl)-9H-fluoren-9(R,S)-yl]amide of 1H-pyrrolo[2,3-b]pyridine-4-carboxylic acid

[4-(5-trifluoromethoxy-1H-benzimidazol-2-yl)-9H-fluoren-9(R,S)-yl]amide of 1H-pyrrolo[2,3-b]pyridine-4-carboxylic acid

[4-(5-cyano-1H-benzimidazol-2-yl)-9H-fluoren-9(R,S)-yl]amide of 1H-pyrrolo[2,3-b]pyridine-4-carboxylic acid D diastereoisomer of [4-(3H-imidazo[4,5-c]pyridin-2-yl)-9H-fluoren-9(R,S)-yl]amide of 2-(3-acetyl-2,2-dimethyl-cyclobutan-1-yl)acetic acid

[4-(6-chloro-1H-benzimidazol-2-yl)-9H-fluoren-9(R,S)-yl]amide of 1H-pyrrolo[2,3-b]pyridine-4-carboxylic acid:

[4-(5-fluoro-6-morpholino-1H-benzimidazole-2-yl)-9H-fluoren-9(R,S)-yl]amide of 1H-pyrrolo[2,3-b]pyridine-4-carboxylic acid

[4-(6-chloro-5-fluoro-1H-benzimidazole-2-yl)-9H-fluoren-9(R,S)-yl]amide of 1H-pyrrolo[2,3-b]pyridine-4-carboxylic acid

[4-(4,5,6,7-tetrahydro-1H-benzimidazol-2-yl)-9H-fluoren-9(R,S)-yl]amide of 1H-pyrrolo[2,3-b]pyridine-4-carboxylic acid

[2-amino-5-(1H-benzimidazol-2-yl)-9H-fluoren-9(R,S)-yl]amide of 1H-pyrrolo[2,3-b]pyridine-4-carboxylic acid

[4-(5-hydroxy-5H-imidazo[4,5-c]pyridin-2-yl)-9H-fluoren-9(R,S)-yl]amide of 1H-pyrrolo[2,3-b]pyridine-4-carboxylic acid

[4-(5-hydroxy-1H-benzimidazole-2-yl)-9H-fluoren-9(R,S)-yl]amide of 1H-pyrrolo[2,3-b]pyridine-4-carboxylic acid

[4-(5-methylaminocarbonyl-1H-benzimidazol-2-yl)-9H-fluoren-9(R,S)-yl]amide of 1H-pyrrolo[2,3-b]pyridine-4-carboxylic acid

[4-(5-dimethylaminocarbonyl-1H-benzimidazol-2-yl)-9H-fluoren-9(R,S)-yl]amide of 1H-pyrrolo[2,3-b]pyridine-4-carboxylic acid

[4-5-(2-dimethylamino-ethyl)aminocarbonyl-1H-benzimidazol-2-yl)-9H-fluoren-9(R,S)-yl]amide of 1H-pyrrolo[2,3-b]pyridine-4-carboxylic acid

[4-(4,5,6,7-tetrafluoro-1H-benzimidazol-2-yl)-9H-fluoren-9(R,S)-yl]amide of 1H-pyrrolo[2,3-b]pyridine-4-carboxylic acid 4-[5-(3-methoxypropyl)aminocarbonyl-1H-benzimidazol-2-yl)-9H-fluoren-9(R,S)-yl]amide of 1H-pyrrolo[2,3-b]pyridine-4-carboxylic acid 4-[5-(4-methyl-piperazine-1-yl)carbonyl-1H-benzimidazol-2-yl)-9H-fluoren-9(R,S)-yl]amide of 1H-pyrrolo[2,3-b]pyridine-4-carboxylic acid

[4-(6-dimethylsulphamoyl-1H-benzimidazol-2-yl)-9H-fluoren-9(R,S)-yl]amide of 1H-pyrrolo[2,3-b]pyridine-4-carboxylic acid

[4-[5-(pyrrolidin-1-yl)carbonyl)-1H-benzimidazol-2-yl)-9H-fluoren-9(R,S)-yl]amide of 1H-pyrrolo[2,3-b]pyridine-4-carboxylic acid dextrorotatory enantiomer of 2-{9(R,S)-[(1H-pyrrolo[2,3-b]pyridine-4-carbonyl)-amino]-9H-fluoren-4-yl}-1H-benzimidazole-5-carboxylic acid {{4-{5-[2-(pyrrolidin-1-yl)ethylaminocarbonyl]-1H-benzimidazole-2-yl}-9H-fluoren-9(R,S)-yl}}amide of 1H-pyrrolo[2,3-b]pyridine-4-carboxylic acid

[4-(6-dimethylamino-1H-benzimidazol-2-yl)-9H-fluoren-9(R,S)-yl]amide of 1H-pyrrolo[2,3-b]pyridine-4-carboxylic acid {4-[6-(4-methyl-piperazin-1-yl)-1H-benzimidazol-2-yl]-9H-fluoren-9(R,S)-yl}-amide of 1H-pyrrolo[2,3-b]pyridine-4-carboxylic acid

[4-[6-(methyl-4(5)-imidazolin-2-yl)-1H-benzimidazol-2-yl]-9H-fluoren-9(R,S)-yl]amide of 1H-pyrrolo[2,3-b]pyridine-4-carboxylic acid {{4-{5-[(3-dimethylamino-propyl)aminocarbonyl]-1H-benzimidazol-2-yl}-9H-fluoren-9(R,S)-yl}}-amide of 1H-pyrrolo[2,3-b]pyridine-4-carboxylic acid {4-[5-fluoro-6-(4-methyl-piperazin-1-yl)-1H-benzimidazol-2-yl]-9H-fluoren-9(R,S)-yl}-amide of 1H-pyrrolo[2,3-b]pyridine-4-carboxylic acid {{4-{5-[(3-dimethylamino-propyl)carbonyloxy]-1H-benzimidazol-2-yl}-9H-fluoren-9(R,S)-yl}}-amide of 1H-pyrrolo[2,3-b]pyridine-4-carboxylic acid

[4-(6-amino-1H-benzimidazol-2-yl)-9H-fluoren-9-(R,S)-yl]amide of 1H-pyrrolo[2,3-b]pyridine-4-carboxylic acid

[4-(6-methyl-1H-benzimidazol-2-yl)-9H-fluoren-9(R,S)-yl]amide of 1H-pyrrolo[2,3-b]pyridine-4-carboxylic acid {{4-{5-[(3-hydroxy-propyl)aminocarbonyl]-1H-benzimidazole-2-yl}-9H-fluoren-9(R,S)-yl}}-amide of 1H-pyrrolo[2,3-b]pyridine-4-carboxylic acid dextrorotatory enantiomer of {4-[5-cyano-1H-benzimidazol-2-yl]-9H-fluoren-9(R,S)-yl}-amide of 1H-pyrrolo[2,3-b]pyridine-4-carboxylic acid

[4-(3H-imidazo[4,5-c]pyridin-2-yl)-9H-fluoren-9(R,S)-yl]amide of 7H-pyrrolo[2,3-d]pyrimidine-4-carboxylic acid

[4-(6-amino-1H-benzimidazol-2-yl)-9H-fluoren-9(R,S)-yl]amide of 1H-pyrrolo[2,3-b]pyridine-4-carboxylic acid dextrorotatory enantiomer of {4-[5-fluoro-1H-benzimidazol-2-yl]-9H-fluoren-9(R,S)-yl}-amide of 1H-pyrrolo[2,3-b]pyridine-4-carboxylic acid methyl ester of 2-{9(R,S)-[(1H-pyrrolo[2,3-b]pyridine-4-carbonyl)-amino]-9H-fluoren-4-yl}-1H-imidazo[4,5-c]pyridine-6-carboxylic acid

[4-(6-fluoro-5-methoxy-1H-benzimidazol-2-yl)-9H-fluoren-9(R,S)-yl]amide of 1H-pyrrolo[2,3-b]pyridine-4-carboxylic acid

[4-(6-fluoro-5-hydroxy-1H-benzimidazol-2-yl)-9H-fluoren-9(R,S)-yl]amide of 1H-pyrrolo[2,3-b]pyridine-4-carboxylic acid {4-[5-fluoro-6-(3-methoxy-propoxy)-1H-benzimidazol-2-yl]-9H-fluoren-9(R,S)-yl}-amide of 1H-pyrrolo[2,3-b]pyridine-4-carboxylic acid {4-[6-(3-dimethylamino-propoxy)-5-fluoro-1H-benzimidazol-2-yl]-9H-fluoren-9(R,S)-yl}-amide of 1H-pyrrolo[2,3-b]pyridine-4-carboxylic acid as well as their prodrugs, said products of formula (I) being in all the possible tautomeric and isomeric forms: racemic, enantiomeric and diastereoisomeric, as well as the pharmaceutically acceptable salts of addition with inorganic and organic acids or with inorganic and organic bases of said products of formula (I).

The invention relates more particularly to the application of the products with the following names as medicinal products:

[4-(3H-imidazo[4,5-c]pyridin-2-yl)-9H-fluoren-9(R,S)-yl] amide of quinoline-5-carboxylic acid the dextrorotatory enantiomer of [4-(3H-imidazo[4,5-c]pyridin-2-yl)-9H-fluoren-9(R,S)-yl]amide of quinoline-5-carboxylic acid 4-(3H-imidazo[4,5-c]pyridin-2-yl)-fluoren-9-one oxime (E).

trifluoroacetate of [4-(3H-imidazo[4,5-c]pyridin-2-yl)-9H-fluoren-9(R,S)-yl]amide of 1H-benzotriazole-5-carboxylic acid N-[4-(3H-imidazo[4,5-c]pyridin-2-yl)-9H-fluoren-9(R,S)-yl]-isonicotinamide trifluoroacetate of [4-(3H-imidazo[4,5-c]pyridin-2-yl)-9H-fluoren-9(R,S)-yl]amide of quinoline-5-carbothioic acid 2-acetylamino-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of quinoline-4-carboxylic acid 2-amino-N-[4-(3H-imidazo[4,5-c]pyridin-2-yl)-9H-fluoren-9(R,S)-yl]-isonicotinamide.

2-ethyl-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 2-amino-pyrimidine-4-carboxylic acid

[4-(3H-imidazo[4,5-c]pyridin-2-yl)-9H-fluoren-9(R,S)-yl] amide of 1H-pyrrolo[2,3-b]pyridine-4-carboxylic acid

[4-(3H-imidazo[4,5-c]pyridin-2-yl)-9H-fluoren-9(R,S)-yl] amide of 1H-pyrrolo[2,3-b]pyridine-3-carboxylic acid 2-bromo-N-[4-(3H-imidazo[4,5-c]pyridin-2-yl)-9H-fluoren-9(R,S)-yl]-isonicotinamide 3-hydroxy-N-[4-(3H-imidazo[4,5-c]pyridin-2-yl)-9H-fluoren-9(R,S)-yl]-isonicotinamide 3-amino-N-[4-(3H-imidazo[4,5-c]pyridin-2-yl)-9H-fluoren-9(R,S)-yl]-isonicotinamide methyl ester of 4-[4-(3H-imidazo[4,5-c]pyridin-2-yl)-9H-fluoren-9(R,S)-ylcarbamoyl]-pyridine-2-carboxylic acid

[4-(3H-imidazo[4,5-c]pyridin-2-yl)-9H-fluoren-9(R,S)-yl] amide of 1H-indazole-4-carboxylic acid

[4-(3H-imidazo[4,5-c]pyridin-2-yl)-9H-fluoren-9(R,S)-yl] amide of 6-bromo-3H-imidazo[4,5-b]pyridine-7-carboxylic acid 4-(3H-imidazo[4,5-c]pyridin-2-yl)-9H-fluoren-9(R,S)-yl ester of isonicotinic acid, as well as their prodrugs, said products of formula (I) being in all the possible tautomeric and isomeric forms: racemic, enantiomeric and diastereoisomeric, as well as the pharmaceutically acceptable salts of addition with inorganic and organic acids or with inorganic and organic bases of said products of formula (I).

The invention relates even more particularly to the application of the products with the following names as medicinal products:

[4-(3H-imidazo[4,5-c]pyridin-2-yl)-9H-fluoren-9(R,S)-yl] amide of quinoline-5-carboxylic acid N-[4-(3H-imidazo[4,5-c]pyridin-2-yl)-9H-fluoren-9(R,S)-yl]-isonicotinamide 2-amino-N-[4-(3H-imidazo[4,5-c]pyridin-2-yl)-9H-fluoren-9(R,S)-yl]-isonicotinamide.

2-ethyl-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 2-amino-pyrimidine-4-carboxylic acid

[4-(3H-imidazo[4,5-c]pyridin-2-yl)-9H-fluoren-9(R,S)-yl] amide of 1H-pyrrolo[2,3-b]pyridine-4-carboxylic acid

[4-(3H-imidazo[4,5-c]pyridin-2-yl)-9H-fluoren-9(R,S)-yl] amide of 1H-pyrrolo[2,3-b]pyridine-3-carboxylic acid 3-amino-N-[4-(3H-imidazo[4,5-c]pyridin-2-yl)-9H-fluoren-9(R,S)-yl]-isonicotinamide

[4-(3H-imidazo[4,5-c]pyridin-2-yl)-9H-fluoren-9(R,S)-yl] amide of 6-bromo-3H-imidazo[4,5-b]pyridine-7-carboxylic acid as well as their prodrugs, said products of formula (I) being in all the possible tautomeric and isomeric forms: racemic, enantiomeric and diastereoisomeric, as well as the pharmaceutically acceptable salts of addition with inorganic and organic acids or with inorganic and organic bases of said products of formula (I).

The products can be administered by the parenteral, oral, perlingual, rectal or topical route.

The invention also relates to pharmaceutical compositions, characterized in that they contain, as active principle, at least one of the medicinal products of general formula (I).

These compositions can be presented in the form of injectable solutions or suspensions, of tablets, coated tablets, capsules, syrups, suppositories, creams, ointments and lotions. These pharmaceutical forms are prepared by the usual methods. The active principle can be incorporated with excipients that are usually employed in these compositions, such as aqueous or non-aqueous vehicles, talc, gum arabic, lactose, starch, magnesium stearate, cocoa butter, fats of animal or vegetable origin, paraffinic derivatives, glycols, various wetting, dispersing or emulsifying agents, and preservatives.

The usual dose, which varies depending on the subject being treated and the particular disorder, can be, for example, from 10 mg to 500 mg per day in humans, by the oral route.

The present invention thus relates to the use of products of formula (I) as defined above or of pharmaceutically acceptable salts of said products of formula (I) for the preparation of medicinal products intended for inhibiting chaperone protein activity.

The present invention thus relates particularly to the use of products of formula (I) as defined above or of pharmaceutically acceptable salts of said products of formula (I) in which the chaperone protein is HSP90.

The present invention also relates to the use of products of formula (I) as defined above or of pharmaceutically acceptable salts of said products of formula (I) in which the protein kinase is in a cellular culture and also said use in a mammal.

The present invention thus relates to the use of products of formula (I) as defined above or of pharmaceutically acceptable salts of said products of formula (I) for the preparation of a medicinal product intended for preventing or treating a disease characterized by disturbance of the activity of a protein kinase and notably such a disease in a mammal.

The present invention relates to the use of products of formula (I) as defined above or of pharmaceutically acceptable salts of said products of formula (I) for the preparation of a medicinal product intended for preventing or treating a disease in the following group: disorders of proliferation of blood vessels, fibrotic disorders, disorders of proliferation of mesangial cells, metabolic disorders, allergies, asthma, thromboses, diseases of the nervous system, retinopathies, psoriasis, rheumatoid arthritis, diabetes, muscular degeneration, oncological diseases, cancers.

The present invention thus relates to the use of products of formula (I) as defined above or of pharmaceutically acceptable salts of said products of formula (I) for the preparation of a medicinal product intended for treating oncological diseases.

The present invention relates particularly to the use of products of formula (I) as defined above or of pharmaceutically acceptable salts of said products of formula (I) for the preparation of a medicinal product intended for treating cancers.

Among these cancers, the present invention relates quite particularly to the treatment of solid tumours and to the treatment of cancers that are resistant to cytotoxic agents The present invention thus relates notably to the use of products of formula (I) as defined above or of pharmaceutically acceptable salts of said products of formula (I) for the preparation of a medicinal product intended for treating cancers including lung, breast and ovarian cancers, glioblastomas, chronic myeloid leukaemias, acute lymphoblastic leukaemias, cancers of the prostate, pancreas and colon, metastatic melanomas, thyroid tumours and renal carcinomas.

Thus, among the main potential indications of Hsp90 inhibitors, we may mention, non-limitatively:

small cell lung cancers, breast cancers, ovarian cancers and glioblastomas overexpressing EGF-R or HER2;
chronic myeloid leukaemias overexpressing Bcr-Abl;
acute lymphoblastic leukaemias overexpressing Flt-3;
cancers of the breast, prostate, lung, pancreas, colon or ovary overexpressing Akt;
metastatic melanomas and thyroid tumours overexpressing the mutated form of the B-Raf protein;
androgen-dependent and androgen-independent prostate cancers;
oestrogen-dependent and oestrogen-independent breast cancers;
renal carcinomas overexpressing HIF-1a or the mutated c-met protein.

The present invention relates even more particularly to the treatment of cancer of the breast, colon and lung.

The present invention also relates to the use of products of formula (I) as defined above or of pharmaceutically acceptable salts of said products of formula (I) for the preparation of a medicinal product intended for chemotherapy of cancers.

As medicinal products according to the present invention intended for chemotherapy of cancers, the products of formula (I) according to the present invention can be used alone or in combination with chemotherapy or radiotherapy or alternatively in combination with other therapeutic agents.

The present invention also relates notably to the pharmaceutical compositions as defined above additionally containing active principles of other medicinal products for cancer chemotherapy.

Said therapeutic agents can be commonly used antitumour agents.

As examples of known inhibitors of protein kinases, we may mention notably butyrolactone, flavopiridol, 2-(2-hydroxyethylamino)-6-benzylamino-9-methyl-purine, olomucine, Glivec, and Iressa.

The products of formula (I) according to the present invention can thus also be used advantageously in combination with antiproliferative agents: as examples of said antiproliferative agents, though without being limited to this list, we may mention aromatase inhibitors, antioestrogens, topoisomerase I inhibitors, topoisomerase II inhibitors, agents acting on microtubules, alkylating agents, histone deacetylase inhibitors, farnesyl transferase inhibitors, COX-2 inhibitors, MMP inhibitors, mTOR inhibitors, antineoplastic antimetabolites, platinum compounds, compounds causing the activity of protein kinases to decrease, and antiangiogenic compounds, gonadorelin agonists, antiandrogens, bengamides, biphosphonates and trastuzumab.

We may thus mention, as examples, antimicrotubule agents such as the taxoids and the vinca alkaloids, alkylating agents such as cyclophosphamide, DNA-intercalating agents such as cis-platinum, agents that interact with topoisomerase such as camptothecin and derivatives, the anthracyclines such as adriamycin, antimetabolites such as 5-fluorouracil and derivatives and analogues.

The present invention therefore relates to products of formula (I) as inhibitors of chaperone proteins, said products of formula (I) being in all the possible tautomeric and isomeric forms: racemic, enantiomeric and diastereoisomeric, as well as the pharmaceutically acceptable salts of addition with inorganic and organic acids or with inorganic and organic bases of said products of formula (I) as well as their prodrugs.

The present invention relates particularly to products of formula (I) as defined above as Hsp90 inhibitors.

The products of formula (I) according to the present invention can be prepared by the application or adaptation of known methods and notably of the methods described in the literature, for example those described by R. C. Larock in: Comprehensive Organic Transformations, VCH Publishers, 1989.

In the reactions described hereunder, it may be necessary to protect reactive functional groups such as, for example, hydroxy, amino, imino, thio or carboxy groups, when the latter are desired in the final product but when their participation is not desired in the reactions of synthesis of products of formula (I). It is possible to use conventional protective groups in accordance with the usual standard practice, such as those described for example by T. W. Greene and P. G. M. Wuts in "Protective Groups in Organic Chemistry" John Wiley and Sons, 1991.

The experimental section hereunder gives non-limiting examples of starting products: other starting products are available commercially or can be prepared by the usual methods known by a person skilled in the art.

EXAMPLES ILLUSTRATING THE INVENTION

The examples whose preparation is given hereunder illustrate the present invention though without limiting it. All the examples described were characterized by proton NMR spectroscopy and by mass spectroscopy, and most of these examples were also characterized by IR spectroscopy.

Example 1

Synthesis of 4-(3H-imidazo[4,5-c]pyridin-2-yl)-fluoren-9-one

Stage 1: In a 1-liter three-necked flask, dissolve 6.75 g of 3,4-diamino-pyridine in 500 ml of dichloromethane, then add, successively at room temperature, 11.49 ml of triethylamine, previously dried over potassium hydroxide, and 10 g of chloride of fluoren-9-one-4-carboxylic acid. After stirring for 4 hours at room temperature, the precipitate formed is drained, washed with a solution of sodium hydrogen carbonate then with water and is dried in a stove at 500 overnight. In this way we obtain 10.5 g of the equimolecular amide mixture, which is used as it is in the next stage.

Stage 2: In a 100-W microwave reactor, heat, at 109° C. for 20 minutes, a solution of 20 g of the amide mixture, obtained previously, in a mixture of 40 ml of trifluoroacetic anhydride, 80 ml of 36% hydrochloric acid and 312 ml of trifluoroacetic acid, the reaction being carried out in 50 ml portions. After cooling, the various operations are combined and 1 L of water and 1 L of dichloromethane are added. The organic phase is separated, then the aqueous phase is brought to pH=8-9 by adding a saturated solution of potassium hydrogen carbonate. The precipitate that formed is drained, washed with water and dried in the stove at 50° C. In this way we obtain 18.8 g of 4-(3H-imidazo[4,5-c]pyridin-2-yl)-fluoren-9-one, in the form of a yellow powder with the following characteristics:

Kofler melting point=236-38° C.
Mass spectrum (E/I): m/z=297 (M$^+$)
$^1$H-NMR spectrum (300 MHz, δ in ppm, DMSO): 7.40 (td, J=7.5 and 1.0 Hz, 1H); 7.49 (td, J=7.5 and 1.0 Hz, 1H); 7.59 (t, J=7.5 Hz, 1H); from 7.62 to 7.73 (m, 3H); 7.82 (dd, J=7.5 and 1.0 Hz, 1H); 7.90 (dd, J=7.5 and 1.0 Hz, 1H); 8.41 (d broad, J=5.5 Hz, 1H); 9.08 (s broad, 1H); from 12.5 to 13.5 (m very spread-out, 1H).

4-(3H-Imidazo[4,5-c]pyridin-2-yl)-fluoren-9-one can also be obtained in one stage either by heating an equimolecular mixture of 3,4-diamino-pyridine and of fluoren-4-one-9-carboxylic acid at 200° in polyphosphoric acid, or by heating in acetic acid between 90 and 100° C.

Example 2

Synthesis of (6-chloropyridin-3-ylmethyl)-amide of 4-(1H-imidazo[4,5-c]pyridin-2-yl)-9H-fluorene-9(R,S)-carboxylic acid In a 5-ml ground-glass tube under an argon atmosphere, dissolve 100 mg of the hydrochloride of 4-(1H-imidazo[4,5-c]pyridin-2-yl)-9H-fluorene-9(R,S)-carboxylic acid obtained in Example 29, in 1 ml of dichloromethane, then add successively 46 μL of triethylamine, 47 μL of N,N'-diisopropylcarbodiimide and 41 mg of 1-hydroxybenzotriazole and stir for 10 minutes. Then add a solution of 43 mg of 5-aminomethyl-2-chloropyridine in 1 ml and stir for 6 hours at room temperature. Pour the reaction mixture into 20 ml of a saturated aqueous solution of sodium hydrogen carbonate and extract twice with 10 ml of dichloromethane then with 10 ml of ethyl acetate. Combine the organic phases and wash with water, dry over sodium sulphate and concentrate under reduced pressure. After purification by flash chromatography on silica gel (40-63 μm), eluting with a mixture of dichloromethane and methanol (95-5 then 90-10 by volume), we obtain 21 mg of (6-chloropyridin-3-ylmethyl)-amide of 4-(1H-imidazo[4,5-c]pyridin-2-yl)-9H-fluorene-9(R,S)-carboxylic acid, in the form of a beige foam with the following characteristics:

Mass spectrum (E/I): m/z=451 (M$^+$)

Example 3

Synthesis of 4-(3H-imidazo[4,5-c]pyridin-2-yl)-9H-fluoren-9(R,S)-ol

In a 25-ml round-bottomed flask under an argon atmosphere, dissolve 100 mg of 4-(3H-imidazo[4,5-c]pyridin-2-yl)-fluoren-9(R,S)-one, obtained in Example 1, in 3 ml of methanol. After cooling to 0° C., add in 2 portions 13 mg of sodium hydroborate and stir for 15 minutes until completely dissolved. Pour the reaction mixture into water, then extract twice with 10 ml of ethyl acetate. Combine the organic phases and wash with water, dry over sodium sulphate then concentrate under reduced pressure. After purification by crystallization in a minimum of diethyl ether, we obtain 88 mg of 4-(3H-imidazo[4,5-c]pyridin-2-yl)-fluoren-9(R,S)-ol, in the form of a light yellow powder with the following characteristics:

Mass spectrum (E/I): m/z=299 (M$^+$)
$^1$H-NMR spectrum (300 MHz, δ in ppm, DMSO): 5.58 (d, J=8.0 Hz, 1H); 6.00 (d, J=8.0 Hz, 1H); 7.19 (t broad, J=7.5 Hz, 1H); 7.31 (t broad, J=7.5 Hz, 2H); 7.50 (t, J=7.5 Hz, 1H); from 7.58 to 7.70 (m, 3H); 7.80 (d broad, J=7.5 Hz, 1H); 8.39 (d, J=5.5 Hz, 1H); 9.02 (s broad, 1H); 13.4 (m, 1H).

Example 4

Synthesis of hydrochloride of the (pyridin-4-ylmethyl)-amide of 4-(3H-imidazo[4,5-c]pyridin-2-yl)-9H-fluorene-9(R,S)-carboxylic acid The procedure used in Example 2 is followed, starting from 100 mg of hydrochloride of 4-(1H-imidazo[4,5-c]pyridin-2-yl)-9H-fluorene-9(R,S)-carboxylic acid, prepared in Example 29, but with 31 μL of 4-picolylamine. After purification by chromatography on silica gel (40-63 μm), eluting with a mixture of dichloromethane and methanol (90-10 by volume), we obtain 29 mg of the hydrochloride of (pyridin-4-ylmethyl)-amide of 4-(3H-imidazo[4,5-c]pyridin-2-yl)-9H-fluorene-9(R,S)-carboxylic acid, in the form of a beige foam with the following characteristics:

Mass spectrum (E/I): m/z=453 (M$^+$)

Example 5

Synthesis of 4-(3H-imidazo[4,5-c]pyridin-2-yl)-fluoren-9-one oxime (Z, E)

In a 500-ml three-necked flask, dissolve 20 g of 4-(3H-imidazo[4,5-c]pyridin-2-yl)-fluoren-9-one, obtained in Example 1, in 328 ml of ethanol, then add successively 14.02 g of hydroxylamine hydrochloride and 27.59 g of dry sodium acetate. After stirring overnight at room temperature, dilute with 328 ml of water. The precipitate that formed is drained, washed with water and dried in the stove at 500. In this way we obtain 18.6 g of equimolecular mixture of the Z and E oximes of 4-(3H-imidazo[4,5-c]pyridin-2-yl)-fluoren-9-one, in the form of a pale yellow powder, witH-NMR purity over 95%, with the following characteristics:

Mass spectrum (E/I): m/z=312 (M$^+$)
$^1$H-NMR spectrum (400 MHz, δ in ppm, DMSO): 7.24 (m, 1H); from 7.30 to 7.37 (m, 1H); 7.40 (m, 0.5H); 7.49 (m, 0.5H); 7.54 (t, J=7.5 Hz, 0.5H); 7.49 (t, J=7.5 Hz, 0.5H); from 7.67 to 7.80 (m, 3H); 7.95 (m, 0.5H); from 8.40 to 8.47 (m, 2H); 8.63 (m, 0.5H); 9.11 (s broad, 1H); from 12.7 to 12.8 (m broad, 1H).

Example 6

Synthesis of 4-(3H-imidazo[4,5-c]pyridin-2-yl)-9H-fluorene-9(R,S)-amine

In a 211-ml autoclave, dissolve 6.99 g of equimolecular mixture of the Z and E oximes of 4-(3H-imidazo[4,5-c]pyridin-2-yl)-fluoren-9-one, obtained in Example 5, in a mixture of 30 ml of ethanol and 30 ml of tetrahydrofuran, add 108 mg of Raney activated nickel then subject it to an initial hydrogen pressure of 1 bar and heat the autoclave at 600° for 20 hours. After cooling, the volume of hydrogen absorbed is 175 ml. After purging with argon, open the autoclave, add 10 g of Celite and then filter (catalyst+Celite). Concentrate the filtrate under reduced pressure. In this way we obtain 5.15 g of 4-(3H-imidazo[4,5-c]pyridin-2-yl)-fluorene-9(R,S)-amine, in the form of a beige powder, with the following characteristics:

Mass spectrum (E/I): m/z=298 (M$^+$)

$^1$H-NMR spectrum (400 MHz, δ in ppm, CD$_3$OD): 4.94 (s, 1H); 7.05 (d broad, J=7.5 Hz, 1H); 7.14 (t broad, J=7.5 Hz, 1H); 7.31 (t broad, J=7.5 Hz, 1H); 7.51 (t, J=7.5 Hz, 1H); 7.61 (d, J=7.5 Hz, 1H); 7.72 (m, 2H); 7.92 (d, J=7.5 Hz, 1H); 8.40 (d, J=6.0 Hz, 1H); 8.99 (s, 1H).

Example 7

Synthesis of 2-(9H-fluoren-4-yl)-3H-imidazo[4,5-c]pyridine

Stage 1: In a 250-ml three-necked flask, stir, for 1 hour at room temperature, 1.99 g of fluorene-4-carboxylic acid in 40 ml of thionyl chloride. After concentration under reduced pressure, dissolve the acid chloride obtained in 40 ml of dichloromethane, then add 1.55 g of 3,4-diaminopyridine and 2.65 ml of triethylamine. Stir overnight at room temperature. Drain the precipitate that formed, and wash with dichloromethane. In this way we obtain 3.08 g of a product containing mainly an equimolecular amide mixture, which is used as it is in the next stage.

Stage 2: In a 25-ml three-necked flask, dissolve 1.3 g of the amide mixture obtained in the preceding stage in 50 ml of dioxan and 5 ml of phosphorus oxychloride. Then stir for 2 hours at 120° C., then add a further 20 ml of phosphorus oxychloride and heat again for 20 hours at 120° C. After concentration under reduced pressure, purify the residue by flash chromatography on silica gel (70-230 mesh), eluting with a mixture of dichloromethane, methanol and ammonia (95-5-0.2 by volume). In this way we obtain 1.68 g of 2-(9H-fluoren-4-yl)-3H-imidazo[4,5-c]pyridine, in the form of an off-white powder with the following characteristics:

Mass spectrum (E/I): m/z=283 (M$^+$)

$^1$H-NMR spectrum (400 MHz, δ in ppm, DMSO): 4.06 (s, 2H); 7.18 (t broad, J=7.5 Hz, 1H); 7.31 (t broad, J=7.5 Hz, 1H); 7.37 (d broad, J=7.5 Hz, 1H); 7.50 (t, J=7.5 Hz, 1H); from 7.60 to 7.68 (m, 3H); 7.81 (d broad, J=7.5 Hz, 1H); 8.39 (d, J=6.0 Hz, 1H); 9.03 (s broad, 1H).

Example 8

Synthesis of N-benzyl-N'-[4-(1H-imidazo[4,5-c] pyridin-2-yl)-fluoren-9-ylidene]-hydrazine, 55/45 mixture of E and Z isomers In a 10-ml round-bottomed flask, dissolve 100 mg of 4-(3H-imidazo[4,5-c]pyridin-2-yl)-fluoren-9-one, obtained in Example 1, in 3 ml of methanol, then add successively 197 mg of benzylhydrazine dihydrochloride and 138 mg of dry sodium acetate and heat at 50-55° C. for 5 hours. Pour the cooled reaction mixture into 10 ml of water, extract with ethyl acetate then twice with dichloromethane. Combine the organic phases, wash with a saturated aqueous solution of sodium chloride, dry over sodium sulphate then concentrate under reduced pressure. After purification by chromatography on silica gel (40-63 μm), eluting with a mixture of dichloromethane and methanol (93-7 by volume), we obtain 37 mg of N-benzyl-N'-[4-(1H-imidazo[4,5-c]pyridin-2-yl)-fluoren-9-ylidene]-hydrazine, in the form of a yellow foam with the following characteristics:

Mass spectrum (E/I): m/z=401 (M$^+$)

Example 9

Synthesis of N-[4-(1H-imidazo[4,5-c]pyridin-2-yl)-fluoren-9-ylidene]-hydrazine, 60/40 mixture of E and Z isomers In a 10-ml round-bottomed flask, dissolve 100 mg of 4-(3H-imidazo[4,5-c]pyridin-2-yl)-fluoren-9-one, obtained in Example 1, in 3 ml of methanol, then add successively 96 μL of hydrazine hydrate and 57.6 μL of acetic acid, then heat at 50-55° C. for 3 hours. Pour the cooled reaction mixture into 10 ml of water. Filter the precipitate that formed, and dissolve again in a mixture of methanol and dichloromethane. After drying over sodium sulphate then concentrating under reduced pressure, purify the residue by crystallization in a minimum of diethyl ether. In this way we obtain 70 mg of N-[4-(1H-imidazo[4,5-c]pyridin-2-yl)-fluoren-9-ylidene]-hydrazine, as a mixture of the Z and E isomers, in the form of a beige powder with the following characteristics:

Mass spectrum (E/I): m/z=311 (M$^+$)

$^1$H-NMR spectrum (400 MHz, δ in ppm, DMSO-d$_6$): from 7.00 to 7.30 (m, 2H); 7.39 (t, J=7.5 Hz, 0.5H); from 7.45 to 7.76 (m, 3H); 7.88 (m, 0.5H); from 8.21 to 8.47 (m, 3H); 9.06 (s broad, 1H); from 13.1 to 13.7 (m very spread-out, 1H).

Example 10

Synthesis of 2-[9(R,S)-fluoro-9H-fluoren-4-yl]-1H-imidazo[4,5-c]pyridine

In a 10-ml round-bottomed flask under an argon atmosphere, dissolve 85 mg of 4-(3H-imidazo[4,5-c]pyridin-2-yl)-fluoren-9-ol, obtained in Example 3, in 3 ml of dichloromethane. Cool the solution obtained to −60° C. then add, dropwise using a syringe, 41 μL of diethylamino sulphur trifluoride (DAST). Leave to return to room temperature and stir for 45 minutes, then pour the reaction mixture into an aqueous solution with 10% of sodium hydrogen carbonate and extract twice with dichloromethane. Combine the organic phases, dry over sodium sulphate and concentrate under reduced pressure. After purification by chromatography on silica gel (40-63 μm), eluting with a mixture of dichloromethane and methanol (95-5 by volume), we obtain 44 mg of 2-[9(R,S)-fluoro-9H-fluoren-4-yl]-1H-imidazo[4,5-c]pyridine, in the form of a white powder with the following characteristics:

Mass spectrum (E/I): m/z=301 (M$^+$)

$^1$H-NMR spectrum (400 MHz, δ in ppm, DMSO-d$_6$): 6.60 (d, J=52.0 Hz, 1H); 7.31 (t broad, J=7.5 Hz, 1H); 7.38 (t broad, J=7.5 Hz, 1H); 7.47 (d broad, J=7.5 Hz, 1H); 7.57 (t, J=7.5 Hz, 1H); 7.67 (d broad, J=5.5 Hz, 1H); 7.70 (d broad, J=7.5 Hz, 1H); 7.77 (d broad, J=7.5 Hz, 1H); 7.78 (d broad, J=7.5 Hz, 1H); 8.38 (d, J=5.5 Hz, 1H); 9.04 (s broad, 1H); from 13.2 to 13.6 (m very spread-out, 1H).

Example 11

Synthesis of O-(pyridin-3-yl)methyl 4-(3H-imidazo [4,5-c]pyridin-2-yl)-fluoren-9-one oxime (Z, E)

In a 10-ml round-bottomed flask, dissolve 100 mg of 4-(3H-imidazo[4,5-c]pyridin-2-yl)-fluoren-9-one, obtained in Example 1, in 3 ml of ethanol, then add successively 66.2 mg of [(pyridin-3-yl)methyl]hydroxylamine dihydrochloride, which can be obtained according to DE 2119012, and 276 mg of dry sodium acetate. After stirring overnight at room temperature, dilute with 30 ml of water. The precipitate that formed is drained, washed with water and dried in the stove at 500. In this way we obtain 43 mg of equimolecular mixture of the Z and E isomers of O-(pyridin-3-yl)methyl 4-(3H-imidazo[4,5-c]pyridin-2-yl)-fluoren-9-one oxime (Z, E), in the form of a yellow powder with the following characteristics:

Mass spectrum (E/I): m/z=476 (M+).

Example 12

Synthesis of N-[4-(3H-imidazo[4,5-c]pyridin-2-yl)-9H-fluoren-9(R,S)-yl]-formamide The 4-(3H-imidazo[4,5-c]pyridin-2-yl)-fluorene-9(R,S)-amine obtained in Example 6 can be crystallized as the triformate by treatment with excess of formic acid in methanol. Dissolve 65 mg of triformate of 4-(3H-imidazo[4,5-c]pyridin-2-yl)-fluorene-9(R,S)-amine in 1.5 ml of a mixture of dimethylformamide and dichloromethane (50-50 by volume), then add 43 mg of EDCI, 30 mg of HOBT and 200 µL of diethylisopropylamine and stir at room temperature for 22 hours. Pour the reaction mixture into 5 ml of a saturated aqueous solution of potassium dihydrogen phosphate, then extract 3 times with 10 ml of ethyl acetate. After purification by HPLC/MS on an X-Terra silica column, carry out gradient elution with water 100% (buffered to pH=9) to acetonitrile 100%, then lyophilization of the fractions containing the product of expected mass, obtaining 6 mg of N-[4-(3H-imidazo[4,5-c]pyridin-2-yl)-9H-fluoren-9(R,S)-yl]-formamide, in the form of a white solid with the following characteristics:

Mass spectrum (E/I): m/z=326 (M+).

Example 13

Synthesis of [4-(1H-imidazo[4,5-c]pyridin-2-yl)-fluoren-(9)-ylidene]-methanol, equimolecular mixture of the Z and E isomers In a 50-ml round-bottomed flask under an argon atmosphere, dissolve 200 mg of 2-(9H-fluoren-4-yl)-3H-imidazo[4,5-c]pyridine, obtained in Example 7, in 10 ml of tetrahydrofuran and cool the solution to −10° C. Then add 2.83 ml of a molar solution of potassium tert-butylate in tetrahydrofuran then 628 mg of ethyl formate. Stir for 12 minutes at −10° C., then add a normal aqueous solution of hydrochloric acid until the pH is neutral and finally 20 ml of ethyl acetate. Decant the organic phase, wash with water, dry over magnesium sulphate and concentrate under reduced pressure. In this way we obtain 95 mg of [4-(1H-imidazo[4,5-c]pyridin-2-yl)-fluoren-(9)-ylidene]-methanol, equimolecular mixture of the Z and E isomers, in the form of a yellow foam, with the following characteristics:

Mass spectrum (E/I): m/z=476 (M+).

Example 14

Synthesis of [4-(3H-imidazo[4,5-c]pyridin-2-yl)-9H-fluoren-9(R,S)-yl]amide of quinoline-5-carboxylic acid In a 50-ml three-necked flask, dissolve 605 mg of 4-(3H-imidazo[4,5-c]pyridin-2-yl)-fluorene-9(R,S)-amine, obtained in Example 6, in 30.17 ml of dimethylformamide, then add successively 530 mg of hydrochloride of 1-(3-dimethylaminopropyl)-3-ethylcarbodiimide (EDCI), 373 mg of 1-hydroxybenzotriazole (HOBT) and 319 mg of quinoline-5-carboxylic acid then stir for 20 hours at room temperature. Then add 100 ml of water, drain the precipitate that formed, and wash with water then with a saturated solution of sodium hydrogen carbonate. The raw solid obtained is purified by flash chromatography on silica gel (70-230 mesh), eluting with a mixture of dichloromethane and methanol (95-5 by volume). In this way we obtain 650 mg (78%) of [4-(3H-imidazo[4,5-c]pyridin-2-yl)-9H-fluoren-9(R,S)-yl]amide of quinoline-5-carboxylic acid, in the form of a pale yellow powder with the following characteristics:

Melting point (Kofler)=254-8° C. (decomposition).

Mass spectrum (E/I): m/z=453 (M+)

$^1$H-NMR spectrum (400 MHz, δ in ppm, DMSO-$d_6$): 6.44 (d, J=8.5 Hz, 1H); 7.27 (t broad, J=7.5 Hz, 1H); 7.39 (t broad, J=7.5 Hz, 1H); 7.48 (m broad, 1H); 7.57 (t, J=8.0 Hz, 1H); from 7.60 to 7.85 (m, 5H); 7.87 (d broad, J=7.5 Hz, 1H); 7.92 (d broad, J=8.0 Hz, 1H); 8.14 (d broad, J=8.5 Hz, 1H); 8.40 (d broad, J=5.5 Hz, 1H); 8.87 (d broad, J=8.5 Hz, 1H); from 8.93 to 9.10 (m spread-out, 1H); 8.99 (dd, J=2.0 and 4.0 Hz, 1H); 9.39 (d, J=8.5 Hz, 1H); from 13.3 to 13.5 (m spread-out, 1H).

Example 14A

Synthesis of the dextrorotatory enantiomer of the [4-(3H-imidazo[4,5-c]pyridin-2-yl)-9H-fluoren-9(R, S)-yl]amide of quinoline-5-carboxylic acid Inject 103 mg of [4-(3H-imidazo[4,5-c]pyridin-2-yl)-9H-fluoren-9(R,S)-yl]amide of quinoline-5-carboxylic acid, obtained in Example 14, into a preparative chiral column containing 600 g of silica Chiracel OJ. Elute with a mixture of n-heptane, methanol, ethanol and triethylamine (50-25-25-0.1 by volume). By recovering the first fraction eluted and concentrating under reduced pressure, we obtain 41.8 mg of the dextrorotatory enantiomer with the following characteristics:

$\alpha^D_{20}$=+131.1+/−1.8° (c=0.5; MeOH).

Example 14B

Synthesis of laevorotatory enantiomer of the [4-(3H-imidazo[4,5-c]pyridin-2-yl)-9H-fluoren-9(R,S)-yl] amide of quinoline-5-carboxylic acid Following the same procedure as in Example 14A, but recovering the second fraction eluted and concentrating under reduced pressure, we obtain 33.1 mg of laevorotatory enantiomer with the following characteristics:

$\alpha^D_{20}$=−123.5+/−1.8° (c=0.5; MeOH).

Example 15

Synthesis of 4-(3H-imidazo[4,5-b]pyridin-2-yl)-fluoren-9-one O-(4-bromo-3-hydroxybenzyl)-oxime The procedure in Example 11 is followed, starting from 100 mg of 4-(3H-imidazo[4,5-c]pyridin-2-yl)-fluoren-9-one, obtained in Example 1, and 42 mg of (4-bromo-3-hydroxybenzyl)hydroxylamine, which can be obtained according to J. Pharm. Exp. Ther. 1971, 179, 619-33, in 3 ml of methanol. In this way we obtain 22 mg of 60/40 mixture of the Z and E isomers of 4-(3H-imidazo[4,5-b]pyridin-2-yl)-fluoren-9-one O-(4-bromo-3-hydroxy-benzyl)-oxime), in the form of a yellow-orange powder, with the following characteristics:

Mass spectrum (E/I): m/z=496 (M+).

Example 16

Synthesis of N-[4-(3H-imidazo[4,5-c]pyridin-2-yl)-9H-fluoren-9(R,S)-yl]-phenethyl-amine In a microwave reactor, add 81 µL of 2-phenyl-ethylamine, 18 µL of diethylisopropylamine and 182 µL of titanium tetraisopropylate to a solution of 84 mg of 4-(3H-imidazo[4,5-c]pyridin-2-yl)-fluoren-9-one, obtained in Example 1, in 0.5 ml of ethanol. Then heat successively at 60° C. for 5 minutes, at 70° C. for 20 minutes, at 100° C. for 15 minutes and finally at 130° C. for 30 minutes. After cooling to room temperature, add 25 mg of sodium cyanohydroborate and stir for 16 hours at room temperature. Pour the reaction mixture into 5 ml of a saturated aqueous solution of potassium dihydrogen phosphate, then extract 3 times with 10 ml of dichloromethane. After purification on silica gel, eluting with mixtures of dichloromethane and methanol (98-2, then 96-4 by volume), we obtain 4.8 mg of N-[4-(3H-imidazo[4,5-c]pyridin-2-yl)-9H-fluoren-9(R,S)-yl]-phenethyl-amine, in the form of a white solid with the following characteristics:

Mass spectrum (E/I): m/z=402 ($M^+$).

Example 17

Synthesis of 2-[4-(3H-imidazo[4,5-c]pyridin-2-yl)-fluoren-(9E,Z)-ylidene]-N-pyridin-3-yl-acetamide Stage 1: In a 100-ml three-necked flask, dissolve 594 mg of 4-(3H-imidazo[4,5-c]pyridin-2-yl)-fluoren-9-one, obtained in Example 1, in 15 ml of acetonitrile and add successively 654 mg of tert-butyloxycarbonyl anhydride and 12 mg of 4-dimethylamino-pyridine. Stir the solution obtained for 20 hours at room temperature, then pour the reaction mixture into 100 ml of ice water and extract 3 times with ethyl acetate. Combine the organic phases and wash with water, dry over magnesium sulphate and concentrate under reduced pressure. In this way we obtain 695 mg of tert-butyl ester of 2-(9-oxo-9H-fluoren-4-yl)-imidazo[4,5-c]pyridine-3-carboxylic acid, in the form of brown crystals, which are used as they are in the next stage.

Stage 2: In a 25-ml three-necked flask under a nitrogen atmosphere, dissolve 695 mg of tert-butyl ester of 2-(9-oxo-9H-fluoren-4-yl)-imidazo[4,5-c]pyridine-3-carboxylic acid, obtained in the preceding stage, in 5 ml of anhydrous tetrahydrofuran, then add 126 mg of sodium hydride and stir for 10 minutes. Then add, dropwise in 30 minutes, a solution of 588 mg of triethyl phosphonoacetate in 5 ml of anhydrous tetrahydrofuran, then stir for 16 hours at room temperature. Concentrate the reaction mixture under reduced pressure, then absorb in a mixture of water and ethyl acetate. Decant the organic phase, wash with water, dry over magnesium sulphate and concentrate under reduced pressure. After purification on silica gel, eluting with mixtures of dichloromethane and ethyl acetate (90-10, then 80-20, then 70-30 by volume), we obtain 432 mg of tert-butyl ester of 2-{9-[1-ethoxycarbonyl-methylidene]-9H-fluoren-4-yl}-3H-pyrrolo[3,2-c]pyridine-3-carboxylic acid, as equimolecular mixture of the Z and E isomers, in the form of a viscous yellow oil, which is used as it is in the next stage.

Stage 3: In a 25-ml three-necked flask, stir for 12 hours at room temperature a solution of 400 mg of tert-butyl ester of 2-{9-[1-ethoxycarbonyl-methylidene]-9H-fluoren-4-yl}-3H-pyrrolo[3,2-c]pyridine-3-carboxylic acid, obtained in the preceding stage, in 10 ml of tetrahydrofuran in the presence of 2 ml of a normal aqueous solution of sodium hydroxide. After concentrating the solvent under reduced pressure, take up the residue in a mixture of water and ethyl acetate. Acidify the aqueous phase to pH=2, then extract 4 times with ethyl acetate. Combine the organic phases and wash with water and concentrate under reduced pressure. Crystallize the white residue obtained in diisopropyl ether. In this way we obtain 60 mg of [4-(3H-imidazo[4,5-c]pyridin-2-yl)-fluoren-9-ylidene]-acetic acid, as 40-60 mixture of the Z and E isomers, in the form of a white powder with the following characteristics:

Mass spectrum (E/I): m/z=339 ($M^+$).

Stage 4: Follow the procedure in Example 14, starting from 45 mg of [4-(3H-imidazo[4,5-c]pyridin-2-yl)-fluoren-9-ylidene]-acetic acid, obtained in the preceding stage, and 18.7 mg of 3-aminopyridine in the presence of 38.1 mg of EDCI and 30.5 mg of HOBT. After purifying by precipitation in water, we obtain 26 mg of 2-[4-(3H-imidazo[4,5-c]pyridin-2-yl)-fluoren-9-ylidene]-N-pyridin-3-yl-acetamide, as 40-60 mixture of the Z and E isomers, in the form of a beige powder with the following characteristics:

Mass spectrum (E/I): m/z=415 ($M^+$).

$^1$H-NMR spectrum (400 MHz, δ in ppm, DMSO): 7.15 (d, J=7.5 Hz, 0.4H); 7.27 (t, J=7.5 Hz, 1H); from 7.30 to 7.49 (m, 3.6H); 7.53 (t, J=7.5 Hz, 0.6H); 7.60 (t, J=7.5 Hz, 0.4H); from 7.62 to 7.75 (m, 2H); 7.92 (d broad, J=7.5 Hz, 0.6H); 8.10 (d, J=7.5 Hz, 0.4H); 8.23 (m broad, 1H); 8.35 (s broad, 1H); 8.41 (d, J=5.5 Hz, 1H); 8.75 (d, J=8.5 Hz, 0.4H); 8.41 (s broad, 1H); 8.95 (d, J=8.5 Hz, 0.6 Hz); 9.05 (s broad, 1H); 10.89 (s, 0.4H); 10.91 (s, 0.6H); from 13.2 to 13.6 (m very spread-out, 1H).

Example 18

Synthesis of N-[4-(3H-imidazo[4,5-c]pyridin-2-yl)-9H-fluoren-9(R,S)-yl]-(1H-indol-5-ylmethyl)-amine In a 5-ml three-necked flask, dissolve 74 mg of 4-(3H-imidazo[4,5-c]pyridin-2-yl)-fluorene-9(R,S)-amine, isolated as the dihydrochloride, in 0.5 ml of ethanol, add 45 mg of 5-formyl-indole and 70 µL of diisopropylethylamine and stir for 2 hours 30 minutes at room temperature. Then add 28 mg of sodium hydroborate and stir for 18 hours at room temperature. Pour the reaction mixture into 5 ml of a saturated aqueous solution of potassium dihydrogen phosphate, then extract 3 times with 10 ml of dichloromethane. After purification on silica gel, eluting with mixtures of dichloromethane and methanol (98-2, then 96-4 by volume), we obtain 34 mg of N-[4-(3H-imidazo[4,5-c]pyridin-2-yl)-9H-fluoren-9(R,S)-yl]-(1H-indol-5-yl-methyl)-amine, in the form of a white solid with the following characteristics:

Mass spectrum (E/I): m/z=427 ($M^+$).

Example 19

Synthesis of 4-(3H-imidazo[4,5-c]pyridin-2-yl)-fluoren-9-one oxime (Z)

Inject 103 mg of 4-(3H-imidazo[4,5-c]pyridin-2-yl)-fluoren-9-one oxime (Z,E), obtained in Example 5, into a preparative chiral column containing 700 g of silica Chiralpak AS (20 µm). Elute with a mixture of n-heptane, methanol, isopropanol and triethylamine (90-2.5-2.5-0.1 by volume).

Recovering the second fraction eluted, and concentrating under reduced pressure, we obtain 23.8 mg of oxime Z.

Example 20

Synthesis of ethyl ester of [4-(3H-imidazo[4,5-c]pyridin-2-yl)-9H-fluoren-9(R,S)-yl]-carbamoic acid In a 25-ml three-necked flask under an argon atmosphere, add 72 μL of ethyl chloroformate to a suspension, cooled to 5° C., of 225 mg of 4-(3H-imidazo[4,5-c]pyridin-2-yl)-fluorene-9(R,S)-amine, obtained in Example 6, in 3 ml of tetrahydrofuran and 113 μL of triethylamine. Stir the reaction mixture for 1 hour, allowing it to return to room temperature, then concentrate under reduced pressure. After purification by silica gel flash chromatography, eluting with a mixture of dichloromethane and methanol (96-4 by volume), we obtain 138 mg of ethyl ester of [4-(3H-imidazo[4,5-c]pyridin-2-yl)-9H-fluoren-9(R,S)-yl]-carbamoic acid, in the form of a pale yellow solid with the following characteristics:
Mass spectrum (E/I): m/z=370 (M+).

Example 21

Synthesis of N-[4-(3H-imidazo[4,5-c]pyridin-2-yl)-9H-fluoren-9(R,S)-yl]-2-(pyridin-3-yl)-acetamide Carry out the procedure as in Example 14, starting from 85.2 mg of 4-(3H-imidazo[4,5-c]pyridin-2-yl)-fluorene-9(R,S)-amine, obtained in Example 6, and 21 mg of (pyridin-3-yl)acetic acid in the presence of 44 mg of EDCI and 31 mg of HOBT in 1 ml of dichloromethane and 1 ml of DMF, for 20 hours. After diluting with 25 ml of water, drain the precipitate that formed, wash with water and dry under reduced pressure at 50° C. In this way we obtain 20 mg of N-[4-(3H-imidazo[4,5-c]pyridin-2-yl)-9H-fluoren-9(R,S)-yl]-2-(pyridin-3-yl)-acetamide, in the form of a beige powder, with the following characteristics:
Mass spectrum (E/I): m/z=417 (M+).

Example 22

Synthesis of N-[4-(3H-imidazo[4,5-c]pyridin-2-yl)-9H-fluoren-9(R,S)-yl]-(1H-indol-6-ylmethyl)-amine Carry out the procedure as in Example 18, starting from 94 mg of dihydrochloride of 4-(3H-imidazo[4,5-c]pyridin-2-yl)-fluorene-9(R,S)-amine, 55 mg of 6-formyl-indole and 90 μL of diisopropylethylamine in 0.7 ml of ethanol for 2 hours at room temperature, then add 28 mg of sodium hydroborate and stir for 1 hour at room temperature. After purification on silica gel, eluting with mixtures of dichloromethane and methanol (95-5 by volume), we obtain 58 mg of N-[4-(3H-imidazo[4,5-c]pyridin-2-yl)-9H-fluoren-9(R,S)-yl]-(1H-indol-6-ylmethyl)-amine, in the form of a pale pink solid with the following characteristics:
Mass spectrum (E/I): m/z=427 (M+).

Example 23

Synthesis of 4-(3H-imidazo[4,5-c]pyridin-2-yl)-fluoren-9-one oxime (E)

Inject 103 mg of 4-(3H-imidazo[4,5-c]pyridin-2-yl)-fluoren-9-one oxime (Z,E), obtained in Example 5, into a preparative chiral column containing 700 g of silica Chiralpak AS (20 μm). Elute with a mixture of n-heptane, methanol, isopropanol and triethylamine (90-2.5-2.5-0.1 by volume). Recovering the first fraction eluted, and concentrating under reduced pressure, we obtain 37 mg of oxime E, which has the following characteristics:
$^1$H-NMR spectrum (300 MHz, δ in ppm, DMSO): from 7.18 to 7.28 (m, 2H); 7.33 (m, 1H); 7.58 (t, J=7.5 Hz, 1H); 7.67 (m spread-out, 1H); 7.72 (d broad, J=7.5 Hz, 1H); 7.76 (d broad, J=7.5 Hz, 1H); 8.40 (d, J=5.5 Hz, 1H); 8.62 (d broad, J=7.5 Hz, 1H); 9.04 (s broad, 1H).

Example 24

Synthesis of trifluoroacetate of 2-(2-amino-thiazol-4-yl)-N-[4-(3H-imidazo[4,5-c]pyridin-2-yl)-9H-fluoren-9(R,S)-yl]-acetamide In a 10-ml three-necked flask under an argon atmosphere, add 210 μL of a 2M solution of trimethylaluminium in toluene to a suspension of 80 mg of 4-(3H-imidazo[4,5-c]pyridin-2-yl)-fluorene-9(R,S)-amine, obtained in Example 6, in 2 ml of toluene and heat at 80° C. for 20 minutes. Again add 90 μL of 2M solution of trimethylaluminium in toluene and heat again for 10 minutes at 80° C. Add 45 mg of ethyl ester of (2-amino-thiazol-4-yl)acetic acid and continue heating at 80° C. for 2 hours. Pour the reaction mixture into 5 ml of a saturated aqueous solution of potassium dihydrogen phosphate, then extract 3 times with 10 ml of dichloromethane. After purification by HPLC/MS on a Symmetry C18 silica column (5 μm), eluting with a gradient of water 100% (containing 0.07% of TFA) to acetonitrile 100% (containing 0.07% of TFA), we obtain 7 mg of trifluoroacetate of 2-(2-amino-thiazol-4-yl)-N-[4-(3H-imidazo[4,5-c]pyridin-2-yl)-9H-fluoren-9(R,S)-yl]-acetamide, in the form of a white solid with the following characteristics:
Mass spectrum (E/I): m/z=438 (M+).

Example 25

Synthesis of 2-(6-chloropyridin-3-yl)-N-[4-(3H-imidazo[4,5-c]pyridin-2-yl)-9H-fluoren-9(R,S)-yl]-acetamide Carry out the procedure as in Example 14, starting from 101.3 mg of 4-(3H-imidazo[4,5-c]pyridin-2-yl)-fluorene-9(R,S)-amine, obtained in Example 6, and 39 mg of (2-chloropyridin-5-yl)acetic acid in the presence of 65.4 mg of EDCI and 46.1 mg of HOBT in 1.8 ml of dichloromethane and 1.8 ml of DMF, for 20 hours. After purifying by crystallization from water, we obtain 16 mg of 2-(6-chloropyridin-3-yl)-N-[4-(3H-imidazo[4,5-c]pyridin-2-yl)-9H-fluoren-9(R,S)-yl]-acetamide, in the form of a yellow powder, with the following characteristics:
Mass spectrum (E/I): m/z=451 (M+).

Example 26

Synthesis of trifluoroacetate of N-[4-(3H-imidazo[4,5-c]pyridin-2-yl)-9H-fluoren-9(R,S)-yl]-quinolin-5-yl-methylamine Carry out the procedure as in Example 18, starting from 100 mg of 4-(3H-imidazo[4,5-c]pyridin-2-yl)-fluorene-9(R,S)-amine, obtained in Example 6, and 59 mg of quinoline-5-carboxaldehyde in 1 ml of ethanol for 3 hours at room temperature, then add 29 mg of sodium hydroborate and stir for 2 hours at room temperature. After purification by HPLC/MS on a Symmetry C18 silica column (5 μm), eluting with a gradient of water 100% (containing 0.07% of TFA) to acetonitrile 100% (containing 0.07% of TFA), we obtain 49.5 mg of trifluoroacetate of N-[4-(3H-imidazo[4,5-c]pyridin-2-yl)-9H-fluoren-9(R,S)-yl]-quinolin-5-yl-methylamine, in the form of a pale yellow solid with the following characteristics:

Mass spectrum (E/I): m/z=439 (M⁺).

Example 27

Synthesis of N-[4-(3H-imidazo[4,5-c]pyridin-2-yl)-9H-fluoren-9(R,S)-yl]-2-(4-methoxy-phenyl)-acetamide Carry out the procedure as in Example 14, starting from 99.2 mg of 4-(3H-imidazo[4,5-c]pyridin-2-yl)-fluorene-9(R,S)-amine, obtained in Example 6, and 37 mg of (4-methoxyphenyl)acetic acid in the presence of 64 mg of EDCI and 45.1 mg of HOBT in 1.5 ml of dichloromethane and 1.5 ml of DMF for 20 hours. After purifying by crystallization from water, we obtain 35 mg of N-[4-(3H-imidazo[4,5-c]pyridin-2-yl)-9H-fluoren-9(R,S)-yl]-2-(4-methoxy-phenyl)-acetamide, in the form of a beige powder, with the following characteristics:

Mass spectrum (E/I): m/z=446 (M⁺).

Example 28

Synthesis of [4-(3H-imidazo[4,5-c]pyridin-2-yl)-9H-fluoren-9(R,S)-yl]-urea trifluoroacetate In a 10-ml three-necked flask under an argon atmosphere, add 210 μL of a 2M solution of trimethylaluminium to a suspension of 80 mg of 4-(3H-imidazo[4,5-c]pyridin-2-yl)-fluorene-9(R,S)-amine, obtained in Example 6, in 1 ml of anhydrous toluene. Stir the suspension obtained for 15 minutes at room temperature then 15 min at 80° C. Then add 30 mg of 2-chloro-ethyl carbamate, and stir for 1 hour at 40° C. After adding 0.5 ml of water, the precipitate that formed is drained. After purification by HPLC/MS on a Symmetry C18 silica column (5 μm), eluting with a gradient of water 100% (containing 0.07% of TFA) to acetonitrile 100% (containing 0.07% of TFA), then lyophilization of the fractions containing the product of the expected mass, we obtain 18 mg of [4-(3H-imidazo[4,5-c]pyridin-2-yl)-9H-fluoren-9(R,S)-yl]-urea trifluoroacetate, in the form of a white solid with the following characteristics:

Mass spectrum (E/I): m/z=341 (M⁺).

Example 29

Synthesis of hydrochloride of 4-(1H-imidazo[4,5-c]pyridin-2-yl)-9H-fluorene-9(R,S)-carboxylic acid Stage 1: In a 500-ml three-necked flask under an argon atmosphere, dissolve 1.4 g of tert-butyl ester of fluorene-4-carboxylic acid, which can be obtained according to Helv. Chim. Acta 1984, 67, 2009-16, in 50 ml of tetrahydrofuran. After cooling to −20° C., add 1.18 g of potassium tert-butylate, then after stirring for 10 minutes at −20° C., add 0.995 g of methyl chloroformate to the purple solution obtained and stir for 1 hour at −20° C. Then dilute the reaction mixture with 200 ml of ethyl acetate, and wash with saturated solution of sodium dihydrogen phosphate. Decant the organic phase, dry over magnesium sulphate and concentrate under reduced pressure. After purification on silica gel (70-230 mesh), eluting with a mixture of dichloromethane and n-heptane (66-34 by volume), we obtain 1.4 g of 4-tert-butyl 9,9-dimethyl ester of fluorene-4,9,9-tricarboxylic acid, in the form of a viscous colourless oil, which is used as it is in the next stage.

Stage 2: In a 500-ml three-necked flask, dissolve 1.4 g of 4-tert-butyl 9,9-dimethyl ester of fluorene-4,9,9-tricarboxylic acid, obtained in the preceding stage, in 10 ml of dichloromethane, then after cooling to 0° C. add 10 ml of trifluoroacetic acid and stir for 1 hour at 0° C. After concentration under reduced pressure, we obtain 1.2 g of 9,9-dimethyl ester of fluorene-4,9,9-tricarboxylic acid in the form of a white powder, which is used as it is in the next stage.

Stage 3: In a 500-ml three-necked flask, stir, for one hour and fifteen minutes at room temperature, 1.2 g of 9,9-dimethyl ester of fluorene-4,9,9-tricarboxylic acid, obtained in the preceding stage, in 35 ml of thionyl chloride. After concentration under reduced pressure, dissolve the acid chloride obtained (1.33 g) in 40 ml of dichloromethane, then add 0.6 g of 3,4-diaminopyridine and stir for one hour and thirty minutes at room temperature. After purification by flash chromatography on silica gel (70-230 mesh), eluting with a mixture of dichloromethane and methanol (96-4 by volume), we obtain 1.3 g of an equimolecular mixture of dimethyl ester of 4-(4-amino-pyridin-3-ylcarbamoyl)-fluorene-9,9-dicarboxylic acid and of dimethyl ester of 4-(3-amino-pyridin-4-ylcarbamoyl)-fluorene-9,9-dicarboxylic acid, in the form of a beige powder, which is used as it is in the next stage.

Stage 4: In a 25-ml three-necked flask, dissolve 1.3 g of the amide mixture obtained in the preceding stage in 35 ml of trifluoroacetic acid, 3.5 ml of trifluoroacetic anhydride and 1.5 ml of 36% hydrochloric acid. Then stir for 2 days at 90° C., then add, in three portions, 8.5 ml of 36% hydrochloric acid and heat again for 60 hours at 90° C. After concentration under reduced pressure, the residue is purified by flash chromatography on silica gel (70-230 mesh), eluting with a mixture of dichloromethane and methanol (95-5 then 90-10 by volume). In this way we obtain 1 g of hydrochloride of 4-(1H-imidazo[4,5-c]pyridin-2-yl)-9H-fluorene-9(R,S)-carboxylic acid, in the form of an off-white powder with the following characteristics:

Mass spectrum (E/I): m/z=363 (M⁺)

Example 30

Synthesis of trifluoroacetate of 4-(3H-imidazo[4,5-c]pyridin-2-yl)-fluoren-9-one semicarbazone (Z, E)

In a 5-ml three-necked flask, stir, for 6 hours at room temperature, a suspension containing 35 mg of 4-(3H-imidazo[4,5-c]pyridin-2-yl)-fluoren-9-one, obtained in Example 1, 29 mg of sodium acetate and 20 mg of semicarbazide hydrochloride in 0.4 ml of an aqueous solution at 50% of ethanol. Then add a further 29 mg of sodium acetate and 20 mg of semicarbazide hydrochloride then stir again for 18 hours at room temperature. After adding 2 ml of water, the precipitate that formed is drained and washed twice with 1 ml of water. After purification by HPLC/MS on a Symmetry C18 silica column (5 μm), eluting with a gradient of water 100% (containing 0.07% of TFA) to acetonitrile 100% (containing 0.07% of TFA), we obtain 5.5 mg of trifluoroacetate of 4-(3H-imidazo[4,5-c]pyridin-2-yl)-fluoren-9-one semicarbazone (Z, E), in the form of a white solid with the following characteristics:

Mass spectrum (E/I): m/z=354 (M⁺).

Example 31

Synthesis of [4-(3H-imidazo[4,5-c]pyridin-2-yl)-9H-fluoren-9(R,S)-yl]amide of 2-hydroxy-quinoline-4-carboxylic acid Carry out the procedure as in Example 14, starting from 298 mg of 4-(3H-imidazo[4,5-c]pyridin-2-yl)-fluorene-9(R,S)-amine, obtained in Example 6, and 189 mg of 2-hydroxyquinoline-4-carboxylic acid in the presence of 211 mg of EDCI and 149 mg of HOBT in 7 ml of DMF for 20 hours. After purifying by precipitation in water, then washing successively with a saturated solution of sodium hydrogen carbonate then isopropanol, we obtain 450 mg of [4-(3H-imidazo[4,5-c]pyridin-2-yl)-9H-fluoren-9(R,S)-yl]amide of 2-hydroxy-quinoline-4-carboxylic acid, in the form of a brown solid, with the following characteristics:

Mass spectrum (E/I): m/z=469 (M$^+$).

Example 32

Synthesis of [4-(3H-imidazo[4,5-c]pyridin-2-yl)-9H-fluoren-9(R,S)-yl]amide of tetrahydropyran-4-carboxylic acid Carry out the procedure as in Example 14, starting from 202 mg of 4-(3H-imidazo[4,5-c]pyridin-2-yl)-fluorene-9(R, S)-amine, obtained in Example 6, and 80 mg of tetrahydropyran-4-carboxylic acid in the presence of 177 mg of EDCI and 125 mg of HOBT in 3.4 ml of DMF for 20 hours. After purifying by precipitation in water, then washing successively with a saturated solution of sodium hydrogen carbonate then petroleum ether, we obtain 253 mg of [4-(3H-imidazo[4,5-c]pyridin-2-yl)-9H-fluoren-9(R,S)-yl]amide of tetrahydro-pyran-4-carboxylic acid, in the form of a white crystalline solid, with the following characteristics:

Mass spectrum (E/I): m/z=410 (M$^+$).

Example 33

Synthesis of the tert-butyl ester of 4-[4-(3H-imidazo[4,5-c]pyridin-2-yl)-9H-fluoren-9(R,S)-ylcarbamoyl]-piperidine-1-carboxylic acid Carry out the procedure as in Example 14, starting from 208 mg of 4-(3H-imidazo[4,5-c]pyridin-2-yl)-fluorene-9(R, S)-amine, obtained in Example 6, and 145.4 mg of tert-butoxycarbonyl-nipecotic acid in the presence of 182 mg of EDCI and 128.5 mg of HOBT in 3.5 ml of DMF for 20 hours. After purifying by precipitation in water, then washing successively with a saturated solution of sodium hydrogen carbonate then petroleum ether, we obtain 195 mg of tert-butyl ester of 4-[4-(3H-imidazo[4,5-c]pyridin-2-yl)-9H-fluoren-9 (R,S)-ylcarbamoyl]-piperidine-1-carboxylic acid, in the form of a beige crystalline solid, with the following characteristics:

Mass spectrum (E/I): m/z=509 (M$^+$).

Example 34

Synthesis of hydrochloride of [4-(3H-imidazo[4,5-c]pyridin-2-yl)-9H-fluoren-9(R,S)-yl]amide of 6-hydroxy-naphthalene-1-carboxylic acid Carry out the procedure as in Example 14, starting from 208 mg of 4-(3H-imidazo[4,5-c]pyridin-2-yl)-fluorene-9(R, S)-amine, obtained in Example 6, and 119 mg of 6-hydroxy-naphthalene-1-carboxylic in the presence of 182 mg of EDCI and 128.5 mg of HOBT in 3.5 ml of DMF for 20 hours. After purification by flash chromatography on silica gel (70-230 M), eluting with a mixture of dichloromethane and methanol (95-5 by volume), we obtain 100 mg of hydrochloride of [4-(3H-imidazo[4,5-c]pyridin-2-yl)-9H-fluoren-9(R,S)-yl] amide of 6-hydroxy-naphthalene-1-carboxylic acid, in the form of a white crystalline solid, with the following characteristics:

Mass spectrum (E/I): m/z=468 (M$^+$).

Example 35

Synthesis of [4-(3H-imidazo[4,5-c]pyridin-2-yl)-9H-fluoren-9(R,S)-yl]amide of isoquinoline-5-carboxylic acid Carry out the procedure as in Example 14, starting from 208 mg of 4-(3H-imidazo[4,5-c]pyridin-2-yl)-fluorene-9(R, S)-amine, obtained in Example 6, and 110 mg of isoquinoline-5-carboxylic acid in the presence of 182 mg of EDCI and 128.5 mg of HOBT in 10.5 ml of DMF for 20 hours. After purification by flash chromatography on silica gel (70-230 M), eluting with a mixture of dichloromethane and methanol (95-5 by volume), we obtain 106 mg of [4-(3H-imidazo[4,5-c]pyridin-2-yl)-9H-fluoren-9(R,S)-yl]amide of isoquinoline-5-carboxylic acid, in the form of a yellow crystalline solid, with the following characteristics:

Mass spectrum (E/I): m/z=453 (M$^+$).

Example 36

Synthesis of 2-furan-3-yl-N-[4-(3H-imidazo[4,5-c]pyridin-2-yl)-9H-fluoren-9(R,S)-yl]-2-oxo-acetamide Carry out the procedure as in Example 14, starting from 351 mg of 4-(3H-imidazo[4,5-c]pyridin-2-yl)-fluorene-9(R, S)-amine, obtained in Example 6, and 150 mg of 3-furylglyoxylic acid in the presence of 308 mg of EDCI and 217 mg of HOBT in 5.9 ml of DMF for 20 hours. After purification by flash chromatography on silica gel (70-230 M), eluting with a mixture of dichloromethane and methanol (97.5-2.5 by volume), we obtain 96 mg of 2-furan-3-yl-N-[4-(3H-imidazo[4, 5-c]pyridin-2-yl)-9H-fluoren-9(R,S)-yl]-2-oxo-acetamide, in the form of a pale yellow crystalline solid, with the following characteristics:

Mass spectrum (E/I): m/z=420 (M$^+$).

Example 37

Synthesis of N-[4-(3H-imidazo[4,5-c]pyridin-2-yl)-9H-fluoren-9(R,S))-yl]-2-pyridin-4-yl-acetamide trifluoroacetate Carry out the procedure as in Example 24, but starting from 50 mg of 4-(3H-imidazo[4,5-c]pyridin-2-yl)-fluorene-9(R, S)-amine, obtained in Example 6, 300 μL of a 2M solution of trimethylaluminium in toluene and 46 μL of ethyl ester of (4-pyridyl)acetic acid in 2 ml of toluene and 0.5 ml of N-methylpyrrolidone for 10 minutes at room temperature then 10 minutes at 60° C. in a microwave reactor. After purification by HPLC/MS on a Symmetry C18 silica column (5 μm), eluting with a gradient of water 100% (containing 0.07% of TFA) to acetonitrile 100% (containing 0.07% of TFA), we obtain 7.8 mg of N-[4-(3H-imidazo[4,5-c]pyridin-2-yl)-9H-fluoren-9 (R,S))-yl]-2-pyridin-4-yl-acetamide trifluoroacetate, in the form of a white solid with the following characteristics:

Mass spectrum (E/I): m/z=417 (M$^+$).

Example 38

Synthesis of [4-(3H-imidazo[4,5-c]pyridin-2-yl)-9H-fluoren-9(R,S)-yl]amide trifluoroacetate of 2H-1-benzopyran-5-carboxylic acid Carry out the procedure as in Example 14, starting from 74 mg of 4-(3H-imidazo[4,5-c]pyridin-2-yl)-fluorene-9(R,S)- amine, obtained in Example 6, and 39 mg of 2H-1-benzopyran-5-carboxylic acid, in the presence of 57.5 mg of EDCI, 40.5 mg of HOBT and 70 μL of diisopropylethylamine in 1 ml of DMF for 24 hours. After purification by HPLC/MS on a Symmetry C18 silica column (5 μm), eluting with a gradient of water 100% (containing 0.07% of TFA) to acetonitrile 100% (containing 0.07% of TFA), we obtain 21 mg of [4-(3H-imidazo[4,5-c]pyridin-2-yl)-9H-fluoren-9(R,S)-yl] amide trifluoroacetate of 2H-1-benzopyran-5-carboxylic acid, in the form of a beige solid with the following characteristics:

Mass spectrum (E/I): m/z=456 ($M^+$).

2H-1-benzopyran-5-carboxylic acid can be obtained according to WO2005012291.

Example 39

Synthesis of [4-(3H-imidazo[4,5-c]pyridin-2-yl)-9H-fluoren-9(R,S)-yl]amide trifluoroacetate of 1H-pyrazole-3-carboxylic acid Carry out the procedure as in Example 14, starting from 75 mg of 4-(3H-imidazo[4,5-c]pyridin-2-yl)-fluorene-9(R,S)-amine, obtained in Example 6, and 42 mg of 1H-pyrazole-4-carboxylic acid, in the presence of 72 mg of EDCI, 51 mg of HOBT and 131 μL of diisopropylethylamine in 1.25 ml of DMF and 1.25 ml of dichloromethane for 24 hours. After purification by HPLC/MS on a Symmetry C18 silica column (5 μm), eluting with a gradient of water 100% (containing 0.07% of TFA) to acetonitrile 100% (containing 0.07% of TFA), we obtain 58.5 mg of [4-(3H-imidazo[4,5-c]pyridin-2-yl)-9H-fluoren-9(R,S)-yl]amide trifluoroacetate of 1H-pyrazole-3-carboxylic acid, in the form of a white solid with the following characteristics:

Mass spectrum (E/I): m/z=392 ($M^+$).

Example 40

Synthesis of N-[4-(3H-imidazo[4,5-c]pyridin-2-yl)-9H-fluoren-9(R,S)-yl]-succinamide trifluoroacetate Carry out the procedure as in Example 14, starting from 74.6 mg of 4-(3H-imidazo[4,5-c]pyridin-2-yl)-fluorene-9(R,S)-amine, obtained in Example 6, and 43.9 mg of succinamic acid, in the presence of 71.9 mg of EDCI, 50.7 mg of HOBT and 131 μL of diisopropylamine in 1.25 ml of dichloromethane and 1.25 ml of DMF for 20 hours. After purification by HPLC/MS on silica Symmetry C18 (5 μm), following the conditions described in Example 28, we obtain 63 mg of N-[4-(3H-imidazo[4,5-c]pyridin-2-yl)-9H-fluoren-9(R,S)-yl]-succinamide trifluoroacetate, in the form of a white solid, with the following characteristics:

Mass spectrum (E/I): m/z=397 ($M^+$).

Example 41

Synthesis of [4-(3H-imidazo[4,5-c]pyridin-2-yl)-9H-fluoren-9(R,S)-yl]amide trifluoroacetate of 1H-benzotriazole-5-carboxylic acid Carry out the procedure as in Example 14, starting from 74.62 mg of 4-(3H-imidazo[4,5-c]pyridin-2-yl)-fluorene-9(R,S)-amine, obtained in Example 6, and 61.2 mg of 1H-benzotriazole-5-carboxylic acid, which can be obtained according to Archiv. Pharm. 1989, 322, 457-59, in the presence of 71.9 mg of EDCI, 50.7 mg of HOBT and 131 μL of diisopropylamine in 1.25 ml of dichloromethane and 1.25 ml of DMF for 20 hours. After purification by HPLC/MS in the conditions described in Example 28, we obtain 66.5 mg of [4-(3H-imidazo[4,5-c]pyridin-2-yl)-9H-fluoren-9(R,S)-yl]amide trifluoroacetate of 1H-benzotriazole-5-carboxylic acid, in the form of a white solid, with the following characteristics:

Mass spectrum (E/I): m/z=443 ($M^+$).

$^1$H-NMR spectrum (300 MHz, δ in ppm, DMSO-$d_6$): 6.41 (d, J=8.5 Hz, 1H); 7.27 (t broad, J=7.5 Hz, 1H); 7.38 (t broad, J=7.5 Hz, 1H); from 7.54 to 7.67 (m, 3H); 7.77 (d broad, J=7.5 Hz, 1H); 7.85 (d broad, J=7.5 Hz, 1H); from 7.88 to 8.13 (m very spread-out, 2H); 8.15 (d broad, J=6.5 Hz, 1H); from 8.50 to 8.70 (m very spread-out, 1H); 8.64 (d, J=6.5 Hz, 1H); 9.37 (d, J=8.5 Hz, 1H); 9.53 (s broad, 1H); from 14.1 to 15.2 (m very spread-out, 1H); from 15.7 to 16.3 (m spread-out, 1H).

Example 42

Synthesis of N-[4-(3H-imidazo[4,5-c]pyridin-2-yl)-9H-fluoren-9(R,S)-yl]-2-(5-mercapto-4H-1,2,4-triazol-3-yl)-acetamide trifluoroacetate Carry out the procedure as in Example 14, starting from 75 mg of 4-(3H-imidazo[4,5-c]pyridin-2-yl)-fluorene-9(R,S)-amine, obtained in Example 6, and 44 mg of (5-mercapto-4H-1,2,4-triazol-3-yl)-acetic acid, in the presence of 72 mg of EDCI, 51 mg of HOBT and 131 μL of diisopropylethylamine in 1.25 ml of DMF and 1.25 ml of dichloromethane for 24 hours. After purification by HPLC/MS on a Symmetry C18 silica column (5 μm), eluting with a gradient of water 100% (containing 0.07% of TFA) to acetonitrile 100% (containing 0.07% of TFA), we obtain 67.5 mg of N-[4-(3H-imidazo[4,5-c]pyridin-2-yl)-9H-fluoren-9(R,S)-yl]-2-(5-mercapto-4H-1,2,4-triazol-3-yl)-acetamide trifluoroacetate, in the form of a pale yellow solid with the following characteristics:

Mass spectrum (E/I): m/z=439 ($M^+$).

Example 43

Synthesis of [4-(3H-imidazo[4,5-c]pyridin-2-yl)-9H-fluoren-9(R,S)-yl]amide of 2-oxo-2,3-dihydro-1H-benzimidazole-5-carboxylic acid Carry out the procedure as in Example 14, starting from 202 mg of 4-(3H-imidazo[4,5-c]pyridin-2-yl)-fluorene-9(R,S)-amine, obtained in Example 6, and 110 mg of 2-oxo-2,3-dihydro-1H-benzimidazole-5-carboxylic acid, in the presence of 177 mg of EDCI and 125 mg of HOBT in 5.9 ml of DMF for 20 hours. After purification by flash chromatography on silica gel (70-230 M), eluting with a mixture of dichloromethane and methanol (95-5 by volume), we obtain 139 mg of [4-(3H-imidazo[4,5-c]pyridin-2-yl)-9H-fluoren-9(R,S)-yl]amide of 2-oxo-2,3-dihydro-1H-benzimidazole-5-carboxylic acid, in the form of a pale yellow crystalline solid, with the following characteristics:

Mass spectrum (E/I): m/z=458 ($M^+$).

Example 44

Synthesis of [4-(3H-imidazo[4,5-c]pyridin-2-yl)-9H-fluoren-9(R,S)-yl]amide of 6-chloro-1H-benzimidazole-4-carboxylic acid Carry out the procedure as in Example 14, starting from 200 mg of 4-(3H-imidazo[4,5-c]pyridin-2-yl)-fluorene-9(R,S)-amine, obtained in Example 6, and 120 mg of 6-chloro-1H-benzimidazole-4-carboxylic acid, in the presence of 175 mg of EDCI and 124 mg of HOBT in 5.8 ml of DMF for 20 hours. After purification by flash chromatography on silica gel (70-230 M), eluting with a mixture of dichloromethane and methanol (95-5 by volume), we obtain 40 mg of [4-(3H-imidazo[4,5-c]pyridin-2-yl)-9H-fluoren-9(R,S)-yl]amide of 6-chloro-1H-benzimidazole-4-carboxylic acid, in the form of a pale yellow crystalline solid, with the following characteristics:

Mass spectrum (E/I): m/z=476 (M$^+$).

Example 45

Synthesis of [4-(3H-imidazo[4,5-c]pyridin-2-yl)-9H-fluoren-9(R,S)-yl]amide of 1H-indazole-5-carboxylic acid Carry out the procedure as in Example 14, starting from 202 mg of 4-(3H-imidazo[4,5-c]pyridin-2-yl)-fluorene-9(R,S)-amine, obtained in Example 6, and 122.5 mg of hydrochloride of 1H-indazole-5-carboxylic acid, in the presence of 177 mg of EDCI, 124 mg of HOBT and 122 µL of diisopropylamine in 5.8 ml of DMF for 20 hours. After purification by flash chromatography on silica gel (70-230 M), eluting with a mixture of dichloromethane and methanol (95-5 by volume), we obtain 87 mg of [4-(3H-imidazo[4,5-c]pyridin-2-yl)-9H-fluoren-9(R,S)-yl]amide of 1H-indazole-5-carboxylic acid, in the form of a pale yellow crystalline solid, with the following characteristics:

Mass spectrum (E/I): m/z=442 (M$^+$).

Example 46

Synthesis of [4-(3H-imidazo[4,5-c]pyridin-2-yl)-9H-fluoren-9(R,S)-yl]amide of 1H-indole-6-carboxylic acid Carry out the procedure as in Example 14, starting from 204 mg of 4-(3H-imidazo[4,5-c]pyridin-2-yl)-fluorene-9(R,S)-amine, obtained in Example 6, and 100 mg of 1H-indole-6-carboxylic acid, in the presence of 179 mg of EDCI and 126 mg of HOBT in 3 ml of DMF for 20 hours. After purification by flash chromatography on silica gel (70-230 M), eluting with a mixture of dichloromethane and methanol (90-10 by volume), we obtain 54 mg of [4-(3H-imidazo[4,5-c]pyridin-2-yl)-9H-fluoren-9(R,S)-yl]amide of 1H-indole-6-carboxylic acid, in the form of a pale yellow solid, with the following characteristics:

Mass spectrum (E/I): m/z=441 (M$^+$).

Example 47

Synthesis of N-[4-(3H-imidazo[4,5-c]pyridin-2-yl)-9H-fluoren-9(R,S)-yl]-isonicotinamide Carry out the procedure as in Example 14, starting from 208 mg of 4-(3H-imidazo[4,5-c]pyridin-2-yl)-fluorene-9(R,S)-amine, obtained in Example 6, and 78 mg of isonicotinic acid, in the presence of 182 mg of EDCI and 128 mg of HOBT in 3.5 ml of DMF for 20 hours. After purification by flash chromatography on silica gel (70-230 M), eluting with a mixture of dichloromethane and methanol (95-5 by volume), we obtain 90 mg of N-[4-(3H-imidazo[4,5-c]pyridin-2-yl)-9H-fluoren-9(R,S)-yl]-isonicotinamide, in the form of a white crystalline solid, with the following characteristics:

Mass spectrum (E/I): m/z=403 (M$^+$).

$^1$H-NMR spectrum (300 MHz, δ in ppm, DMSO-d$_6$): 6.36 (d, J=8.5 Hz, 1H); 7.26 (t broad, J=7.5 Hz, 1H); 7.34 (t broad, J=7.5 Hz, 1H); from 7.48 to 7.60 (m, 3H); from 7.65 to 7.77 (m, 3H); 7.87 (d broad, J=6.0 Hz, 2H); 8.39 (d, J=5.5 Hz, 1H); 8.75 (d broad, J=6.0 Hz, 2H); 9.04 (s broad, 1H); 9.47 (d, J=8.5 Hz, 1H); from 13.0 to 14.0 (m very spread-out, 1H).

Example 48

Synthesis of N-[4-(3H-imidazo[4,5-c]pyridin-2-yl)-9H-fluoren-9(R,S)-yl]-nicotinamide Carry out the procedure as in Example 14, starting from 208 mg of 4-(3H-imidazo[4,5-c]pyridin-2-yl)-fluorene-9(R,S)-amine, obtained in Example 6, and 78 mg of nicotinic acid, in the presence of 182 mg of EDCI and 128 mg of HOBT in 3.5 ml of DMF for 20 hours. After purification by flash chromatography on silica gel (70-230 M), eluting with a mixture of dichloromethane and methanol (95-5 by volume), we obtain 78 mg of N-[4-(3H-imidazo[4,5-c]pyridin-2-yl)-9H-fluoren-9(R,S)-yl]-nicotinamide, in the form of a pale green, crystalline solid, with the following characteristics:

Mass spectrum (E/I): m/z=403 (M$^+$).

Example 49

Synthesis of hydrochloride of [4-(3H-imidazo[4,5-c]pyridin-2-yl)-9H-fluoren-9(R,S)-yl]amide of 4-oxo-pentanoic acid Carry out the procedure as in Example 14, starting from 208 mg of 4-(3H-imidazo[4,5-c]pyridin-2-yl)-fluorene-9(R,S)-amine, obtained in Example 6, and 73.6 mg of laevulinic acid, in the presence of 182 mg of EDCI and 128 mg of HOBT in 3.5 ml of DMF for 20 hours. After purification by flash chromatography on silica gel (70-230 M), eluting with a mixture of dichloromethane and methanol (95-5 by volume), we obtain 62 mg of hydrochloride of [4-(3H-imidazo[4,5-c]pyridin-2-yl)-9H-fluoren-9(R,S)-yl]amide of 4-oxo-pentanoic acid, in the form of a white crystalline solid, with the following characteristics:

Mass spectrum (E/I): m/z=396 (M$^+$).

Example 50

Synthesis of hydrochloride of 3-hydroxy-N-[4-(3H-imidazo[4,5-c]pyridin-2-yl)-9H-fluoren-9(R,S)-yl]-benzamide Carry out the procedure as in Example 14, starting from 208 mg of 4-(3H-imidazo[4,5-c]pyridin-2-yl)-fluorene-9(R,S)-amine, obtained in Example 6, and 87.5 mg of 3-hydroxy-benzoic acid, in the presence of 182 mg of EDCI and 128 mg of HOBT in 3.5 ml of DMF for 20 hours. After purification by flash chromatography on silica gel (70-230 M), eluting with a mixture of dichloromethane and methanol (95-5 by volume), we obtain 34 mg of hydrochloride of 3-hydroxy-N-[4-(3H-imidazo[4,5-c]pyridin-2-yl)-9H-fluoren-9(R,S)-yl]-benzamide, in the form of a pale green, crystalline solid, with the following characteristics:

Mass spectrum (E/I): m/z=418 (M$^+$).

Example 51

Synthesis of [4-(3H-imidazo[4,5-c]pyridin-2-yl)-9H-fluoren-9(R,S)-yl]amide trifluoroacetate of morpholine-4-carboxylic acid In a 10-ml round-bottomed flask under an argon atmosphere, dissolve 34 mg of 4-(3H-imidazo[4,5-c]pyridin-2- yl)-fluorene-9(R,S)-amine, obtained in Example 6, in 0.5 ml of tetrahydrofuran containing 9.5 µL of pyridine, then add 23 mg of p-nitrophenyl chloroformate and stir for 2 hours at 20° C. Then add 2 µL of pyridine and an additional 2.5 mg of p-nitrophenyl chloroformate and stir again for 2 hours at room temperature. Finally add 70 µL of morpholine in solution in 0.5 ml of dichloromethane and stir for 3 days at room temperature. Concentrate the reaction mixture under reduced pressure. After purification by HPLC/MS in the conditions described in Example 28, we obtain 4.7 mg of [4-(3H-imidazo[4,5-c]pyridin-2-yl)-9H-fluoren-9(R,S)-yl]amide trifluoroacetate of morpholine-4-carboxylic acid, in the form of a yellow solid, with the following characteristics:

Mass spectrum (E/I): m/z=411 (M$^+$)

Example 52

Synthesis of [4-(3H-imidazo[4,5-c]pyridin-2-yl)-9H-fluoren-9(R,S)-yl]amide trifluoroacetate of 5-dimethylamino-naphthalene-1-sulphonic acid In a 10-ml round-bottomed flask under an argon atmosphere, dissolve 72 mg of 4-(3H-imidazo[4,5-c]pyridin-2-yl)-fluorene-9(R,S)-amine, obtained in Example 6, in 1.2 ml of tetrahydrofuran containing 40 µL of triethylamine, then add 72 mg of dansyl chloride and stir for 3 days at room temperature. Concentrate the reaction mixture under reduced pressure. After purification by HPLC/MS in the conditions described in Example 28, we obtain 18.5 mg of [4-(3H-imidazo[4,5-c]pyridin-2-yl)-9H-fluoren-9(R,S)-yl]amide trifluoroacetate of 5-dimethylamino-naphthalene-1-sulphonic acid, in the form of a yellow solid, with the following characteristics:

Mass spectrum (E/I): m/z=531 (M$^+$).

$^1$H-NMR spectrum (400 MHz, δ in ppm, DMSO-d$_6$): 2.90 (s, 6H); 5.42 (d, J=9.0 Hz, 1H); 6.85 (d broad, J=7.5 Hz, 1H); from 7.07 to 7.16 (m, 2H); 7.20 (d broad, J=8.0 Hz, 1H); from 7.32 to 7.40 (m, 2H); 7.47 (d broad, J=8.0 Hz, 1H); from 7.63 to 7.72 (m, 3H); 8.20 (m spread-out, 1H); 8.36 (d broad, J=8.0 Hz, 1H); 8.43 (d broad, J=8.0 Hz, 1H); 8.57 (d broad, J=8.5 Hz, 1H); 8.65 (d, J=6.5 Hz, 1H); 8.90 (d, J=9.0 Hz, 1H); from 9.55 to 9.64 (m very spread-out, 1H); from 14.4 to 14.9 (m very spread-out, 1H).

Example 53

Synthesis of [4-(3H-imidazo[4,5-c]pyridin-2-yl)-9H-fluoren-9(R,S)-yl]amide of 1H-indole-4-carboxylic acid Carry out the procedure as in Example 14, starting from 75 mg of 4-(3H-imidazo[4,5-c]pyridin-2-yl)-fluorene-9(R,S)-amine, obtained in Example 6, and 60 mg of 1H-indole-4-carboxylic acid, in the presence of 72 mg of EDCI, 51 mg of HOBT and 131 µL of diisopropylethylamine in 1.25 ml of DMF and 1.25 ml of dichloromethane for 24 hours. After purification by HPLC/MS on a Symmetry C18 silica column (5 µm), eluting with a gradient of water 100% (containing 0.07% of TFA) to acetonitrile 100% (containing 0.07% of TFA), then flash chromatography on a silica cartridge SCX MegaBond Elut, eluting with methanol, we obtain 54.5 mg of the [4-(3H-imidazo[4,5-c]pyridin-2-yl)-9H-fluoren-9(R,S)-yl]amide of 1H-indole-4-carboxylic acid, in the form of a pale yellow solid with the following characteristics:

Mass spectrum (E/I): m/z=441 (M$^+$)

Example 54

Synthesis of [4-(3H-imidazo[4,5-c]pyridin-2-yl)-9H-fluoren-9(R,S)-yl]amide of 6-amino-naphthalene-1-carboxylic acid Stage 1: Carry out the procedure as in Example 14, starting from 414 mg of 4-(3H-imidazo[4,5-c]pyridin-2-yl)-fluorene-9(R,S)-amine, obtained in Example 6, and 274 mg of 6-nitro-naphthalene-1-carboxylic acid, in the presence of 363 mg of EDCI and 256 mg of HOBT in 3.5 ml of DMF for 20 hours. After purification by flash chromatography on silica gel (70-230 M), eluting with a mixture of dichloromethane and methanol (95-5 by volume), we obtain 300 mg of [4-(3H-imidazo[4,5-c]pyridin-2-yl)-9H-fluoren-9(R,S)-yl]amide of 6-nitro-naphthalene-1-carboxylic acid, in the form of a yellow crystalline solid, with the following characteristics:

Mass spectrum (E/I): m/z=497 (M$^+$).

Stage 2: Hydrogenate 524 mg of [4-(3H-imidazo[4,5-c]pyridin-2-yl)-9H-fluoren-9(R,S)-yl]amide of 6-nitro-naphthalene-1-carboxylic acid, obtained as in the preceding stage, in solution in 30 ml of ethanol and 40 ml of dimethylformamide, at room temperature in an autoclave under a pressure of 1 bar for 20 hours, in the presence of 16 mg of palladium on carbon at 10%. After filtration on Celite, concentrate the filtrate under reduced pressure. After purification by flash chromatography on silica gel (70-230 M), eluting with a mixture of dichloromethane and methanol (95-5 by volume), we obtain 176 mg of [4-(3H-imidazo[4,5-c]pyridin-2-yl)-9H-fluoren-9(R,S)-yl]amide of 6-amino-naphthalene-1-carboxylic acid, in the form of a white crystalline solid, with the following characteristics:

Mass spectrum (E/I): m/z=467 (M$^+$).

Example 55

Synthesis of [4-(3H-imidazo[4,5-c]pyridin-2-yl)-9H-fluoren-9(R,S)-yl]amide trifluoroacetate of quinoline-5-carbothioic acid Dissolve 157 mg of [4-(3H-imidazo[4,5-c]pyridin-2-yl)-9H-fluoren-9(R,S)-yl]amide of quinoline-5-carboxylic acid, obtained as in Example 14, in 10 ml of dioxan and heat for 15 hours at a temperature close to 100° C. in the presence of 80 mg of Lawesson's reagent. After cooling, concentrate the reaction mixture under reduced pressure. After purification by HPLC/MS in the conditions described in Example 28, we obtain 42 mg of [4-(3H-imidazo[4,5-c]pyridin-2-yl)-9H-fluoren-9(R,S)-yl]amide trifluoroacetate of quinoline-5-carbothioic acid, in the form of a yellow crystalline solid, with the following characteristics:

Mass spectrum (E/I): m/z=469 (M$^+$)

$^1$H-NMR spectrum (300 MHz, δ in ppm, DMSO-d$_6$): 7.31 (t broad, J=7.5 Hz, 1H); from 7.37 to 7.49 (m, 2H); from 7.60 to 7.70 (m, 4H); from 7.75 to 7.84 (m, 2H); 7.90 (d broad, J=7.5 Hz, 1H); 8.06 (d broad, J=8.0 Hz, 1H); 8.11 (d broad, J=8.0 Hz, 1H); 8.22 (d broad, J=6.5 Hz, 1H); from 8.64 to 8.73 (m, 2H); 8.96 (dd, J=2.0 and 4.0 Hz, 1H); 9.59 (s broad, 1H); 11.32 (d, J=9.0 Hz, 1H); from 14.2 to 15.0 (m very spread-out, 2H).

Example 56

Synthesis of N-[4-(3H-imidazo[4,5-c]pyridin-2-yl)-9H-fluoren-9(R,S)-yl]-1-oxynicotinamide Carry out the procedure as in Example 14, starting from 212 mg of 4-(3H-imidazo[4,5-c]pyridin-2-yl)-fluorene-9(R,S)-amine, obtained in Example 6, and 90 mg of N-oxide of nicotinic acid, in the presence of 186 mg of EDCI and 131 mg of HOBT in 5.2 ml of DMF for 20 hours. After purification by flash chromatography on silica gel (70-230 M), eluting with a mixture of dichloromethane and methanol (95-5 by volume), we obtain 109 mg of N-[4-(3H-imidazo[4,5-c]pyridin-2-yl)-9H-fluoren-9(R,S)-yl]-1-oxynicotinamide, in the form of a pale green, crystalline solid, with the following characteristics:

Mass spectrum (E/I): m/z=419 ($M^+$).

Example 57

Synthesis of tert-butyl ester of {(S)-2-carbamoyl-1-[4-(3H-imidazo[4,5-c]pyridin-2-yl)-9H-fluoren-9(R,S)-ylcarbamoyl]-ethyl}-carbamoic acid Carry out the procedure as in Example 14, starting from 212 mg of 4-(3H-imidazo[4,5-c]pyridin-2-yl)-fluorene-9(R,S)-amine, obtained in Example 6, and 150 mg of N-Boc-asparagine, in the presence of 186 mg of EDCI and 131 mg of HOBT in 5.2 ml of DMF for 20 hours. After purifying by precipitation in water, then washing successively with a saturated solution of sodium hydrogen carbonate then with petroleum ether, we obtain 220 mg of tert-butyl ester of {(S)-2-carbamoyl-1-[4-(3H-imidazo[4,5-c]pyridin-2-yl)-9H-fluoren-9(R,S)-ylcarbamoyl]-ethyl}-carbamoic acid, in the form of a yellow crystalline solid with the following characteristics:

Mass spectrum (E/I): m/z=512 ($M^+$).

Example 58

Synthesis of N-[4-(3H-imidazo[4,5-c]pyridin-2-yl)-9H-fluoren-9(R,S)-yl]-2-ureido-acetamide Carry out the procedure as in Example 14, starting from 212 mg of 4-(3H-imidazo[4,5-c]pyridin-2-yl)-fluorene-9(R,S)-amine, obtained in Example 6, and 76.4 mg of hydantoic acid, in the presence of 186 mg of EDCI and 131 mg of HOBT in 5.2 ml of DMF for 20 hours. After purifying by precipitation in water, then washing successively with a saturated solution of sodium hydrogen carbonate then with petroleum ether, we obtain 161 mg of N-[4-(3H-imidazo[4,5-c]pyridin-2-yl)-9H-fluoren-9(R,S)-yl]-2-ureido-acetamide, in the form of a yellow crystalline solid with the following characteristics:

Mass spectrum (E/I): m/z=398 ($M^+$).

Example 59

Synthesis of tert-butyl ester of {(R)-1-carbamoyl-2-[4-(3H-imidazo[4,5-c]pyridin-2-yl)-9H-fluoren-9(R,S)-ylcarbamoyl]-ethyl}-carbamoic acid Carry out the procedure as in Example 14, starting from 297 mg of 4-(3H-imidazo[4,5-c]pyridin-2-yl)-fluorene-9(R,S)-amine, obtained in Example 6, and 210 mg of N-Boc-isoasparagine, in the presence of 260 mg of EDCI and 183 mg of HOBT in 7.3 ml of DMF for 20 hours. After purifying by precipitation in water, then washing successively with a saturated solution of sodium hydrogen carbonate, then with methanol and then with petroleum ether, we obtain 176 mg of tert-butyl ester of {(R)-1-carbamoyl-2-[4-(3H-imidazo[4,5-c]pyridin-2-yl)-9H-fluoren-9(R,S)-ylcarbamoyl]-ethyl}-carbamoic acid, in the form of a pale yellow crystalline solid with the following characteristics:

Mass spectrum (E/I): m/z=512 ($M^+$).

Example 60

Synthesis of [4-(3H-imidazo[4,5-c]pyridin-2-yl)-9H-fluoren-9(R,S)-yl]amide of 1-oxo-indan-4-carboxylic acid Carry out the procedure as in Example 14, starting from 183 mg of 4-(3H-imidazo[4,5-c]pyridin-2-yl)-fluorene-9(R,S)-amine, obtained in Example 6, and 100 mg of indanone-4-carboxylic acid, in the presence of 163 mg of EDCI and 115 mg of HOBT in 4.6 ml of DMF for 20 hours. After purification by flash chromatography on silica gel (70-230 M), eluting with a mixture of dichloromethane and methanol (95-5 by volume), we obtain 84 mg of [4-(3H-imidazo[4,5-c]pyridin-2-yl)-9H-fluoren-9(R,S)-yl]amide of 1-oxo-indan-4-carboxylic acid, in the form of a white crystalline solid, with the following characteristics:

Mass spectrum (E/I): m/z=456 ($M^+$).

Example 61

Synthesis of tert-butyl ester of {(R)-2-carbamoyl-1-[4-(3H-imidazo[4,5-c]pyridin-2-yl)-9H-fluoren-9(R,S)-ylcarbamoyl]-ethyl}-carbamoic acid.

Carry out the procedure as in Example 14, starting from 212.3 mg of 4-(3H-imidazo[4,5-c]pyridin-2-yl)-fluorene-9(R,S)-amine, obtained in Example 6, and 150 mg of N-Boc-D-asparagine, in the presence of 186 mg of EDCI and 131 mg of HOBT in 5.2 ml of DMF for 20 hours. After purification by flash chromatography on silica gel (70-230 M), eluting with a mixture of dichloromethane and methanol (95-5 by volume), we obtain 280 mg of tert-butyl ester of {(R)-2-carbamoyl-1-[4-(3H-imidazo[4,5-c]pyridin-2-yl)-9H-fluoren-9(R,S)-ylcarbamoyl]-ethyl}-carbamoic acid, in the form of a white crystalline solid with the following characteristics:

Mass spectrum (E/I): m/z=512 ($M^+$).

Example 62

Synthesis of (R)-2-amino-N4-[4-(3H-imidazo[4,5-c]pyridin-2-yl)-9H-fluoren-9(R,S)-yl]-succinamide Dissolve 144 mg of tert-butyl ester of {(R)-1-carbamoyl-2-[4-(3H-imidazo[4,5-c]pyridin-2-yl)-9H-fluoren-9(R,S)-ylcarbamoyl]-ethyl}-carbamoic acid, obtained in Example 59, in 5 ml of dioxan and add 1 ml of a 4M solution of hydrochloric acid in dioxan. After stirring for 5 hours at room temperature, dry the solid that formed. After washing successively with a saturated aqueous solution of sodium hydrogen carbonate, then with dichloromethane, we obtain 145 mg of (R)-2-amino-N4-[4-(3H-imidazo[4,5-c]pyridin-2-yl)-9H-fluoren-9(R,S)-yl]-succinamide, in the form of a pale green, crystalline solid, with the following characteristics:

Mass spectrum (E/I): m/z=412 ($M^+$).

Example 63

Synthesis of the hydrochloride of (S)-2-amino-N1-[4-(3H-imidazo[4,5-c]pyridin-2-yl)-9H-fluoren-9(R,S)-yl]-succinamide Dissolve 200 mg of tert-butyl ester of {(S)-2-carbamoyl-1-[4-(3H-imidazo[4,5-c]pyridin-2-yl)-9H-fluoren-9(R,S)-ylcarbamoyl]-ethyl}-carbamoic acid, obtained in Example 57, in 5 ml of dioxan and 4 ml of dichloromethane, then add 0.87 ml of a 4M solution of hydrochloric acid in dioxan. After stirring for 15 hours at room temperature, dry the solid that formed. After washing successively with a mixture of dichloromethane and methanol (95-5 by volume), we obtain 54 mg of the hydrochloride of (S)-2-amino-N1-[4-(3H-imidazo[4,5-c]pyridin-2-yl)-9H-fluoren-9(R,S)-yl]-succinamide, in the form of a pale yellow crystalline solid, with the following characteristics:

Mass spectrum (E/I): m/z=412 (M$^+$).

Example 64

Synthesis of [4-(3H-imidazo[4,5-c]pyridin-2-yl)-9H-fluoren-9(R,S)-yl]amide of isoquinoline-1-carboxylic acid Carry out the procedure as in Example 14, starting from 202.5 mg of 4-(3H-imidazo[4,5-c]pyridin-2-yl)-fluorene-9(R,S)-amine, obtained in Example 6, and 106.8 mg of isoquinoline-1-carboxylic acid, in the presence of 177.4 mg of EDCI and 125 mg of HOBT in 5.9 ml of DMF for 20 hours. After purification by flash chromatography on silica gel (70-230 M), eluting with a mixture of dichloromethane and methanol (95-5 by volume), we obtain 80 mg of [4-(3H-imidazo[4,5-c]pyridin-2-yl)-9H-fluoren-9(R,S)-yl]amide of isoquinoline-1-carboxylic acid, in the form of a pale yellow crystalline solid, with the following characteristics:

Mass spectrum (E/I): m/z=453 (M$^+$).

Example 65

Synthesis of the hydrochloride of (R)-2-amino-N1-[4-(3H-imidazo[4,5-c]pyridin-2-yl)-9H-fluoren-9(R,S)-yl]-succinamide Dissolve 244 mg of tert-butyl ester of {(R)-2-carbamoyl-1-[4-(3H-imidazo[4,5-c]pyridin-2-yl)-9H-fluoren-9(R,S)-ylcarbamoyl]-ethyl}-carbamoic acid, obtained in Example 61, in 5 ml of dichloromethane, then add 1 ml of a 4M solution of hydrochloric acid in dioxan. After stirring for 5 hours at room temperature, drain the solid that formed, and wash with water. We obtain 160 mg of the hydrochloride of (R)-2-amino-N1-[4-(3H-imidazo[4,5-c]pyridin-2-yl)-9H-fluoren-9(R,S)-yl]-succinamide, in the form of a pale yellow crystalline solid, with the following characteristics:

Mass spectrum (E/I): m/z=412 (M$^+$).

Example 66

Synthesis of 2-acetylamino-N-[4-(3H-imidazo[4,5-c]pyridin-2-yl)-9H-fluoren-9(R,S)-yl]-isonicotinamide Carry out the procedure as in Example 14, starting from 212.3 mg of 4-(3H-imidazo[4,5-c]pyridin-2-yl)-fluorene-9(R,S)-amine, obtained in Example 6, and 116.6 mg of 2-acetylamino-isonicotinic acid, in the presence of 186 mg of EDCI and 131 mg of HOBT in 5.2 ml of DMF for 20 hours. After purification by flash chromatography on silica gel (70-230 M), eluting with a mixture of dichloromethane and ethanol (95-5 by volume), we obtain 108 mg of 2-acetylamino-N-[4-(3H-imidazo[4,5-c]pyridin-2-yl)-9H-fluoren-9(R,S)-yl]-isonicotinamide, in the form of a pale yellow solid, with the following characteristics:

Mass spectrum (E/I): m/z=460 (M$^+$).

$^1$H-NMR spectrum (300 MHz, δ in ppm, DMSO-d$_6$): 2.12 (s, 3H); 6.34 (d, J=8.5 Hz, 1H); 7.25 (t broad, J=7.5 Hz, 1H); 7.34 (t broad, J=7.5 Hz, 1H); from 7.48 to 7.59 (m, 4H); from 7.62 to 7.76 (m, 3H); from 8.37 to 8.44 (m, 2H); 8.55 (s broad, 1H); 9.04 (s broad, 1H); 8.43 (d, J=8.5 Hz, 1H); 10.6 (s broad, 1H); 13.4 (m very spread-out, 1H).

Example 67

Synthesis of [4-(3H-imidazo[4,5-c]pyridin-2-yl)-9H-fluoren-9(R,S)-yl]amide of quinoline-4-carboxylic acid Carry out the procedure as in Example 14, starting from 212.3 mg of 4-(3H-imidazo[4,5-c]pyridin-2-yl)-fluorene-9(R,S)-amine, obtained in Example 6, and 112 mg of quinoline-4-carboxylic acid, in the presence of 186 mg of EDCI and 131 mg of HOBT in 5.2 ml of DMF for 20 hours. After purification by washing successively with a saturated aqueous solution of sodium hydrogen carbonate then with dichloromethane, we obtain 213 mg of [4-(3H-imidazo[4,5-c]pyridin-2-yl)-9H-fluoren-9(R,S)-yl]amide of quinoline-4-carboxylic acid, in the form of a pale yellow solid, with the following characteristics:

Mass spectrum (E/I): m/z=453 (M$^+$).

Example 68

Synthesis of 4-(1H-benzimidazol-2-yl)-fluoren-9-one oxime (Z,E)

Stage 1: Carry out the procedure as in stage 1 of Example 1, starting from 2.01 g of o-phenylenediamine in 5 ml of dichloromethane, 3.4 ml of triethylamine and 3 g of chloride of fluoren-4-one-9-carboxylic acid. After stirring for 2 hours and 30 minutes at room temperature, pour the reaction mixture into water and extract with dichloromethane. Wash the organic phases with a saturated aqueous solution of sodium hydrogen carbonate, dry over magnesium sulphate and concentrate under reduced pressure. After purification by making a paste in diethyl ether, we obtain 3.4 g of the (2-aminophenyl)amide of 9-oxo-9H-fluorene-4-carboxylic acid, which is used as it is in the next stage, and has the following characteristics:

Mass spectrum (E/I): m/z=314 (M$^+$).

Stage 2: In a 50-ml three-necked flask under an argon atmosphere, heat, at 80° C. for 2 hours, a solution of 3 g of the (2-amino-phenyl)amide of 9-oxo-9H-fluorene-4-carboxylic acid obtained in the preceding stage, in 150 ml of acetic acid. After cooling, the precipitate that formed is drained. After purification by silica gel flash chromatography, eluting with mixtures of dichloromethane and ethyl acetate (90-10 then 80-20 and finally 70-30 by volume), we obtain 1.73 g of 4-(1H-benzimidazol-2-yl)-fluoren-9-one in the form of a yellow powder, which is used as it is in the next stage, with the following characteristics:

Mass spectrum (E/I): m/z=296 (M$^+$).

Stage 3: Carry out the procedure as in Example 5, starting from 1.7 g of 4-(1H-benzimidazol-2-yl)-fluoren-9-one, obtained in the preceding stage, 1.196 g of hydroxylamine hydrochloride and 2.53 g of sodium acetate heated at 60° C. for 3 hours in 30 ml of ethanol. After concentration of the solvent under reduced pressure, the residue is taken up successively in water, then in toluene and finally is made into a paste in diethyl ether, obtaining 1.62 g of 4-(1H-benzimidazol-2-yl)-fluoren-9-one oxime, as a 50-50 mixture of the Z and E isomers, in the form of a pale yellow powder, with the following characteristics:

Mass spectrum (E/I): m/z=311 (M$^+$).

Example 69

Synthesis of 4-(6-fluoro-1H-benzimidazol-2-yl)-fluoren-9-one

Stage 1: Carry out the procedure as in stage 1 of Example 1, starting from 2.34 g of 4-fluoro-benzene-1,2-diamine in 5 ml of dichloromethane, 3.445 ml of triethylamine and 3 g of chloride of fluoren-4-one-9-carboxylic acid. After stirring overnight at room temperature, we obtain 3.37 g (82%) of the equimolecular amide mixture, which is used as it is in the next stage.

Stage 2: In a 50-ml three-necked flask under an argon atmosphere, heat, at 100° C. for 4 hours, a solution of 3.37 g of the amide mixture obtained in the preceding stage, in 168 ml of acetic acid. After cooling, the precipitate that formed is drained then triturated with diethyl ether and drained again. After washing in diethyl ether, then drying in the stove at 35° C. under reduced pressure, we obtain 2.81 g of 4-(1H-benzimidazol-2-yl)-fluoren-9-one, in the form of a yellow powder with the following characteristics:

Mass spectrum (E/I): m/z=314 ($M^+$).

Example 70

Synthesis of 4-(6-fluoro-1H-benzimidazol-2-yl)-fluoren-9-one oxime (Z,E)

Carry out the procedure as in Example 5, starting from 2.6 g of 4-(1H-benzimidazol-2-yl)-fluoren-9-one, obtained in Example 69, 1.744 g of hydroxylamine hydrochloride and 3.43 g of sodium acetate at room temperature for 20 hours in 45 ml of ethanol. After concentrating the solvent under reduced pressure, the residue is taken up successively in water, then in toluene and is finally made into a paste in diethyl ether, obtaining 1.94 g of 4-(6-fluoro-1H-benzimidazol-2-yl)-fluoren-9-one oxime, as 40-60 mixture of the Z and E isomers, in the form of a pale yellow powder, with the following characteristics:

Mass spectrum (E/I): m/z=329 ($M^+$).

Example 71

Synthesis of 4-(6-fluoro-1H-benzimidazol-2-yl)-9H-fluoren-9(R,S)-ylamine

Carry out the procedure as in Example 6, starting from 1.7 g of 4-(6-fluoro-1H-benzimidazol-2-yl)-fluoren-9-one oxime (Z,E), obtained in Example 70, and 6 mg of Raney Nickel in 90 ml of ethanol and 90 ml of tetrahydrofuran for 4 hours at 60° C. under a hydrogen pressure of 1 bar. After purification by making a paste in diisopropyl ether, we obtain 1.58 g of 4-(6-fluoro-1H-benzimidazol-2-yl)-9H-fluoren-9(R,S)-ylamine, in the form of a beige powder with the following characteristics:

Mass spectrum (E/I): m/z=315 ($M^+$).
melting point (Kofler)=170-72° C.

Examples 72 and 73

Synthesis of N-[4-(3H-imidazo[4,5-c]pyridin-2-yl)-9H-fluoren-9(R,S)-yl]-acetamide and of 2-amino-N-[4-(3H-imidazo[4,5-c]pyridin-2-yl)-9H-fluoren-9(R,S)-yl]-isonicotinamide Carry out the procedure as in Example 14, starting from 300 mg of 4-(3H-imidazo[4,5-c]pyridin-2-yl)-fluorene-9(R,S)-amine, obtained in Example 6, and 153.3 mg of 2-amino-isonicotinic acid, in the presence of 319 mg of EDCI and 225 mg of HOBT in 17 ml of DMF for 20 hours. After purification by flash chromatography on silica gel (70-230 mesh), eluting with a mixture of dichloromethane and methanol (90-10 by volume), we obtain:

a) by recovering the first chromatographed fraction, 22 mg of N-[4-(3H-imidazo[4,5-c]pyridin-2-yl)-9H-fluoren-9(R,S)-yl]-acetamide, in the form of a white foam, with the following characteristics:

Mass spectrum (E/I): m/z=340 ($M^+$).

b) by recovering the second chromatographed fraction, 30 mg of 2-amino-N-[4-(3H-imidazo[4,5-c]pyridin-2-yl)-9H-fluoren-9(R,S)-yl]-isonicotinamide, in the form of a white foam, with the following characteristics:

Mass spectrum (E/I): m/z=418 ($M^+$).

$^1$H-NMR spectrum (300 MHz, δ in ppm, DMSO-$d_6$): 6.11 (s broad, 2H); 6.31 (d, J=8.5 Hz, 1H); from 6.90 to 6.95 (m, 2H); 7.24 (t broad, J=7.5 Hz, 1H); 7.33 (t broad, J=7.5 Hz, 1H); from 7.45 to 7.57 (m, 3H); 7.62 (m very spread-out, 1H); from 7.66 to 7.72 (m, 2H); 7.99 (d, J=5.5 Hz, 1H); 8.40 (d, J=5.5 Hz, 1H); from 8.93 to 9.10 (m spread-out, 1H); 9.19 (d, J=8.5 Hz, 1H); from 13.2 to 13.5 (m very spread-out, 1H).

Example 74

Synthesis of 1-furan-2-ylmethyl-3-[4-(3H-imidazo[4,5-c]pyridin-2-yl)-9H-fluoren-9(R,S)-yl]-urea Carry out the procedure as in Example 77, starting from 75 mg of 4-(3H-imidazo[4,5-c]pyridin-2-yl)-fluorene-9(R,S)-amine, obtained in Example 6, and 29 µL of furfuryl isocyanate in 1.25 ml of tetrahydrofuran containing 41 µL of triethylamine for 3 hours at room temperature. The residue obtained is taken up in 5 ml of dichloromethane, then drained and washed with dichloromethane. In this way we obtain 90 mg of 1-furan-2-ylmethyl-3-[4-(3H-imidazo[[4,5-c]pyridin-2-yl)-9H-fluoren-9(R,S)-yl]-urea, in the form of a white solid with the following characteristics:

Mass spectrum (E/I): m/z=421 ($M^+$).

Example 75

Synthesis of 1-(4-fluorobenzyl)-3-[4-(3H-imidazo[4,5-c]pyridin-2-yl)-9H-fluoren-9(R,S)-yl]-urea Carry out the procedure as in Example 77, starting from 75 mg of 4-(3H-imidazo[4,5-c]pyridin-2-yl)-fluorene-9(R,S)-amine, obtained in Example 6, and 33.6 µL of 4-fluorobenzyl isocyanate in 1.25 ml of tetrahydrofuran containing 41 µL of triethylamine for 3 hours at room temperature. The residue obtained is taken up in 5 ml of dichloromethane, then drained and washed with dichloromethane. In this way we obtain 96 mg of 1-(4-fluorobenzyl)-3-[4-(3H-imidazo[4,5-c]pyridin-2-yl)-9H-fluoren-9(R,S)-yl]-urea, in the form of a pale yellow solid with the following characteristics:

Mass spectrum (E/I): m/z=449 ($M^+$).

Example 76

Synthesis of 1-(3,5-dimethyl-isoxazol-4-yl)-3-[4-(3H-imidazo[4,5-c]pyridin-2-yl)-9H-fluoren-9(R,S)-yl]-urea Carry out the procedure as in Example 77, starting from 75 mg of 4-(3H-imidazo[4,5-c]pyridin-2-yl)-fluorene-9(R,S)-amine, obtained in Example 6, and 36.5 mg of 3,5-dimethylisoxazol-4-yl isocyanate in 1.25 ml of tetrahydrofuran containing 41 µL of triethylamine for 3 hours at room temperature. The residue obtained is taken up in 5 ml of dichloromethane, then drained and washed with dichloromethane. In this way we obtain 95 mg of 1-(3,5-dimethyl-isoxazol-4-yl)-3-[4-(3H-imidazo[4,5-c]pyridin-2-yl)-9H-fluoren-9(R,S)-yl]-urea, in the form of a white solid with the following characteristics:

Mass spectrum (E/I): m/z=436 (M$^+$).

Example 77

Synthesis of ethyl ester of 3-{3-[4-(3H-imidazo[4,5-c]pyridin-2-yl)-9H-fluoren-9(R,S)-yl]-ureido}-propionic acid Add 35 µL of ethyl 3-isocyanato-propionate to a solution of 75 mg of 4-(3H-imidazo[4,5-c]pyridin-2-yl)-fluorene-9(R,S)-amine, obtained in Example 6, in 1.25 ml of tetrahydrofuran containing 41 µL of triethylamine. The white suspension obtained is stirred for 3 hours at room temperature, then concentrated under reduced pressure. The residue obtained is taken up in 5 ml of dichloromethane, then drained and washed with dichloromethane. In this way we obtain 80 mg of ethyl ester of 3-{3-[4-(3H-imidazo[4,5-c]pyridin-2-yl)-9H-fluoren-9(R,S)-yl]-ureido}-propionic acid, in the form of a white solid with the following characteristics:

Mass spectrum (E/I): m/z=441 (M$^+$).

Example 78

Synthesis of ethyl ester of {3-[4-(3H-imidazo[4,5-c]pyridin-2-yl)-9H-fluoren-9(R,S)-yl]-ureido}-acetic acid Carry out the procedure as in Example 77, starting from 75 mg of 4-(3H-imidazo[4,5-c]pyridin-2-yl)-fluorene-9(R,S)-amine, obtained in Example 6, and 33 µL of ethyl isocyanatoacetate. In this way we obtain 81 mg of ethyl ester of {3-[4-(3H-imidazo[4,5-c]pyridin-2-yl)-9H-fluoren-9(R,S)-yl]-ureido}-acetic acid, in the form of a white solid with the following characteristics:

Mass spectrum (E/I): m/z=427 (M$^+$).

Example 79

Synthesis of trifluoroacetate of 3-{3-[4-(3H-imidazo[4,5-c]pyridin-2-yl)-9H-fluoren-9(R,S)-yl]-ureido}-propionamide Stage 1: Carry out the procedure as in Example 77, starting from 75 mg of 4-(3H-imidazo[4,5-c]pyridin-2-yl)-fluorene-9(R,S)-amine, obtained in Example 6, and 41 µL of ethyl 3-isocyanatopropionate. In this way we obtain 80 mg of ethyl ester of 3-{3-[4-(3H-imidazo[4,5-c]pyridin-2-yl)-9H-fluoren-9(R,S)-yl]-ureido}-propionic acid, in the form of a white solid with the following characteristics:

Mass spectrum (E/I): m/z=441 (M$^+$).

Stage 2: A solution of 15 mg of ethyl ester of 3-{3-[4-(3H-imidazo[4,5-c]pyridin-2-yl)-9H-fluoren-9(R,S)-yl]-ureido}-propionic acid, obtained in the preceding stage, in 2 ml of 7N ammonia in methanol is heated in a sealed tube in a microwave reactor for 20 minutes at 120° C. then for 35 minutes at 130° C. After concentration, then purification by HPLC/MS on a Symmetry C18 silica column (5 µm), eluting with a gradient of water 100% (containing 0.07% of TFA) to acetonitrile 100% (containing 0.07% of TFA), we obtain 3.5 mg of trifluoroacetate of 3-{3-[4-(3H-imidazo[4,5-c]pyridin-2-yl)-9H-fluoren-9(R,S)-yl]-ureido}-propionamide, in the form of a white solid with the following characteristics:

Mass spectrum (E/I): m/z=412 (M$^+$).

Example 80

Synthesis of 3-[4-(3H-imidazo[4,5-c]pyridin-2-yl)-9H-fluoren-9(R,S)-yl]-imidazolidine-2,4-dione In microwave apparatus (Emrgs™ Personal Chemistry), heat, for 15 minutes at 120° C., 15 mg of ethyl ester of {3-[4-(3H-imidazo[4,5-c]pyridin-2-yl)-9H-fluoren-9(R,S)-yl]-ureido}-acetic acid, obtained in Example 78, in 2 ml of a 7M solution of ammonia in methanol. After concentration under reduced pressure, the residue is taken up in a minimum of diethyl ether and drained. In this way we obtain 13 mg of 3-[4-(3H-imidazo[4,5-c]pyridin-2-yl)-9H-fluoren-9(R,S)-yl]-imidazolidine-2,4-dione, in the form of a pale yellow solid with the following characteristics:

Mass spectrum (E/I): m/z=381 (M$^+$).

$^1$H-NMR spectrum (400 MHz, δ in ppm, DMSO-d$_6$): from 3.80 to 4.20 (m very spread-out, 2H); from 6.02 to 6.23 (m spread-out, 1H); from 7.17 to 7.32 (m, 2H); from 7.32 to 7.49 (m, 2H); from 7.53 to 7.62 (m, 2H); from 7.67 to 7.78 (m, 2H); from 7.80 to 8.61 (m very spread-out, 1H); 8.28 (d broad, J=5.5 Hz, 1H); 8.96 (s, 1H); from 12.5 to 14.0 (m very spread-out, 1H).

Example 81

Synthesis of N-[4-(3H-imidazo[4,5-c]pyridin-2-yl)-9H-fluoren-9(R,S)-yl]-1-oxyisonicotinamide Carry out the procedure as in Example 14, starting from 298 mg of 4-(3H-imidazo[4,5-c]pyridin-2-yl)-fluorene-9(R,S)-amine, obtained in Example 6, and 139 mg of the N-oxide of isonicotinic acid, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 45 mg of N-[4-(3H-imidazo[4,5-c]pyridin-2-yl)-9H-fluoren-9(R,S)-yl]-1-oxyisonicotinamide, in the form of a beige solid, with the following characteristics:

Mass spectrum (E/I): m/z=419 (M$^+$).

Example 82

Synthesis of 2-ethyl-N-[4-(3H-imidazo[4,5-c]pyridin-2-yl)-9H-fluoren-9(R,S)-yl]-isonicotinamide Carry out the procedure as in Example 14, starting from 298 mg of 4-(3H-imidazo[4,5-c]pyridin-2-yl)-fluorene-9(R, S)-amine, obtained in Example 6, and 151.2 mg of 2-ethyl-isonicotinic acid, which can be obtained according to J. Biol. Chem. 2002, 277, 12824-29, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 310 mg of 2-ethyl-N-[4-(3H-imidazo[4,5-c]pyridin-2-yl)-9H-fluoren-9(R,S)-yl]-isonicotinamide, in the form of a beige solid, with the following characteristics:

Mass spectrum (E/I): m/z=431 (M$^+$).

Example 83

Synthesis of [4-(1H-benzimidazol-2-yl)-9H-fluoren-9(R,S)-yl]amide of quinoline-5-carboxylic acid Stage 1: Carry out the procedure as in Example 6, starting from 1.57 g of 4-(1H-benzimidazol-2-yl)-fluoren-9-one oxime (Z,E), obtained in Example 68, and 5.6 mg of Raney Nickel in 80 ml of ethanol and 80 ml of tetrahydrofuran for 4 hours at 60° C. under a hydrogen pressure of 1 bar. After purification by making a paste in diisopropyl ether, we obtain 1.31 g of 4-(1H-benzimidazol-2-yl)-9H-fluoren-9(R,S)-ylamine, in the form of a white powder, with the following characteristics:

Mass spectrum (E/I): m/z=297 (M$^+$).

Stage 2: Carry out the procedure as in Example 14, starting from 200 mg of 4-(1H-benzimidazol-2-yl)-9H-fluoren-9(R,S)-ylamine, obtained in the preceding stage, and 120 mg of quinoline-5-carboxylic acid, in the presence of 193 mg of EDCI and 135 mg of HOBT in 2 ml of DMF for 20 hours. After purification by silica gel flash chromatography, eluting with a mixture of dichloromethane and methanol (95-5 by volume), we obtain 125 mg of [4-(1H-benzimidazol-2-yl)-9H-fluoren-9(R,S)-yl]amide of quinoline-5-carboxylic acid, in the form of a pale yellow powder, with the following characteristics:

Mass spectrum (E/I): m/z=493 (M$^+$).

$^1$H-NMR spectrum (300 MHz, δ in ppm, DMSO-d$_6$): 6.43 (d, J=8.5 Hz, 1H); from 7.21 to 7.33 (m, 3H); 7.37 (t broad, J=7.5 Hz, 1H); from 7.52 to 7.61 (m, 3H); from 7.65 to 7.90 (m, 7H); 8.14 (d broad, J=8.5 Hz, 1H); 8.87 (d broad, J=8.5 Hz, 1H); 8.99 (dd, J=2.0 and 4.0 Hz, 1H); 9.37 (d, J=8.5 Hz, 1H); 12.9 (s broad, 1H).

Example 84

Synthesis of [4-(6-fluoro-1H-benzimidazol-2-yl)-9H-fluoren-9(R,S)-yl]amide of quinoline-5-carboxylic acid Carry out the procedure as in Example 14, starting from 200 mg of 4-(6-fluoro-1H-benzimidazol-2-yl)-9H-fluoren-9(R,S)-ylamine, obtained in Example 71, and 113 mg of quinoline-5-carboxylic acid, in the presence of 182.4 mg of EDCI and 128.5 mg of HOBT in 2 ml of DMF for 20 hours. After purification by silica gel flash chromatography, eluting with a mixture of dichloromethane and methanol (95-5 by volume), we obtain 134 mg of [4-(6-fluoro-1H-benzimidazol-2-yl)-9H-fluoren-9(R,S)-yl]amide of quinoline-5-carboxylic acid, in the form of a pale yellow powder, with the following characteristics:

Mass spectrum (E/I): m/z=470 (M$^+$).

$^1$H-NMR spectrum (400 MHz, δ in ppm, DMSO-d$_6$): 6.43 (d, J=8.5 Hz, 1H); 7.14 (t broad, J=10.0 Hz, 1H); 7.26 (t broad, J=7.5 Hz, 1H); 7.38 (t broad, J=7.5 Hz, 1H); 7.55 (t, J=7.5 Hz, 2H); from 7.35 to 7.61 (m very spread-out, 2H); from 7.65 to 7.70 (m, 2H); 7.73 (d broad, J=7.5 Hz, 1H); 7.80 (m, 1H); from 7.86 to 7.90 (m, 2H); 8.14 (d broad, J=8.5 Hz, 1H); 8.86 (d broad, J=8.5 Hz, 1H); 8.99 (dd, J=2.0 and 4.0 Hz, 1H); 9.38 (d, J=8.5 Hz, 1H); 13.1 (s broad, 1H).

Example 85

Synthesis of [4-(3H-imidazo[4,5-c]pyridin-2-yl)-9H-fluoren-9-yl]amide of 2-cyclopropyl-quinoline-4-carboxylic acid Carry out the procedure as in Example 14, starting from 364 mg of 4-(3H-imidazo[4,5-c]pyridin-2-yl)-fluorene-9(R,S)-amine, obtained in Example 6, and 286 mg of 2-cyclopropyl-quinoline-4-carboxylic acid, in the presence of 234 mg of EDCI and 165 mg of HOBT in 10 ml of DMF for 20 hours. After purification by washing successively with a saturated aqueous solution of sodium hydrogen carbonate then with water and diisopropyl ether, we obtain 344 mg of [4-(3H-imidazo[4,5-c]pyridin-2-yl)-9H-fluoren-9-yl]amide of 2-cyclopropyl-quinoline-4-carboxylic acid, in the form of a beige powder, with the following characteristics:

Mass spectrum (E/I): m/z=493 (M$^+$).

Example 86

Synthesis of [4-(3H-imidazo[4,5-c]pyridin-2-yl)-9H-fluoren-9-yl]amide of pyridazine-4-carboxylic acid Carry out the procedure as in Example 14, starting from 298 mg of 4-(3H-imidazo[4,5-c]pyridin-2-yl)-fluorene-9(R,S)-amine, obtained in Example 6, and 124 mg of pyridazine-4-carboxylic acid, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 210 mg of [4-(3H-imidazo[4,5-c]pyridin-2-yl)-9H-fluoren-9-yl]amide of pyridazine-4-carboxylic acid, in the form of a brown powder, with the following characteristics:

Mass spectrum (E/I): m/z=404 (M$^+$).

Example 87

Synthesis of 2-chloro-N-[4-(3H-imidazo[4,5-c]pyridin-2-yl)-9H-fluoren-9(R,S)-yl]-isonicotinamide Carry out the procedure as in Example 14, starting from 298 mg of 4-(3H-imidazo[4,5-c]pyridin-2-yl)-fluorene-9(R,S)-amine, obtained in Example 6, and 157.6 mg of 2-chloro-isonicotinic acid, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 405 mg of 2-chloro-N-[4-(3H-imidazo[4,5-c]pyridin-2-yl)-9H-fluoren-9(R,S)-yl]-isonicotinamide, in the form of a brown powder, with the following characteristics:

Mass spectrum (E/I): m/z=437 (M$^+$).

Example 88

Synthesis of [4-(3H-imidazo[4,5-c]pyridin-2-yl)-9H-fluoren-9-yl]amide of 2,6-dihydroxypyrimidine-4-carboxylic acid Carry out the procedure as in Example 14, starting from 298 mg of 4-(3H-imidazo[4,5-c]pyridin-2-yl)-fluorene-9(R,S)-amine, obtained in Example 6, and 156 mg of 2,6-dihydroxypyrimidine-4-carboxylic acid, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 365 mg of [4-(3H-imidazo[4,5-c]pyridin-2-yl)-9H-fluoren-9-yl]amide of 2,6-dihydroxypyrimidine-4-carboxylic acid, in the form of a brown powder, with the following characteristics:

Mass spectrum (E/I): m/z=436 (M$^+$).

Example 89

Synthesis of [4-(3H-imidazo[4,5-c]pyridin-2-yl)-9H-fluoren-9-yl]amide of 2-hydroxypyrimidine-4-carboxylic acid Carry out the procedure as in Example 14, starting from 298 mg of 4-(3H-imidazo[4,5-c]pyridin-2-yl)-fluorene-9(R,S)-amine, obtained in Example 6, and 140 mg of 2-hydroxypyrimidine-4-carboxylic acid, in the presence of 211 mg of EDCI and 148.6 mg of HOBT in 7.2 ml of DMF for 20 hours. After purification by washing successively with a saturated aqueous solution of sodium hydrogen carbonate then with water and isopropanol, we obtain 195 mg of [4-(3H-imidazo[4,5-c]pyridin-2-yl)-9H-fluoren-9-yl]amide of 2-hydroxypyrimidine-4-carboxylic acid, in the form of a brown powder, with the following characteristics:

Mass spectrum (E/I): m/z=420 (M$^+$).

Example 90

Synthesis of [4-(3H-imidazo[4,5-c]pyridin-2-yl)-9H-fluoren-9-yl]amide of 2-methyl-quinoline-5-carboxylic acid Carry out the procedure as in Example 14, starting from 200 mg of 4-(3H-imidazo[4,5-c]pyridin-2-yl)-fluorene-9(R,S)-amine, obtained in Example 6, and 138 mg of 2-methyl-quinoline-5-carboxylic acid, which can be obtained according to J. Med. Chem. 2002, 4647, in the presence of 128.4 mg of EDCI and 90.5 mg of HOBT in 5.5 ml of DMF for 20 hours. After purification by washing successively with a saturated aqueous solution of sodium hydrogen carbonate then with water and diisopropyl ether, we obtain 70 mg of [4-(3H-imidazo[4,5-c]pyridin-2-yl)-9H-fluoren-9-yl]amide of 2-methyl-quinoline-5-carboxylic acid, in the form of a pale yellow powder, with the following characteristics:

Mass spectrum (E/I): m/z=467 (M$^+$).

Example 91

Synthesis of [4-(3H-imidazo[4,5-c]pyridin-2-yl)-9H-fluoren-9-yl]amide of 2-amino-pyrimidine-4-carboxylic acid Carry out the procedure as in Example 14, starting from 214.5 mg of 4-(3H-imidazo[4,5-c]pyridin-2-yl)-fluorene-9(R,S)-amine, obtained in Example 6, and 100 mg of 2-amino-pyrimidine-4-carboxylic acid, in the presence of 151.6 mg of EDCI and 107 mg of HOBT in 5 ml of DMF for 20 hours. After purification by washing successively with a saturated aqueous solution of sodium hydrogen carbonate then with water and isopropanol, we obtain 190 mg of [4-(3H-imidazo[4,5-c]pyridin-2-yl)-9H-fluoren-9-yl]amide of 2-amino-pyrimidine-4-carboxylic acid, in the form of a beige powder, with the following characteristics:

Mass spectrum (E/I): m/z=419 (M$^+$).

Example 92

Synthesis of [4-(3H-imidazo[4,5-c]pyridin-2-yl)-9H-fluoren-9(R,S)-yl]amide of 1H-pyrrolo[2,3-b]pyridine-4-carboxylic acid Carry out the procedure as in Example 14, starting from 300 mg of 4-(3H-imidazo[4,5-c]pyridin-2-yl)-fluorene-9(R,S)-amine, obtained in Example 6, and 171 mg of 1H-indazole-4-carboxylic acid, in the presence of 212 mg of EDCI and 150 mg of HOBT in 10 ml of DMF for 20 hours. After purification by washing successively with a saturated aqueous solution of sodium hydrogen carbonate then with water and isopropanol, we obtain 245 mg of [4-(3H-imidazo[4,5-c]pyridin-2-yl)-9H-fluoren-9(R,S)-yl]amide of 1H-pyrrolo[2,3-b]pyridine-4-carboxylic acid, in the form of an off-white powder, with the following characteristics:

Mass spectrum (E/I): m/z=442 (M$^+$).

melting point (Kofler)=236° C.

Example 93

Synthesis of [4-(3H-imidazo[4,5-c]pyridin-2-yl)-9H-fluoren-9-yl]amide of 6-hydroxypyrimidine-4-carboxylic acid Carry out the procedure as in Example 14, starting from 106.55 mg of 4-(3H-imidazo[4,5-c]pyridin-2-yl)-fluorene-9(R,S)-amine, obtained in Example 6, and 50 mg of 6-hydroxypyrimidine-4-carboxylic acid, in the presence of 75.3 mg of EDCI and 53 mg of HOBT in 2.5 ml of DMF for 20 hours. After purification by washing successively with a saturated aqueous solution of sodium hydrogen carbonate then with water and isopropanol, we obtain 65 mg of [4-(3H-imidazo[4,5-c]pyridin-2-yl)-9H-fluoren-9-yl]amide of 6-hydroxypyrimidine-4-carboxylic acid, in the form of a brown powder, with the following characteristics:

Mass spectrum (E/I): m/z=420 (M$^+$).

6-Hydroxypyrimidine-4-carboxylic acid can be obtained by hydrolysis of the methyl ester of 6-hydroxypyrimidine-4-carboxylic acid, which can be obtained according to J. Med. Chem. 2000, 43, 3995-4002.

Example 94

Synthesis of 2-hydroxymethyl-N-[4-(3H-imidazo[4,5-c]pyridin-2-yl)-9H-fluoren-9(R,S)-yl]-isonicotinamide Carry out the procedure as in Example 14, starting from 97.4 mg of 4-(3H-imidazo[4,5-c]pyridin-2-yl)-fluorene-9(R,S)-amine, obtained in Example 6, and 50 mg of 2-hydroxymethyl-isonicotinic acid, in the presence of 68.8 mg of EDCI and 48.5 mg of HOBT in 2.5 ml of DMF for 20 hours. After purification by washing successively with a saturated aqueous solution of sodium hydrogen carbonate then with water and isopropanol, we obtain 70 mg of 2-hydroxymethyl-N-[4-(3H-imidazo[4,5-c]pyridin-2-yl)-9H-fluoren-9(R,S)-yl]-isonicotinamide, in the form of a beige powder, with the following characteristics:

Mass spectrum (E/I): m/z=433 (M$^+$).

2-Hydroxymethyl-isonicotinic acid can be obtained by saponification of the methyl ester of 2-hydroxymethyl-isonicotinic acid, which can be obtained according to E.P. 533131.

Example 95

Synthesis of 2-fluoro-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 141 mg of 2-fluoro-isonicotinic acid, in the presence of 211 mg of EDCI and 148.65 mg of HOBT in 7 ml of DMF for 20 hours. After purification by washing successively with a saturated aqueous solution of sodium hydrogen carbonate then with water and isopropanol, we obtain 290 mg of 2-fluoro-N-[4-(3H- imidazo[4,5-c]pyridin-2-yl)-9H-fluoren-9(R,S)-yl]-isonicotinamide, in the form of a beige powder, with the following characteristics:

Mass spectrum (E/I): m/z=421 (M$^+$).

Example 96

Synthesis of N-[4-(3H-imidazo[4,5-c]pyridin-2-yl)-9H-fluoren-9(R,S)-yl]-3-methyl-isonicotinamide Carry out the procedure as in Example 14, starting from 298.4 mg of 4-(3H-imidazo[4,5-c]pyridin-2-yl)-fluorene-9(R,S)-amine, obtained in Example 6, and 137 mg of 3-methyl-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 290 mg of N-[4-(3H-imidazo[4,5-c]pyridin-2-yl)-9H-fluoren-9(R,S)-yl]-3-methyl-isonicotinamide, in the form of a beige powder, with the following characteristics:

Mass spectrum (E/I): m/z=417 (M$^+$).

Example 97

Synthesis of the hydrochloride of [4-(3H-imidazo[4,5-c]pyridin-2-yl)-9H-fluoren(R,S)-9-yl]amide of 1,8-naphthyridine-4-carboxylic acid Carry out the procedure as in Example 14, starting from 298.4 mg of 4-(3H-imidazo[4,5-c]pyridin-2-yl)-fluorene-9(R,S)-amine, obtained in Example 6, and 174.2 mg of hydrochloride of 1,8-naphthyridine-4-carboxylic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 435 mg of hydrochloride of [4-(3H-imidazo[4,5-c]pyridin-2-yl)-9H-fluoren-9(R,S)-yl]amide of 1,8-naphthyridine-4-carboxylic acid, in the form of a light brown powder, with the following characteristics:

Mass spectrum (E/I): m/z=4547 (M$^+$).

Example 98

Synthesis of 3-bromo-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 202 mg of 3-bromo-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 435 mg of 3-bromo-N-[4-(3H-imidazo[4,5-c]pyridin-2-yl)-9H-fluoren-9(R,S)-yl]-isonicotinamide, in the form of a brown powder, with the following characteristics:

Mass spectrum (E/I): m/z=482 (M$^+$).

Example 99

Synthesis of [4-(3H-imidazo[4,5-c]pyridin-2-yl)-9H-fluoren(R,S)-9-yl]amide of 1H-pyrrolo[2,3-b]pyridine-3-carboxylic acid Carry out the procedure as in Example 14, starting from 298 mg of 4-(3H-imidazo[4,5-c]pyridin-2-yl)-fluorene-9(R,S)-amine, obtained in Example 6, and 170 mg of 1H-pyrrolo[2,3-b]pyridine-3-carboxylic acid, which can be prepared according to WO 04111048, in the presence of 287 mg of EDCI and 202 mg of HOBT in 5 ml of DMF for 20 hours. After purification by silica gel flash chromatography, eluting with a mixture of dichloromethane and methanol (90-10 by volume), we obtain 155 mg of [4-(3H-imidazo[4,5-c]pyridin-2-yl)-9H-fluoren(R,S)-9-yl]amide of 1H-pyrrolo[2,3-b]pyridine-3-carboxylic acid, in the form of a white powder, with the following characteristics:

Mass spectrum (E/I): m/z=442 (M$^+$).
Melting point (Kofler)=225° C. (decomp.).

1H-Pyrrolo[2,3-b]pyridine-3-carboxylic acid can be prepared according to WO 04111048.

Example 100

Synthesis of N-[4-(3H-imidazo[4,5-c]pyridin-2-yl)-9H-fluoren-9(R,S)-yl]-2(R,S)-(pyridin-3-yl)-propionamide Carry out the procedure as in Example 14, starting from 200 mg of 4-(3H-imidazo[4,5-c]pyridin-2-yl)-fluorene-9(R,S)-amine, obtained in Example 6, and 138.3 mg of hydrochloride of 2-(pyridin-3-yl)propanoic acid, in the presence of 128.4 mg of EDCI, 45.3 mg of HOBT and 104 µL of triethylamine in 5 ml of DMF for 20 hours. After purification by silica gel flash chromatography, eluting with a mixture of dichloromethane and methanol (90-10 by volume), we obtain 444 mg of N-[4-(3H-imidazo[4,5-c]pyridin-2-yl)-9H-fluoren-9(R,S)-yl]-2(R,S)-(pyridin-3-yl)-propionamide, in the form of a yellow powder, with the following characteristics:

Mass spectrum (E/I): m/z=431 (M$^+$).

The hydrochloride of 2-(pyridin-3-yl)propanoic acid can be obtained according to WO 95 10516.

Example 101

Synthesis of [4-(3H-imidazo[4,5-c]pyridin-2-yl)-9H-fluoren-9(R,S)-yl]amide of 1-methyl-1H-pyrrolo[2,3-b]pyridine-3-carboxylic acid Carry out the procedure as in Example 14, starting from 298 mg of 4-(3H-imidazo[4,5-c]pyridin-2-yl)-fluorene-9(R,S)-amine, obtained in Example 6, and 185 mg of 1-methyl-1H-pyrrolo[2,3-b]pyridine-3-carboxylic acid, in the presence of 287 mg of EDCI and 202 mg of HOBT in 5 ml of DMF for 20 hours. After purification by silica gel flash chromatography, eluting with a mixture of dichloromethane and methanol (90-10 by volume), we obtain 165 mg of [4-(3H-imidazo[4,5-c]pyridin-2-yl)-9H-fluoren-9(R,S)-yl]amide of 1-methyl-1H-pyrrolo[2,3-b]pyridine-3-carboxylic acid, in the form of an off-white solid, with the following characteristics:

Mass spectrum (E/I): m/z=456 (M$^+$).
Melting point (Kofler)=204° C. (decomp.).

1-Methyl-1H-pyrrolo[2,3-b]pyridine-3-carboxylic acid can be obtained according to WO 96 11929.

Example 102

Synthesis of 2-bromo-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 202 mg of 2-bromo-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 345 mg of 2-bromo-N-[4-(3H-imidazo[4,5-c]pyridin-2-yl)-9H-fluoren-9(R,S)-yl]-isonicotinamide, in the form of a brown powder, with the following characteristics:
Mass spectrum (E/I): m/z=482 (M$^+$).

Example 103

Synthesis of 3-hydroxy-N-[4-(3H-imidazo[4,5-c]pyridin-2-yl)-9H-fluoren-9(R,S)-yl]-isonicotinamide Carry out the procedure as in Example 14, starting from 400 mg of 4-(3H-imidazo[4,5-c]pyridin-2-yl)-fluorene-9(R,S)-amine, obtained in Example 6, and 196 mg of 3-hydroxy-isonicotinic acid, in the presence of 211 mg of EDCI and 148.6 mg of HOBT in 7 ml of DMF for 20 hours. After purification by silica gel flash chromatography, eluting with a mixture of dichloromethane and methanol (90-10 by volume), we obtain 250 mg of 3-hydroxy-N-[4-(3H-imidazo[4,5-c]pyridin-2-yl)-9H-fluoren-9(R,S)-yl]-isonicotinamide, in the form of a beige solid, with the following characteristics:
Mass spectrum (E/I): m/z=419 (M$^+$).

Example 104

Synthesis of 3-amino-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 138 mg of 3-amino-isonicotinic acid, in the presence of 211 mg of EDCI and 148.6 mg of HOBT in 7 ml of DMF for 20 hours. After purification by silica gel flash chromatography, eluting with a mixture of dichloromethane and methanol (95-5 by volume), we obtain 176 mg of 3-amino-N-[4-(3H-imidazo[4,5-c]pyridin-2-yl)-9H-fluoren-9(R,S)-yl]-isonicotinamide, in the form of a pale yellow solid, with the following characteristics:
Mass spectrum (E/I): m/z=418 (M$^+$).

Example 105

Synthesis of 2-cyano-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 148 mg of 2-cyano-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 388 mg of 2-cyano-N-[4-(3H-imidazo[4,5-c]pyridin-2-yl)-9H-fluoren-9(R,S)-yl]-isonicotinamide, in the form of a brown powder, with the following characteristics:
Mass spectrum (E/I): m/z=428 (M$^+$).

Example 106

Synthesis of N-[4-(6-methoxy-1H-benzimidazol-2-yl)-9H-fluoren-9(R,S)-yl]-isonicotinamide Stage 1: Carry out the procedure as in stage 1 of Example 1, starting from 2.562 g of 4-methoxy-o-phenylenediamine in 150 ml of dichloromethane, 3.445 ml of triethylamine and 3 g of chloride of fluoren-4-one-9-carboxylic acid, stirring for 20 hours at room temperature. After purification by flash chromatography on silica gel (40-63 μm), eluting with a mixture of dichloromethane and methanol (98-2 by volume), we obtain 2.97 g of a mixture of regioisomeric amides, which is used as it is in the next stage.

Stage 2: In a 500-ml three-necked flask under an argon atmosphere, heat, at 100° C. for 5 hours, a solution of 2.97 g of the amide mixture obtained in the preceding stage, in 150 ml of acetic acid. After cooling, the precipitate that formed is drained. After purification by flash chromatography on silica gel (40-63 μm), eluting with a mixture of dichloromethane and methanol (99-1 by volume), we obtain 1.71 g of 4-(6-methoxy-1H-benzimidazol-2-yl)-9H-fluoren-9-one, in the form of a brown powder, which is used as it is in the next stage.

Stage 3: Carry out the procedure as in Example 5, starting from 1 g of 4-(6-methoxy-1H-benzimidazol-2-yl)-9H-fluoren-9-one, obtained in the preceding stage, 0.639 g of hydroxylamine hydrochloride and 1.257 g of sodium acetate stirred at room temperature for 20 hours in 17 ml of ethanol. After purification by making a paste in diisopropyl ether, we obtain 959 mg of 4-(6-methoxy-1H-benzimidazol-2-yl)-9H-fluoren-9-one oxime, as a 50-50 mixture of the Z and E isomers, in the form of a chestnut-brown powder, with the following characteristics:
Mass spectrum (E/I): m/z=341 (M$^+$).
$^1$H-NMR spectrum (300 MHz, δ in ppm, DMSO-d$_6$): 3.92 (s, 3H); 6.78 (d broad, J=8.5 Hz, 0.5 Hz); 6.93 (d broad, J=8.5 Hz, 0.5H); from 7.25 to 7.52 (m, 4H); from 7.59 to 7.72 (m, 1H); from 7.79 to 7.92 (m, 2.5H); 8.08 (d broad, J=8.5 Hz, 0.5H); 8.47 (d broad, J=8.5 Hz, 0.5H); 8.73 (d broad, J=8.5 Hz, 0.5H).

Stage 4: Carry out the procedure as in Example 6, starting from 900 mg of 4-(6-methoxy-1H-benzimidazol-2-yl)-9H-fluoren-9-one oxime (Z,E), obtained in the preceding stage, and 1.55 mg of Raney Nickel in 50 ml of ethanol and 50 ml of tetrahydrofuran for 16 hours at 60° C. under a hydrogen pressure of 1 bar. After purification by making a paste in diisopropyl ether, we obtain 631 mg of 4-(6-methoxy-1H-benzimidazol-2-yl)-9H-fluoren-9(R,S)-ylamine, in the form of a brown powder, with the following characteristics:
Mass spectrum (E/I): m/z=327 (M$^+$).

Stage 5: Carry out the procedure as in Example 14, starting from 300 mg of 4-(6-methoxy-1H-benzimidazol-2-yl)-9H-fluoren-9(R,S)-ylamine, obtained in the preceding stage, and 118.6 mg of isonicotinic acid, in the presence of 263.4 mg of EDCI and 185.7 mg of HOBT in 3 ml of DMF for 20 hours. After purification by successive flash chromatography on an Isolute silica cartridge, eluting with mixtures of ethyl acetate and methanol (99-1 then 98-2 by volume), we obtain 9.1 mg of N-[4-(6-methoxy-1H-benzimidazol-2-yl)-9H-fluoren-9(R,S)-yl]-isonicotinamide, in the form of a beige powder, with the following characteristics:
Mass spectrum (E/I): m/z=432 (M$^+$).

Example 107

Synthesis of 4-(6-hydroxy-1H-benzimidazol-2-yl)-fluoren-9-one oxime (Z,E)

Stage 1: In a 50-ml three-necked flask under an argon atmosphere, dissolve 700 mg of 4-(6-methoxy-1H-benzimidazol-2-yl)-9H-fluoren-9-one, obtained in stage 2 of Example 106, in 10 ml of dichloromethane, then add dropwise 5.35 ml of a 1M solution of boron tribromide in dichloromethane and stir for 20 hours at room temperature. Pour the reaction mixture into 50 ml of water. The precipitate that forms is drained and washed with water then with toluene and finally dried. After purification by silica gel flash chromatography, eluting with a mixture of dichloromethane and methanol (90-10 by volume), we obtain 363 mg of 4-(6-hydroxy-1H-benzimidazol-2-yl)-fluoren-9-one, in the form of a brown powder, with the following characteristics:

Mass spectrum (E/I): m/z=312 (M$^+$).

Stage 2: Carry out the procedure as in Example 5, starting from 571 mg of 4-(6-hydroxy-1H-benzimidazol-2-yl)-fluoren-9-one, obtained in the preceding stage, 381 mg of hydroxylamine hydrochloride and 750 mg of sodium acetate stirred at room temperature for 20 hours in 11 ml of ethanol. After purification by making a paste in diisopropyl ether, we obtain 539 mg of 4-(6-hydroxy-1H-benzimidazol-2-yl)-fluoren-9-one oxime, as a 50-50 mixture of the Z and E isomers, in the form of a chestnut-brown powder, with the following characteristics:

Mass spectrum (E/I): m/z=327 (M$^+$).

Example 108

Synthesis of methyl ester of 4-[4-(3H-imidazo[4,5-c]pyridin-2-yl)-9H-fluoren-9(R,S)-ylcarbamoyl]-pyridine-2-carboxylic acid Carry out the procedure as in Example 14, starting from 597 mg of 4-(3H-imidazo[4,5-c]pyridin-2-yl)-fluorene-9(R,S)-amine, obtained in Example 6, and 362 mg of the 2-methyl ester of pyridine-2,4-dicarboxylic acid, in the presence of 422 mg of EDCI and 297 mg of HOBT in 14 ml of DMF for 20 hours. After purification by silica gel flash chromatography, eluting with a mixture of dichloromethane and methanol (90-10 by volume), we obtain 610 mg of methyl ester of 4-[4-(3H-imidazo[4,5-c]pyridin-2-yl)-9H-fluoren-9(R,S)-ylcarbamoyl]-pyridine-2-carboxylic acid, in the form of a beige solid, with the following characteristics:

Mass spectrum (E/I): m/z=461 (M$^+$).

The 2-methyl ester of pyridine-2,4-dicarboxylic acid can be obtained according to EP 479177.

Example 109

Synthesis of 4-[4-(3H-imidazo[4,5-c]pyridin-2-yl)-9H-fluoren-9(R,S)-ylcarbamoyl]-pyridine-2-carboxylic acid In a 50-ml three-necked flask, dissolve 500 mg of methyl ester of 4-[4-(3H-imidazo[4,5-c]pyridin-2-yl)-9H-fluoren-9(R,S)-ylcarbamoyl]-pyridine-2-carboxylic acid, obtained in Example 108, in 20 ml of methanol, then add a solution of 60.8 mg of potassium hydroxide in 10 ml of water and stir at room temperature for 20 hours. Concentrate the reaction mixture under reduced pressure, re-dissolve in 50 ml of water and extract twice with 50 ml of diethyl ether. Acidify the aqueous phase to pH=4 by adding normal aqueous solution of hydrochloric acid. The precipitate that form is drained, washed with water and with diisopropyl ether. In this way we obtain 410 mg of 4-[4-(3H-imidazo[4,5-c]pyridin-2-yl)-9H-fluoren-9(R,S)-ylcarbamoyl]-pyridine-2-carboxylic acid, in the form of a beige solid with the following characteristics:

Mass spectrum (E/I): m/z=447 (M$^+$).

Example 110

Synthesis of N-[4-(3H-imidazo[4,5-b]pyridin-2-yl)-9H-fluoren-9(R,S)-yl]-isonicotinamide Stage 1: Carry out the procedure as in stage 1 of Example 1, starting from 2.023 g of 2,3-diamino-pyridine in 150 ml of dichloromethane, 3.445 ml of triethylamine and 3 g of chloride of fluoren-4-one-9-carboxylic acid for 20 hours of stirring at room temperature. After purification by flash chromatography on silica gel (40-63 µm), eluting with mixtures of dichloromethane and methanol (98-2 then 95-5 by volume), we obtain 1.495 g of the mixture of regioisomeric amides, which is used as it is in the next stage.

Stage 2: In a 250-ml three-necked flask under an argon atmosphere, heat, at 100° C. for 2 hours and 30 minutes, a solution of 1.49 g of the amide mixture obtained in the preceding stage, in 75 ml of acetic acid. After cooling, the precipitate that formed is drained. After purification by making a paste in diisopropyl ether, we obtain 1.40 g of 4-(3H-imidazo[4,5-b]pyridin-2-yl)-9H-fluoren-9-one in the form of a yellow powder, which is used as it is in the next stage.

Stage 3: Carry out the procedure as in Example 5, starting from 1.4 g of 4-(3H-imidazo[4,5-b]pyridin-2-yl)-9H-fluoren-9-one, obtained in the preceding stage, 1 g of hydroxylamine hydrochloride and 1.93 g of sodium acetate stirred at room temperature for 20 hours in 25 ml of ethanol. After purification by silica gel flash chromatography, eluting with mixtures of dichloromethane and ammonia as 7M solution in methanol (90-10 then 85-15 by volume), we obtain 1.32 g of 4-(3H-imidazo[4,5-b]pyridin-2-yl)-9H-fluoren-9-one oxime, as a 50-50 mixture of the Z and E isomers, in the form of a beige powder, with the following characteristics:

Mass spectrum (E/I): m/z=312 (M$^+$).

$^1$H-NMR spectrum (300 MHz, δ in ppm, DMSO-d$_6$): 7.26 (t broad, J=7.5 Hz, 0.5H); from 7.30 to 7.48 (m, 2H); from 7.57 to 7.69 (m, 1.5H); from 7.77 to 7.86 (m, 2.5H); 8.04 (d broad, J=8.5 Hz, 0.5H); 8.48 (d broad, J=8.5 Hz, 0.5H); from 8.67 to 8.75 (m, 1.5H); 8.78 (d broad, J=5.5 Hz, 1H).

Stage 4: Carry out the procedure as in Example 6, starting from 1.30 g of 4-(3H-imidazo[4,5-b]pyridin-2-yl)-9H-fluoren-9-one oxime (Z,E), obtained in the preceding stage, and 2.45 mg of Raney Nickel in 65 ml of ethanol and 65 ml of tetrahydrofuran for 5 hours at 60° C. under a hydrogen pressure of 1 bar. After purification by making a paste in diisopropyl ether, we obtain 1.06 g of 4-(3H-imidazo[4,5-b]pyridin-2-yl)-9H-fluoren-9(R,S)-ylamine, in the form of a white powder, with the following characteristics:

Mass spectrum (E/I): m/z=298 (M$^+$).

Stage 5: Carry out the procedure as in Example 14, starting from 300 mg of 4-(3H-imidazo[4,5-b]pyridin-2-yl)-9H-fluoren-9(R,S)-ylamine, obtained in the preceding stage, and 130 mg of isonicotinic acid, in the presence of 289.3 mg of EDCI and 204 mg of HOBT in 3 ml of DMF for 20 hours. After purification by washing successively with a saturated aqueous solution of sodium hydrogen carbonate then with water and making a paste in diisopropyl ether, we obtain 227 mg of N-[4-(3H-imidazo[4,5-b]pyridin-2-yl)-9H-fluoren-9(R,S)-yl]-isonicotinamide, in the form of a beige powder, with the following characteristics:

Mass spectrum (E/I): m/z=403 (M$^+$).

$^1$H-NMR spectrum (300 MHz, δ in ppm, DMSO-d$_6$): 6.38 (s, 1H); 7.29 (t broad, J=7.5 Hz, 1H); 7.39 (t broad, J=7.5 Hz, 1H); 7.60 (t, J=7.5 Hz, 1H); from 7.63 to 7.70 (m, 2H); from 7.74 to 7.85 (m, 2H); 7.88 (d broad, J=7.5 Hz, 1H); 8.34 (d broad, J=6.0 Hz, 2H); 8.67 (d broad, J=8.5 Hz, 1H); 8.77 (d broad, J=5.0 Hz, 1H); 9.04 (d broad, J=6.0 Hz, 2H).

Example 111

Synthesis of [4-(3H-imidazo[4,5-c]pyridin-2-yl)-9H-fluoren-9(R,S)-yl]amide of 1H-indazole-4-carboxylic acid Carry out the procedure as in Example 14, starting from 300 mg of 4-(3H-imidazo[4,5-c]pyridin-2-yl)-fluorene-9(R,S)-amine, obtained in Example 6, and 171 mg of 1H-indazole-4-carboxylic acid, in the presence of 212 mg of EDCI and 150 mg of HOBT in 3 ml of DMF for 20 hours. After purification by silica gel flash chromatography, eluting with a mixture of dichloromethane and methanol (90-10 by volume), we obtain 154 mg of [4-(3H-imidazo[4,5-c]pyridin-2-yl)-9H-fluoren-9(R,S)-yl]amide of 1H-indazole-4-carboxylic acid, in the form of a yellow solid, with the following characteristics:

Mass spectrum (E/I): m/z=442 ($M^+$).
Melting point (Kofler)=230-35° C.

Example 112

Synthesis of 4-{[4-(3H-imidazo[4,5-c]pyridin-2-yl)-9H-fluoren-9(R,S)-yl]amide}-2-[(3-methoxy-propyl)-amide] of pyridine-2,4-dicarboxylic acid Carry out the procedure as in Example 14, starting from 62.6 mg of 4-(3H-imidazo[4,5-c]pyridin-2-yl)-fluorene-9(R,S)-amine, obtained in Example 6, and 50 mg of 2-[(3-methoxy-propyl)-amide] of pyridine-2,4-dicarboxylic acid, in the presence of 44.3 mg of EDCI and 31.2 mg of HOBT in 2 ml of DMF for 20 hours. After purification by washing successively with a saturated aqueous solution of sodium hydrogen carbonate then with water and isopropanol, we obtain 70 mg of 4-{[4-(3H-imidazo[4,5-c]pyridin-2-yl)-9H-fluoren-9(R,S)-yl]amide}2-[(3-methoxy-propyl)-amide] of pyridine-2,4-dicarboxylic acid, in the form of a beige powder, with the following characteristics:

Mass spectrum (E/I): m/z=518 ($M^+$).

Example 113

Synthesis of [4-(3H-imidazo[4,5-c]pyridin-2-yl)-9H-fluoren-9(R,S)-yl]amide of 2-(furan-2-yl)-quinoline-4-carboxylic acid Carry out the procedure as in Example 14, starting from 298.4 mg of 4-(3H-imidazo[4,5-c]pyridin-2-yl)-fluorene-9(R,S)-amine, obtained in Example 6, and 239 mg of 2-(furan-2-yl)-quinoline-4-carboxylic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 440 mg of [4-(3H-imidazo[4,5-c]pyridin-2-yl)-9H-fluoren-9(R,S)-yl]amide of 2-(furan-2-yl)-quinoline-4-carboxylic acid, in the form of a brown powder, with the following characteristics:

Mass spectrum (E/I): m/z=519 ($M^+$).

Example 114

Synthesis of 3-fluoro-N-[4-(3H-imidazo[4,5-c]pyridin-2-yl)-9H-fluoren-9(R,S)-yl]-isonicotinamide Carry out the procedure as in Example 14, starting from 298.4 mg of 4-(3H-imidazo[4,5-c]pyridin-2-yl)-fluorene-9(R,S)-amine, obtained in Example 6, and 141 mg of 3-fluoro-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 350 mg of 3-fluoro-N-[4-(3H-imidazo[4,5-c]pyridin-2-yl)-9H-fluoren-9(R,S)-yl]-isonicotinamide, in the form of a brown powder, with the following characteristics:

Mass spectrum (E/I): m/z=421 ($M^+$).

Example 115

Synthesis of 3-amino-N-[4-(3H-imidazo[4,5-c]pyridin-2-yl)-9H-fluoren-9(R,S)-yl]-benzamide Carry out the procedure as in Example 14, starting from 300 mg of 4-(3H-imidazo[4,5-c]pyridin-2-yl)-fluorene-9(R,S)-amine, obtained in Example 6, and 137 mg of 3-aminobenzoic acid, in the presence of 211 mg of EDCI and 148.6 mg of HOBT in 3 ml of DMF for 20 hours. After purification by silica gel flash chromatography, eluting with a mixture of dichloromethane and methanol (90-10 by volume), we obtain 230 mg of 3-amino-N-[4-(3H-imidazo[4,5-c]pyridin-2-yl)-9H-fluoren-9(R,S)-yl]-benzamide, in the form of a pale yellow solid, with the following characteristics:

Mass spectrum (E/I): m/z=417 ($M^+$).

Example 116

Synthesis of N-[4-(3H-imidazo[4,5-c]pyridin-2-yl)-9H-fluoren-9(R,S)-yl]-2-methylamino-isonicotinamide In a 30-ml autoclave, heat for 20 hours at 90° C., a solution of 230 mg of 2-bromo-N-[4-(3H-imidazo[4,5-c]pyridin-2-yl)-9H-fluoren-9(R,S)-yl]-isonicotinamide, obtained in Example 102, in 6 ml of ethanol and 6 ml of methylamine. Concentrate the reaction mixture under reduced pressure, then purify by silica gel flash chromatography, eluting with mixtures of dichloromethane and methanol (97.5-2.5 then 95-5 by volume). In this way we obtain, after washing with a decinormal aqueous solution of sodium hydroxide, 20 mg of N-[4-(3H-imidazo[4,5-c]pyridin-2-yl)-9H-fluoren-9(R,S)-yl]-2-methylamino-isonicotinamide, in the form of a brown solid with the following characteristics:

Mass spectrum (E/I): m/z=432 ($M^+$).

Example 117

Synthesis of N-[4-(6-hydroxy-1H-benzimidazol-2-yl)-9H-fluoren-9(R,S)-yl]-isonicotinamide Stage 1: Carry out the procedure as in Example 6, starting from 500 mg of 4-(6-hydroxy-1H-benzimidazol-2-yl)-fluoren-9-one oxime (Z,E), obtained in Example 107, and 5 mg of Raney Nickel in 25 ml of ethanol and 25 ml of tetrahydrofuran for 5 hours at 60° C. under a hydrogen pressure of 1 bar. After purification by making a paste in diisopropyl ether, we obtain 385 mg of 4-(6-hydroxy-1H-benzimidazol-2-yl)-fluoren-9(R,S)-ylamine, in the form of a brown powder, with the following characteristics:

Mass spectrum (E/I): m/z=313 ($M^+$).

Stage 2: Carry out the procedure as in Example 14, starting from 300 mg of 4-(6-hydroxy-1H-benzimidazol-2-yl)-fluoren-9(R,S)-ylamine, obtained in the preceding stage, and 130 mg of isonicotinic acid, in the presence of 275 mg of EDCI and 194 mg of HOBT in 3 ml of DMF for 20 hours. After purification by washing successively with a saturated aqueous solution of sodium hydrogen carbonate then with water and making a paste in diisopropyl ether, we obtain 87 mg of N-[4-(6-hydroxy-1H-benzimidazol-2-yl)-9H-fluoren-9(R,S)-yl]-isonicotinamide, in the form of a beige powder, with the following characteristics:

Mass spectrum (E/I): m/z=418 (M$^+$).

Example 118

Synthesis of [4-(3H-imidazo[4,5-c]pyridin-2-yl)-9H-fluoren-9(R,S)-yl]amide of 6-bromo-3H-imidazo[4,5-b]pyridine-7-carboxylic acid Carry out the procedure as in Example 14, starting from 149 mg of 4-(3H-imidazo[4,5-c]pyridin-2-yl)-fluorene-9(R,S)-amine, obtained in Example 6, and 121 mg of 6-bromo-3H-imidazo[4,5-b]pyridine-7-carboxylic acid, in the presence of 105.4 mg of EDCI and 74.3 mg of HOBT in 3.5 ml of DMF for 20 hours. After purification by silica gel flash chromatography, eluting with a mixture of dichloromethane and methanol (90-10 by volume), we obtain 100 mg of [4-(3H-imidazo[4,5-c]pyridin-2-yl)-9H-fluoren-9(R,S)-yl]amide of 6-bromo-3H-imidazo[4,5-b]pyridine-7-carboxylic acid, in the form of a pale green solid, with the following characteristics:

Mass spectrum (E/I): m/z=522 (M$^+$).

Example 119

Synthesis of [4-(3H-imidazo[4,5-c]pyridin-2-yl)-9H-fluoren-9(R,S)-yl]amide of 2-piperidin-1-yl-quinoline-4-carboxylic acid Carry out the procedure as in Example 14, starting from 298.4 mg of 4-(3H-imidazo[4,5-c]pyridin-2-yl)-fluorene-9(R,S)-amine, obtained in Example 6, and 256.3 mg of 2-piperidin-1-yl-quinoline-4-carboxylic acid (or 2-piperidino-cinchoninic acid), in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 495 mg of [4-(3H-imidazo[4,5-c]pyridin-2-yl)-9H-fluoren-9(R,S)-yl]amide of 2-piperidin-1-yl-quinoline-4-carboxylic acid, in the form of a yellow powder, with the following characteristics:

Mass spectrum (E/I): m/z=536 (M$^+$).

Example 120

Synthesis of N-[4-(3H-imidazo[4,5-c]pyridin-2-yl)-9H-fluoren-9(R,S)-yl]-2-pyrrolidin-1-yl-isonicotinamide Carry out the procedure as in Example 14, starting from 298.4 mg of 4-(3H-imidazo[4,5-c]pyridin-2-yl)-fluorene-9(R,S)-amine, obtained in Example 6, and 199.2 mg of 2-pyrrolidin-1-yl-isonicotinic acid, in the presence of 211 mg of EDCI and 148.6 mg of HOBT in 7 ml of DMF for 20 hours. After purification by washing successively with a saturated aqueous solution of sodium hydrogen carbonate then with water and isopropanol, we obtain 260 mg of N-[4-(3H-imidazo[4,5-c]pyridin-2-yl)-9H-fluoren-9(R,S)-yl]-2-pyrrolidin-1-yl-isonicotinamide, in the form of a yellow powder, with the following characteristics:

Mass spectrum (E/I): m/z=472 (M$^+$).

Example 121

Synthesis of 2-hydroxy-N-[4-(3H-imidazo[4,5-c]pyridin-2-yl)-9H-fluoren-9(R,S)-yl]-6-methyl-isonicotinamide Carry out the procedure as in Example 14, starting from 298.4 mg of 4-(3H-imidazo[4,5-c]pyridin-2-yl)-fluorene-9(R,S)-amine, obtained in Example 6, and 153 mg of 2-hydroxy-6-methyl-isonicotinic acid, in the presence of 211 mg of EDCI and 148.6 mg of HOBT in 7 ml of DMF for 20 hours. After purification by silica gel flash chromatography, eluting with a mixture of dichloromethane and methanol (90-10 by volume), we obtain 340 mg of 2-hydroxy-N-[4-(3H-imidazo[4,5-c]pyridin-2-yl)-9H-fluoren-9(R,S)-yl]-6-methyl-isonicotinamide, in the form of a beige solid, with the following characteristics:

Mass spectrum (E/I): m/z=433 (M$^+$).

Example 122

Synthesis of 4-(3H-imidazo[4,5-c]pyridin-2-yl)-9H-fluoren-9(R,S)-yl ester of isonicotinic acid In a 25-ml round-bottomed flask under an argon atmosphere, dissolve 299.3 mg of 4-(3H-imidazo[4,5-c]pyridin-2-yl)-fluoren-9(R,S)-ol, obtained in Example 3, in 5 ml of pyridine. To this solution, cooled to 0° C., add 356 mg of hydrochloride of the chloride of isonicotinic acid; then stir for 18 hours at room temperature. The reaction mixture is concentrated then poured into 10 ml of water. The precipitate that formed is drained and washed successively with 10 ml of a saturated aqueous solution of sodium hydrogen carbonate, twice with 10 ml of water and twice with 10 ml of diisopropyl ether. In this way we obtain, after drying under reduced pressure at 50° C., 335 mg of 4-(3H-imidazo[4,5-c]pyridin-2-yl)-9H-fluoren-9(R,S)-yl ester of isonicotinic acid, in the form of a pale yellow powder with the following characteristics:

Mass spectrum (E/I): m/z=404 (M$^+$).

Example 123

Synthesis of 2-chloro-N-[4-(3H-imidazo[4,5-c]pyridin-2-yl)-9H-fluoren-9(R,S)-yl]-6-methyl-isonicotinamide The procedure used in Example 14 is followed, starting from 400 mg of 4-(3H-imidazo[4,5-c]pyridin-2-yl)-fluorene-9(R,S)-amine, obtained in Example 6, and 241.6 mg of 2-chloro-methyl-isonicotinic acid, in the presence of 270 mg of EDCI and 91 mg of HOBT in 7 ml of DMF for 20 hours. After purification by washing successively with a saturated aqueous solution of sodium hydrogen carbonate then with water and isopropanol, we obtain 332 mg of 2-chloro-N-[4-(3H-imidazo[4,5-c]pyridin-2-yl)-9H-fluoren-9(R,S)-yl]-6-methyl-isonicotinamide, in the form of a beige solid, with the following characteristics:

Mass spectrum (E/I): m/z=433 (M$^+$).
Melting point (Kofler)=250° C.

Example 124

Synthesis of 4-(3H-imidazo[4,5-c]pyridin-2-yl)-9H-fluoren-9(R,S)-yl of 5-quinolinecarboxylic acid Introduce successively into a 50 ml round-bottomed flask, 347 mg of 5-quinolinecarboxylic acid, two drops of dimethylformamide and 15 ml of dichloromethane. After cooling to 0° C., add 206 µl of oxalyl chloride and stir for 1 hour at room temperature. Evaporate off the solvent and then add 300 mg of 4-(3H-imidazo[4,5-c]pyridin-2-yl)fluoren-9(R,S)-ol, synthesized as in Example 3, in solution in a mixture of 5 ml of pyridine and 2 ml of dichloromethane. After 5 minutes at ambient temperature, add 1 ml of water, and then the solvent is evaporated off. The pasty reaction medium is poured into 20 ml of saturated aqueous sodium hydrogen carbonate solution. The solid obtained is filtered off and then successively washed with water (2×10 ml) and with diisopropyl ether (2×10 ml). After purification by flash chromatography on silica gel (40-63 µm), eluting with a mixture of dichloromethane and methanol (95-05 by volume), we obtain 120 mg of 4-(3H-imidazo[4,5-c]pyridin-2-yl)-9H-fluoren-9(R,S)-yl of 5-quinolinecarboxylic acid, in the form of an off-white foam with the following characteristics:

Mass spectrum (LCMS): m=455 (MH+).
$^1$H-NMR spectrum (300 MHz, δ in ppm, DMSO-d6):

Example 125

Synthesis of N-[4-(3H-imidazo[4,5-c]pyridin-2-yl)-9H-fluoren-9(R,S)-yl]amide of 2-tert-butoxycarbonylaminoisonicotinic acid The procedure used in Example 14 is followed, starting from 3.2 g of 4-(3H-imidazo[4,5-c]pyridin-2-yl)fluorene-9(R,S)-amine obtained in Example 6, and 2.6 g of 2-tert-butoxycarbonylaminoisonicotinic acid, in the presence of 2.3 g of EDCI and 1.6 g of HOBT in 80 ml of DMF for 20 hours. After successive washes with a saturated aqueous solution of sodium hydrogen carbonate, with water and then with isopropyl ether, we obtain 5.4 g of N-[4-(3H-imidazo[4,5-c]pyridin-2-yl)-9H-fluoren-9(R,S)-yl]amide of 2-tert-butoxycarbonylaminoisonicotinic acid, in the form of a beige solid with the following characteristics:

Mass spectrum (E/I): m/z=518 (M+).
The 2-tert-butoxycarbonylaminoisonicotinic acid can be obtained according to WO 2001074788.

Example 126

Synthesis of N-[4-(3H-imidazo[4,5-c]pyridin-2-yl)-9H-fluoren-9(R,S)-yl]isophthalamide The procedure used in Example 14 is followed, starting from 325 mg of 4-(3H-imidazo[4,5-c]pyridin-2-yl)fluorene-9(R,S)-amine, obtained in Example 6, and 180 mg of isophthalamic acid, in the presence of 230 mg of EDCI and 162 mg of HOBT in 8 ml of DMF for 20 hours. After successive washes with a saturated aqueous solution of sodium hydrogen carbonate, with water and then with isopropyl ether, we obtain 380 mg of N-[4-(3H-imidazo[4,5-c]pyridin-2-yl)-9H-fluoren-9(R,S)-yl]isophthalamide, in the form of a beige solid with the following characteristics:

Mass spectrum (E/I): m/z=445 (M+).
The isophthalamic acid can be obtained according to WO 2000021920.

Example 127

Synthesis of N-[4-(3H-imidazo[4,5-c]pyridin-2-yl)-9H-fluoren-9(R,S)-yl]-4-methoxybenzamide The procedure used in Example 14 is followed, starting from 400 mg of 4-(3H-imidazo[4,5-c]pyridin-2-yl)fluorene-9(R,S)amine, obtained in Example 6, and 200 mg of 4-methoxybenzoic acid, in the presence of 270 mg of EDCI and 91 mg of HOBT in 14 ml of DMF for 20 hours. After successive washes with a saturated aqueous solution of sodium hydrogen carbonate and then with water, the crude mixture is purified by flash chromatography on silica gel, eluting with a mixture of dichloromethane and methanol (95-05 by volume), we obtain 78 mg of N-[4-(3H-imidazo[4,5-c]pyridin-2-yl)-9H-fluoren-9(R,S)-yl]-4-methoxybenzamide, in the form of a white solid with the following characteristics:

Mass spectrum (LC/MS): m/z=432 (M+).
Melting point (Kofler)=194° C.

Example 128

Synthesis of N-[4-(3H-imidazo[4,5-c]pyridin-2-yl)-9H-fluoren-9(R,S)-yl]amide of 3-chloro-6-methoxyquinoline-4-carboxylic acid The procedure used in Example 14 is followed, starting from 300 mg of 4-(3H-imidazo[4,5-c]pyridin-2-yl)-fluorene-9(R,S)-amine, obtained in Example 6, and 238 mg of 3-chloro-6-methoxyquinoline-4-carboxylic acid, in the presence of 211 mg of EDCI and 148 mg of HOBT in 7 ml of DMF for 20 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (95-05 by volume), we obtain 310 mg of N-[4-(3H-imidazo[4,5-c]pyridin-2-yl)-9H-fluoren-9(R,S)-yl]amide of 3-chloro-6-methoxyquinoline-4-carboxylic acid, in the form of a white powder with the following characteristics:

Mass spectrum (E/I): m/z=517 (M+).

Example 129

Synthesis of 4-amino-N-[4-(3H-imidazo[4,5-c]pyridin-2-yl)-9H-fluoren-9(R,S)-yl]benzamide hydrochloride Stage 1: The procedure used in Example 14 is followed, starting from 800 mg of 4-(3H-imidazo[4,5-c]pyridin-2-yl)fluorene-9(R,S)-amine, obtained in Example 6, and 640 mg of 4-tert-butoxycarbonylaminobenzoic acid, in the presence of 540 mg of EDCI and 180 mg of HOBT in 14 mg of DMF for 20 hours. After successive washes with a saturated aqueous solution of sodium hydrogen carbonate and then with water, the crude mixture is purified by flash chromatography on silica gel, eluting with a mixture of dichloromethane and methanol (95-05 by volume), we obtain 168 mg of the tert-butyl ester of 4-[4-(3H-imidazo[4,5-c]pyridin-2-yl)-9H-fluoren-9(R,S)-ylcarbamoyl]phenyl}-carbamoic acid, in the form of a white solid with the following characteristics:

Mass spectrum (LC/MS): m/z=517 (M+).
Stage 2: Dissolve 88 mg of tert-butyl ester of 4-[4-(3H-imidazo[4,5-c]pyridin-2-yl)-9H-fluoren-9(R,S)-ylcarbamoyl]phenyl}carbamoic acid, obtained in stage 1, in 5 ml of dichloromethane and add 6 ml of a 4M solution of hydrochloric acid in dioxane. After stirring for 20 hours at room temperature, the solid that forms is drained. After washing with twice 3 ml of isopropyl ether and drying, we obtain 89 mg of 4-amino-N-[4-(3H-imidazo[4,5-c]pyridin-2-yl)-9H-fluoren-9(R,S)-yl]benzamide hydrochloride, in the form of a white powder with the following characteristics:

Mass spectrum (LC/MS): m/z=417 (M+).

Example 130

Synthesis of N-[4-(3H-imidazo[4,5-c]pyridin-2-yl)-9H-fluoren-9(R,S)-yl]amide of 3-hydroxyquinoline-4-carboxylic acid The procedure used in Example 14 is followed, starting from 370 mg of 4-(3H-imidazo[4,5-c]pyridin-2-yl)-fluorene-9(R,S)-amine, obtained in Example 6, and 300 mg of 3-hydroxyquinoline-4-carboxylic acid, in the presence of 240 mg of EDCI and 84 mg of HOBT in 5 ml of DMF for 15 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (90-10 by volume), we obtain 73 mg of N-[4-(3H-imidazo[4,5-c]pyridin-2-yl)-9H-fluoren-9(R,S)-yl]amide of 3-hydroxyquinoline-4-carboxylic acid, in the form of a yellow solid with the following characteristics:

Mass spectrum (LC/MS): m/z=511 (M+).
Melting point (Kofler)=250° C.

The 3-hydroxyquinoline-4-carboxylic acid can be obtained according to Organic Syntheses, 40, 54-60; 1960.

Example 131

Synthesis of N-[4-(3H-imidazo[4,5-c]pyridin-2-yl)-9H-fluoren-9(R,S)-yl]amide of 2-amino-5-chloropyrimidine-4-carboxylic acid The procedure used in Example 14 is followed, starting from 8.6 g of 4-(3H-imidazo[4,5-c]pyridin-2-yl)fluorene-9(R,S)-amine obtained in Example 6, and 5 g of 2-amino-5-chloropyrimidine-4-carboxylic acid, in the presence of 5.6 g of EDCI and 1.9 g of HOBT in 115 ml of DMF for 15 hours. After successive washes with a saturated aqueous solution of sodium hydrogen carbonate and then with water, the crude mixture is purified by flash chromatography on silica gel, eluting with a mixture of dichloromethane and 7N solution of ammoniacal methanol (95-05 by volume), we obtain 6.1 g of N-[4-(3H-imidazo[4,5-c]pyridin-2-yl)-9H-fluoren-9(R,S)-yl]amide of 2-amino-5-chloropyrimidine-4-carboxylic acid, in the form of a white powder with the following characteristics:

Mass spectrum (E/I): m/z=453 (MH+).
Melting point (Kofler)=216° C.

Example 132

Synthesis of [4-(3H-imidazo[4,5-c]pyridin-2-yl)-9H-fluoren-9(R,S)-yl]amide of 3-bromo-1H-pyrrolo[2,3-b]pyridine-4-carboxylic acid In a 100 ml round-bottomed flask, dissolve 700 mg of [4-(3H-imidazo[4,5-c]pyridin-2-yl)-9H-fluoren-9(R,S)-yl] amide of 1H-pyrrolo[2,3-b]pyridine-4-carboxylic acid, obtained as in Example 92, in 15 ml of glacial acetic acid. After cooling to 10° C., add 89.4 µl of bromine and stir for 10 minutes at room temperature. Water is added (1 ml) and the solvent is then evaporated off. The solid obtained is washed successively with water, a saturated aqueous solution of sodium hydrogen carbonate and then water. After purification by flash chromatography on silica gel (40-63 µm), eluting with a mixture of dichloromethane and methanol (90-10 by volume), we obtain 670 mg of [4-(3H-imidazo[4,5-c]pyridin-2-yl)-9H-fluoren-9(R,S)-yl]amide of 3-bromo-1H-pyrrolo[2,3-b]pyridine-4-carboxylic acid, in the form of a yellow foam with the following characteristics:

Mass spectrum (LCMS): m=521 (MH+).

Examples 133 to 150

The products of Examples 133 to 150 were prepared in parallel according to the following procedure:

71 mg (0.370 mmol, 1.1 eq) of EDCI hydrochloride and 50 mg (0.370 mmol, 1.1 eq) of HOBT are added to 100 mg (0.335 mmol) of amine and x mg (0.335 mmol, 1.0 eq) of acid in 2.5 ml of DMF. When the acid is in the form of hydrochloride, 47 µl (0.335 mmol, 1.0 eq) of TEA are added. The reaction medium is stirred for 20 h at room temperature (25° C.) and then concentrated.

The solid or pasty crude product is taken up in 4 ml of water and filtered, and washed successively with 4 ml of water, 2 times 4 ml of a saturated aqueous solution of sodium hydrogen carbonate, 4 ml of water and then 2 times 5 ml of isopropyl ether.

The products isolated under the above conditions have an LC/MS purity of greater than 90% under the following conditions:

Column Hypersil Gold C18 3×50 mm (particle diameter: 3 µm)

U.V. detection DAD (200<λ<400 nm)

Gradient of solvents A (water containing 0.1% of formic acid) and B (acetonitrile) at a flow rate of 0.8 ml/min

| Time (min) | % A | % B |
|---|---|---|
| 0 | 95 | 5 |
| 5 | 5 | 95 |
| 5.5 | 5 | 95 |
| 6.5 | 95 | 5 |
| 7 | 95 | 5 |

When a supplementary purification was necessary, the conditions of this purification are described in the table below, which also contains the masses obtained and the characteristics of the compounds of Examples 133 to 150

(Mass Spectrum and Retention Time by LC/MS Analysis)

| Example | Mass obtained (mg) | Mass spectrum (MH+) | LC/MS retention time (min) | Supplementary purification conditions |
|---|---|---|---|---|
| 133 | 113 | 499 | 4.18 | |
| 134 | 72 | 435 | 3.69 | |
| 135 | 68 | 423 | 3.64 | |
| 136 | 112 | 504 | 3.33 | |
| 137 | 76 | 474 | 2.73 | |
| 138 | 75 | 439 | 2.51 | |
| 139 | 91 | 423 | 3 | |
| 140 | 104 | 475 | 3.36 | |
| 141 | 101 | 434 | 2.6 | |
| 142 | 40 | 447 | 3.43 | 0.5 mm prep silica plate 7N $CH_2Cl_2$/$NH_3$ in MeOH 96/4 |
| 143 | 53 | 473 | 3.14 | 0.5 mm prep silica plate 7N $CH_2Cl_2$/$NH_3$ in MeOH 96/4 |
| 144 | 45 | 495 | 2.6 | Crystallization from 80/20 $CH_2Cl_2$/MeOH |
| 145 | 27 | 465 | 3.26 | 0.5 mm prep silica plate 7N $CH_2Cl_2$/$NH_3$ in MeOH 96/4 |

-continued

| Example | Mass obtained (mg) | Mass spectrum (MH+) | LC/MS retention time (min) | Supplementary purification conditions |
|---|---|---|---|---|
| 146 | 74 | 512 | 2.78 | Crystallization from 80/20 $CH_2Cl_2$/MeOH |
| 147 | 77 | 451 | 2.5 | 0.5 mm prep silica plate 7N $CH_2Cl_2$/$NH_3$ in MeOH 95/5 |
| 148 | 100 | 528 | 2.59 | 0.5 mm prep silica plate 7N $CH_2Cl_2$/$NH_3$ in MeOH 95/5 |
| 149 | 81 | 507 | 2.65 | |
| 150 | 95 | 475 | 2.67 | |

The compound of Example 145 can also be characterized by the following NMR spectrum (400 MHz—δ in ppm—DMSO-d6): 0.80 (s, 3H); 1.33 (s, 3H); 1.80 (m, 1H); 1.89 (m, 1H); 2.00 (s, 3H); 2.17 (dd, J=8.5 and 14.0 Hz, 1H); 2.25 (dd, J=7.5 and 14.0 Hz, 1H); 2.40 (m, 1H); 2.96 (m, 1H); 6.10 (d, J=8.5 Hz, 1H); 7.22 (t, J=7.5 Hz, 1H); 7.32 (t, J=7.5 Hz, 1H); from 7.44 to 7.53 (m, 3H); from 7.59 to 7.69 (m, 3H); 8.37 (d, J=5.5 Hz, 1H); 8.52 (d, J=8.5 Hz, 1H); 9.02 (s, 1H); 13.4 (m very spread-out, 1H).

Example 151

[4-(3H-imidazo[4,5-c]pyridin-2-yl)-9H-fluoren-9(R,S)-yl]amide of indole-3-carboxylic acid The procedure used in Example 14 is followed, starting from 298 mg of 4-(3H-imidazo[4,5-c]pyridin-2-yl)fluorene-9(R,S)-amine, obtained in Example 6, and 169 mg of indole-3-carboxylic acid, in the presence of 211 mg of EDCI and 149 mg of HOBT in 5 ml of DMF for 72 hours. After purification by flash chromatography on silica gel (15-40 μm), eluting with a mixture of methanol-dichloromethane (10/90 by volume), we recover 112 mg of [4-(3H-imidazo[4,5-c]pyridin-2-yl)-9H-fluoren-9(R,S)-yl]amide of indole-3-carboxylic acid, in the form of a beige powder with the following characteristics:

Melting point (Kofler)=210° C. decomposition.
$^1$H-NMR spectrum (300 MHz, DMSO-d6) δ in ppm: 6.43 (d, J=8.5 Hz, 1H); from 7.12 to 7.27 (m, 3H); 7.33 (dt, J=1.5 and 7.5 Hz, 1H); from 7.41 to 7.72 (m, 6H); 7.75 (d broad, J=7.5 Hz, 1H); 8.11 (d, J=3.0 Hz, 1H); 8.31 (m, 1H); 8.40 (d, J=5.5 Hz, 1H); 8.55 (d, J=8.5 Hz, 1H); 9.05 (s broad, 1H); 11.55 (m broad, 1H); 13.35 (m broad, 1H).
Mass spectrum (ES): m/z=442 (MH+).

Example 152

Synthesis of the dextrorotatory enantiomer of [4-(3H-imidazo[4,5-c]pyridin-2-yl)-9H-fluoren-9(R,S)-yl]amide of 1H-pyrrolo[2,3-b]pyridine-4-carboxylic acid 8 g of [4-(3H-imidazo[4,5-c]pyridin-2-yl)-9H-fluoren-9(R,S)-yl]amide of 1H-pyrrolo[2,3-b]pyridine-4-carboxylic acid, obtained in Example 92, are purified, in the supercritical phase, on a preparative chiral column 5 cm in diameter, containing 350 g of 20 μm of Chiralcel silica, in 20 successive injections. Elute, at a flow rate of 250 ml/min, with 100 bar of carbon dioxide in the presence of 30% of methanol and 0.1% of triethylamine as cosolvent. By recovering and concentrating under reduced pressure the first fractions eluted, we obtain 3.59 g of dextrorotatory enantiomer, in the form of a white powder with the following characteristics:

$^1$H-NMR spectrum (300 MHz, DMSO-d6, δ in ppm): 6.42 (d, J=8.5 Hz, 1H); 6.90 (m, 1H); 7.25 (t, J=7.5 Hz, 1H); 7.35 (t, J=7.5 Hz, 1H); 7.47 (d, J=5.0 Hz, 1H); from 7.50 to 7.57 (m, 2H); from 7.60 to 7.72 (m, 4H); 7.79 (d, J=7.5 Hz, 1H); 8.29 (d, J=5.0 Hz, 1H); 8.37 (d, J=5.5 Hz, 1H); 9.04 (s broad, 1H); 9.28 (d, J=8.5 Hz, 1H); 11.85 (s broad, 1H); 13.35 (m spread-out, 1H).
αD20=+136.5+/−2° (c=0.507; DMSO).

Example 153

Synthesis of the levorotatory enantiomer of [4-(3H-imidazo[4,5-c]pyridin-2-yl)-9H-fluoren-9(R,S)-yl]amide of 1H-pyrrolo[2,3-b]pyridine-4-carboxylic acid Following the same procedure as in Example 153, but recovering the second fractions eluted and concentrating under reduced pressure, we obtain 3.53 g of levorotatory enantiomer with the following characteristics:
αD20=−117.5+/−2° (c=0.5; DMSO).

Example 154

Synthesis of N-[4-(3H-imidazo[4,5-c]pyridin-2-yl)-9H-fluoren-9(R,S)-yl]amide of 3-hydroxy-2-methylquinoline-4-carboxylic acid The procedure used in Example 14 is followed, starting from 200 mg of 4-(3H-imidazo[4,5-c]pyridin-2-yl)fluorene-9(R,S)-amine, obtained in Example 6, and 143 mg of 3-hydroxy-2-methylquinoline-4-carboxylic acid, in the presence of 135 mg of EDCI and 45 mg of HOBT in 2 ml of DMF for 20 hours. After successive washes with a saturated aqueous solution of sodium hydrogen carbonate and then with water, the crude mixture is purified by flash chromatography on silica gel, eluting with a mixture of dichloromethane and methanol (95-05 by volume), and we obtain 16 mg of N-[4-(3H-imidazo[4,5-c]pyridin-2-yl)-9H-fluoren-9(R,S)-yl] amide of 3-hydroxy-2-methylquinoline-4-carboxylic acid, in the form of a yellow solid with the following characteristics:
Mass spectrum (LC/MS): m/z=483 (M+).
Melting point (Kofler)=240° C.

Example 155

Synthesis of N-[4-(3H-imidazo[4,5-c]pyridin-2-yl)-9H-fluoren-9(R,S)-yl]-3,5-dimethoxybenzamide The procedure used in Example 14 is followed, starting from 150 mg of 4-(3H-imidazo[4,5-c]pyridin-2-yl)fluorene-9(R,S)-amine, obtained in Example 6, and 92 mg of 3,5-dimethoxybenzoic acid, in the presence of 98 mg of EDCI and 34 mg of HOBT in 2 ml of DMF for 20 hours. After successive washes with a saturated aqueous solution of sodium hydrogen carbonate and then with water, the crude mixture is purified by flash chromatography on silica gel, eluting with a mixture of dichloromethane and methanol (95-05 by volume), and we obtain 18 mg of N-[4-(3H-imidazo[4,5-c]pyridin-2-yl)-9H-fluoren-9(R,S)-yl]-3,5-dimethoxybenzamide, in the form of a white foam with the following characteristics:
Mass spectrum (E/I): m/z=462 (M+).

Example 156

[4-(3H-imidazo[4,5-c]pyridin-2-yl)-9H-fluoren-9(R,S)-yl]amide of bromo-6-hydroxy-2-quinoline-4-carboxylic acid The procedure used in Example 14 is followed, starting from 298 mg of 4-(3H-imidazo[4,5-c]pyridin-2-yl)fluorene-9(R,S)-amine, obtained in Example 6, and 282 mg of bromo-6-hydroxy-2-quinoline-4-carboxylic acid, in the presence of 211 mg of EDCI and 149 mg of HOBT in 5 ml of DMF for 20 hours. After evaporation to dryness under vacuum, the residue is taken up with 100 ml of ethyl acetate and 50 ml of a saturated solution of sodium bicarbonate. The mixture is filtered over sintered glass and the solid is dried under vacuum at 40° C. We obtain 513 mg of [4-(3H-imidazo[4,5-c]pyridin-2-yl)-9H-fluoren-9(R,S)-yl]amide of bromo-6-hydroxy-2-quinoline-4-carboxylic acid, in the form of a beige solid with the following characteristics:

$^1$H-NMR spectrum (400 MHz, DMSO-d6) δ in ppm: 6.29 (d, J=8.5 Hz, 1H); 6.72 (s, 1H); 7.22 (t broad, J=7.5 Hz, 1H); from 7.26 to 7.34 (m, 2H); 7.42 (m, 2H); 7.64 (d broad, J=8.0 Hz, 1H); 7.68 (m broad, 1H); 7.73 (dd, J=2.0 and 8.5 Hz, 1H); 7.84 (m broad, 1H); 8.02 (m broad, 1H); 8.09 (d, J=2.0 Hz, 1H); 8.27 (m broad, 1H); 8.79 (s broad, 1H); 9.51 (d, J=8.5 Hz, 1H); 12.2 (m spread-out, 2H).

Mass spectrum (ES): m/z=548 (MH+).

Example 157

Synthesis of N-[4-(3H-imidazo[4,5-c]pyridin-2-yl)-9H-fluoren-9(R,S)-yl]amide of 9H-purine-6-carboxylic acid The procedure used in Example 14 is followed, starting from 300 mg of 4-(3H-imidazo[4,5-c]pyridin-2-yl)fluorene-9(R,S)-amine, obtained in Example 6, and 182 mg of 9H-purine-6-carboxylic acid, in the presence of 212 mg of EDCI and 70 mg of HOBT in 4 ml of DMF for 15 hours. After successive washes with a saturated aqueous solution of sodium hydrogen carbonate, with water and then with isopropyl ether, we obtain 400 mg of N-[4-(3H-imidazo[4,5-c]pyridin-2-yl)-9H-fluoren-9(R,S)-yl]amide of 9H-purine-6-carboxylic acid, in the form of a white solid with the following characteristics:

Mass spectrum (E/I): m/z=444 (M+).

Example 158

Synthesis of N-[4-(3H-imidazo[4,5-c]pyridin-2-yl)-9H-fluoren-9(R,S)-yl]amide of 2-amino-6-methylpyrimidine-4-carboxylic acid The procedure used in Example 14 is followed, starting from 300 mg of 4-(3H-imidazo[4,5-c]pyridin-2-yl)fluorene-9(R,S)-amine, obtained in Example 6, and 170 mg of 2-amino-6-methylpyrimidine-4-carboxylic acid, in the presence of 212 mg of EDCI and 68 mg of HOBT in 4 ml of DMF for 4 hours. After successive washes with a saturated aqueous solution of sodium hydrogen carbonate and then with water, the crude mixture is purified by flash chromatography on silica gel, elution being carried out with a mixture of dichloromethane and a 7N solution of ammoniacal methanol (95-05 by volume), and we obtain 50 mg of N-[4-(3H-imidazo[4,5-c]pyridin-2-yl)-9H-fluoren-9(R,S)-yl]amide of 2-amino-6-methylpyrimidine-4-carboxylic acid, in the form of a pale yellow solid with the following characteristics:

Mass spectrum (E/I): m/z=433 (M+).
Melting point (Kofler)=210° C.

Example 159

Synthesis of 2-ethyl-6-hydroxy-N-[4-(3H-imidazo[4,5-c]pyridin-2-yl)-9H-fluoren-9(R,S)-yl]isonicotinamide The procedure used in Example 14 is followed, starting from 300 mg of 4-(3H-imidazo[4,5-c]pyridin-2-yl)fluorene-9(R,S)-amine, obtained in Example 6, and 185 mg of 2-ethyl-6-hydroxyisonicotinic acid, in the presence of 212 mg of EDCI and 68 mg of HOBT in 7 ml of DMF for 20 hours. After successive washes with a saturated aqueous solution of sodium hydrogen carbonate, with water and then with isopropyl ether, we obtain 330 mg of 2-ethyl-6-hydroxy-N-[4-(3H-imidazo[4,5-c]pyridin-2-yl)-9H-fluoren-9(R,S)-yl]isonicotin-amide, in the form of a pale yellow powder with the following characteristics:

Mass spectrum (LC/MS): m/z=447 (M+).

The 2-ethyl-6-hydroxyisonicotinic acid can be obtained according to EP542059.

Example 160

Synthesis of 3,5-dichloro-N-[4-(3H-imidazo[4,5-c]pyridin-2-yl)-9H-fluoren-9(R,S)-yl]isonicotinamide The procedure used in Example 14 is followed, starting from 300 mg of 4-(3H-imidazo[4,5-c]pyridin-2-yl)fluorene-9(R,S)-amine, obtained in Example 6, and 193 mg of 3,5-dichloroisonicotinic acid, in the presence of 212 mg of EDCI and 68 mg of HOBT in 10 ml of DMF for 15 hours. After successive washes with a saturated aqueous solution of sodium hydrogen carbonate and then with water, the crude mixture is purified by flash chromatography on silica gel, eluting with a mixture of dichloromethane and methanol (90-10 by volume), and we obtain 250 mg of 3,5-dichloro-N-[4-(3H-imidazo[4,5-c]pyridin-2-yl)-9H-fluoren-9(R,S)-yl]isonicotinamide, in the form of a white solid with the following characteristics:

Mass spectrum (LC/MS): m/z=472 (M+).
Melting point (Kofler)=240° C.

Example 161

Synthesis of [4-(3H-imidazo[4,5-c]pyridin-2-yl)-9H-fluoren-9(R,S)-yl]amide of 5-amino-3H-1,2,3-triazole-4-carboxylic acid The procedure used in Example 14 is followed, starting from 300 mg of 4-(3H-imidazo[4,5-c]pyridin-2-yl)fluorene-9(R,S)-amine, obtained in Example 6, and 135 mg of 5-amino-3H-1,2,3-triazole-4-carboxylic acid in 3 ml of dimethylformamide, in the presence of 289 mg of 1-(3-dimethylaminopropyl)-3-ethylcarbodiimide hydrochloride (EDCI) and 204 mg of 1-hydroxybenzotriazole (HOBT), for 20 hours at room temperature. After purification by flash chromatography on silica gel (40-63 μm), eluting with a mixture of dichloromethane and methanol (9/1 then 85/15 by volume), we obtain 100 mg of [4-(3H-imidazo[4,5-c]pyridin-2-yl)-9H-fluoren-9(R,S)-yl]amide of 5-amino-3H-1,2,3-triazole-4-carboxylic acid, in the form of a pale yellow powder with the following characteristics:

Mass spectrum (LCMS): m/z=408 (M+).

Example 162

Synthesis of N-[4-(3H-imidazo[4,5-c]pyridin-2-yl)-9H-fluoren-9(R,S)-yl]amide of 6-methyl-2-methylaminopyrimidine-4-carboxylic acid The procedure used in Example 14 is followed, starting from 90 mg of 4-(3H-imidazo[4,5-c]pyridin-2-yl)fluorene-9(R,S)-amine, obtained in Example 6, and 50 mg of 6-methyl-2-methylaminopyrimidine-4-carboxylic acid, in the presence of 64 mg of EDCI and 20 mg of HOBT in 2 ml of DMF for 6 hours. After successive washes with a saturated aqueous solution of sodium hydrogen carbonate and then with water, the crude mixture is purified by flash chromatography on silica gel, eluting with a mixture of dichloromethane and methanol (90-10 by volume), and we obtain 35 mg of N-[4-(3H-imidazo[4,5-c]pyridin-2-yl)-9H-fluoren-9(R,S)-yl]amide of 6-methyl-2-methylamino-pyrimidine-4-carboxylic acid, in the form of a white powder with the following characteristics:

Mass spectrum (LC/MS): m/z=447 (M+).

Melting point (Kofler)=196° C.

The 6-methyl-2-methylaminopyrimidine-4-carboxylic acid can be obtained by hydrolysis of the corresponding methyl ester according to Helvetica Chimica Acta, 81(2), 231-235; 1998.

Example 163

Synthesis of N-[4-(3H-imidazo[4,5-c]pyridin-2-yl)-9H-fluoren-9(R,S)-yl]amide of 5-amino-2,6-dihydroxypyrimidine-4-carboxylic acid The procedure used in Example 14 is followed, starting from 300 mg of 4-(3H-imidazo[4,5-c]pyridin-2-yl)fluorene-9(R,S)-amine, obtained in Example 6, and 172 mg of 5-amino-2,6-dihydroxypyrimidine-4-carboxylic acid, in the presence of 212 mg of EDCI and 68 mg of HOBT in 15 ml of DMF for 15 hours. After successive washes with a saturated aqueous solution of sodium hydrogen carbonate and then with water, the crude mixture is purified by flash chromatography silica gel, eluting with a mixture of dichloromethane and methanol (90-10 by volume), and we obtain 210 mg of N-[4-(3H-imidazo[4,5-c]pyridin-2-yl)-9H-fluoren-9(R,S)-yl]amide of 5-amino-2,6-dihydroxy-pyrimidine-4-carboxylic acid, in the form of a white powder with the following characteristics:

Mass spectrum (LC/MS): m/z=451 (M+).

Example 164

Synthesis of N-[4-(9H-purin-8-yl)-9H-fluoren-9(R,S)-yl]amide of isonicotinic acid Stage 1: The procedure used in stage 1 of Example 1 is followed, starting from 2 g of 4,5-diaminopyrimidine in 150 ml of dichloromethane, 3.4 ml of triethylamine and 3 g of fluoren-4-one-9-carboxylic acid chloride. After stirring for 20 hours at room temperature, the reaction medium is poured onto a saturated aqueous solution of sodium hydrogen carbonate and extracted with dichloromethane. The organic phases are washed with water, dried over magnesium sulphate and concentrated under reduced pressure. After purification by flash chromatography on silica gel (40-63 μm), eluting with a mixture of dichloromethane and methanol (98/2 then 95/5 by volume), we obtain 1.1 g of (5-aminopyrimidin-4-yl)amide of 9-oxo-9H-fluorene-4-carboxylic acid, which is used as it is in the next stage, with the following characteristics:

Mass spectrum (E/I): m/z=316 (M+).

Stage 2: In a 250 ml round-bottomed flask under an argon atmosphere, heat, at 95° C. for 5 hours, a solution of 1.1 g of (5-aminopyrimidin-4-yl)amide of 9-oxo-9H-fluorene-4-carboxylic acid, obtained in the previous step, in 55 ml of acetic acid. After cooling, bring to dryness under reduced pressure. Purify by flash chromatography on silica gel (40-63 μm), eluting with a mixture of dichloromethane and methanol (98/2 by volume), followed by making a paste in isopropyl ether, and, in this way, we obtain 565 mg of 4-(9H-purin-8-yl)fluoren-9-one, in the form of a pale yellow powder, which is used as it is in the following stage, with the following characteristics:

Mass spectrum (E/I): m/z=298 (M+).

$^1$H-NMR spectrum (400 MHz, δ in ppm, DMSO-d6): 7.42 (t, J=7.5 Hz, 1H); 7.50 (dt, J=1.0 and 7.5 Hz, 1H); 7.61 (t, J=7.5 Hz, 1H); 7.67 (d, J=7.5 Hz, 1H); 7.70 (d, J=7.5 Hz, 1H); 7.86 (d, J=8.0 Hz, 1H); 7.92 (d, J=7.5 Hz, 1H); 9.00 (s, 1H); 9.25 (s, 1H); 14.5 (s broad, 1H).

Stage 3: The procedure used in Example 5 is followed, starting from 564 mg of 4-(9H-purin-8-yl)fluoren-9-one, obtained in the previous step, 394 mg of hydroxylamine hydrochloride and 776 mg of sodium acetate in 12 ml of ethanol for 20 h at room temperature. After concentration of the solvent under reduced pressure, the residue is taken up successively with water, then toluene and, finally, made into a paste with diisopropyl ether, and in this way, we obtain 502 mg of 4-(9H-purin-8-yl)fluoren-9-one oxime (Z,E), as a 50-50 mixture of the Z and E isomers, in the form of an off-white powder with the following characteristics:

Mass spectrum (LCMS): m/z=313 (M+).

Stage 4: The procedure used in Example 6 is followed, in an autoclave, starting from 450 mg of 4-(9H-purin-8-yl)fluoren-9-one oxime (Z,E), obtained in the previous stage, in solution in a mixture of 25 ml of ethanol and 25 ml of tetrahydrofuran, in the presence of Raney activated nickel, under an initial hydrogen pressure of 1 bar, at 600 for 20 hours. After filtration of the catalyst over Celite, and concentration of the filtrate under reduced pressure, in this way, we obtain 384 mg of 4-(9H-purin-8-yl)-9H-fluorene-9(R,S)-amine, in the form of a beige powder with the following characteristics:

Mass spectrum (EI): m/z=299 (M+).

$^1$H-NMR spectrum (400 MHz, δ in ppm, DMSO-d6): 4.83 (s, 1H); 7.17 (t, J=7.5 Hz, 1H); 7.31 (t, J=7.5 Hz, 1H); 7.48 (t, J=7.5 Hz, 1H); 7.57 (d broad, J=8.0 Hz, 1H); 7.65 (d, J=7.5 Hz, 1H); 7.69 (d, J=7.5 Hz, 1H); 7.86 (d, J=7.5 Hz, 1H); 8.90 (s, 1H); 9.11 (s, 1H).

Stage 5: The procedure used in Example 14 is followed, starting from 300 mg of 4-(9H-purin-8-yl)-9H-fluoren-9(R,S)-amine, obtained in the previous step, and 129 mg of isonicotinic acid in 3 ml of dimethylformamide, in the presence of 288 mg of 1-(3-dimethylaminopropyl)-3-ethylcarbodiimide (EDCI) and 204 mg of 1-hydroxybenzotriazole (HOBT) for 20 hours at room temperature. After purification by flash chromatography on silica gel (40-63 μm), eluting with a mixture of dichloromethane and methanol (95/5 then 9/1 by volume), we obtain 230 mg of N-[4-(9H-purin-8-yl)-9H-fluoren-9(R,S)-yl]amide of isonicotinic acid, in the form of a beige powder with the following characteristics:

Mass spectrum (EI/LCMS): m/z=404 (M+).

$^1$H-NMR spectrum (400 MHz, δ in ppm, DMSO-d6): 6.37 (d, J=8.5 Hz, 1H); 7.28 (t, J=7.5 Hz, 1H); 7.36 (t, J=7.5 Hz, 1H); 7.54 (t, J=7.5 Hz, 1H); 7.60 (m, 2H); 7.72 (d, J=7.5 Hz, 1H); 7.77 (d, J=7.5 Hz, 1H); 7.88 (d broad, J=6.0 Hz, 2H); 8.75 (d broad, J=6.0 Hz, 2H); 9.00 (s, 1H); 9.22 (s broad, 1H); 9.48 (d, J=8.5 Hz, 1H); 13.95 (m spread-out, 1H).

Example 165

Synthesis of N-[4-(3H-imidazo[4,5-c]pyridin-2-yl)-9H-fluoren-9(R,S)-yl]amide of 3-aminoquinoline-4-carboxylic acid The procedure used in Example 14 is followed, starting from 300 mg of 4-(3H-imidazo[4,5-c]pyridin-2-yl)fluorene-9(R,S)-amine, obtained in Example 6, and 189 mg of 3-aminoquinoline-4-carboxylic acid, in the presence of 212 mg of EDCI and 68 mg of HOBT in 7 ml of DMF for 15 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (95-05 by volume), and we obtain 230 mg of N-[4-(3H-imidazo[4,5-c]pyridin-2-yl)-9H-fluoren-9(R,S)-yl]amide of 3-aminoquinoline-4-carboxylic acid, in the form of a white powder with the following characteristics:

Mass spectrum (E/I): m/z=468 (M+).
Melting point (Kofler)=234° C.

The 3-aminoquinoline-4-carboxylic acid can be obtained according to Journal of Heterocyclic Chemistry, 17 (3), 465-73; 1980.

Example 166

Synthesis of N-[4-(3H-imidazo[4,5-c]pyridin-2-yl)-9H-fluoren-9(R,S)-yl]amide of 6-methoxyquinoline-4-carboxylic acid The procedure used in Example 14 is followed, starting from 300 mg of 4-(3H-imidazo[4,5-c]pyridin-2-yl)fluorene-9(R,S)-amine, obtained in Example 6, and 300 mg of 6-methoxyquinoline-4-carboxylic acid, in the presence of 422 mg of EDCI and 297 mg of HOBT in 7 ml of DMF for 15 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (95-05 by volume), and we obtain 180 mg of N-[4-(3H-imidazo[4,5-c]pyridin-2-yl)-9H-fluoren-9(R,S)-yl]amide of 6-methoxy-quinoline-4-carboxylic acid in the form of a yellow solid with the following characteristics:

Mass spectrum (E/I): m/z=483 (M+).

Example 167 and 172

Synthesis of N-[4-(3H-imidazo[4,5-c]pyridin-2-yl)-9H-fluoren-9(R,S)-yl]amide of 3,4-diaminobenzoic acid and of N-[4-(3H-imidazo[4,5-c]pyridin-2-yl)-9H-fluoren-9(R,S)-yl]amide of 4-amino-3-hydroxybenzoic acid Stage 1: The procedure used in Example 14 is followed, starting from 600 mg of 4-(3H-imidazo[4,5-c]pyridin-2-yl)fluorene-9(R,S)-amine, obtained in Example 6, and 424 mg of 3,4-dinitrobenzoic acid, in the presence of 422 mg of EDCI and 300 mg of HOBT in 14 ml of DMF for 15 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (95-05 by volume), and we obtain 215 mg of N-[4-(3H-imidazo[4,5-c]pyridin-2-yl)-9H-fluoren-9(R,S)-yl]amide of 3,4-dinitrobenzoic acid, in the form of a yellow solid with the following characteristics:

Mass spectrum (E/I): m/z=492 (M+).

Stage 2: In a 45 ml autoclave, dissolve 365 mg of N-[4-(3H-imidazo[4,5-c]pyridin-2-yl)-9H-fluoren-9(R,S)-yl]amide of 3,4-dinitrobenzoic acid, obtained in stage 1, in a mixture of 60 ml of ethanol, add 78 mg of 10% palladium-on-charcoal, and then subject to an initial hydrogen pressure of 1 bar for 20 hours. After cooling, the volume of hydrogen absorbed is 100 ml. After purging with argon, open the autoclave, filter over celite and rinse with ethanol. The filtrate is concentrated under reduced pressure and purified by flash chromatography on silica gel, eluting with a mixture of dichloromethane and a 7N solution of ammoniacal methanol (95-05 by volume), and we obtain:

firstly, 70 mg of N-[4-(3H-imidazo[4,5-c]pyridin-2-yl)-9H-fluoren-9(R,S)-yl]amide of 3,4-diaminobenzoic acid, in the form of a yellow foam with the following characteristics:

Mass spectrum (E/I): m/z=432 (M+);

and, secondly, 150 mg of N-[4-(3H-imidazo[4,5-c]pyridin-2-yl)-9H-fluoren-9(R,S)-yl]amide of 4-amino-3-hydroxybenzoic acid, in the form of a yellow foam with the following characteristics:

Mass spectrum (E/I): m/z=433 (M+).

Example 168

Synthesis of 3,5-dihydroxy-N-[4-(3H-imidazo[4,5-c]pyridin-2-yl)-9H-fluoren-9(R,S)-yl]benzamide The procedure used in Example 14 is followed, starting from 300 mg of 4-(3H-imidazo[4,5-c]pyridin-2-yl)fluorene-9(R,S)-amine, obtained in Example 6, and 308 mg of 3,5-dihydroxybenzoic acid, in the presence of 422 mg of EDCI and 297 mg of HOBT in 7 ml of DMF for 20 hours. After successive washes with a saturated aqueous solution of sodium hydrogen carbonate and then with water, the crude mixture is purified by preparative HPLC on a Kromasil C8 column, eluting with a mixture of water supplemented with 0.1% of trifluoroacetic acid and methanol (80-20 by volume), and 170 mg of 3,5-dihydroxy-N-[4-(3H-imidazo[4,5-c]pyridin-2-yl)-9H-fluoren-9(R,S)-yl]benzamide are obtained in the form of a pale yellow foam with the following characteristics:

Mass spectrum (E/I): m/z=483 (M+).

Example 169

Synthesis of [4-(3H-imidazo[4,5-c]pyridin-2-yl)-9H-fluoren-9(R,S)-yl]amide of 1H-imidazole-4-carboxylic acid The procedure used in Example 14 is followed, starting from 300 mg of 4-(3H-imidazo[4,5-c]pyridin-2-yl)fluorene-9(R,S)-amine, obtained in Example 6, and 118 mg of 1H-imidazole-4-carboxylic acid in 3 ml of dimethylformamide, in the presence of 289 mg of 1-(3-dimethylaminopropyl)-3-ethylcarbodiimide hydrochloride (EDCI) and 204 mg of 1-hydroxybenzotriazole (HOBT), for 20 hours at room temperature. After purification by flash chromatography on silica gel (40-63 μm), eluting with a mixture of dichloromethane and 7N ammonia in methanol (95/5 then 9/1 by volume), we obtain 52 mg of [4-(3H-imidazo[4,5-c]pyridin-2-yl)-9H-fluoren-9(R,S)-yl]amide of 1H-imidazole-4-carboxylic acid, in the form of a beige powder with the following characteristics:

Mass spectrum (EI/LCMS): m/z=392 (M+).

Example 170

Synthesis of [4-(3H-imidazo[4,5-c]pyridin-2-yl)-9H-fluoren-9(R,S)-yl]amide of 5-amino-2H-1,2,4-triazole-3-carboxylic acid The procedure used in Example 14 is followed, starting from 300 mg of 4-(3H-imidazo[4,5-c]pyridin-2-yl)fluorene-9(R,S)-amine, obtained in Example 6, and 144 mg of 5-amino-2H-1,2,4-triazole-3-carboxylic acid in 5 ml of dimethylformamide, in the presence of 289 mg of 1-(3-dimethylaminopropyl)-3-ethylcarbodiimide hydrochloride (EDCI) and 204 mg of 1-hydroxy-benzotriazole (HOBT), for 20 hours at room temperature. After purification by flash chromatography on silica gel (40-63 µm), eluting with a mixture of dichloromethane and methanol (9/1 then 8/2 by volume), we obtain 124 mg of [4-(3H-imidazo[4,5-c]pyridin-2-yl)-9H-fluoren-9(R,S)-yl]amide of 5-amino-2H-1,2,4-triazole-3-carboxylic acid, in the form of an off-white powder with the following characteristics:

Mass spectrum (EI/CI): m/z=408 (M+).

Example 171

Synthesis of N-[4-(3H-imidazo[4,5-c]pyridin-2-yl)-9H-fluoren-9(R,S)-yl]amide of 2-methylbenzoxazole-4-carboxylic acid The procedure used in Example 14 is followed, starting from 300 mg of 4-(3H-imidazo[4,5-c]pyridin-2-yl)fluorene-9(R,S)-amine, obtained in Example 6, and 178 mg of 2-methylbenzoxazole-4-carboxylic acid, in the presence of 212 mg of EDCI and 68 mg of HOBT in 7 ml of DMF for 20 hours. After successive washes with a saturated aqueous solution of sodium hydrogen carbonate, with water and then with isopropyl ether, we obtain 310 mg of N-[4-(3H-imidazo[4,5-c]pyridin-2-yl)-9H-fluoren-9(R,S)-yl]amide of 2-methylbenzoxazole-4-carboxylic acid, in the form of a grey powder with the following characteristics:

Mass spectrum (LC/MS): m/z=457 (M+).
Melting point (Kofler)=200° C.

Example 172

Synthesis of [4-(3H-imidazo[4,5-c]pyridin-2-yl)-9H-fluoren-9(R,S)-yl]amide of 4-amino-3-hydroxybenzoic acid The procedure used in Example 14 is followed, starting from 300 mg of 4-(3H-imidazo[4,5-c]pyridin-2-yl)fluorene-9(R,S)-amine, obtained in Example 6, and 153 mg of 4-amino-3-hydroxybenzoic acid in 5 ml of dimethylformamide, in the presence of 289 mg of 1-(3-dimethylaminopropyl)-3-ethylcarbodiimide hydrochloride (EDCI) and 204 mg of 1-hydroxybenzotriazole (HOBT), for 20 hours at room temperature. After purification by flash chromatography on silica gel (40-63 µm), eluting with a mixture of dichloromethane and methanol (8/2 then 5/5 by volume), we obtain 100 mg of [4-(3H-imidazo[4,5-c]pyridin-2-yl)-9H-fluoren-9(R,S)-yl]amide of 4-amino-3-hydroxybenzoic acid, in the form of an off-white powder with the following characteristics:

Mass spectrum (EI/CI): m/z=433 (M+).

Example 173

Synthesis of 2-carbamoyl-N-[4-(3H-imidazo[4,5-c]pyridin-2-yl)-9H-fluoren-9(R,S)-yl]isonicotinamide The procedure used in Example 14 is followed, starting from 300 mg of 4-(3H-imidazo[4,5-c]pyridin-2-yl)fluorene-9(R,S)-amine, obtained in Example 6, and 175 mg of carbamoyl-2-isonicotinic acid, in the presence of 210 mg of EDCI and 148 mg of HOBT in 7 ml of DMF for 20 hours. After successive washes with a saturated aqueous solution of sodium hydrogen carbonate, with water, and then with isopropanol, we obtain 160 mg of 2-carbamoyl-N-[4-(3H-imidazo[4,5-c]pyridin-2-yl)-9H-fluoren-9(R,S)-yl]isonicotinamide, in the form of a brown solid with the following characteristics:

Mass spectrum (E/I): m/z=446 (M+).

Example 174

Synthesis of N-[4-(3H-imidazo[4,5-c]pyridin-2-yl)-9H-fluoren-9(R,S)-yl]amide of pyridine-3,4-dicarboxylic acid 3-methyl ester The procedure used in Example 14 is followed, starting from 300 mg of 4-(3H-imidazo[4,5-c]pyridin-2-yl)-fluorene-9(R,S)-amine, obtained in Example 6, and 183 mg of pyridine-3,4-dicarboxylic acid 3-methyl ester, in the presence of 212 mg of EDCI and of 68 mg of HOBT in 7 ml of DMF for 20 hours. After successive washes with a saturated aqueous solution of sodium hydrogen carbonate, with water, ethyl acetate then with isopropyl ether, we obtain 110 mg of N-[4-(3H-imidazo[4,5-c]pyridin-2-yl)-9H-fluoren-9(R,S)-yl] amide of pyridine-3,4-dicarboxylic acid 3-methyl ester in the form of a white solid, with the following characteristics:

Mass spectrum (E/I): m/z=461 (M+).
Melting point (Kofler)=196° C.

Example 175

Synthesis of [4-(3H-imidazo[4,5-c]pyridin-2-yl)-9H-fluoren-9(R,S)-yl]amide of 5-hydroxy-4H-1,2,4-triazole-3-carboxylic acid The procedure used in Example 14 is followed, starting from 330 mg of 4-(3H-imidazo[4,5-c]pyridin-2-yl)fluorene-9(R,S)-amine, obtained in Example 6, and 150 mg of 5-hydroxy-4H-1,2,4-triazole-3-carboxylic acid in 3.3 ml of dimethylformamide, in the presence of 318 mg of 1-(3-dimethylaminopropyl)-3-ethylcarbodiimide hydrochloride (EDCI) and 224 mg of 1-hydroxybenzotriazole (HOBT), for 20 hours at room temperature. After purification by flash chromatography on silica gel (40-63 µm), eluting with a mixture of dichloromethane and methanol (9/1 by volume), we obtain 164 mg of [4-(3H-imidazo[4,5-c]pyridin-2-yl)-9H-fluoren-9(R,S)-yl]amide of 5-hydroxy-4H-1,2,4-triazole-3-carboxylic acid, in the form of a white powder with the following characteristics:

Mass spectrum (EI): m/z=409 (M+).

Example 176

Synthesis of N-[4-(3H-imidazo[4,5-c]pyridin-2-yl)-9H-fluoren-9(R,S)-yl]amide of pyrimidine-4-carboxylic acid The procedure used in Example 14 is followed, starting from 300 mg of 4-(3H-imidazo[4,5-c]pyridin-2-yl)fluorene-9(R,S)-amine, obtained in Example 6, and 126 mg of pyrimidine-4-carboxylic acid, in the presence of 212 mg of EDCI and 68 mg of HOBT in 7 ml of DMF for 6 hours. After successive washes with a saturated aqueous solution of sodium hydrogen carbonate, with water, and then with isopropyl ether, we obtain 90 mg of N-[4-(3H-imidazo[4,5-c]pyridin-2-yl)-9H-fluoren-9(R,S)-yl]amide of pyrimidine-4-carboxylic acid in the form of a brown solid with the following characteristics:
Mass spectrum (E/I): m/z=404 (M+).
Melting point (Kofler)=192° C.

Example 177

Synthesis of N-[4-(3H-imidazo[4,5-c]pyridin-2-yl)-9H-fluoren-9(R,S)-yl]amide of 1,3-dioxo-2,3-dihydro-1H-isoindole-5-carboxylic acid The procedure used in Example 14 is followed, starting from 300 mg of 4-(3H-imidazo[4,5-c]pyridin-2-yl)fluorene-9(R,S)-amine, obtained in Example 6, and 192 mg of 1,3-dioxo-2,3-dihydro-1H-isoindole-5-carboxylic acid, in the presence of 212 mg of EDCI and 150 mg of HOBT in 7 ml of DMF for 20 hours. After successive washes with a saturated aqueous solution of sodium hydrogen carbonate, with water, with methanol, and then with isopropyl ether, we obtain 122 mg of N-[4-(3H-imidazo[4,5-c]pyridin-2-yl)-9H-fluoren-9(R,S)-yl]amide of 1,3-dioxo-2,3-dihydro-1H-isoindole-5-carboxylic acid, in the form of a yellow powder with the following characteristics:
Mass spectrum (E/I): m/z=471 (M+).
Melting point (Kofler)=258° C.

Example 178

Synthesis of 4-hydroxy-N-[4-(3H-imidazo[4,5-c]pyridin-2-yl)-9H-fluoren-9(R,S)-yl]benzamide The procedure used in Example 14 is followed, starting from 300 mg of 4-(3H-imidazo[4,5-c]pyridin-2-yl)fluorene-9(R,S)-amine, obtained in Example 6, and 139 mg of 4-hydroxybenzoic acid, in the presence of 212 mg of EDCI and 150 mg of HOBT in 7 ml of DMF for 20 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (90-10 by volume), and we obtain 283 mg of 4-hydroxy-N-[4-(3H-imidazo[4,5-c]pyridin-2-yl)-9H-fluoren-9(R,S)-yl]benzamide, in the form of a yellow solid with the following characteristics:
Mass spectrum (E/I): m/z=418 (M+)

Example 179

Synthesis of 2,4-dihydroxy-N-[4-(3H-imidazo[4,5-c]pyridin-2-yl)-9H-fluoren-9(R,S)-yl]benzamide The procedure used in Example 14 is followed, starting from 300 mg of 4-(3H-imidazo[4,5-c]pyridin-2-yl)fluorene-9(R,S)-amine, obtained in Example 6, and 155 mg of 2,4-dihydroxybenzoic acid, in the presence of 212 mg of EDCI and 150 mg of HOBT in 7 ml of DMF for 20 hours. After successive washes with a saturated aqueous solution of sodium hydrogen carbonate and then with water, the crude mixture is purified by flash chromatography on silica gel, eluting with a mixture of dichloromethane and a 7N solution of ammoniacal methanol (90-10 by volume), and we obtain 168 mg of 2,4-dihydroxy-N-[4-(3H-imidazo[4,5-c]pyridin-2-yl)-9H-fluoren-9(R,S)-yl]benzamide, in the form of a yellow solid with the following characteristics:
Mass spectrum (E/I): m/z=434 (M+).

Example 180

[4-(3H-imidazo[4,5-c]pyridin-2-yl)-9H-fluoren-9(R,S)-yl]amide of 6-chloro-1H-pyrrolo[2,3-b]pyridine-3-carboxylic acid Stage 1: 2.9 ml of trichloroacetyl chloride are added to a suspension of 5.2 g of aluminium chloride in 4.5 ml of anhydrous dichloromethane. The mixture is stirred for 30 minutes at room temperature under argon, and then 2.0 g of 6-chloro-1H-pyrrolo[2,3-b]pyridine, which can be prepared according to Synthesis 1992, 661, are added in small fractions and the mixture is refluxed for 3 hours. After cooling to room temperature, the reaction mixture is poured over 80 g of ice. The pasty solid is recovered by decanting, taken up with 15 ml of water and 8 ml of 35% sodium hydroxide and then heated at 90° C. for 15 minutes. After cooling, the reaction medium is filtered, the filtrate which has been acidified with hydrochloric acid is concentrated, and the solid is filtered off and air-dried. In this way, we obtain a beige solid containing 50% of 6-chloro-1H-pyrrolo[2,3-b]pyridine-3-carboxylic acid, which is used as it is in the following stage, with the following characteristics:
$^1$H-NMR spectrum (400 MHz—DMSO-d6) δ in ppm: 7.28 (d, J=8.5 Hz, 1H); 8.16 (d, J=3.0 Hz, 1H); 8.31 (d, J=8.5 Hz, 1H); 12.35 (m spread-out, 1H); 12.6 (s broad, 1H).
Mass spectrum (ES): m/z=197 (MH+).

Stage 2: The procedure used in Example 14 is followed, starting from 298 mg of 4-(3H-imidazo[4,5-c]pyridin-2-yl)fluorene-9(R,S)-amine, obtained in Example 6, and 216 mg of crude 6-chloro-1H-pyrrolo[2,3-b]pyridine-3-carboxylic acid, prepared previously, in the presence of 211 mg of EDCI and 149 mg of HOBT, in 15 ml of DMF for 42 hours. The reaction medium is poured into 75 ml of water and then extracted with 3 times 35 ml of a mixture of dichloromethane and methanol (90/10 by volume). The organic phases are washed with 35 ml of distilled water, 35 ml of a saturated solution of sodium bicarbonate and, finally, 35 ml of water, dried over sodium sulphate and evaporated to dryness under vacuum. The residue is chromatographed on silica gel, eluting with a mixture of dichloromethane and methanol (90/10 by volume). After evaporation to dryness under vacuum, the residue is triturated with 3.5 ml of ethyl ether and the solid is filtered off and dried under vacuum at 40° C. We obtain 200 mg of [4-(3H-imidazo[4,5-c]pyridin-2-yl)-9H-fluoren-9(R,S)-yl]amide of 6-chloro-1H-pyrrolo[2,3-b]pyridine-3-carboxylic acid, in the form of a beige solid with the following characteristics:
$^1$H-NMR spectrum (400 MHz—DMSO-d6) δ in ppm: 6.41 (d, J=8.5 Hz, 1H); 7.25 (t, J=7.5 Hz, 1H); 7.31 (d, J=8.5 Hz, 1H); 7.33 (t partially masked, J=7.5 Hz, 1H); 7.50 (d partially masked, J=7.5 Hz, 1H); 7.52 (t, J=7.5 Hz, 1H); 7.59 (d, J=7.5 Hz, 1H); 7.63 (m spread-out, 1H); 7.69 (d, J=7.5 Hz, 1H); 7.75 (d, J=7.5 Hz, 1H); 8.26 (d, J=3.0 Hz, 1H); 8.40 (d broad, J=5.5 Hz, 1H); 8.61 (d, J=8.5 Hz, 1H); 8.78 (d, J=8.5 Hz, 1H); 9.07 (m spread-out, 1H); 12.35 (d, J=3.0 Hz, 1H); 13.45 (m spread-out, 1H).
Mass spectrum (ES): m/z=477 (MH+).

Example 181

Synthesis of [4-(3H-imidazo[4,5-c]pyridin-2-yl)-9H-fluoren-9(R,S)-yl]amide of 3-benzylisoxazole-5-carboxylic acid The procedure used in Example 14 is followed, starting from 280 mg of 4-(3H-imidazo[4,5-c]pyridin-2-yl)fluorene-9(R,S)-amine, obtained in Example 6, and 200 mg of 3-benzylisoxazole-5-carboxylic acid in 3 ml of dimethylformamide, in the presence of 270 mg of 1-(3-dimethylaminopropyl)-3-ethylcarbodiimide hydrochloride (EDCI) and 190 mg of 1-hydroxybenzotriazole (HOBT), for 20 hours at room temperature. After purification by flash chromatography on silica gel (40-63 μm), eluting with a mixture of dichloromethane and methanol (95/5 by volume), we obtain 235 mg of [4-(3H-imidazo[4,5-c]pyridin-2-yl)-9H-fluoren-9(R,S)-yl]amide of 3-benzylisoxazole-5-carboxylic acid, in the form of a white powder with the following characteristics:

Melting point (Kofler)=192-194° C.
Mass spectrum (LCMS): m/z=485 (M+).

Example 182

Synthesis of [4-(3H-imidazo[4,5-c]pyridin-2-yl)-9H-fluoren-9(R,S)-yl]amide of 5-(4-hydroxyphenyl)-3H-1,2,3-triazole-4-carboxylic acid The procedure used in Example 14 is followed, starting from 280 mg of 4-(3H-imidazo[4,5-c]pyridin-2-yl)fluorene-9(R,S)-amine, obtained in Example 6, and 200 mg of 5-(4-hydroxyphenyl)-3H-1,2,3-triazole-4-carboxylic acid in 3 ml of dimethylformamide, in the presence of 270 mg of 1-(3-dimethylaminopropyl)-3-ethylcarbodiimide hydrochloride (EDCI) and 190 mg of 1-hydroxybenzo-triazole (HOBT), for 20 hours at room temperature. After purification by flash chromatography on silica gel (40-63 μm), eluting with a mixture of dichloromethane and methanol (95/5 then 9/1 by volume) and then a mixture of dichloromethane and 7N ammonia in methanol (9/1 by volume) and, finally, a mixture of dichloromethane and methanol (8/2 by volume), we obtain 163 mg of [4-(3H-imidazo[4,5-c]pyridin-2-yl)-9H-fluoren-9(R,S)-yl]amide of 5-(4-hydroxyphenyl)-3H-1,2,3-triazole-4-carboxylic acid, in the form of a white powder with the following characteristics:

Mass spectrum (LCMS): m/z=485 (M+).

Example 183

Synthesis of [4-(5-cyano-6-fluoro-1H-benzimidazol-2-yl)-9H-fluoren-9(R,S)-yl]amide of 1H-pyrrolo[2,3-b]pyridine-4-carboxylic acid At room temperature, stir 20 mg of 4,5-diamino-2-fluorobenzonitrile, which can be prepared according to WO9926941A1, 40 mg of [4-formyl-9H-fluoren-9(R,S)-yl]amide of 1H-pyrrolo[2,3-b]pyridine-4-carboxylic acid, which can be obtained as in stage 6 of Example 234, and 18 mg of ferric chloride in solution in 2 ml of dimethylformamide. The stirring is stopped after 60 hours and the solvent is evaporated off under reduced pressure. The dark oil obtained is purified by flash chromatography on silica gel, eluting with a gradient of mixtures of dichloromethane and methanol (from 100/0 to 90/10 by volume) so as to give 22 mg of [4-(5-cyano-6-fluoro-1H-benzimidazol-2-yl)-9H-fluoren-9(R,S)-yl]amide of 1H-pyrrolo[2,3-b]pyridine-4-carboxylic acid, in the form of a beige powder with the following characteristic:

Mass spectrum (ESI+): m/z=485 (MH+).

Example 184

Synthesis of [4-(3H-imidazo[4,5-c]pyridin-2-yl)-9H-fluoren-9(R,S)-yl]amide of 2-amino-4-methylthiazole-5-carboxylic acid The procedure used in Example 14 is followed, starting from 300 mg of 4-(3H-imidazo[4,5-c]pyridin-2-yl)fluorene-9(R,S)-amine, obtained in Example 6, and 167 mg of 2-amino-4-methylthiazole-5-carboxylic acid, which can be obtained according to WO2004/099156, in 3 ml of dimethylformamide, in the presence of 289 mg of 1-(3-dimethylaminopropyl)-3-ethylcarbodiimide hydrochloride (EDCI) and 204 mg of 1-hydroxybenzotriazole (HOBT), for 20 hours at room temperature. After purification by flash chromatography on silica gel (40-63 μm), eluting with a mixture of dichloromethane and methanol (95/5 then 9/1 by volume), we obtain 85.2 mg of [4-(3H-imidazo[4,5-c]pyridin-2-yl)-9H-fluoren-9(R,S)-yl]amide of 2-amino-4-methylthiazole-5-carboxylic acid, in the form of a beige powder with the following characteristics:

Melting point (Kofler)=224-226° C.
Mass spectrum (EI): m/z=438 (M+).

Example 185

Synthesis of [4-(1H-benzimidazol-2-yl)-9H-fluoren-9(R,S)-yl]amide of 2-amino-5-chloropyrimidine-4-carboxylic acid The procedure used in Example 14 is followed, starting from 300 mg of 4-(1H-benzimidazol-2-yl)-9H-fluoren-9(R,S)-ylamine, obtained in Example 83, and 193 mg of 2-amino-5-chloropyrimidine-4-carboxylic acid in 3 ml of dimethylformamide, in the presence of 213 mg of 1-(3-dimethylaminopropyl)-3-ethylcarbodiimide hydrochloride (EDCI) and 68 mg of 1-hydroxybenzotriazole (HOBT), for 20 hours at room temperature. After purification by flash chromatography on silica gel (40-63 μm), eluting with a mixture of dichloromethane and methanol (98/2 by volume), we obtain 270 mg of [4-(1H-benzimidazol-2-yl)-9H-fluoren-9(R,S)-yl]amide of 2-amino-5-chloropyrimidine-4-carboxylic acid, in the form of a pale yellow powder with the following characteristics:

Mass spectrum (EI/LCMS): m/z=452 (M+).
$^1$H-NMR spectrum (400 MHz, δ in ppm, DMSO-d6): 6.25 (d, J=8.5 Hz, 1H); 7.12 (s broad, 2H); from 7.21 to 7.33 (m, 3H); 7.36 (t, J=7.5 Hz, 1H); from 7.51 to 7.60 (m, 4H); 7.66 (d, J=8.5 Hz, 1H); 7.70 (d, J=7.5 Hz, 1H); 7.76 (d, J=7.5 Hz, 1H); 8.39 (s, 1H); 9.31 (d, J=85 Hz, 1H); 12.95 (s, 1H).

Example 186

Synthesis of [4-(5-fluoro-1H-benzimidazol-2-yl)-9H-fluoren-9(R,S)-yl]amide of 2-amino-5-chloropyrimidine-4-carboxylic acid The procedure used in Example 14 is followed, starting from 300 mg of 4-(6-fluoro-1H-benzimidazol-2-yl)-9H-fluoren-9(R,S)-ylamine, obtained in Example 71, and 181 mg of 2-amino-5-chloropyrimidine-4-carboxylic acid in 3 ml of dimethylformamide, in the presence of 200 mg of 1-(3-dimethylaminopropyl)-3-ethylcarbodiimide hydrochloride (EDCI) and 64 mg of 1-hydroxybenzotriazole (HOBT), for 20 hours at room temperature. After purification by successive flash chromatographies on silica gel (40-63 μm), eluting with a mixture of dichloromethane and methanol (98/2 by volume), and then on alumina gel 90, eluting with a mixture of dichloromethane and methanol (98/2 by volume), we obtain 186 mg of [4-(5-fluoro-1H-benzimidazol-2-yl)-9H-fluoren-9(R,S)-yl]amide of 2-amino-5-chloropyrimidine-4-carboxylic acid, in the form of a beige powder with the following characteristics:

Mass spectrum (EI/LCMS): m/z=470 (M+).
$^1$H-NMR spectrum (400 MHz, δ in ppm, DMSO-d6): 6.24 (d, J=8.5 Hz, 1H); 7.11 (s broad, 2H); 7.14 (m partially masked, 1H); 7.25 (t, J=7.5 Hz, 1H); 7.36 (t broad, J=7.5 Hz, 1H); 7.46 (m spread-out, 1H); from 7.50 to 7.58 (m, 3H); 7.63 (m spread-out partially masked, 1H); 7.66 (d, J=7.5 Hz, 1H); 7.70 (d, J=7.5 Hz, 1H); 8.39 (s, 1H); 9.31 (d, J=8.5 Hz, 1H); 13.05 (m spread-out, 1H).

Example 187

Synthesis of [4-(3H-imidazo[4,5-c]pyridin-2-yl)-9H-fluoren-9(R,S)-yl]amide of pyrimidine-5-carboxylic acid The procedure used in Example 14 is followed, starting from 300 mg of 4-(3H-imidazo[4,5-c]pyridin-2-yl)fluorene-9(R,S)-amine, obtained in Example 6, and 127 mg of pyrimidine-5-carboxylic acid, in the presence of 212 mg of EDCI and 68 mg of HOBT in 7 ml of DMF for 15 hours. After successive washes with a saturated aqueous solution of sodium hydrogen carbonate, with water, and then with isopropyl ether, the crude mixture is purified by preparative HPLC on an Xterra RP 18, 5 μm column, eluting with a mixture of 35% acetonitrile and NH$_4$HCO$_3$ buffer (20 mmol, pH=9), and we obtain 67 mg of [4-(3H-imidazo[4,5-c]pyridin-2-yl)-9H-fluoren-9(R,S)-yl]amide of pyrimidine-5-carboxylic acid, in the form of a beige solid with the following characteristics:

Mass spectrum (E/I): m/z=404 (M+).
Melting point (Kofler)=192° C.

Example 188

Synthesis of [4-(5-fluoro-1H-benzimidazol-2-yl)-9H-fluoren-9(R,S)-yl]amide of 1H-pyrrolo[2,3-b]pyridine-4-carboxylic acid The procedure used in Example 14 is followed, starting from 300 mg of 4-(6-fluoro-1H-benzimidazol-2-yl)-9H-fluoren-9(R,S)-ylamine, obtained in Example 71, and 170 mg of 1H-pyrrolo[2,3-b]pyridine-4-carboxylic acid, which can be obtained according to WO 2003/000688, in 3 ml of dimethylformamide, in the presence of 200 mg of 1-(3-dimethylaminopropyl)-3-ethylcarbodiimide hydrochloride (EDCI) and 64 mg of 1-hydroxybenzotriazole (HOBT), for 20 hours at room temperature. After purification by flash chromatography on silica gel (40-63 μm), eluting with a mixture of dichloromethane and methanol (98/2 by volume), we obtain 243 mg of [4-(5-fluoro-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Mass spectrum (LCMS): m/z=459 (M+).
$^1$H-NMR spectrum (400 MHz, δ in ppm, DMSO-d6): 6.41 (d, J=8.5 Hz, 1H); 6.91 (dd, J=2.0 and 3.5 Hz, 1H); 7.14 (m, 1H); 7.25 (t, J=7.5 Hz, 1H); 7.34 (t, J=7.5 Hz, 1H); 7.38 (m partially masked, 1H); 7.46 (d, J=5.0 Hz, 1H); 7.52 (t, J=7.5 Hz, 1H); from 7.55 to 7.67 (m, 4H); 7.75 (d, J=7.5 Hz, 1H); 7.79 (m partially masked, 1H); 8.30 (d, J=5.0 Hz, 1H); 9.28 (d, J=8.5 Hz, 1H); 11.85 (s broad, 1H); 13.05 (s broad, 1H).

Example 189

[4-(3H-imidazo[4,5-c]pyridin-2-yl)-9H-fluoren-9(R,S)-yl]amide of isoquinoline-4-carboxylic acid The procedure used in Example 14 is followed, starting from 298 mg of 4-(3H-imidazo[4,5-c]pyridin-2-yl)fluorene-9(R,S)-amine, obtained in Example 6, and 173 mg of isoquinoline-4-carboxylic acid, in the presence of 211 mg of EDCI and 68 mg of HOBT, in 5 ml of DMF for 20 hours. After purification by flash chromatography on alumina, eluting with a mixture of methanol and dichloromethane (5/95 by volume), and then crystallization from 20 ml of isopropyl ether, we obtain 40 mg of [4-(3H-imidazo[4,5-c]pyridin-2-yl)-9H-fluoren-9(R,S)-yl]amide of isoquinoline-4-carboxylic acid, in the form of a beige solid with the following characteristics:

Melting point (Kofler)=200° C.
$^1$H-NMR spectrum (400 MHz, DMSO-d6) δ in ppm: 6.44 (d, J=8.5 Hz, 1H); 7.27 (t, J=7.5 Hz, 1H); 7.39 (t, J=7.5 Hz, 1H); 7.51 (d, J=7.5 Hz, 1H); 7.57 (t, J=7.5 Hz, 1H); 7.67 (d broad, J=5.5 Hz, 1H); 7.71 (d, J=7.5 Hz, 1H); 7.78 (m, 2H); 7.95 (m, 2H); 8.23 (d, J=8.5 Hz, 1H); 8.39 (d, J=5.5 Hz, 1H); 8.46 (d, J=8.5 Hz, 1H); 8.75 (s, 1H); 9.04 (s, 1H); 9.42 (s, 1H); 9.47 (d, J=8.5 Hz, 1H); 13.4 (m spread-out, 1H).
Mass spectrum (ES): m/z=454 (MH+).

Example 190

Synthesis of [4-(3H-imidazo[4,5-c]pyridin-2-yl)-9H-fluoren-9(R,S)-yl]amide of 2,3-dimethylquinoxaline-5-carboxylic acid The procedure used in Example 14 is followed, starting from 300 mg of 4-(3H-imidazo[4,5-c]pyridin-2-yl)fluorene-9(R,S)-amine, obtained in Example 6, and 24 mg of 2,3-dimethylquinoxaline-5-carboxylic acid in 3 ml of dimethylformamide, in the presence of 212 mg of 1-(3-dimethylaminopropyl)-3-ethylcarbodiimide hydrochloride (EDCI) and 68 mg of 1-hydroxybenzotriazole (HOBT), for 20 hours at room temperature. After purification by flash chromatography on silica gel (40-63 μm), eluting with a mixture of dichloromethane and methanol (95/5 by volume), we obtain 295 mg of [4-(3H-imidazo[4,5-c]pyridin-2-yl)-9H-fluoren-9(R,S)-yl]amide of 2,3-dimethylquinoxaline-5-carboxylic acid, in the form of a pale yellow powder with the following characteristics:

Mass spectrum (EI): m/z=482 (M+).

Example 191

Synthesis of [4-(3H-imidazo[4,5-c]pyridin-2-yl)-9H-fluoren-9(R,S)-yl]amide of 3-amino-1H-pyrazole-4-carboxylic acid The procedure used in Example 14 is followed, starting from 300 mg of 4-(3H-imidazo[4,5-c]pyridin-2-yl)fluorene-9(R,S)-amine, obtained in Example 6, and 141 mg of 3-amino-1H-pyrazole-4-carboxylic acid in 3 ml of dimethylformamide, in the presence of 289 mg of 1-(3-dimethylaminopropyl)-3-ethylcarbodiimide hydrochloride (EDCI) and 204 mg of 1-hydroxybenzotriazole (HOBT), for 20 hours at room temperature. After purification by HPLC on a 5 μm XTERRA silica RP18 column (30×150 mm), eluting with a mixture (75/25) of acetonitrile and buffer, pH=9 (aqueous ammonia/ammonium formate, 20 mmol), we obtain 8 mg of [4-(3H-imidazo[4,5-c]pyridin-2-yl)-9H-fluoren-9(R,S)-yl]amide of 3-amino-1H-pyrazole-4-carboxylic acid, in the form of a white solid with the following characteristics:

Mass spectrum (EI/LCMS): m/z=407 (M+).
$^1$H-NMR spectrum (300 MHz; DMSO-d6; δ in ppm): 6.25 (d, J=8.5 Hz, 1H); 7.10 (s broad, 2H); 7.25 (t, J=7.5 Hz, 1H); 7.36 (t, J=7.5 Hz, 1H); from 7.48 to 7.59 (m, 3H); 7.65 (d, J=5.5 Hz, 1H); from 7.68 to 7.74 (m, 2H); 8.37 (d, J=5.5 Hz, 1H); 8.39 (s, 1H); 9.01 (s, 1H); 9.31 (d, J=8.5 Hz, 1H).

Example 192

Synthesis of the dextrorotatory enantiomer of N-[4-(3H-imidazo[4,5-c]pyridin-2-yl)-9H-fluoren-9(R,S)-yl]amide of 2-amino-5-chloropyrimidine-4-carboxylic acid 150 mg of N-[4-(3H-imidazo[4,5-c]pyridin-2-yl)-9H-fluoren-9(R,S)-yl]amide of 2-amino-5-chloropyrimidine-4-carboxylic acid, obtained in Example 131, are injected onto a preparative chiral column containing 300 g of 10 μm Whelk 01 RR silica. Elution is carried out with a mixture of n-heptane, methanol, ethanol and triethylamine (60-10-30-0.2 by volume). By recovering the first fraction eluted and concentrating under reduced pressure, we obtain 70.9 mg of dextrorotatory enantiomer with the following characteristics:
αD20=+117.3+/−2° (c=0.5; MeOH).

Example 193

Synthesis of the levorotatory enantiomer of N-[4-(3H-imidazo[4,5-c]pyridin-2-yl)-9H-fluoren-9(R,S)-yl]amide of 2-amino-5-chloropyrimidine-4-carboxylic acid Using the procedure in Example 192, but recovering the second fraction eluted and concentrating under reduced pressure, we obtain 68.7 mg of levorotatory enantiomer with the following characteristics:
αD200=−77+/−2° (c=0.3; MeOH).

Example 194

Synthesis of [4-(3H-imidazo[4,5-c]pyridin-2-yl)-9H-fluoren-9(R,S)-yl]amide of 1H-benzimidazole-4-carboxylic acid The procedure used in Example 14 is followed, starting from 300 mg of 4-(3H-imidazo[4,5-c]pyridin-2-yl)-fluorene-9(R,S)-amine, obtained in Example 6, and 179 mg of 1H-benzimidazole-4-carboxylic acid in 3 ml of dimethylformamide, in the presence of 212 mg of 1-(3-dimethylaminopropyl)-3-ethylcarbodiimide hydrochloride (EDCI) and 68 mg of 1-hydroxybenzotriazole (HOBT), for 20 hours at room temperature. After purification by flash chromatography on silica gel (40-63 μm), eluting with a mixture of dichloromethane and methanol (95/5 then 9/1 by volume), in this way, we obtain 144 mg of [4-(3H-imidazo[4,5-c]pyridin-2-yl)-9H-fluoren-9(R,S)-yl]amide of 1H-benzimidazole-4-carboxylic acid, in the form of an off-white powder with the following characteristics:
Mass spectrum (EI): m/z=442 (M+).

Example 195

Synthesis of [4-(3H-imidazo[4,5-c]pyridin-2-yl)-9H-fluoren-9(R,S)-yl]amide of 3-methylquinoxaline-5-carboxylic acid The procedure used in Example 14 is followed, starting from 300 mg of 4-(3H-imidazo[4,5-c]pyridin-2-yl)fluorene-9(R,S)-amine, obtained in Example 6, 200 mg of 3-methylquinoxaline-5-carboxylic acid, 212 mg of 1-(3-dimethylaminopropyl)-3-ethylcarbodiimide hydrochloride (EDCI), and 68 mg of 1-hydroxybenzotriazole (HOBT) in 3 ml of dimethylformamide, for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and methanol (95/5 by volume). After forming a paste with diisopropyl ether, in this way we obtain 308 mg (65%) of [4-(3H-imidazo[4,5-c]pyridin-2-yl)-9H-fluoren-9(R,S)-yl]amide of 3-methylquinoxaline-5-carboxylic acid, in the form of a beige powder with the following characteristics:
Melting point (Kofler)=>260° C.
Mass spectrum (LCMS): m/z=468 (M+).
$^1$H-NMR spectrum (400 MHz, δ in ppm, DMSO-d6): 2.59 (s, 3H); 6.44 (d, J=7.5 Hz, 1H); 7.28 (t, J=7.5 Hz, 1H); 7.38 (t, J=7.5 Hz, 1H); 7.47 (d broad, J=8.0 Hz, 1H); 7.57 (t, J=7.5 Hz, 1H); 7.67 (m broad, 1H); 7.71 (d, J=7.5 Hz, 1H); 7.81 (d, J=7.5 Hz, 1H); 7.94 (t, J=7.5 Hz, 1H); 7.98 (d, J=7.5 Hz, 1H); 8.25 (d broad, J=7.5 Hz, 1H); 8.39 (d, J=5.5 Hz, 1H); 8.55 (d broad, J=7.5 Hz, 1H); 8.95 (s, 1H); 9.04 (s broad, 1H); 10.6 (d, J=7.5 Hz, 1H); 13.4 (m spread-out, 1H).

Example 196

Synthesis of [4-(3H-imidazo[4,5-c]pyridin-2-yl)-9H-fluoren-9(R,S)-yl]amide of quinoxaline-5-carboxylic acid The procedure used in Example 14 is followed, starting from 300 mg of 4-(3H-imidazo[4,5-c]pyridin-2-yl)fluorene-9(R,S)-amine, obtained in Example 6, 192 mg of quinoxaline-5-carboxylic acid, 212 mg of 1-(3-dimethylaminopropyl)-3-ethylcarbodiimide hydrochloride (EDCI) and 68 mg of 1-hydroxybenzotriazole (HOBT) in 3 ml of dimethylformamide, for 20 hours at room temperature. Bring the dimethylformamide to dryness, add water, then drain the precipitate that formed and then wash with water, then with a saturated solution of 10% sodium hydrogen carbonate and again with water. The crude solid obtained is dried and then purified by flash chromatography on silica gel (40-63 μm), eluting with a mixture of dichloromethane and methanol (95/5 by volume). After forming a paste with diisopropyl ether, in this way we obtain 294 mg of [4-(3H-imidazo[4,5-c]pyridin-2-yl)-9H-fluoren-9(R,S)-yl]amide of quinoxaline-5-carboxylic acid, in the form of a pale yellow solid with the following characteristics:
Melting point (Kofler)=>260° C.
Mass spectrum (EI/LC/MS): m/z=454 (M+).
$^1$H-NMR spectrum (400 MHz, δ in ppm, DMSO-d6): 6.50 (d, J=8.0 Hz, 1H); 7.27 (t, J=7.5 Hz, 1H); 7.36 (t, J=7.5 Hz, 1H); 7.46 (d broad, J=8.0 Hz, 1H); 7.55 (t, J=7.5 Hz, 1H); 7.67 (d broad, J=5.5 Hz, 1H); 7.71 (m, 2H); 7.89 (d, J=7.5 Hz, 1H); 8.05 (t, J=8.0 Hz, 1H); 8.32 (d broad, J=8.0 Hz, 1H); 8.40 (d, J=5.5 Hz, 1H); 8.62 (d broad, J=7.5 Hz, 1H); 8.97 (d, J=2.0 Hz, 1H); 9.04 (m broad, 2H); 10.35 (d, J=8.0 Hz, 1H); 13.4 (m spread-out, 1H).

Example 197

Synthesis of [4-(3H-imidazo[4,5-c]pyridin-2-yl)-9H-fluoren-9(R,S)-yl]amide of 2-furan-2-yl-3H-benzimidazole-4-carboxylic acid The procedure used in Example 14 is followed, starting from 300 mg of 4-(3H-imidazo[4,5-c]pyridin-2-yl)fluorene-9(R,S)-amine, obtained in Example 6, 253 mg of 2-furan-2-yl-3H-benzimidazole-4-carboxylic acid, 212 mg of 1-(3-dimethylaminopropyl)-3-ethylcarbodiimide hydrochloride (EDCI) and 68 mg of 1-hydroxybenzotriazole (HOBT) in 3 ml of dimethylformamide, for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and ammonia as a 7N solution in methanol (9/1 by volume). After forming a paste with diisopropyl ether, in this way we obtain 195 mg of [4-(3H-imidazo[4,5-c]pyridin-2-yl)-9H-fluoren-9(R,S)-yl]amide of 2-furan-2-yl-3H-benzimidazole-4-carboxylic acid, in the form of a beige powder with the following characteristics:

Melting point (Kofler)=252° C.
Mass spectrum (LC/MS): m/z=508 (M+).

Example 198

Synthesis of [4-(3H-imidazo[4,5-c]pyridin-2-yl)-9H-fluoren-9(R,S)-yl]amide of 2-thiophen-2-yl-3H-benzimidazole-4-carboxylic acid The procedure used in Example 14 is followed, starting from 300 mg of 4-(3H-imidazo[4,5-c]pyridin-2-yl)fluorene-9(R,S)-amine, obtained in Example 6, 270 mg of 2-thiophen-2-yl-3H-benzimidazole-4-carboxylic acid, 212 mg of 1-(3-dimethylaminopropyl)-3-ethylcarbodiimide hydrochloride (EDCI) and 68 mg of 1-hydroxybenzotriazole (HOBT) in 3 ml of dimethylformamide for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and ammonia as a 7N solution in methanol (95/5 then 9/1 by volume). After forming a paste with diisopropyl ether, in this way we obtain 347 mg of [4-(3H-imidazo[4,5-c]pyridin-2-yl)-9H-fluoren-9(R,S)-yl]amide of 2-thiophen-2-yl-3H-benzimidazole-4-carboxylic acid in the form of an off-white powder with the following characteristics:

Melting point (Kofler)=>260° C.
Mass spectrum (LCMS): m/z=524 (M+).

Example 199

Synthesis of [4-(3H-imidazo[4,5-c]pyridin-2-yl)-9H-fluoren-9(R,S)-yl]amide of quinoxaline-6-carboxylic acid The procedure used in Example 14 is followed, but starting from 300 mg of 4-(3H-imidazo[4,5-c]pyridin-2-yl)-9H-fluorene-9(R,S)-amine, obtained in Example 6, 193 mg of quinoxaline-6-carboxylic acid, 212 mg of 1-(3-dimethylaminopropyl)-3-ethylcarbodiimide hydrochloride (EDCI) and 68 mg of 1-hydroxybenzotriazole (HOBT) in 3 ml of dimethylformamide, for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and methanol (95/5 then 9/1 by volume). After forming a paste with diisopropyl ether, in this way we obtain 306 mg of [4-(3H-imidazo[4,5-c]pyridin-2-yl)-9H-fluoren-9(R,S)-yl]amide of quinoxaline-6-carboxylic acid, in the form of an off-white powder with the following characteristics:

Melting point (Kofler)=>260° C.
Mass spectrum (LC/MS): m/z=454 (M+).

Example 200

Synthesis of [4-(9H-purin-8-yl)-9H-fluoren-9(R,S)-yl]amide of 1H-pyrrolo[2,3-b]pyridine-4-carboxylic acid The procedure used in Example 14 is followed, but starting from 100 mg of 4-(9H-purin-8-yl)-fluorene-9(R,S)-amine, obtained in Example 164, 60 mg of 1H-pyrrolo-[2,3-b]pyridine-4-carboxylic acid, 70 mg of 1-(3-dimethylaminopropyl)-3-ethylcarbodiimide hydrochloride (EDCI) and 23 mg of 1-hydroxybenzotriazole (HOBT) in 1 ml of dimethylformamide, for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and methanol (98/2 then 95/5 by volume). After forming a paste with diisopropyl ether, in this way we obtain 53.3 mg of [4-(9H-purin-8-yl)-9H-fluoren-9(R,S)-yl]amide of 1H-pyrrolo-[2,3-b]pyridine-4-carboxylic acid, in the form of a beige powder with the following characteristics:

Melting point (Kofler)=>260° C.
Mass spectrum (LCMS): m/z=443 (M+).
$^1$H-NMR spectrum (300 MHz, δ in ppm, DMSO-d6): 6.41 (d, J=8.5 Hz, 1H); 6.91 (dd, J=2.0 and 3.5 Hz, 1H); 7.27 (t, J=7.5 Hz, 1H); 7.36 (t, J=7.5 Hz, 1H); 7.47 (d, J=5.0 Hz, 1H); 7.55 (t, J=7.5 Hz, 1H); from 7.58 to 7.66 (m, 3H); 7.73 (d, J=7.5 Hz, 1H); 7.82 (d, J=7.5 Hz, 1H); 8.30 (d, J=5.0 Hz, 1H); 9.00 (s, 1H); 9.22 (s, 1H); 9.29 (d, J=8.5 Hz, 1H); 11.85 (m broad, 1H); 13.95 (m spread-out, 1H).

Example 201

Synthesis of [4-(3H-imidazo[4,5-c]pyridin-2-yl)-9H-fluoren-9(R,S)-yl]amide of 2-hydroxyquinazoline-4-carboxylic acid The procedure used in Example 14 is followed, but starting from 400 mg of 4-(3H-imidazo[4,5-c]pyridin-2-yl)fluorene-9(R,S)-amine, obtained in Example 6, 283 mg of 1-(3-dimethylaminopropyl)-3-ethylcarbodiimide hydrochloride (EDCI), 91 mg of 1-hydroxybenzotriazole (HOBT) and 255 mg of 2-hydroxyquinazoline-4-carboxylic acid in 10 ml of dimethylformamide, for 20 hours at room temperature. Then add 100 ml of water and drain the precipitate that formed and then wash with water then with a saturated solution of sodium hydrogen carbonate. The crude solid obtained is purified by flash chromatography on silica gel (70-230 mesh), eluting with a mixture of dichloromethane and ammonia at 7N in methanol (90/10 by volume). In this way we obtain 50 mg of [4-(3H-imidazo[4,5-c]pyridin-2-yl)-9H-fluoren-9(R,S)-yl] amide of 2-hydroxyquinazoline-4-carboxylic acid, in the form of a pale yellow powder with the following characteristics:

Melting point (Kofler)>260° C.
Mass spectrum (LCMS): m/z=470 (M+).

Example 202

Synthesis of the hydrochloride of [4-(3H-imidazo[4,5-c]pyridin-2-yl)-9H-fluoren-9(R,S)-yl]amide of 6-(2-aminoethylamino)nicotinic acid Stage 1: The procedure used in Example 14 is followed, but starting from 645 mg of 4-(3H-imidazo[4,5-c]pyridin-2-yl)fluorene-9(R,S)-amine, obtained in Example 6, 456 mg of 1-(3-dimethylaminopropyl)-3-ethylcarbodiimide hydrochloride (EDCI), 146 mg of 1-hydroxybenzotriazole (HOBT) and 608 mg of 6-(2-tert-butoxycarbonylaminoethylamino)nicotinic acid in 15 ml of dimethylformamide, for 20 hours at room temperature. Then add 50 ml of water, and drain the precipitate that formed and then wash with water then with a saturated solution of sodium hydrogen carbonate. The crude solid obtained is purified by flash chromatography on silica gel (70-230 mesh), eluting with a mixture of dichloromethane and methanol (90/10 by volume). In this way, we obtain 540 mg of [4-(3H-imidazo[4,5-c]pyridin-2-yl)-9H-fluoren-9(R,S)-yl]amide of 6-(2-tert-butoxycarbonylaminoethylamino)nicotinic acid, in the form of a beige powder with the following characteristic:

Mass spectrum (LCMS): m/z=561 (M+).

Stage 2: Dissolve 320 mg of [4-(3H-imidazo[4,5-c]pyridin-2-yl)-9H-fluoren-9(R,S)-yl]amide of 6-(2-tert-butoxycarbonylaminoethylamino)nicotinic acid, obtained above, in 10 ml of dioxane, then add 2 ml of a 4M solution of hydrochloric acid in dioxane. After stirring for 20 hours at room temperature, the solid that formed is drained and washed with ethanol then with ethyl ether. In this way, we obtain 280 mg of hydrochloride of [4-(3H-imidazo[4,5-c]pyridin-2-yl)-9H-fluoren-9(R,S)-yl]amide of 6-(2-aminoethylamino)nicotinic acid, in the form of a pale yellow powder with the following characteristics:

Melting point (Kofler)>260° C.
Mass spectrum (LCMS): m/z=571 (M+).

Example 203

Synthesis of [4-(1H-benzimidazol-2-yl)-9H-fluoren-9(R,S)-yl]amide of 1H-pyrrolo[2,3-b]pyridine-4-carboxylic acid The procedure used in Example 14 is followed, but starting from 300 mg of 4-(1H-benzimidazol-2-yl)-9H-fluoren-9(R,S)-ylamine, obtained in Example 83, 180 mg of 1H-pyrrolo-[2,3-b]pyridine-4-carboxylic acid, 213 mg of 1-(3-dimethylaminopropyl)-3-ethylcarbodiimide hydrochloride (EDCI) and 68 mg of 1-hydroxybenzotriazole (HOBT) in 3 ml of dimethylformamide, for 20 hours at room temperature. Bring the dimethylformamide to dryness, add water, and drain the precipitate that formed and then wash with water then with a saturated solution of 10% sodium hydrogen carbonate and again with water. The crude solid obtained is dried and then purified by flash chromatography on silica gel (40-63 μm), eluting with a mixture of dichloromethane and methanol (98/2 by volume) and then with a mixture of dichloromethane and ammonia as a 7N solution in methanol (95/5 by volume). After forming a paste with diisopropyl ether, in this way we obtain 202 mg of 4-(1H-benzimidazol-2-yl)-9H-fluoren-9(R,S)-yl]amide of 1H-pyrrolo-[2,3-b]pyridine-4-carboxylic acid, in the form of an off-white powder with the following characteristics:

Melting point (Kofler)=220° C.
Mass spectrum (EI): m/z=441 (M+).

NMR spectrum (300 MHz, δ in ppm, DMSO-d6): 6.41 (d, J=8.5 Hz, 1H); 6.91 (m broad, 1H); 7.24 (t, J=7.5 Hz, 1H); 7.28 (m broad, 2H); 7.34 (t, J=7.5 Hz, 1H); 7.47 (d, J=5.5 Hz, 1H); 7.52 (t, J=7.5 Hz, 1H); from 7.58 to 7.64 (m, 4H); 7.66 (d, J=7.5 Hz, 1H); 7.76 (d, J=7.5 Hz, 1H); 7.76 (m spread-out partially masked, 1H); 8.30 (d, J=5.5 Hz, 1H); 9.28 (d, J=8.5 Hz, 1H); 11.85 (m broad, 1H); 12.95 (m broad, 1H).

Example 204

Synthesis of [4-(5-trifluoromethyl-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 2.6 g of 3,4-diaminobenzotrifluoromethyl in 85 ml of dichloromethane, 3.4 ml of triethylamine and 3 g of fluoren-4-one-9-carboxylic acid chloride. After stirring for 20 hours at room temperature, the reaction medium is poured into water and extracted with dichloromethane. The organic phases are washed with a saturated aqueous solution of 10% sodium hydrogen carbonate, dried over magnesium sulphate and concentrated under reduced pressure. After purification by flash chromatography on silica gel (40-63 μm), eluting with dichloromethane then with a mixture of dichloromethane and methanol (98/2 by volume), in this way we obtain 2.6 g of (2-amino-5-trifluoromethylphenyl)amide of 9-oxo-9H-fluorene-4-carboxylic acid, in the form of a yellow powder, which is used as it is in the following stage, with the following characteristics:

Mass spectrum (LC/MS): m/z=382 (M+).

Stage 2: The procedure used in Example 68 is followed. In a 500 ml round-bottomed flask under an argon atmosphere, heat, at 120° C. for 1 h 15 min, a solution of 2.6 g of (2-amino-5-trifluoromethylphenyl)amide of 9-oxo-9H-fluorene-4-carboxylic acid, obtained in the previous stage, in 130 ml of acetic acid. After cooling, bring to dryness under reduced pressure. Purify by flash chromatography on silica gel (40-63 μm), eluting with a mixture of dichloromethane and methanol (98/2 by volume), then with a mixture of dichloromethane and ammonia as a 7N solution in methanol. After forming a paste with diisopropyl ether, we obtain 2.1 g of 4-(5-trifluoromethyl-1H-benzimidazol-2-yl)-9H-fluoren-9-one, in the form of an orange-coloured resin, which is used as it is in the following stage, with the following characteristics:

Mass spectrum (EI/LC/MS): m/z=364 (M+).

$^1$H-NMR spectrum (300 MHz, δ in ppm, DMSO-d6): 7.40 (t broad, J=7.5 Hz, 1H); 7.50 (dt, J=1.5 and 7.5 Hz, 1H); 7.60 (t, J=7.5 Hz, 1H); from 7.61 to 7.71 (m, 3H); 7.83 (d broad, J=7.5 Hz, 1H); 7.88 (m, 2H); 8.08 (s broad, 1H); 13.5 (m very spread-out, 1H).

Stage 3: The procedure used in Example 5 is followed, but starting from 2.1 g of 4-(5-trifluoromethyl-1H-benzimidazol-2-yl)-9H-fluoren-9-one, obtained in the previous stage, 1.2 g of hydroxylamine hydrochloride and 2.4 g of sodium acetate in 100 ml of ethanol for 20 h at room temperature. After concentrating the solvent under reduced pressure, the residue is taken up successively with water, then toluene, brought to dryness and, finally, made into paste in diisopropyl ether, filtered and washed twice. In this way, we obtain 2.3 g of 4-(5-trifluoromethyl-1H-benzimidazol-2-yl)-9H-fluoren-9-one oxime (Z,E), as a 50-50 mixture of Z and E isomers, in the form of a beige powder with the following characteristics:

Mass spectrum (LCMS): m/z=379 (M+).

Stage 4: The procedure used in Example 6 is followed. In a 528 ml autoclave, dissolve 2.2 g of 4-(5-trifluoromethyl-1H-benzimidazol-2-yl)-9H-fluoren-9-one oxime (Z,E), obtained in the previous stage, in a mixture of 80 ml of ethanol and 80 ml of tetrahydrofuran, add a spatula of Raney activated nickel and then subject to an initial hydrogen pressure of 1 bar and heat the autoclave at 600 for 4 hours. After cooling, the volume of hydrogen absorbed is 412 ml. After filtration of the catalyst over Celite, concentrate under reduced pressure. In this way, we obtain 1.73 g of 4-(5-trifluoromethyl-1H-benzimidazol-2-yl)-9H-fluorene-9(R,S)-amine, in the form of a grey foam with the following characteristics:

Mass spectrum (LC/MS): m/z=365 (M+).

Stage 5: The procedure used in Example 14 is followed, but starting from 365 mg of 4-(5-trifluoromethyl-1H-benzimidazol-2-yl)-9H-fluorene-9(R,S)-amine, obtained in the previous stage, 178 mg of 1H-pyrrolo-[2,3-b]pyridine-4-carboxylic acid, 210 mg of 1-(3-dimethylaminopropyl)-3-ethylcarbodiimide hydrochloride (EDCI) and 68 mg of 1-hydroxybenzotriazole (HOBT) in 3.6 ml of dimethylformamide, for 20 hours at room temperature. Bring the dimethylformamide to dryness, add water, and drain the precipitate that formed and then wash with water then with a 10% saturated solution of sodium hydrogen carbonate and again with water. The crude solid obtained is dried and then purified by flash chromatography on silica gel (40-63 μm), eluting with a mixture of dichloromethane and methanol (98/2 then 95/5 by volume). After forming a paste with diisopropyl ether containing a small amount of dichloromethane, in this way we obtain 221 mg of 4-(5-trifluoromethyl-1H-benzimidazol-2-yl)-9H-fluoren-9(R,S)-yl]amide of 1H-pyrrolo[2,3-b]pyridine-4-carboxylic acid, in the form of a beige powder with the following characteristics:

Melting point (Kofler)=220° C.

Mass spectrum (LC/MS): m/z=509 (M+).

$^1$H-NMR spectrum (400 MHz, δ in ppm, DMSO-d6): 6.42 (d, J=8.5 Hz, 1H); 6.91 (dd, J=2.0 and 3.5 Hz, 1H); 7.26 (t, J=7.5 Hz, 1H); 7.35 (t, J=7.5 Hz, 1H); 7.47 (d, J=5.0 Hz, 1H); 7.54 (t, J=7.5 Hz, 1H); from 7.55 to 7.64 (m, 4H); 7.70 (d, J=7.5 Hz, 1H); 7.79 (d, J=7.5 Hz, 1H); 7.86 (m spread-out, 1H); 8.05 (m spread-out, 1H); 8.30 (d, J=5.0 Hz, 1H); 9.28 (d, J=8.5 Hz, 1H); 11.85 (m broad, 1H); 13.4 (m spread-out, 1H).

Example 205

Synthesis of [4-(5-methoxycarbonyl-1H-benzimidazol-2-yl)-9H-fluoren-9(R,S)-yl]amide of 1H-pyrrolo [2,3-b]pyridine-4-carboxylic acid Stage 1: The procedure used in stage 1 of Example 1 is followed, but starting from 4.9 g of methyl 3,4-diaminobenzoate in 170 ml of dichloromethane, 6.9 ml of triethylamine and 6 g of fluoren-4-one-9-carboxylic acid chloride. After stirring for 20 hours at room temperature, the precipitate that formed is filtered off, washed with water, then with a 10% saturated aqueous solution of sodium hydrogen carbonate and again with water. After forming a paste with diisopropyl ether, in this way we obtain 6.5 g of (2-amino-5-methoxycarbonylphenyl)amide of 9-oxo-9H-fluorene-4-carboxylic acid, in the form of a yellow powder, which is used as it is in the following stage, with the following characteristics:

Mass spectrum (LC/MS): m/z=372 (M+).

Stage 2: The procedure used in Example 68 is followed. In a 1 l round-bottomed flask under an argon atmosphere, heat, at 135° C. for 2 hours, a solution of 6.5 g of (2-amino-5-methoxycarbonylphenyl)amide of 9-oxo-9H-fluorene-4-carboxylic acid, obtained in the previous stage, in 320 ml of acetic acid. After cooling, bring to dryness under reduced pressure. After forming a paste with diisopropyl ether, we obtain 6.1 g of methyl ester of 2-(9H-fluoren-9-on-4-yl)benzimidazole-4-carboxylic acid, in the form of a yellow powder, which is used as it is in the following stage, with the following characteristics:

Mass spectrum (EI): m/z=354 (M+).

NMR spectrum (400 MHz, δ in ppm, DMSO-d6): 3.90 (s, 3H); 7.40 (t broad, J=7.5 Hz, 1H); 7.50 (dt, J=1.5 and 7.5 Hz, 1H); 7.59 (t, J=7.5 Hz, 1H); 7.69 (d, J=7.5 Hz, 1H); 7.73 (d, J=7.5 Hz, 1H); 7.77 (d, J=8.5 Hz, 1H); 7.82 (dd, J=1.0 and 7.5 Hz, 1H); 7.90 (dd, J=1.0 and 8.0 Hz, 1H); 7.94 (dd, J=1.5 and 8.5 Hz, 1H); 8.31 (s broad, 1H); 13.1 (m very spread-out, 1H).

Stage 3: The procedure used in Example 5 is followed, but starting from 6.1 g of methyl ester of 2-(9H-fluoren-9-on-4-yl)benzimidazole-4-carboxylic acid, obtained in the previous stage, 3.6 g of hydroxylamine hydrochloride and 7 g of sodium acetate in 300 ml of ethanol stirred for 4 h at room temperature and then at 80° C. for 2 hours. After concentrating the solvent under reduced pressure, the residue is taken up successively with water then toluene, brought to dryness and, finally, made into a paste in diisopropyl ether. In this way, we obtain 6.1 g of methyl ester of 2-(9H-fluoren-9-oximino-4-yl)benzimidazole-4-carboxylic acid, as a 50-50 mixture of Z and E isomers, in the form of a pale yellow powder, which is used as it is in the following stage, with the following characteristics:

Mass spectrum (EI/CI): m/z=369 (M+).

Stage 4: The procedure used in Example 6 is followed. In a 955 ml autoclave, dissolve 6.1 g of methyl ester of 2-(9H-fluoren-9-oximino-4-yl)benzimidazole-4-carboxylic acid, obtained in the previous stage, in a mixture of 230 ml of ethanol and 230 ml of tetrahydrofuran, add a spatula of Raney activated nickel and then subject to an initial hydrogen pressure of 1 bar and heat the autoclave at 600 for 6 hours. After cooling, the volume of hydrogen absorbed is 979 ml. After filtration of the catalyst over Celite, concentrate the filtrate under reduced pressure. The crude solid obtained is made into a paste with diisopropyl ether, and in this way, we obtain 5.7 g of methyl ester of 2-(9H-fluorene-9(R,S)-amino-4-yl)benzimidazole-4-carboxylic acid, in the form of a beige powder, which is used as it is in the following stage, with the following characteristics:

Mass spectrum (LC/MS): m/z=355 (M+).

Stage 5: The procedure used in Example 14 is followed, but starting from 2.5 g of methyl ester of 2-(9H-fluoren-9(R,S)-amino-4-yl)benzimidazole-4-carboxylic acid, obtained in the previous stage, 1.25 g of 1H-pyrrolo-[2,3-b]pyridine-4-carboxylic acid, 1.48 g of 1-(3-dimethylaminopropyl)-3-ethylcarbodiimide hydrochloride (EDCI) and 475 mg of 1-hydroxybenzotriazole (HOBT) in 25 ml of dimethylformamide, for 20 hours at room temperature. Bring the dimethylformamide to dryness, add water, and drain the precipitate that formed and then wash with water then with a 10% saturated solution of sodium hydrogen carbonate and again with water. The crude solid obtained is dried and then purified by flash chromatography on silica gel (40-63 μm), eluting with a mixture of dichloromethane and methanol (98/2 then 95/5 by volume). After forming a paste with diisopropyl ether, in this way we obtain 2.35 g of [4-(5-methoxycarbonyl-1H-benzimidazol-2-yl)-9H-fluoren-9(R,S)-yl]amide of 1H-pyrrolo [2,3-b]pyridine-4-carboxylic acid, in the form of a beige powder with the following characteristics:

Melting point (Kofler)=222-226° C.

Mass spectrum (LC/MS): m/z=499 (M+).

$^1$H-NMR spectrum (400 MHz, δ in ppm, DMSO-d6): for this compound, a 50%-50% mixture of tautomers is observed with: 3.91 (s, 3H); 6.42 (d, J=8.5 Hz, 1H); 6.91 (dd, J=2.0 and 3.5 Hz, 1H); 7.26 (t, J=7.5 Hz, 1H); 7.35 (t, J=7.5 Hz, 1H); 7.47 (d, J=5.0 Hz, 1H); 7.54 (m, 1.5H); 7.63 (m, 2.5H); 7.70

(m, 1.5H); 7.78 (d, J=7.5 Hz, 1H); from 7.84 to 7.99 (m, 1.5H); 8.19 (s broad, 0.5H); 8.30 (d, J=5.0 Hz, 1H); 8.38 (s broad, 0.5H); 9.29 (d, J=8.5 Hz, 1H); 11.85 (m broad, 1H); 13.35 (m broad, 1H).

Example 206

Synthesis of [4-(5-carboxy-1H-benzimidazol-2-yl)-9H-fluoren-9(R,S)-yl]amide of 1H-pyrrolo[2,3-b]pyridine-4-carboxylic acid In a 30 ml round-bottomed flask under argon, dissolve 500 mg of [4-(5-methoxycarbonyl-1H-benzimidazol-2-yl)-9H-fluoren-9(R,S)-yl]amide of 1H-pyrrolo[2,3-b]pyridine-4-carboxylic acid, obtained in Example 205, in 10 ml of methanol, then add 2.4 ml of a 1.25 M aqueous solution of lithium hydroxide, then reflux for 20 hours. The reaction medium is cooled and acidified to pH 4-5 with a 1M aqueous solution of hydrochloric acid. The crude solid is dried and then purified by flash chromatography on silica gel (40-63 µm), eluting with a mixture of dichloromethane and methanol (9/1 then 8/2 by volume). After forming a paste with diisopropyl ether, in this way we obtain 210 mg of [4-(5-carboxy-1H-benzimidazol-2-yl)-9H-fluoren-9(R,S)-yl]amide of 1H-pyrrolo[2,3-b]pyridine-4-carboxylic acid, in the form of a white powder with the following characteristics:

Melting point (Kofler)=>260° C.

Mass spectrum (LC/MS): m/z=485 (M+).

$^1$H-NMR spectrum (400 MHz, δ in ppm, DMSO-d6): for this compound, a 50%-50% mixture of tautomers is observed: 6.42 (d, J=8.5 Hz, 1H); 6.91 (dd, J=2.0 and 3.5 Hz, 1H); 7.26 (t, J=7.5 Hz, 1H); 7.35 (t, J=7.5 Hz, 1H); 7.46 (d, J=5.0 Hz, 1H); 7.53 (t, J=7.5 Hz, 1H); from 7.56 to 7.67 (m, 3.5H); 7.70 (d, J=8.0 Hz, 1H); 7.78 (d, J=8.0 Hz, 1H); 7.82 (m, 0.5H); from 7.87 to 7.97 (m, 1H); 8.17 (s broad, 0.5H); 8.30 (d, J=5.0 Hz, 1H); 8.35 (s broad, 0.5H); 9.29 (d, J=8.5 Hz, 1H); 11.85 (m broad, 1H); 12.7 (m very spread-out, 1H); 13.25 (m broad, 1H).

Example 207

Synthesis of [4-(4-methyl-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 2.932 g of 2,3-diaminotoluene, 5.622 ml of triethylamine and 4.85 g of fluoren-4-one-9-carboxylic acid chloride in 100 ml of dichloromethane. After stirring for 20 hours at room temperature, the precipitate that formed is filtered off, washed with dichloromethane, with water, then with a 10% saturated aqueous solution of sodium hydrogen carbonate and, finally, with water. After forming a paste with diisopropyl ether, in this way we obtain 5 g of (2-amino-6-methylphenyl)amide of 9-oxo-9H-fluorene-4-carboxylic acid, in the form of an orange powder, which is used as it is in the following stage, with the following characteristics:

Mass spectrum (LC/MS/ES/+/−): m/z=328 (M+).

Stage 2: The procedure used in Example 68 is followed. In a 250 ml round-bottomed flask under an argon atmosphere, reflux, for 6 hours, a suspension of 5 g of (2-amino-6-methylphenyl)amide of 9-oxo-9H-fluorene-4-carboxylic acid, obtained in the previous stage, in 100 ml of acetic acid. After cooling, bring to dryness under reduced pressure. Take the residue up in 25 ml of water then bring to pH=8 by addition of a saturated aqueous solution of sodium hydrogen carbonate. The precipitate that formed is filtered off, washed with water, and made into a paste with diisopropyl ether, and in this way, we obtain 4.7 g of 4-(4-methyl-1H-benzimidazol-2-yl)-9H-fluoren-9-one, in the form of an orange powder, which is used as it is in the following stage, with the following characteristics:

Mass spectrum (EI): m/z=310 (M+).

Stage 3: The procedure used in Example 5 is followed, but starting from 4.7 g of 4-(4-methyl-1H-benzimidazol-2-yl)-9H-fluoren-9-one, obtained in the previous stage, 3.16 g of hydroxylamine hydrochloride and 6.21 g of sodium acetate in 65 ml of ethanol, stirred for 20 hours at room temperature. After concentrating the solvent under reduced pressure, the residue is taken up successively with water, filtered, washed with water, and made into a paste with diisopropyl ether. In this way, we obtain 4 g of 4-(4-methyl-1H-benzimidazol-2-yl)-9H-fluoren-9-one oxime (Z,E), as a 60-40 mixture of Z and E isomers, in the form of a beige powder which is used as it is in the following stage.

Stage 4: The procedure used in Example 6 is followed, but starting from 4 g of 4-(4-methyl-1H-benzimidazol-2-yl)-9H-fluoren-9-one oxime (Z,E), obtained in the previous stage, and 0.7 g of Raney nickel in 100 ml of ethanol and 100 ml of tetrahydrofuran for 10 hours at 60° C. under an initial hydrogen pressure of one bar. After filtration of the catalyst, and then purification by formation of a paste in diisopropyl ether, in this way we obtain 2.7 g of 4-(4-methyl-1H-benzimidazol-2-yl)-9H-fluoren-9(R,S)-ylamine, in the form of a beige powder which is used as it is in the following stage.

Stage 5: The procedure used in Example 14 is followed, but starting from 311 mg of 4-(4-methyl-1H-benzimidazo-2-yl)-9H-fluoren-9(R,S)-ylamine, obtained in the previous stage, 162 mg of 1H-pyrrolo-[2,3-b]pyridine-4-carboxylic acid, 211 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. After purification by flash chromatography on silica gel (40-63 µm), eluting with a mixture of dichloromethane and methanol (95/5 by volume), then forming a paste with dichloromethane, in this way we obtain 255 mg of [4-(4-methyl-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Mass spectrum (LC/MS/ES+/−): m/z=455 (M+).

$^1$H-NMR spectrum (400 MHz, δ in ppm, DMSO-d6): for this compound, a 50%-50% mixture of tautomers is observed with: 2.55 (s, 1.5H); 2.62 (s, 1.5H); 6.41 (d, J=8.5 Hz, 1H); 6.90 (d broad, J=3.5 Hz, 1H); 7.07 (d, J=7.5 Hz, 1H); 7.17 (t, J=7.5 Hz, 1H); 7.24 (m broad, 1H); 7.33 (t, J=7.5 Hz, 1H); 7.39 (m broad, 0.5H); 7.47 (d, J=5.0 Hz, 1H); 7.51 (t, J=7.5 Hz, 1H); 7.51 (m masked, 0.5H); from 7.55 to 7.64 (m, 2.5H); 7.67 (d, J=7.5 Hz, 1H); from 7.70 to 7.78 (m, 1.5H); 8.30 (d, J=5.0 Hz, 1H); 9.28 (d broad, J=8.5 Hz, 1H); 11.85 (m broad, 1H); 13.4 (m broad, 1H).

Example 208

Synthesis of [4-(5-carboxamido-1H-benzimidazol-2-yl)-9H-fluoren-9(R,S)-yl]amide of 1H-pyrrolo[2,3-b]pyridine-4-carboxylic acid In a 10 ml round-bottomed flask, dissolve 300 mg of [4-(5-carboxy-1H-benzimidazol-2-yl)-9H-fluoren-9(R,S)-yl] amide of 1H-pyrrolo[2,3-b]pyridine-4-carboxylic acid, obtained in Example 206, in 3.5 ml of dimethylformamide, then add successively 66 mg of ammonium chloride, 480 mg of benzotriazol-1-yl-oxytrispyrrolidinophosphonium hexafluorophosphate (PYBOP), 125 mg of 1-hydroxybenzotriazole (HOBT) and 0.41 ml of N,N-diisopropylethylamine (DIPEA), then stir for 20 hours at room temperature. Bring the dimethylformamide to dryness and add water and ethyl acetate, and filter the precipitate that formed and then wash with water then with a 10% saturated solution of sodium hydrogen carbonate and again with water. After formation of a paste with diisopropyl ether, in this way we obtain 100 mg of [4-(5-carboxamido-1H-benzimidazol-2-yl)-9H-fluoren-9(R,S)-yl]amide of 1H-pyrrolo-[2,3-b]pyridine-4-carboxylic acid, in the form of an off-white powder with the following characteristics:

Melting point (Kofler)=>260° C.

Mass spectrum (LC/MS): m/z=484 (M+).

Example 209

Synthesis of N-[4-(1H-imidazo[4,5-c]pyridin-2-yl)-9H-fluoren-9(R,S)-yl]amide of cyclohexan-3-one-4(R,S)-carboxylic acid The procedure used in Example 14 is followed, but starting from 100 mg of (1H-imidazo[4,5-c]pyridin-2-yl)-9H-fluoren-9(R,S)-ylamine, obtained in Example 6, 47 mg of cyclohexan-3-one-4(R,S)-carboxylic acid, 71 mg of 1-(3-dimethylaminopropyl)-3-ethylcarbodiimide hydrochloride (EDCI) and 50 mg of 1-hydroxybenzotriazole (HOBT) in 2.5 ml of dimethylformamide, for 20 hours at room temperature. After purification by flash chromatography on silica gel (40-63 µm), eluting with a mixture of dichloromethane and methanol (98/2 by volume), in this way we obtain 123 mg of N-[4-(1H-imidazo[4,5-c]pyridin-2-yl)-9H-fluoren-9(R,S)-yl]amide of cyclohexan-3-one-4(R,S)-carboxylic acid, in the form of a white powder with the following characteristics:

Mass spectrum (EI): m/z=422 (M+).

Example 210

Synthesis of [4-(5,7-difluoro-1H-benzimidazol-2-yl)]-9H-fluoren-9(R,S)-yl]amide of 1H-pyrrolo[2,3-b]pyridine-4-carboxylic acid Stage 1: The procedure used in stage 1 of Example 1 is followed, but starting from 2.1 g of 1,2-diamino-3,5-difluorobenzene, 3.4 ml of triethylamine and 3 g of fluoren-4-one-9-carboxylic acid chloride in 85 ml of dichloromethane. After stirring for 20 hours at room temperature, the precipitate is filtered off, and washed with dichloromethane, with water, then with a 10% saturated aqueous solution of sodium hydrogen carbonate and again with water. After drying and then forming a paste with diisopropyl ether, in this way we obtain 2.8 g of (2-amino-3,5-difluorophenyl)amide of 9-oxo-9H-fluorene-4-carboxylic acid, in the form of a pale yellow powder, which is used as it is in the following stage, with the following characteristics:

Mass spectrum (EI): m/z=350 (M+).

Stage 2: The procedure used in Example 68 is followed. In a 500 ml round-bottomed flask under an argon atmosphere, heat, at 135° C. for 10 hours, a solution of 2.8 g of (2-amino-3,5-difluorophenyl)amide of 9-oxo-9H-fluorene-4-carboxylic acid, obtained in the previous stage, in 140 ml of acetic acid. After cooling, bring to dryness under reduced pressure. After formation of a paste with diisopropyl ether, we obtain 2.6 g of 4-(5,7-difluoro-1H-benzimidazol-2-yl)-9H-fluoren-9-one, in the form of a pale green powder, which is used as it is in the following stage, with the following characteristics:

Mass spectrum (EI): m/z=332 (M+).

Stage 3: The procedure used in Example 5 is followed, but starting from 2.6 g of 4-(5,7-difluoro-1H-benzimidazol-2-yl)-9H-fluoren-9-one, obtained in the previous stage, 1.6 g of hydroxylamine hydrochloride and 3.2 g of sodium acetate in 130 ml of ethanol, stirred for 20 hours at room temperature. After concentrating the solvent under reduced pressure, the residue is taken up successively with water then with toluene, brought to dryness, and finally made into a paste in diisopropyl ether. In this way, we obtain 1.85 g of 4-(5,7-difluoro-1H-benzimidazol-2-yl)-9H-fluoren-9-one oxime (Z,E), as a 50-50 mixture of Z and E isomers, in the form of a beige powder, which is used as it is in the following stage, with the following characteristics:

Mass spectrum (EI/CI/LC/MS): m/z=347 (M+).

Stage 4: The procedure used in Example 6 is followed. In a 211 ml autoclave, dissolve 1.85 g of 4-(5,7-difluoro-1H-benzimidazol-2-yl)-9H-fluoren-9-one oxime (Z,E), obtained in the previous stage, in a mixture of 70 ml of ethanol and 70 ml of tetrahydrofuran, add a spatula of Raney activated nickel and then subject to an initial hydrogen pressure of 1 bar and heat the autoclave at 60° for 6 hours. After cooling, the volume of hydrogen absorbed is 342 ml. After filtration of the catalyst, the filtrate is concentrated under reduced pressure and then taken up in a mixture of dichloromethane with a small amount of methanol and dried over magnesium sulphate, and the crude solid obtained is made into a paste with diisopropyl ether. In this way, we obtain 1.32 g of 4-(5,7-difluoro-1H-benzimidazol-2-yl)-9H-fluorene-9(R,S)-amine, in the form of a grey powder, which is used as it is in the following stage, with the following characteristics:

Mass spectrum (EI): m/z=333 (M+).

Stage 5: The procedure used in Example 14 is followed, but starting from 330 mg of 4-(5,7-difluoro-1H-benzimidazol-2-yl)-9H-fluorene-9(R,S)-amine, obtained in the previous stage, 177 mg of 1H-pyrrolo-[2,3-b]pyridine-4-carboxylic acid, 209 mg of 1-(3-dimethylaminopropyl)-3-ethylcarbodiimide hydrochloride (EDCI) and 67 mg of 1-hydroxybenzotriazole (HOBT) in 3.3 ml of dimethylformamide for 20 hours at room temperature. Bring the dimethylformamide to dryness, add water, then drain the precipitate that formed and then wash with water then with a 10% saturated solution of sodium hydrogen carbonate and again with water. The crude solid obtained is dried and then purified by flash chromatography on silica gel (40-63 µm), eluting with a mixture of dichloromethane and methanol (98/2 then 95/5 by volume). After forming a paste in diisopropyl ether, in this way we obtain 280 mg of 4-(5,7-difluoro-1H-benzimidazol-2-yl)]-9H-fluoren-9(R,S)-yl]amide of 1H-pyrrolo[2,3-b]pyridine-4-carboxylic acid, in the form of an off-white powder with the following characteristics:

Melting point (Kofler)=238-240° C.

Mass spectrum (EI): m/z=477 (M+).

$^1$H-NMR spectrum (400 MHz, δ in ppm, DMSO-d6): 6.41 (d, J=8.5 Hz, 1H); 6.91 (m broad, 1H); 7.16 (t broad, J=10.5 Hz, 1H); from 7.23 to 7.41 (m masked, 1H); 7.27 (t, J=7.5 Hz, 1H); 7.36 (t, J=7.5 Hz, 1H); 7.47 (d, J=5.0 Hz, 1H); 7.52 (m, 2H); 7.62 (m, 2H); 7.67 (d, J=7.5 Hz, 1H); 7.78 (d, J=7.5 Hz, 1H); 8.30 (d, J=5.0 Hz, 1H); 9.29 (d, J=8.5 Hz, 1H); 11.85 (m broad, 1H); 13.4 (m spread-out, 1H).

Example 211

[4-(6-sulphamoyl-1H-benzimidazol-2-yl)-9H-fluoren-9(R,S)-yl]amide of 1H-pyrrolo[2,3-b]pyridine-4-carboxylic acid Stage 1: In a 250 ml round-bottomed flask, dissolve 0.94 g of 4-sulphonamidobenzene-1,2-diamine in 15 ml of tetrahydrofuran, then add, successively at 0° C., 1.21 g of fluoren-4-one-9-carboxylic acid chloride and 0.42 g of sodium hydrogen carbonate. After stirring for 1 hour at room temperature, the mixture is brought to 40° C. for 2 hours. Add 10 ml of water then 10 ml of a 1M aqueous solution of hydrochloric acid and then extract with diethyl ether. The aqueous phase is decanted, then brought to pH=10 by the addition of a 1M aqueous solution of sodium hydroxide and extracted with 3 times 20 ml of ethyl acetate. After concentrating the ethyl acetate to dryness, in this way we obtain 80 mg of a crude mixture containing predominantly (2-amino-4-sulphamoylphenyl)amide of 9-oxo-9H-fluorene-4-carboxylic acid.

Stage 2: In a 10 ml round-bottomed flask, the mixture obtained in the previous stage in 15 ml of acetic acid and heat to 110° C. for 2 hours. After cooling and concentration of the solvent, add 5 ml of water and the aqueous phase is brought to pH=8-9 by the addition of a saturated solution of potassium hydrogen carbonate. The crude solid obtained is purified by flash chromatography on silica gel (40-63 μm), eluting with a mixture of dichloromethane and ammonia at 7N in methanol (90/10 by volume). In this way, we obtain 58 mg of 2-(9-oxo-9H-fluoren-4-yl)-1H-benzimidazole-5-sulphonamide, in the form of a yellow powder with the following characteristics:

Mass spectrum (E/I): m/z=376 (M+).

Stage 3: The procedure used in Example 5 is followed, but starting from 56 mg of 2-(9-oxo-9H-fluoren-4-yl)-1H-benzimidazole-5-sulphonamide, obtained in the previous stage, 31 mg of hydroxylamine hydrochloride and 62 mg of sodium acetate in 5 ml of ethanol, stirred for 1 h at room temperature and then at 80° C. for 3 hours. After concentration of the solvent under reduced pressure, the residue is taken up successively with water then with toluene, brought to dryness and, finally, made into a paste in diisopropyl ether. In this way, we obtain 50 mg of 2-[9(Z,E)-hydroxyimino-9H-fluoren-4-yl]-1H-benzimidazole-5-sulphonamide, as a 50-50 mixture of Z and E isomers, in the form of an amber powder, which is used as it is in the following stage, with the following characteristics:

Mass spectrum (EI/CI): m/z=391 (M+).

Stage 4: The procedure used in Example 6 is followed. In a 25 ml autoclave, dissolve 50 mg of 2-[9(Z,E)-hydroxyimino-9H-fluoren-4-yl]-1H-benzimidazole-5-sulphonamide, obtained in the previous stage, in a mixture of 5 ml of ethanol and 5 ml of tetrahydrofuran, add a spatula of Raney activated nickel and then subject to an initial hydrogen pressure of 1 bar and heat the autoclave at 60° C. for 12 hours. After cooling, the volume of hydrogen absorbed is 20 ml. After filtration of the catalyst, concentration of the solvent under reduced pressure and purification by forming a paste with diisopropyl ether, in this way we obtain 45 mg of 2-[9(R,S)-amino-9H-fluoren-4-yl]-1H-benzimidazole-5-sulphonamide, in the form of a beige powder, which is used as it is in the following stage, with the following characteristics:

Mass spectrum (LC/MS): m/z=377 (M+).

Stage 5: The procedure used in Example 14 is followed, but starting from 35 mg of 2-[9(R,S)-amino-9H-fluoren-4-yl]-1H-benzimidazole-5-sulphonamide, obtained in the previous stage, 16 mg of 1H-pyrrolo-[2,3-b]pyridine-4-carboxylic acid, 20 mg of 1-(3-dimethylaminopropyl)-3-ethylcarbodiimide hydrochloride (EDCI) and 14 mg of 1-hydroxybenzotriazole (HOBT) in 5 ml of dimethylformamide, for 20 hours at room temperature. After purification by flash chromatography on silica gel (40-63 μm), eluting with a mixture of dichloromethane and ammonia at 7N in methanol (90/10 by volume), in this way we obtain 19 mg of [4-(6-sulphamoyl-1H-benzoimidazol-2-yl)-9H-fluoren-9(R,S)-yl]amide of 1H-pyrrolo[2,3-b]pyridine-4-carboxylic acid, in the form of an amber powder with the following characteristics:

Mass spectrum (LC/MS): m/z=521 (M+).

$^1$H-NMR spectrum (400 MHz, δ in ppm, DMSO-d6): for this compound, a 50/50 mixture of tautomers is observed with: 6.41 (d, J=8.5 Hz, 1H); 6.91 (m broad, 1H); from 7.23 to 7.38 (m, 4H); 7.47 (d, J=5.0 Hz, 1H); from 7.49 to 7.66 (m, 4H); 7.70 (d, J=7.5 Hz, 1H); 7.73 to 7.86 (m, 4H); 8.15 (m spread-out, 1H); 8.29 (d, J=5.0 Hz, 1H); 9.29 (d, J=8.5 Hz, 1H); 11.85 (m broad, 1H); 13.4 (m spread-out, 1H).

Example 212

Synthesis of 4-(4,5-difluoro-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 0.793 g of 1,2-diamino-3,4-difluorobenzene, 1.406 ml of triethylamine and 1.213 g of fluoren-4-one-9-carboxylic acid chloride in 25 ml of dichloromethane. After stirring for 20 hours at room temperature, the precipitate that formed is filtered off, and washed with water, then with a 10% saturated aqueous solution of sodium hydrogen carbonate and, finally, with water. After forming a paste with diisopropyl ether, in this way we obtain 1.7 g of (6-amino-2,3-difluorophenyl)amide of 9-oxo-9H-fluorene-4-carboxylic acid, in the form of an orange powder, which is used as it is in the following stage, with the following characteristics:

Mass spectrum (LC/MS/ES/+/−): m/z=350 (M+).

Stage 2: The procedure used in Example 68 is followed. In a 100 ml round-bottomed flask under an argon atmosphere, heat, at 115° C. for 6 hours, a suspension of 1.7 g of (6-amino-2,3-difluorophenyl)amide of 9-oxo-9H-fluorene-4-carboxylic acid, obtained in the previous stage, in 35 ml of acetic acid. After cooling, bring to dryness under reduced pressure. Take the residue up in water and bring to pH=8 by adding a 10% saturated aqueous solution of sodium hydrogen carbonate, with water. The precipitate that formed is filtered off, washed with water, and rinsed with diisopropyl ether. In this way, we obtain 1.5 g of 4-(4,5-difluoro-1H-benzimidazol-2-yl)-9H-fluoren-9-one, in the form of an orange powder, which is used as it is in the following stage, with the following characteristics:

Mass spectrum (EI): m/z=332 (M+).

Stage 3: The procedure used in Example 5 is followed, but starting from 1.5 g of 4-(4,5-difluoro-1H-benzimidazol-2-yl)-9H-fluoren-9-one, obtained in the previous stage, 0.941 g of hydroxylamine hydrochloride and 1.85 g of sodium acetate in 25 ml of ethanol, stirred for 20 h at room temperature. After concentration of the solvent under reduced pressure, the residue is taken up with water, filtered, washed with water, and made into a paste with diisopropyl ether. In this way, we obtain 1.5 g of 4-(4,5-difluoro-1H-benzimidazol-2-yl)-9H-fluoren-9-one oxime (Z,E) as a 50-50 mixture of Z and E isomers, in the form of a beige powder which is used as it is in the following stage.

Stage 4: The procedure used in Example 6 is followed, but starting from 4 g of 4-(4,5-difluoro-1H-benzimidazol-2-yl)-9H-fluoren-9-one oxime (Z,E), obtained in the previous stage, and 0.27 g of Raney nickel in 35 ml of ethanol and 35 ml of tetrahydrofuran for 10 hours at 60° C. under an initial hydrogen pressure of one bar. After filtration of the catalyst, and purification by forming a paste in diisopropyl ether, in this way we obtain 1 g of 4-(4,5-difluoro-1H-benzimidazol- 2-yl)-9H-fluoren-9(R,S)-ylamine, in the form of a beige powder which is used as it is in the following stage.

Stage 5: The procedure used in Example 14 is followed, but starting from 333 mg of 4-(4,5-difluoro-1H-benzimidazol-2-yl)-9H-fluoren-9(R,S)-ylamine, obtained in the previous stage, 162 mg of 1H-pyrrolo-[2,3-b]pyridine-4-carboxylic acid, 211 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. After purification by flash chromatography on silica gel (40-63 µm), eluting with a mixture of dichloromethane and 7N ammoniacal methanol (97.5/2.5 by volume), and then formation of a paste with dichloromethane, in this way we obtain 296 mg of [4-(4,5-difluoro-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Mass spectrum (LC/MS/ES+/−): m/z=477 (M+).

$^1$H-NMR spectrum (400 MHz, δ in ppm, DMSO-d6): 6.41 (d, J=8.5 Hz, 1H); 6.91 (dd, J=2.0 and 3.5 Hz, 1H); 7.27 (t, J=7.5 Hz, 1H); 7.33 (m partially masked, 1H); 7.36 (t, J=7.5 Hz, 1H); 7.44 (m spread-out, 1H); 7.47 (d, J=5.0 Hz, 1H); 7.50 (d partially masked, J=8.0 Hz, 1H); 7.53 (t, J=7.5 Hz, 1H); 7.63 (m, 2H); 7.68 (d, J=7.5 Hz, 1H); 7.79 (d, J=7.5 Hz, 1H); 8.30 (d, J=5.0 Hz, 1H); 9.29 (d, J=8.5 Hz, 1H); 11.85 (m broad, 1H); 13.4 (m spread-out, 1H).

Example 213

Synthesis of [4-(5-trifluoromethoxy-1H-benzimidazol-2-yl)-9H-fluoren-9(R,S)-yl]amide of 1H-pyrrolo [2,3-b]pyridine-4-carboxylic acid Stage 1: The procedure used in stage 1 of Example 1 is followed, but starting from 1 g of 1,2-diamino-4-(trifluoromethoxy)benzene, 1.3 ml of triethylamine and 1.15 g of fluoren-4-one-9-carboxylic acid chloride in 30 ml of dichloromethane. After stirring for 20 hours at room temperature, the precipitate that formed is filtered off, and washed with dichloromethane, with water, and then with a 10% saturated aqueous solution of sodium hydrogen carbonate and, finally, with water. After drying and formation of a paste with diisopropyl ether, in this way we obtain 485 mg of (2-amino-4-trifluoromethoxyphenyl)amide of 9-oxo-9H-fluoren-4-carboxylic acid, in the form of a yellow powder, which is used as it is in the following stage, with the following characteristics:

Mass spectrum (EI): m/z=350 (M+).

Stage 2: The procedure used in Example 68 is followed. In a 250 ml round-bottomed flask under an argon atmosphere, heat, at 135° C. for 2 hours, a solution of 1.12 g of of (2-amino-4-trifluoromethoxyphenyl)amide of 9-oxo-9H-fluoren-4-carboxylic acid, obtained in the previous stage, in 50 ml of acetic acid. After cooling, bring to dryness under reduced pressure. The crude product is purified by flash chromatography on silica gel (40-63 µm), eluting with a mixture of dichloromethane and methanol (95/5 by volume). After formation of a paste with diisopropyl ether, we obtain 550 mg of 4-(5-trifluoromethoxy-1H-benzimidazol-2-yl)-9H-fluoren-9-one, in the form of a pale yellow powder, which is used as it is in the following stage, with the following characteristics:

Mass spectrum (EI): m/z=380 (M+).

Stage 3: The procedure used in Example 5 is followed, but starting from 1 g of 4-(5-trifluoromethoxy-1H-benzimidazol-2-yl)-9H-fluoren-9-one, obtained in the previous stage, 580 mg of hydroxylamine hydrochloride and 1.1 g of sodium acetate in 50 ml of ethanol, stirred for 20 h at room temperature. After concentration of the solvent under reduced pressure, the residue is taken up successively with water and then with toluene, and brought to dryness. The crude product is purified by flash chromatography on silica gel (40-63 µm), eluting with a mixture of dichloromethane and methanol (98/2 by volume). In this way, we obtain 730 mg of 4-(5-trifluoromethoxy-1H-benzimidazol-2-yl)-9H-fluoren-9-one oxime (Z,E) as a 50-50 mixture of Z and E isomers, in the form of a pale yellow foam, which is used as it is in the following stage, with the following characteristics:

Mass spectrum (EI/LC/MS): m/z=395 (M+).

Stage 4: The procedure used in Example 6 is followed. In a 111 ml autoclave, dissolve 730 mg of 4-(5-trifluoromethoxy-1H-benzimidazol-2-yl)-9H-fluoren-9-one oxime (Z,E), obtained in the previous stage, in a mixture of 25 ml of ethanol and 25 ml of tetrahydrofuran, add a spatula of Raney activated nickel and then subject to an initial hydrogen pressure of 1 bar and heat the autoclave at 600 for 4 hours. After cooling, the volume of hydrogen absorbed is 122 ml. After filtration of the catalyst over Celite, the filtrate is concentrated under reduced pressure and then taken up in dichloromethane and dried over magnesium sulphate. In this way, we obtain 640 mg of 4-(5-trifluoromethoxy-1H-benzimidazol-2-yl)-9H-fluorene-9(R,S)amine, in the form of a beige foam, which is used as it is in the following stage, with the following characteristics:

Mass spectrum (LC/MS): m/z=381 (M+).

Stage 5: The procedure used in Example 14 is followed, but starting from 300 mg of 4-(5-trifluoromethoxy-1H-benzimidazol-2-yl)-9H-fluorene-9(R,S)-amine, obtained in the previous stage, 140 mg of 1H-pyrrolo-[2,3-b]pyridine-4-carboxylic acid, 166 mg of 1-(3-dimethylaminopropyl)-3-ethylcarbodiimide hydrochloride (EDCI) and 53 mg of 1-hydroxybenzotriazole (HOBT) in 3 ml of dimethylformamide, for 20 hours at room temperature. Bring the dimethylformamide to dryness, add water and drain the precipitate that formed and then wash with water then with a 10% saturated solution of sodium hydrogen carbonate and again with water. The crude solid obtained is dried and then purified by flash chromatography on silica gel (40-63 µm), eluting with a mixture of dichloromethane and methanol (98/2 then 95/5 by volume). After formation of a paste with diisopropyl ether, in this way we obtain 213 mg of [4-(5-trifluoromethoxy-1H-benzimidazol-2-yl)-9H-fluoren-9(R,S)-yl]amide of 1H-pyrrolo[2,3-b]pyridine-4-carboxylic acid, in the form of a white powder with the following characteristics:

Melting point (Kofler)=204-206° C.

Mass spectrum (LC/MS): m/z=525 (M+).

$^1$H-NMR spectrum (400 MHz, δ in ppm, DMSO-d6): for this batch, a mixture of tautomers is observed with: 6.41 (d, J=8.5 Hz, 1H); 6.91 (dd, J=2.0 and 3.5 Hz, 1H); 7.26 (m, 2H); 7.35 (dt, J=1.5 and 7.5 Hz, 1H); 7.47 (d, J=5.0 Hz, 1H); 7.52 (t, J=7.5 Hz, 1H); from 7.57 to 7.80 (m, 7H); 8.30 (d, J=5.0 Hz, 1H); 9.28 (d, J=8.5 Hz, 1H); 11.86 (m broad, 1H); 13.3 (m spread-out, 1H).

Examples 214, 215, 217 and 218

Separation of the 4 enantiomers of [4-(3H-imidazo [4,5-c]pyridin-2-yl)-9H-fluoren-9(R,S)-yl]amide of 2-(3-acetyl-2,2-di-methylcyclobutan-1-yl)acetic acid Stage 1: Separation of the diastereoisomer pairs 180 mg of [4-(3H-imidazo[4,5-c]pyridin-2-yl)-9H-fluoren-9(R,S)-yl]amide of 2-(3-acetyl-2,2-dimethylcyclobutan-1-yl)acetic acid, obtained as in Example 145, are chromatographed on a 20 µM Chiralpak AD silica column, 35 cm long and 8 cm in diameter, eluting at a flow rate of 150 ml/min with a mixture of n-heptane, ethanol and methanol (85/10/5 by volume). By recovering the first fraction eluted, in this way we obtain 82.6 mg of the pair of diastereoisomers A and C. By recovering the second fraction eluted, in this way we obtain 85 mg of the pair of diastereoisomers B and D.

Stage 2: Resolution of the diastereoisomer pairs

Chromatograph, separately, 82.6 mg of the pair of diastereoisomers A and C and 85 mg of the pair of diastereoisomers B and D, on a Chiralpak OJ-H silica column, 25 cm long and 2 cm in diameter, eluting with a supercritical mobile phase consisting of carbon dioxide, ethanol and trifluoroacetic acid (70/30/0.1 by volume), at a flow rate of 100 ml/min under a pressure of 126 bars. In this way we obtain:

42.3 mg of diastereosiomer A (Example 217): αD20=+ 104+/−2° (c=0.5; DMSO).

37.6 mg of diastereosiomer C (Example 215): αD20=− 81.2+/−1.8° (c=0.5; DMSO).

42.3 mg of diastereosiomer B (Example 214): αD20=+ 102.3+/−2° (c=0.5; DMSO).

36.4 mg of diastereosiomer D (Example 218): αD20=−91+/− 2.1° (c=0.5; DMSO).

Example 216

Synthesis of [4-(5-cyano-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 2.4 g of 3,4-diaminobenzonitrile and 30 ml of tetrahydrofuran, 4.6 ml of triethylamine and 4 g of fluoren-4-one-9-carboxylic acid chloride in 115 ml of dichloromethane. After stirring for 20 hours at room temperature, the precipitate that formed is filtered off, and washed with dichloromethane, with water, and then with a 10% saturated aqueous solution of sodium hydrogen carbonate and, finally, with water. After formation of a paste with diisopropyl ether, in this way we obtain 3.8 g of (2-amino-5-cyanophenyl) amide of 9-oxo-9H-fluorene-4-carboxylic acid, in the form of a beige powder, which is used as it is in the following stage, with the following characteristics:

Mass spectrum (EI): m/z=339 (M+).

Stage 2: The procedure used in Example 68 is followed. In a 500 ml round-bottomed flask under an argon atmosphere, heat, at 135° C. for 4 hours, a solution of 3.8 g of (2-amino-5-cyanophenyl)amide of 9-oxo-9H-fluorene-4-carboxylic acid, obtained in the previous stage, in 190 ml of acetic acid. After cooling, bring to dryness under reduced pressure. After formation of a paste with diisopropyl ether, we obtain 3.7 g of 4-(5-cyano-1H-benzimidazol-2-yl)-9H-fluoren-9-one, in the form of a beige powder, which is used as it is in the following stage, with the following characteristics:

Mass spectrum (EI/LC/MS): m/z=321 (M+).

$^1$H-NMR spectrum (400 MHz, δ in ppm, DMSO-d6): 7.40 (t, J=7.5 Hz, 1H); 7.49 (dt, J=1.5 and 7.5 Hz, 1H); 7.58 (t, J=7.5 Hz, 1H); from 7.65 to 7.72 (m, 3H); 7.83 (m, 2H); 7.90 (d broad, J=8.0 Hz, 1H); 8.26 (s broad, 1H); 13.0 (m very spread-out, 1H).

Stage 3: The procedure used in Example 5 is followed, but starting from 3.7 g of 4-(5-cyano-1H-benzimidazol-2-yl)-9H-fluoren-9-one, obtained in the previous stage, 2.4 g of hydroxylamine hydrochloride and 4.7 g of sodium acetate in 185 ml of ethanol, stirred for 20 h at room temperature. After concentration of the solvent under reduced pressure, the residue is taken up successively with water, and then with toluene, and brought to dryness. The crude product is purified by flash chromatography on silica gel (40-63 µm), eluting with a mixture of dichloromethane and ammonia as a 7N solution in methanol (98/2 then 95/5 by volume). In this way, we obtain 2.11 g of 4-(5-cyano-1H-benzimidazol-2-yl)-9H-fluoren-9-one oxime (Z,E) as a 50-50 mixture of Z and E isomers, in the form of a beige solid, which is used as it is in the following stage, with the following characteristics:

Mass spectrum (LC/MS/ES+/−): m/z=336 (M+).

Stage 4: In a 100 ml round-bottomed flask under an argon atmosphere, dissolve 1.58 g of an equimolar mixture of 4-(5-cyano-1H-benzimidazol-2-yl)-9H-fluoren-9-one oxime (Z,E), obtained in the previous stage, in a mixture of 10 ml of ethanol and 10 ml of water and 10 ml of acetic acid, at room temperature, add 1.2 g of zinc in three stages, and stir for approximately one hour to two hours between each addition. Add Celite and filter. The filtrate is concentrated under pressure. The crude product is purified by flash chromatography on silica gel (40-63 µm), eluting with a mixture of dichloromethane and methanol (9/1 by volume) and then a mixture of dichloromethane and ammonia as a 7N solution in methanol (95/5 by volume). In this way, we obtain 1.4 g of 4-(5-cyano-1H-benzimidazol-2-yl)-9H-fluorene-9(R,S)-amine, in the form of a white powder, which is used as it is in the following stage.

Stage 5: The procedure used in Example 14 is followed, but starting from 1.4 g of 4-(5-cyano-1H-benzimidazol-2-yl)-9H-fluorene-9(R,S)-amine, obtained in the previous stage, 720 mg of 1H-pyrrolo-[2,3-b]pyridine-4-carboxylic acid, 850 mg of 1-(3-dimethylaminopropyl)-3-ethylcarbodiimide hydrochloride (EDCI) and 300 mg of 1-hydroxybenzotriazole (HOBT) in 15 ml of dimethylformamide for 20 hours at room temperature. Bring the dimethylformamide to dryness, add water, and drain the precipitate that formed and then wash with water, then with a 10% saturated solution of sodium hydrogen carbonate and again with water. The crude solid obtained is dried and then purified by flash chromatography on silica gel (40-63 µm), eluting with a mixture of dichloromethane and methanol (98/2 then 95/5 by volume). After formation of a paste with diisopropyl ether, in this way we obtain 1.6 g of [4-(5-cyano-1H-benzimidazol-2-yl)-9H-fluoren-9(R,S)-yl]amide of 1H-pyrrolo[2,3-b]pyridine-4-carboxylic acid, in the form of a pinkish powder with the following characteristics:

Melting point (Kofler)=>260° C.

Mass spectrum (LC/MS/ES+/−): m/z=466 (M+).

$^1$H-NMR spectrum (400 MHz, δ in ppm, DMSO-d6): 6.41 (d, J=8.5 Hz, 1H); 6.91 (dd, J=2.0 and 3.5 Hz, 1H); 7.25 (t, J=7.5 Hz, 1H); 7.35 (t, J=7.5 Hz, 1H); 7.46 (d, J=5.0 Hz, 1H); 7.53 (t, J=7.5 Hz, 1H); from 7.57 to 7.67 (m, 4H); 7.71 (d, J=7.5 Hz, 1H); 7.77 (d, J=7.5 Hz, 1H); 7.81 (d broad, J=8.5 Hz, 1H); 8.22 (s broad, 1H); 8.30 (d, J=5.0 Hz, 1H); 9.28 (d, J=8.5 Hz, 1H); 11.85 (m broad, 1H); 13.5 (m very spread-out, 1H).

Example 219

(6-chloro-1H-benzimidazol-2-yl)-9H-fluoren-9(R,S)-yl]amide of 1H-pyrrolo[2,3-b]pyridine-4-carboxylic acid Stage 1: To a mixture of 2.84 g of chloro-4-diamino-1,2-benzene and 5.6 ml of triethylamine in 80 ml of dichloromethane, add, under argon and at room temperature, 4.35 g of 9-fluorenone-4-carboxylic acid chloride dropwise over a period of 30 minutes. The reaction medium is stirred overnight at room temperature under argon. After stirring for half an hour, the appearance of a precipitate is noted. The following day, the reaction medium is filtered and the solid is washed successively with 50 ml of dichloromethane, 50 ml of water, twice 50 ml of a saturated solution of sodium bicarbonate and, finally, 50 ml of water. The yellow solid is taken up with 100 ml of toluene and the whole is evaporated to dryness under vacuum. The residue is triturated in 150 ml of diisopropyl ether, filtered and dried under vacuum at 40° C. overnight. In this way, we obtain 3.05 g of (2-amino-4-chlorophenyl)amide of 9-oxo-9H-fluorene-4-carboxylic acid in the form of a beige powder with the following characteristics:

Melting point (Kofler)=226° C.

TLC (SiO$_2$) Rf=0.6 (methanol-dichloromethane 10/90 by volume).

Stage 2: A mixture of 3.0 g of (2-amino-4-chlorophenyl) amide of 9-oxo-9H-fluorene-4-carboxylic acid in 120 ml of glacial acetic acid is refluxed for 2.5 hours. Allow the mixture to return to room temperature and evaporate the reaction medium to dryness under vacuum. The residue is taken up with 75 ml of dichloromethane, and the organic phase is washed with twice 50 ml of a saturated solution of sodium bicarbonate, and 50 ml of a saturated solution of sodium chloride. After drying over magnesium sulphate, the organic phase is evaporated to dryness under vacuum. In this way, we obtain 3.12 g of 4-(6-chloro-1H-benzimidazol-2-yl)-9H-fluoren-9-one in the form of a beige foam with the following characteristics:

TLC (SiO$_2$) Rf=0.6 (methanol-dichloromethane 10/90 by volume).

Stage 3: Stir, at room temperature under argon, a mixture of 2.0 g of 4-(6-chloro-1H-benzimidazol-2-yl)-9H-fluoren-9-one, 1.26 g of hydroxylamine hydrochloride and 2.48 g of sodium acetate in 100 ml of ethanol. The following day, evaporate the reaction medium to dryness under vacuum, take the residue up with 100 ml of dichloromethane and wash with 100 ml of water. The organic phase is dried over magnesium sulphate and evaporated to dryness under vacuum. After drying at 40° C. under vacuum, we obtain 1.88 g of 4-(6-chloro-1H-benzimidazol-2-yl)-9H-fluoren-9-one oxime (Z, E) in the form of a beige solid with the following characteristics:

Melting point (Kofler)=200° C. (decomposition).

TLC (SiO$_2$) Rf=0.4 (methanol-dichloromethane 10/90 by volume).

$^1$H-NMR spectrum (400 MHz—δ in ppm—DMSO-d6): for this batch, we observe a 50%/50% mixture of isomers with: from 7.21 to 7.41 (m, 3.5H); 7.51 (t, J=7.5 Hz, 0.5H); 7.52 (d broad, J=8.0 Hz, 0.5H); 7.56 (t, J=7.5 Hz, 0.5H); from 7.63 to 7.77 (m, 3.5H); 7.91 (d broad, J=7.5 Hz, 0.5H); 8.43 (d broad, J=7.5 Hz, 0.5H); 8.60 (d broad, J=8.0 Hz, 0.5H); from 12.5 to 13.5 (m spread-out, 2H).

Stage 4: Stir, at room temperature, a mixture of 345 mg of 4-(6-chloro-1H-benzimidazol-2-yl)-9H-fluoren-9-one oxime (Z, E) in a mixture of 2 ml of acetic acid, 2 ml of ethanol and 2 ml of water in the presence of 65 mg of powdered zinc. After 1 hour and 3 hours, add, each time, a further 65 mg of powdered zinc and maintain the stirring for approximately 4 hours. Add Celite, filter over sintered glass and wash the precipitate with 200 ml of a mixture of methanol and dichloromethane (20/80 by volume). The filtrate is evaporated to dryness under vacuum, add twice 50 ml of toluene and re-evaporate, each time, to dryness under vacuum. The residue is chromatographed on silica gel, eluting with a mixture of dichloromethane-7N solution of ammonia in methanol (90/10 by volume). In this way, we obtain 275 mg of 4-(6-chloro-1H-benzimidazol-2-yl)-9H-fluorene-9(R,S)-amine in the form of a beige foam with the following characteristics:

TLC (SiO$_2$) Rf=0.5 (methanol-dichloromethane 20/80 by volume).

Stage 5: Stir, at room temperature, a mixture of 238 mg of 4-(6-chloro-1H-benzimidazol-2-yl)-9H-fluorene-9(R,S)-amine, 152 mg of 1-(3-dimethylaminopropyl)-3-ethylcarbodiimide hydrochloride (EDCI), 106 mg of 1-hydroxybenzotriazole (HOBT) and 128 mg of 1H-pyrrolo[2,3-b]pyridine-4-carboxylic acid in 5 ml of dry dimethylformamide. After 2 hours, evaporate the reaction medium to dryness under vacuum, take the residue up with 50 ml of a saturated solution of sodium bicarbonate, triturate the suspension, and filter the precipitate over sintered glass. The solid is washed with 80 ml of saturated solution of sodium bicarbonate and then 80 ml of water. The solid is taken up in 75 ml of toluene and the whole is evaporated to dryness under vacuum. The solid is chromatographed on silica gel, eluting with a mixture of methanol and dichloromethane (7.5/92.5 by volume). In this way, we obtain 180 mg of (6-chloro-1H-benzimidazol-2-yl)-9H-fluoren-9(R,S)-yl]amide of 1H-pyrrolo[2,3-b]pyridine-4-carboxylic acid, in the form of a beige foam with the following characteristics:

Melting point (Kofler)=212° C. (decomp).

TLC (SiO$_2$) Rf=0.3 (methanol-dichloromethane 10/90 by volume).

NMR spectrum (400 MHz—δ in ppm—DMSO-d6) 6.41 (d, J=8.5 Hz, 1H); 6.91 (dd, J=2.0 and 3.5 Hz, 1H); 7.26 (t, J=7.5 Hz, 1H); 7.31 (dd, J=2.0 and 8.5 Hz, 1H); 7.35 (t, J=7.5 Hz, 1H); 7.47 (d, J=5.0 Hz, 1H); 7.52 (t, J=7.5 Hz, 1H); 7.55 (d, J=8.0 Hz, 1H); 7.62 (m, 2H); from 7.64 to 7.78 (m spread-out, 2H); 7.66 (d, J=7.5 Hz, 1H); 7.77 (d, J=7.5 Hz, 1H); 8.29 (d, J=5.0 Hz, 1H); 9.28 (d, J=8.5 Hz, 1H); 11.85 (m broad, 1H); 13.15 (m spread-out, 1H).

Example 220

(6-bromo-1H-benzimidazol-2-yl)-9H-fluoren-9(R, S)-yl]amide of 1H-pyrrolo[2,3-b]pyridine-4-carboxylic acid Stage 1: To a mixture of 2 g of bromo-4-diamino-1,2-benzene and 3.0 ml of triethylamine in 60 ml of dichloromethane, add, under argon and at room temperature, 2.36 g of 9-fluorenone-4-carboxylic acid chloride in small portions over a period of 20 minutes. The reaction medium is stirred overnight at room temperature under argon. After stirring for half an hour, the appearance of a precipitate is noted. The following day, the reaction medium is filtered and the solid is washed successively with 50 ml of dichloromethane, 50 ml of water, twice 50 ml of a saturated solution of sodium bicarbonate and, finally, 50 ml of water. The yellow solid is triturated in 100 ml of diisopropyl ether, filtered and dried under vacuum at 40° C. overnight. In this way, we obtain 1.61 g of (2-amino-4-bromophenyl)amide of 9-oxo-9H-fluorene-4-carboxylic acid, in the form of a pale yellow solid with the following characteristics:

Melting point (Kofler)=252° C.

TLC (SiO$_2$) Rf=0.5 (methanol-dichloromethane 10/90 by volume).

Stage 2: A mixture of 1.61 g of (2-amino-4-bromophenyl) amide of 9-oxo-9H-fluorene-4-carboxylic acid in 80 ml of glacial acetic acid is refluxed for 2.5 hours. Allow to return to ambient temperature and evaporate the reaction medium to dryness under vacuum. The residue is taken up with 50 ml of dichloromethane, and the organic phase is washed with twice 50 ml of a saturated solution of sodium bicarbonate and 50 ml of a saturated solution of sodium chloride. After drying over magnesium sulphate, the organic phase is evaporated to dryness under vacuum. The residue is chromatographed on silica gel, eluting with a mixture of methanol and dichloromethane (5/95 by volume). In this way, we obtain 1.5 g of 4-(6-bromo-1H-benzimidazol-2-yl)-9H-fluoren-9-one, with the following characteristics:

TLC (SiO$_2$) Rf=0.6 (methanol-dichloromethane 10:90 by volume).

$^1$H-NMR spectrum (400 MHz—δ in ppm—DMSO-d6): 7.39 (dt, J=1.0 and 7.5 Hz, 1H); 7.44 (dd, J=2.0 and 8.5 Hz, 1H); 7.49 (dt, J=1.0 and 7.5 Hz, 1H); 7.57 (t, J=7.5 Hz, 1H); from 7.63 to 7.70 (m, 3H); 7.81 (dd, J=1.0 and 7.5 Hz, 1H); 7.86 (dd, J=1.0 and 7.5 Hz, 1H); 7.90 (d broad, J=2.0 Hz, 1H); 13.2 (m spread-out, 1H).

Stage 3: Stir, at room temperature under argon, a mixture of 1.13 g of 4-(6-bromo-1H-benzimidazol-2-yl)-9H-fluoren-9-one, 0.628 g of hydroxylamine hydrochloride and 1.24 g of sodium acetate in 50 ml of ethanol. The following day, evaporate the reaction medium to dryness under vacuum, take the residue up with 100 ml of water, filter off the solid, and then wash it with 100 ml of water. After drying at 40° C. under vacuum, we obtain 1.17 g of 4-(6-bromo-1H-benzimidazol-2-yl)-9H-fluoren-9-one oxime (Z, E), with the following characteristics:

TLC (SiO$_2$) Rf=0.4 (methanol-dichloromethane 10/90 by volume).

Stage 4: Stir, at ambient temperature, a mixture of 390 mg of 4-(6-bromo-1H-benzimidazol-2-yl)-9H-fluoren-9-one oxime (Z, E) in a mixture of 2 ml of acetic acid, 2 ml of ethanol and 2 ml of water in the presence of 65 mg of powdered zinc. After half an hour, add a further 65 mg of powdered zinc and maintain the stirring for approximately 3 hours. Add Celite, filter over sintered glass and wash the precipitate with 200 ml of a mixture of methanol and dichloromethane (20/80 by volume). Evaporate the filtrate to dryness under vacuum, add twice 50 ml of toluene and, each time, re-evaporate to dryness under vacuum. The residue is chromatographed on silica gel, eluting with a mixture of dichloromethane and a 7N solution of ammonia in methanol (90/10 by volume). In this way, we obtain 69 mg of 4-(6-bromo-1H-benzimidazol-2-yl)-9H-fluoren-9(R,S)-amine, in the form of a beige foam with the following characteristics:

TLC (SiO$_2$) Rf=0.5 (methanol-dichloromethane 20/80 by volume).

Stage 5: Stir, at room temperature, a mixture of 220 mg of 4-(6-bromo-1H-benzimidazol-2-yl)-9H-fluoren-9(R,S)-amine, 123 mg of 1-(3-dimethylaminopropyl)-3-ethylcarbodiimide hydrochloride (EDCI), 87 mg of 1-hydroxybenzotriazole (HOBT) and 105 mg of 1H-pyrrolo[2,3-b]pyridine-4-carboxylic acid in 5 ml of dry dimethylformamide. After 1.5 hours, evaporate the reaction medium to dryness under vacuum, take the residue up with 50 ml of a saturated solution of sodium bicarbonate, triturate the suspension and filter the precipitate over sintered glass. The solid is washed with 75 ml of saturated solution of sodium bicarbonate and then 100 ml of water. The solid is taken up in toluene and the whole is evaporated to dryness under vacuum. The solid is chromatographed on silica gel, eluting with a mixture of methanol and dichloromethane (5/95 by volume). In this way, we obtain 214 mg of (6-bromo-1H-benzimidazol-2-yl)-9H-fluoren-9 (R,S)-yl]amide of 1H-pyrrolo-[2,3-b]pyridine-4-carboxylic acid, in the form of an off-white solid with the following characteristics:

Melting point (Kofler)=206° C. (decomp).

TLC (SiO$_2$) Rf=0.4 (methanol-dichloromethane 10/90 by volume).

NMR spectrum (400 MHz—δ in ppm—DMSO-d6): 6.41 (d, J=8.5 Hz, 1H); 6.91 (dd, J=2.0 and 3.5 Hz, 1H); 7.26 (t broad, J=7.5 Hz, 1H); 7.35 (d broad, J=7.5 Hz, 1H); 7.42 (dd, J=2.0 and 8.5 Hz, 1H); 7.47 (d, J=5.0 Hz, 1H); 7.51 (t, J=7.5 Hz, 1H); 7.56 (d broad, J=7.5 Hz, 1H); from 7.60 to 7.69 (m, 4H); 7.76 (d broad, J=7.5 Hz, 1H); 7.87 (m spread-out, 1H); 8.30 (d, J=5.0 Hz, 1H); 9.28 (d, J=8.5 Hz, 1H); 10.85 (m broad, 1H); 13.15 (m spread-out, 1H).

Example 221

Synthesis of 4-(5-fluoro-6-morpholino-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 1.5 g of 1,2-diamino-4-fluoro-5-morpholino-benzene in 50 ml of dichloromethane and 15 ml of tetrahydrofuran, 1.95 ml of triethylamine and 1.7 g of fluoren-4-one-9-carboxylic acid chloride. After stirring for 20 hours at room temperature, the precipitate that formed is filtered off, and washed with dichloromethane, with water, then with a 10% saturated aqueous solution of sodium hydrogen carbonate and, finally, with water. After formation of a paste with diisopropyl ether, in this way we obtain 2.2 g of (2-amino-5-fluoro-4-morpholinophenyl)amide of 9-oxo-9H-fluorene-4-carboxylic acid in the form of an orange powder, which is used as it is in the following stage, with the following characteristics:

Mass spectrum (LC/MS/ES/+/−): m/z=417 (M+).

Stage 2: The procedure used in Example 68 is followed. In a 500 ml round-bottomed flask under an argon atmosphere, heat, at 135° C. for 4 hours, a solution of 2.2 g of (2-amino-5-fluoro-4-morpholinophenyl)amide of 9-oxo-9H-fluorene-4-carboxylic acid, obtained in the previous stage, in 110 ml of acetic acid. After cooling, bring to dryness under reduced pressure. The crude solid obtained is purified by flash chromatography on silica gel (40-63 µm), eluting with a mixture of dichloromethane and ammonia as a 7N solution in methanol (98/2 by volume). After formation of a paste with diisopropyl ether, we obtain 1.8 g of 4-(5-fluoro-6-morpholino-1H-benzimidazol-2-yl)-9H-fluoren-9-one, in the form of a yellow powder, which is used as it is in the following stage, with the following characteristics:

Mass spectrum (LC/MS/ES/+/−): m/z=399 (M+).

Stage 3: The procedure used in Example 5 is followed, but starting from 1.8 g of 4-(5-fluoro-6-morpholino-1H-benzimidazol-2-yl)-9H-fluoren-9-one, obtained in the previous stage, 956 mg of hydroxylamine hydrochloride and 1.9 g of sodium acetate in 95 ml of ethanol, stirred for 20 h at room temperature and then heated at 60° C. for 2 hours. After concentration of the solvent under reduced pressure, the residue is taken up successively with water and then with toluene, brought to dryness. The crude product is purified by flash chromatography on silica gel (40-63 µm), eluting with a mixture of dichloromethane and methanol (98/2 by volume) and then with a mixture of dichloromethane and ammonia as a 7N solution in methanol (98/2 then 95/5 by volume). After formation of a paste with diisopropyl ether, in this way we obtain 1.7 g of 4-(5-fluoro-6-morpholino-1H-benzimidazol-2-yl)-9H-fluoren-9-one oxime (Z,E), as a 50-50 mixture of Z and E isomers, in the form of a pale yellow powder, which is used as it is in the following stage, with the following characteristics:

Mass spectrum (LC/MS/ES+/−): m/z=414 (M+).

Stage 4: The procedure used in Example 6 is followed. In a 211 ml autoclave, dissolve 1.7 g of 4-(5-fluoro-6-morpholino-1H-benzimidazol-2-yl)-9H-fluoren-9-one oxime (Z,E), obtained in the previous stage, in a mixture of 58 ml of ethanol and 58 ml of tetrahydrofuran, add a spatula of Raney activated nickel and then subject to an initial hydrogen pressure of 1 bar and heat the autoclave at 600 for 5 hours. After cooling, the volume of hydrogen absorbed is 250 ml. After filtration over Celite, the filtrate is concentrated under reduced pressure and then taken up in dichloromethane and dried over magnesium sulphate. The crude product is purified by flash chromatography on silica gel (40-63 µm), eluting with a mixture of dichloromethane and ammonia as a 7N solution in methanol (9/1 by volume). After formation of a paste with diisopropyl ether, in this way we obtain 732 mg of 4-(5-fluoro-6-morpholino-1H-benzimidazol-2-yl)-9H-fluorene-9(R,S)-amine, in the form of a white powder, which is used as it is in the following stage, with the following characteristics:

Mass spectrum (EI/CI): m/z=400 (M+).

Stage 5: The procedure used in Example 14 is followed, but starting from 350 mg of 4-(5-fluoro-6-morpholino-1H-benzimidazol-2-yl)-9H-fluorene-9(R,S)-amine, obtained in the previous stage, 156 mg of 1H-pyrrolo-[2,3-b]pyridine-4-carboxylic acid, 184 mg of 1-(3-dimethylaminopropyl)-3-ethylcarbodiimide hydrochloride (EDCI) and 59 mg of 1-hydroxybenzotriazole (HOBT) in 3.5 ml of dimethylformamide, for 20 hours at room temperature. Bring the dimethylformamide to dryness, add water, and drain the precipitate that formed and then wash with water then with a 10% saturated solution of sodium hydrogen carbonate and again with water. The crude solid obtained is dried and then purified by flash chromatography on silica gel (40-63 µm), eluting with a mixture of dichloromethane and methanol (95/5 then 9/1 by volume) and then of dichloromethane and ammonia as a 7N solution in methanol (9/1 then 85/15 by volume). After formation of a paste with diisopropyl ether, in this way we obtain 127 mg of [4-(5-fluoro-6-morpholino-1H-benzimidazol-2-yl)-9H-fluoren-9(R,S)-yl]amide of 1H-pyrrolo[2,3-b]-pyridine-4-carboxylic acid, in the form of a white powder with the following characteristics:

Mass spectrum (LC/MS/ES+/−): m/z=544 (M+).

$^1$H-NMR spectrum (400 MHz, δ in ppm, DMSO-d6): for this compound, a mixture of tautomers is observed with: 3.05 (m, 4H); 3.81 (m, 4H); 6.40 (d, J=8.5 Hz, 1H); 6.91 (m broad, 1H); from 7.10 to 7.66 (m, 9H); 7.46 (d, J=5.0 Hz, 1H); 7.74 (d broad, J=7.5 Hz, 1H); 8.29 (d, J=5.0 Hz, 1H); 9.27 (d, J=8.5 Hz, 1H); 11.85 (m broad, 1H); 12.85 (m broad, 1H).

Example 222

Synthesis of 4-(6-chloro-5-fluoro-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 1 g of 1,2-diamino-4-chloro-5-fluorobenzene, 1.75 ml of triethylamine and 1.5 g of fluoren-4-one-9-carboxylic acid chloride in 45 ml of dichloromethane. After stirring for 20 hours at room temperature, the precipitate that formed is filtered off, and washed with dichloromethane, with water, then with a 10% saturated aqueous solution of sodium hydrogen carbonate and, finally, with water. After formation of a paste with diisopropyl ether, in this way we obtain 1.5 g of (2-amino-5-chloro-4-fluorophenyl) amide of 9-oxo-9H-fluorene-4-carboxylic acid, in the form of a yellow powder, which is used as it is in the following stage, with the following characteristics:

Mass spectrum (LC/MS/ES+/−): m/z=366 (M+).

Stage 2: The procedure used in Example 68 is followed. In a 500 ml round-bottomed flask under an argon atmosphere, heat, at 135° C. for 4 hours, a solution of 1.5 g of (2-amino-5-chloro-4-fluorophenyl)amide of 9-oxo-9H-fluorene-4-carboxylic acid, obtained in the previous stage, in 75 ml of acetic acid. After cooling, bring to dryness under reduced pressure. After formation of a paste with diisopropyl ether, we obtain 1.3 g of 4-(6-chloro-5-fluoro-1H-benzimidazol-2-yl)-9H-fluoren-9-one, in the form of a yellow powder, which is used as it is in the following stage, with the following characteristics:

Mass spectrum (EI): m/z=348 (M+).

$^1$H-NMR spectrum (400 MHz, δ in ppm, DMSO-d6): 7.40 (t, J=7.5 Hz, 1H); 7.49 (t, J=7.5 Hz, 1H); 7.57 (t, J=7.5 Hz, 1H); 7.67 (m, 2H); 7.74 (d, J=9.5 Hz, 1H); 7.81 (d, J=8.0 Hz, 1H); 7.86 (d, J=8.0 Hz, 1H); 7.91 (d, J=7.0 Hz, 1H); 13.0 (m very spread-out, 1H).

Stage 3: The procedure used in Example 5 is followed, but starting from 1.3 g of 4-(6-chloro-5-fluoro-1H-benzimidazol-2-yl)-9H-fluoren-9-one, obtained in the previous stage, 800 mg of hydroxylamine hydrochloride and 1.6 g of sodium acetate in 70 ml of ethanol, stirred for 20 h at room temperature. After concentration of the solvent under reduced pressure, the residue is taken up successively with water, and then with toluene, brought to dryness. After formation of a paste with diisopropyl ether, in this way we obtain 1.1 g of 4-(6-chloro-5-fluoro-1H-benzimidazol-2-yl)-9H-fluoren-9-one oxime (Z,E), as a 50-50 mixture of Z and E isomers, in the form of an off-white powder, which is used as it is in the following stage, with the following characteristics:

Mass spectrum (LC/MS/EI): m/z=363 (M+).

Stage 4: The procedure used in Example 216 is followed. In a 100 ml round-bottomed flask under an argon atmosphere, dissolve 1.1 g of 4-(6-chloro-5-fluoro-1H-benzimidazol-2-yl)-9H-fluoren-9-one oxime (Z,E), obtained in the previous stage, in a mixture of 6.7 ml of ethanol and 6.7 ml of water and 6.7 ml of acetic acid, at room temperature, add 782 mg of zinc in three stages, and, between each addition, stir for approximately one to two hours. Add Celite and filter. The filtrate is concentrated under pressure. The crude product is purified by flash chromatography on silica gel (40-63 µm), eluting with a mixture of dichloromethane and ammonia as a 7N solution in methanol (9/1 by volume). After formation of a paste with diisopropyl ether, in this way we obtain 860 mg of 4-(6-chloro-5-fluoro-1H-benzimidazol-2-yl)-9H-fluorene-9(R, S)-amine, in the form of an off-white powder, which is used as it is in the following stage, with the following characteristics:

Mass spectrum (LC/MS/ES/+/−): m/z=349 (M+).

Stage 5: The procedure used in Example 14 is followed, but starting from 350 mg of 4-(6-chloro-5-fluoro-1H-benzimidazol-2-yl)-9H-fluorene-9(R,S)-amine, obtained in the previous stage, 178 mg of 1H-pyrrolo[2,3-b]pyridine-4-carboxylic acid, 211 mg of 1-(3-dimethylaminopropyl)-3-ethylcarbodiimide hydrochloride (EDCI) and 67 mg of 1-hydroxybenzotriazole (HOBT) in 3.5 ml of dimethyl sulphoxide, for 20 hours at room temperature. Add water, drain the precipitate that formed and then wash with water then with a 10% saturated solution of sodium hydrogen carbonate and again with water. The crude solid obtained is dried and then purified by flash chromatography on silica gel (40-63 µm), eluting with a mixture of dichloromethane and methanol (98/2 then 95/5 by volume). After formation of a paste with diisopropyl ether, in this way we obtain 296 mg of 4-(6-chloro-5-fluoro-1H-benzimidazol-2-yl)-9H-fluoren-9(R,S)-yl]amide of 1H-pyrrolo [2,3-b]pyridine-4-carboxylic acid, in the form of an off-white powder with the following characteristics:

Mass spectrum (LC/MS/ES+/−): m/z=493 (M+).

$^1$H-NMR spectrum (400 MHz, δ in ppm, DMSO-d6): 6.40 (d, J=8.5 Hz, 1H); 6.91 (dd, J=2.0 and 3.5 Hz, 1H); 7.26 (t broad, J=7.5 Hz, 1H); 7.35 (t broad, J=7.5 Hz, 1H); 7.46 (d, J=5.0 Hz, 1H); 7.52 (t, J=7.5 Hz, 1H); 7.57 (d broad, J=8.0 Hz, 1H); 7.62 (m, 2H); 7.66 (d broad, J=7.5 Hz, 1H); 7.72 (d broad, J=9.5 Hz, 1H); 7.77 (d, J=8.0 Hz, 1H); 7.88 (m spread-out, 1H); 8.30 (d, J=5.0 Hz, 1H); 9.28 (d, J=8.5 Hz, 1H); 11.85 (m broad, 1H); 13.25 (m very spread-out, 1H).

Example 223

[4-(4,5,6,7-tetrahydro-1H-benzimidazol-2-yl)-9H-fluoren-9-yl]-amide of 1H-pyrrolo[2,3-b]pyridine-4-carboxylic acid Stage 1: The procedure used in stage 1 of Example 1 is followed, but starting from 1.29 g of cis-cyclohexane-1,2-diamine in 100 ml of dichloromethane, 1.52 g of triethylamine and 1.82 g of fluoren-4-one-9-carboxylic acid chloride for 20 hours at room temperature. After treatment as in stage 1 of Example 1, we obtain 700 mg of (2-aminocyclohexyl)amide of 9-oxo-9H-fluorene-4-carboxylic acid, in the form of a yellow powder, which is used as it is in the following stage, with the following characteristics:
Mass spectrum (LC/MS/ES/+/−): m/z=321 (M+).

Stage 2: In a 25 ml round-bottomed flask, heat, at 150° C. for 30 minutes, 0.68 g of (2-aminocyclohexyl)amide of 9-oxo-9H-fluorene-4-carboxylic acid, obtained in the previous stage, in 5 ml of polyphosphoric acid (PPA). After cooling, neutralize to pH=6 by adding a 38% aqueous solution of sodium hydroxide. The precipitate that formed is filtered and then purified by flash chromatography on silica gel (40-63 µm), eluting with a mixture of dichloromethane and methanol (90/10 by volume). In this way, we obtain 0.36 g of 4-(3a,4,5,6,7,7a-hexahydro-1H-benzimidazol-2-yl)-9H-fluoren-9-one, in the form of a yellow powder, which is used as it is in the following stage, with the following characteristics:
Mass spectrum (LC/MS/ES/+/−): m/z=303 (M+).

Stage 3: In a 20 ml sealed tube, dissolve 330 mg of 4-(3a,4,5,6,7,7a-hexahydro-1H-benzimidazol-2-yl)-9H-fluoren-9-one, obtained in the previous stage, in 12 ml of dimethyl sulphoxide and then heat at 200° C. for one hour. After cooling, add 30 ml of water and then extract 3 times with 100 ml of ethyl acetate. The crude solid obtained is purified by flash chromatography on silica gel (40-63 µm), eluting with a mixture of dichloromethane and methanol (97/3 by volume). In this way, we obtain 210 mg of 4-(4,5,6,7-tetrahydro-1H-benzimidazol-2-yl)-9H-fluoren-9-one, in the form of a yellow powder, which is used as it is in the following stage, with the following characteristics:
Mass spectrum (LC/MS/ES/+/−): m/z=301 (M+).

Stage 4: The procedure used in Example 5 is followed, but starting from 200 mg of 4-(4,5,6,7-tetrahydro-1H-benzimidazol-2-yl)-9H-fluoren-9-one, obtained in the previous stage, 139 mg of hydroxylamine hydrochloride and 273 mg of sodium acetate in 22 ml of ethanol, stirred for 1 h at room temperature and then for 3 hours at 80° C. After concentration of the solvent under reduced pressure, the residue is taken up successively with water and then with toluene, brought to dryness and, finally, made into a paste with diisopropyl ether. In this way, we obtain 44 mg of 4-(4,5,6,7-tetrahydro-1H-benzimidazol-2-yl)-9H-fluoren-9-one oxime (Z,E), as a 50-50 mixture of Z and E isomers, in the form of an amber powder, which is used as it is in the following stage, with the following characteristics:
Mass spectrum (EI/CI): m/z=316 (M+).

Stage 5: The procedure used in Example 6 is followed. In a 25 ml autoclave, dissolve 43 mg of 4-(4,5,6,7-tetrahydro-1H-benzimidazol-2-yl)-9H-fluoren-9-one oxime (Z,E), obtained in the previous stage, in a mixture of 4 ml of ethanol and 4 ml of tetrahydrofuran, add a spatula of Raney activated nickel and then subject to a hydrogen pressure of 1 bar and heat the autoclave at 600 for 12 hours. After cooling, the volume of hydrogen absorbed is 12 ml. After filtration of the catalyst, concentration to dryness under reduced pressure and purification by formation of a paste with diisopropyl ether, in this way we obtain 40 mg of 4-(4,5,6,7-tetrahydro-1H-benzimidazol-2-yl)-9H-fluoren-9(R,S)-ylamine, in the form of a beige powder, which is used as it is in the following stage, with the following characteristics:
Mass spectrum (LC/MS): m/z=302 (M+).

Stage 6: The procedure used in Example 14 is followed, but starting from 35 mg of 4-(4,5,6,7-tetrahydro-1H-benzimidazol-2-yl)-9H-fluoren-9(RS)-ylamine, obtained in the previous stage, 20 mg of 1H-pyrrolo-[2,3-b]pyridine-4-carboxylic acid, 26 mg of 1-(3-dimethylaminopropyl)-3-ethylcarbodiimide hydrochloride (EDCI) and 18 mg of 1-hydroxybenzotriazole (HOBT) in 4 ml of dimethylformamide, for 20 hours at room temperature. After purification by flash chromatography on silica gel (70-230 mesh), eluting with a mixture of dichloromethane and ammonia at 7N in methanol (90/10 by volume), in this way we obtain 19 mg of [4-(4,5,6,7-tetrahydro-1H-benzimidazol-2-yl)-9H-fluoren-9-yl]amide of 1H-pyrrolo[2,3-b]pyridine-4-carboxylic acid, in the form of an amber powder with the following characteristics:
Mass spectrum (LC/MS): m/z=446 (M+).
$^1$H-NMR spectrum (400 MHz, δ in ppm, DMSO-d6): 1.83 (m, 4H); from 2.55 to 2.67 (m broad, 4H); 6.34 (d, J=85 Hz, 1H); 6.90 (dd, J=1.5 and 3.5 Hz, 1H); from 7.26 to 7.35 (m, 2H); 7.39 (t, J=7.5 Hz, 1H); from 7.44 to 7.49 (m, 2H); from 7.50 to 7.60 (m, 2H); 7.61 (dd, J=2.0 and 3.5 Hz, 1H); 8.10 (d broad, J=8.0 Hz, 1H); 8.28 (d, J=5.0 Hz, 1H); 9.22 (d, J=8.5 Hz, 1H); 11.85 (m broad, 1H); 12.0 (s, 1H).

Example 224

Synthesis of 4-(5,6-difluoro-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 1 g of 1,2-diamino-4,5-difluorobenzene, 1.9 ml of triethylamine and 1.7 g of fluoren-4-one-9-carboxylic acid chloride in 50 ml of dichloromethane. After stirring for 20 hours at room temperature, the precipitate that formed is filtered off, and washed with dichloromethane, with water, then with a 10% saturated aqueous solution of sodium hydrogen carbonate and, finally, with water. After formation of a paste with diisopropyl ether, in this way we obtain 1.4 g of (2-amino-4,5-difluorophenyl)amide of 9-oxo-9H-fluorene-4-carboxylic acid, in the form of a yellow powder, which is used as it is in the following stage, with the following characteristics:
Mass spectrum (LC/MS/ES/+/−): m/z=350 (M+).

Stage 2: The procedure used in Example 68 is followed. In a 250 ml round-bottomed flask under an argon atmosphere, heat, at 135° C. for 4 hours, a solution of 1.4 g of (2-amino-4,5-difluorophenyl)amide of 9-oxo-9H-fluorene-4-carboxylic acid, obtained in the previous stage, in 70 ml of acetic acid. After cooling, bring to dryness under reduced pressure. The crude solid obtained is purified by flash chromatography on silica gel (40-63 µm), eluting with a mixture of dichloromethane and ammonia as a 7N solution in methanol (98/2 by volume). After formation of a paste with diisopropyl ether, we obtain 1.1 g of 4-(5,6-difluoro-1H-benzimidazol-2-yl)-9H-fluoren-9-one, in the form of a yellow powder, which is used as it is in the following stage, with the following characteristics:
Mass spectrum (LC/MS/ES/+/−): m/z=332 (M+).

Stage 3: The procedure used in Example 5 is followed, but starting from 1.1 g of 4-(5,6-difluoro-1H-benzimidazol-2-yl)-9H-fluoren-9-one, obtained in the previous stage, 690 mg of hydroxylamine hydrochloride and 1.4 g of sodium acetate in 60 ml of ethanol, stirred for 20 h at room temperature. After concentration of the solvent under reduced pressure, the residue is taken up successively with water, and then with toluene, and brought to dryness. After formation of a paste with diisopropyl ether, in this way we obtain 830 mg of 4-(5,6-difluoro-1H-benzimidazol-2-yl)-9H-fluoren-9-one oxime (Z,E), as a 50-50 mixture of Z and E isomers, in the form of a beige powder, which is used as it is in the following stage, with the following characteristics:

Mass spectrum (LC/MS/ES/+/−): m/z=347 (M+).

Stage 4: The procedure used in Example 216 is followed. In a 100 ml round-bottomed flask under an argon atmosphere, dissolve 830 mg of 4-(5,6-difluoro-1H-benzimidazol-2-yl)-9H-fluoren-9-one oxime (Z,E), obtained in the previous stage, in a mixture of 5.5 ml of ethanol and 5.5 ml of water and 5.5 ml of acetic acid, at room temperature, add 624 mg of zinc in three stages, and, between each addition, stir for approximately one hour to two hours. Add Celite and filter. The filtrate is concentrated under pressure. The crude product is purified by flash chromatography on silica gel (40-63 µm), eluting with a mixture of dichloromethane and ammonia as a 7N solution in methanol (98/2 by volume). After formation of a paste with diisopropyl ether, in this way we obtain 653 mg of 4-(5,6-difluoro-1H-benzimidazol-2-yl)-9H-fluorene-9(R,S)-amine, in the form of a white powder, which is used as it is in the following stage, with the following characteristics:

Mass spectrum (LC/MS/ES/+/−): m/z=333 (M+).

Stage 5: The procedure used in Example 14 is followed, but starting from 330 mg of 4-(5,6-difluoro-1H-benzimidazol-2-yl)-9H-fluoren-9(R,S)-amine, obtained in the previous stage, 178 mg of 1H-pyrrolo[2,3-b]pyridine-4-carboxylic acid, 211 mg of 1-(3-dimethylaminopropyl)-3-ethylcarbodiimide hydrochloride (EDCI) and 67 mg of 1-hydroxybenzotriazole (HOBT) in 3.5 ml of dimethylformamide for 20 hours at room temperature. Bringing the dimethylformamide to dryness, add water and drain the precipitate that formed and then wash with water then with a 10% saturated solution of sodium hydrogen carbonate and, finally, with water. The crude solid obtained is dried and then purified by flash chromatography on silica gel (40-63 µm), eluting with a mixture of dichloromethane and methanol (98/2 then 95/5 by volume). After formation of a paste with diisopropyl ether, in this way we obtain 259 mg of 4-(5,6-difluoro-1H-benzimidazol-2-yl)-9H-fluoren-9(R,S)-yl]-amide of 1H-pyrrolo[2,3-b]pyridine-4-carboxylic acid, in the form of a white powder with the following characteristics:

Mass spectrum (LC/MS/ES+/−): m/z=477 (M+).

$^1$H-NMR spectrum (400 MHz, δ in ppm, DMSO-d6): 6.40 (d, J=8.5 Hz, 1H); 6.91 (d broad, J=3.5 Hz, 1H); 7.25 (t broad, J=7.5 Hz, 1H); 7.35 (t broad, J=7.5 Hz, 1H); 7.46 (d, J=5.0 Hz, 1H); 7.51 (t, J=7.5 Hz, 1H); from 7.54 to 7.79 (m, 7H); 8.29 (d, J=5.0 Hz, 1H); 9.27 (d, J=8.5 Hz, 1H); 11.85 (m broad, 1H); 13.2 (m spread-out, 1H).

Example 225

Synthesis of [4-(5-methyl-5H-imidazo[4,5-c]pyridin-2-yl)-9H-fluoren-9-yl]amide of 1H-pyrrolo[2,3-b]pyridine-4-carboxylic acid In a 5 ml single-necked round-bottomed flask, dissolve 442 mg of [4-(3H-imidazo[4,5-c]pyridin-2-yl)-9H-fluoren-9-yl]amide of 1H-pyrrolo[2,3-b]pyridine-4-carboxylic acid, obtained in Example 92, in 4 ml of dimethylformamide. A solution of 62 µl of methyl iodide in 1 ml of dimethylformamide is added dropwise to the yellow solution obtained. After stirring overnight at room temperature, TLC and LC/MS analysis of the reaction medium reveals that the starting product has been completely used up. The brown oil, obtained after evaporation of the solvent under reduced pressure, is purified by flash chromatography on a silica column (gradient CH$_2$Cl$_2$/MeOH: from 100/0 to 80/20). In this way, we obtain 343 mg of [4-(5-methyl-5H-imidazo-[4,5-c]pyridin-2-yl)-9H-fluoren-9-yl]amide of 1H-pyrrolo[2,3-b]pyridine-4-carboxylic acid, in the form of an off-white powder with the following characteristics:

Mass spectrum (EI): m/z=456 (M+).

NMR spectrum (400 MHz, δ in ppm, DMSO-d6): 4.29 (s, 3H); 6.39 (d, J=8.5 Hz, 1H); 6.91 (dd, J=2.0 and 3.5 Hz, 1H); 7.21 (t broad, J=7.5 Hz, 1H); 7.31 (t broad, J=7.5 Hz, 1H); 7.44 (t partially masked, J=7.5 Hz, 1H); 7.47 (d, J=5.0 Hz, 1H); 7.58 (d broad, J=8.0 Hz, 1H); 7.62 (t broad, J=3.5 Hz, 1H); 7.67 (d broad, J=8.0 Hz, 1H); 7.85 (d, J=7.0 Hz, 1H); 7.91 (d broad, J=8.0 Hz, 1H); 8.15 (d broad, J=7.0 Hz, 1H); 8.25 (d broad, J=8.0 Hz, 1H); 8.29 (d, J=5.0 Hz, 1H); 9.09 (s broad, 1H); 9.25 (d, J=8.5 Hz, 1H); 11.85 (m broad, 1H).

Example 226

Synthesis of [2-amino-5-(1H-benzimidazol-2-yl)-9H-fluoren-9(R,S)-yl]amide of 1H-pyrrolo[2,3-b]pyridine-4-carboxylic acid Stage 1: In a 50 ml three-necked flask, place 1.615 g of 7-nitro-9-oxo-9H-fluorene-4-carboxylic acid, which can be obtained according to WO2003057145, in suspension in 30 ml of dichloromethane, and then add successively 567 µl of oxalyl chloride and 1 drop of dimethylformamide. After stirring for 4 hours at room temperature, add 0.779 g of 1,2-diaminobenzene and 1.686 ml of triethylamine. After stirring for 20 hours at room temperature, the precipitate that formed is filtered off, and washed with water, then with a 10% saturated aqueous solution of sodium hydrogen carbonate and, finally, with water. After formation of a paste with diisopropyl ether, in this way we obtain 1.6 g of (2-aminophenyl)amide of 7-nitro-9-oxo-9H-fluoren-4-carboxylic acid, in the form of an orange powder, which is used as it is in the following stage, with the following characteristics:

Mass spectrum (LC/MS/ES/+/−): m/z=359 (M+).

Stage 2: The procedure used in Example 68 is followed. In a 100 ml round-bottomed flask under an argon atmosphere, heat, at 130° C. for 4 hours, a suspension of 1.6 g of (2-aminophenyl)amide of 7-nitro-9-oxo-9H-fluorene-4-carboxylic acid, obtained in the previous stage, in 30 ml of acetic acid. After cooling, the insoluble material that formed is filtered off, and washed successively with water, with a saturated aqueous solution of sodium hydrogen carbonate and then with water. After purification by flash chromatography on silica gel (40-63 µm), eluting with a mixture of dichloromethane and 7N ammoniacal methanol (9/1 by volume), then formation of a paste in diisopropyl ether, in this way we obtain 550 mg of 5-(1H-benzimidazol-2-yl)-2-nitro-9H-fluoren-9-one, in the form of a yellow powder, which is used as it is in the following stage, with the following characteristics:

Mass spectrum (EI): m/z=341 (M+).

NMR spectrum (400 MHz, δ in ppm, DMSO-d6+TFAd) 7.44 (d, J=8.0 Hz, 1H); 7.67 (m, 2H); 7.84 (t, J=7.5 Hz, 1H); 7.96 (m, 2H); 8.10 (d broad, J=7.5 Hz, 2H); from 7.33 to 7.39 (m, 2H).

Stage 3: In a 100 ml round-bottomed flask under argon, 550 mg of 5-(1H-benzimidazol-2-yl)-2-nitro-9H-fluoren-9-one, obtained in the previous stage, are stirred for 2 hours at reflux, in the presence of 2.513 g of iron and 313 µl of a 37% aqueous solution of hydrochloric acid, in 3.2 ml of water and 25 ml of ethanol. After cooling, filter the insoluble material over Celite, then wash with water and with a saturated aqueous solution of sodium hydrogen carbonate. This insoluble material is then taken up in dimethylformamide. After concentration of the dimethylformamide under reduced pressure, the crude product obtained is purified by flash chromatography on silica gel (40-63 µm), eluting with a mixture of dichloromethane and 7N ammoniacal methanol (95/5 by volume). In this way, we obtain 0.45 g of 2-amino-5-(1H-benzimidazol-2-yl)-9H-fluoren-9-one, in the form of a brown powder which is used as it is in the following stage.

Mass spectrum (EI): m/z=311 (M+).

Stage 4: In a 100 ml round-bottomed flask under argon, 0.3 g of 2-amino-5-(1H-benzimidazol-2-yl)-9H-fluoren-9-one, obtained in the previous stage, are stirred in 10 ml of acetonitrile, for 20 hours at room temperature, in the presence of 0.631 g of tert-butyl dicarbonate and 11.8 mg of 4-dimethylaminopyridine. After concentration of the solvent under reduced pressure, the residue is dissolved in 50 ml of ethyl acetate and the organic phase is then washed with water, dried over magnesium sulphate and concentrated to dryness under reduced pressure. The crude solid obtained is purified by flash chromatography on silica gel (40-63 µm), eluting with a mixture of ethyl acetate and dichloromethane (5/95 by volume). In this way, we obtain 0.3 g of 5-[1-(tert-butoxycarbonyl)benzimidazol-2-yl]-7-(tert-butoxy-carbonylamino)-9H-fluoren-9-one, in the form of a yellow foam which is used as it is in the following stage.

Mass spectrum (EI): m/z=511 (M+).

Stage 5: The procedure used in Example 5 is followed, but starting from 300 mg of 5-[1-(tert-butoxycarbonyl)benzimidazol-2-yl]-7-(tert-butoxycarbonyl-amino)-9H-fluoren-9-one, obtained in the previous stage, 122 mg of hydroxylamine hydrochloride and 240 mg of sodium acetate in 4 ml of ethanol, stirred for 20 h at room temperature. After formation of a paste with diisopropyl ether, in this way we obtain 250 mg of 5-[1-(tert-butoxycarbonyl)-benzimidazol-2-yl]-7-(tert-butoxycarbonylamino)-9H-fluoren-9-one oxime (Z,E), as a 50/50 mixture of Z and E isomers, in the form of an orange powder, which is used as it is in the following stage, with the following characteristics:

Mass spectrum (EI): m/z=526 (M+).

Stage 6: The procedure used in Example 6 is followed, but starting from 250 mg of 5-[1-(tert-butoxycarbonyl)benzimidazol-2-yl]-7-(tert-butoxycarbonyl-amino)-9H-fluoren-9-one oxime (Z,E), obtained in the previous stage, and 29 mg of Raney nickel in 4 ml of ethanol and 4 ml of tetrahydrofuran for 10 hours at 60° C. under an initial hydrogen pressure of one bar. After filtration of the catalyst, and purification by formation of a paste in diisopropyl ether, in this way we obtain 250 mg of 5-[1-(tert-butoxycarbonyl)benzimidazol-2-yl]-7-(tert-butoxycarbonylamino)-9H-fluoren-9(R,S)-ylamine, in the form of an orange powder which is used as it is in the following stage.

Stage 7: The procedure used in Example 14 is followed, but starting from 250 mg of 5-[1-(tert-butoxycarbonyl)benzimidazol-2-yl]-7-(tert-butoxycarbonyl-amino)-9H-fluoren-9(R,S)-ylamine, obtained in the previous stage, 79 mg of 1H-pyrrolo[2,3-b]pyridine-4-carboxylic acid, 103 mg of 1-(3-dimethyl-aminopropyl)-3-ethylcarbodiimide hydrochloride (EDCI) and 72 mg of 1-hydroxybenzotriazole (HOBT) in 3.5 ml of dimethylformamide, for 72 hours at room temperature.

After purification by formation of a paste with diisopropyl ether, in this way we obtain 300 mg of {5-[1-(tert-butoxycarbonyl)-benzimidazol-2-yl]-7-(tert-butoxycarbonylamino)-9H-fluoren-9(R,S)-yl}amide of 1H-pyrrolo[2,3-b]pyridine-4-carboxylic acid, in the form of an orange powder with the following characteristics:

Mass spectrum (LC/MS/ES+/−): m/z=656 (M+).

Stage 8: In a 100 ml round-bottomed flask under argon, dissolve 300 mg of {5-[1-(tert-butoxycarbonyl)benzimidazol-2-yl]-7-(tert-butoxycarbonylamino)-9H-fluoren-9(R,S)-yl}amide of 1H-pyrrolo[2,3-b]pyridine-4-carboxylic acid, obtained in the previous stage, in 1.5 ml of dioxane, and then run in, dropwise, 1.45 ml of a 4N solution of hydrochloric acid into the dioxane and stir for 20 hours at room temperature. After concentration of the solvent under reduced pressure, the reaction medium is taken up in water, and brought to pH=8 by the addition of a saturated aqueous solution of sodium hydrogen carbonate. The precipitate that formed is drained, and then purified by flash chromatography on silica gel (40-63 µm), eluting with a mixture of dichloromethane and methanol (95/5 by volume). In this way, we obtain 15 mg of [2-amino-5-(1H-benzimidazol-2-yl)-9H-fluoren-9(R,S)-yl]amide of 1H-pyrrolo[2,3-b]pyridine-4-carboxylic acid, in the form of a yellow powder with the following characteristics:

Mass spectrum (LC/MS/ES+/−): m/z=456 (M+).

$^1$H-NMR spectrum (400 MHz, δ in ppm, DMSO-d6): 5.39 (s broad, 2H); 6.25 (d, J=8.5 Hz, 1H); 6.39 (dd, J=2.0 and 8.5 Hz, 1H); 6.81 (s broad, 1H); 6.93 (dd, J=2.0 and 3.5 Hz, 1H); from 7.20 to 7.35 (m, 4H); 7.48 (d, J=5.0 Hz, 1H); from 7.51 to 7.64 (m, 4H); 7.75 (m broad, 1H); 8.29 (d, J=5.0 Hz, 1H); 9.20 (d, J=8.5 Hz, 1H); 11.85 (m broad, 1H); 12.8 (m broad, 1H).

Example 227

Synthesis of [4-(5-methyl-4,5,6,7-tetrahydro-3H-imidazo[4,5-c]-pyridin-2-yl)-9H-fluoren-9-yl]amide of 1H-pyrrolo[2,3-b]pyridine-4-carboxylic acid Add, at room temperature and under argon, 174 mg of sodium borohydride to the suspension of 70 mg of [4-(5-methyl-5H-imidazo[4,5-c]pyridin-2-yl)-9H-fluoren-9-yl] amide of 1H-pyrrolo[2,3-b]pyridine-4-carboxylic acid, obtained as in Example 225, in 7 ml of anhydrous methanol. Disappearance of the starting product is observed by TLC after stirring for 1 h at room temperature. The addition of 2 ml of a saturated solution of ammonium chloride makes it possible to neutralize the excess hydride. After evaporation of the solvent under reduced pressure, the solid residue is purified by flash chromatography on a silica column (gradient CH$_2$Cl$_2$/MeOH: from 100/0 to 70/30). We obtain 70 mg of [4-(5-methyl-4,5,6,7-tetrahydro-3H-imidazo[4,5-c]pyridin-2-yl)-9H-fluoren-9-yl]amide of 1H-pyrrolo[2,3-b]pyridine-4-carboxylic acid, in the form of a white powder with the following characteristics:

Mass spectrum (ESI+): m/z=461 (MH+).

$^1$H-NMR spectrum (400 MHz, δ in ppm, DMSO-d6): 2.90 (s, 3H); 3.04 (m broad, 2H); 3.50 (m broad, 2H); 4.24 (m broad, 2H); 6.35 (d, J=8.5 Hz, 1H); 6.89 (m broad, 1H); 7.28 (t, J=7.5 Hz, 1H); 7.34 (t, J=7.5 Hz, 1H); 7.43 (t, J=7.5 Hz, 1H); 7.46 (d, J=5.0 Hz, 1H); 7.53 (d, J=7.5 Hz, 1H); 7.58 (d, J=7.5 Hz, 1H); 7.61 (t, J=3.5 Hz, 1H); 7.64 (d, J=7.5 Hz, 1H);

7.92 (d broad, J=7.5 Hz, 1H); 8.28 (d, J=5.0 Hz, 1H); 9.28 (d, J=8.5 Hz, 1H); 11.95 (m broad, 1H); 12.8 (m spread-out, 1H).

Example 228

Synthesis of 4-(5-methoxy-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 10 g of 1,2-diamino-4-methoxybenzene, 20 ml of triethylamine and 17 g of fluoren-4-one-9-carboxylic acid chloride in 600 ml of dichloromethane. After stirring for 20 hours at room temperature, the precipitate that formed is filtered off, and washed with dichloromethane, with water, then with a 10% saturated aqueous solution of sodium hydrogen carbonate and, finally, with water. After formation of a paste with diisopropyl ether, in this way we obtain 6.2 g of (2-amino-4-methoxyphenyl)amide of 9-oxo-9H-fluorene-4-carboxylic acid, in the form of a brown powder, which is used as it is in the following stage, with the following characteristics:

Mass spectrum (EI): m/z=344 (M+).

Stage 2: The procedure used in Example 68 is followed. In a 1 l round-bottomed flask under an argon atmosphere, heat, at 110° C. for 5 hours, a solution of 6.2 g of (2-amino-4-methoxyphenyl)amide of 9-oxo-9H -fluorene-4-carboxylic acid, obtained in the previous stage, in 300 ml of acetic acid. After cooling, bring to dryness under reduced pressure. The crude solid obtained is purified by flash chromatography on silica gel (40-63 µm) eluting with a mixture of dichloromethane and methanol (99/1 then 98/2 by volume). After formation of a paste with diisopropyl ether, we obtain 5.1 g of 4-(5-methoxy-1H-benzimidazole-2-yl)-9H-fluoren-9-one, in the form of a yellow powder, which is used as it is in the following stage, with the following characteristics:

Mass spectrum (EI): m/z=326 (M+).

$^1$H-NMR spectrum (400 MHz, δ in ppm, DMSO-d6): 3.84 (s, 3H); 6.92 (dd, J=2.0 and 8.5 Hz, 1H); 7.15 (m broad, 1H); 7.39 (t, J=7.5 Hz, 1H); 7.49 (t, J=7.5 Hz, 1H); 7.56 (t, J=7.5 Hz, 1H); 7.59 (m broad, 1H); 7.67 (d, J=8.0 Hz, 1H); from 7.74 to 7.79 (m, 2H); 7.83 (d, J=7.5 Hz, 1H); 12.9 (m spread-out, 1H).

Stage 3: The procedure used in Example 5 is followed, but starting from 1 g of 4-(5-methoxy-1H-benzimidazol-2-yl)-9H-fluoren-9-one, obtained in the previous stage, 640 mg of hydroxylamine hydrochloride and 1.3 g of sodium acetate in 17 ml of ethanol, stirred for 20 h at room temperature. After concentration of the solvent under reduced pressure, the residue is taken up successively with water, then with toluene, brought to dryness. After formation of a paste with diisopropyl ether, in this way we obtain 890 mg of 4-(5-methoxy-1H-benzimidazol-2-yl)-9H-fluoren-9-one oxime (Z,E), as a 50-50 mixture of Z and E isomers, in the form of a beige powder, which is used as it is in the following stage, with the following characteristics:

Mass spectrum (EI): m/z=341 (M+).

Stage 4: The procedure used in Example 216 is followed. In a 100 ml round-bottomed flask under an argon atmosphere, dissolve 890 mg of 4-(5-methoxy-1H-benzimidazol-2-yl)-9H-fluoren-9-one oxime (Z,E), obtained in the previous stage, in a mixture of 5.9 ml of ethanol and 5.9 ml of water and 5.9 ml of acetic acid, at ambient temperature, add 682 mg of zinc in three stages, and, between each addition, stir for approximately one hour to two hours. Add Celite and filter. The filtrate is concentrated under pressure. The crude product is purified by flash chromatography on silica gel (40-63 µm), eluting with a mixture of dichloromethane and ammonia as a 7N solution in methanol (95/5 by volume). After formation of a paste with diisopropyl ether, in this way we obtain 716 mg of 4-(5-methoxy-1H-benzimidazol-2-yl) -9H-fluorene-9(R,S)-amine, in the form of a beige powder, which is used as it is in the following stage, with the following characteristics:

Mass spectrum (LC/MS/ES/+/−): m/z=327 (M+).

Stage 5: The procedure used in Example 14 is followed, but starting from 330 mg of 4-(5-methoxy-1H-benzimidazol-2-yl)-9H-fluorene-9(R,S)-amine, obtained in the previous stage, 180 mg of 1H-pyrrolo[2,3-b]pyridine-4-carboxylic acid, 213 mg of 1-(3-dimethylaminopropyl)-3-ethylcarbodiimide hydrochloride (EDCI) and 68 mg of 1-hydroxybenzotriazole (HOBT) in 3.5 ml of dimethylformamide, for 20 hours at room temperature. Bring the dimethylformamide to dryness, add water and drain the precipitate that formed and then wash with water then with a 10% saturated solution of sodium hydrogen carbonate and, finally, with water. The crude solid obtained is dried and then purified by flash chromatography on silica gel (40-63 µm), eluting with a mixture of dichloromethane and methanol (95/5 by volume). After formation of a paste with diisopropyl ether, in this way we obtain 278 mg of 4-(5-methoxy-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Mass spectrum (LC/MS/ES+/−): m/z=471 (M+).

$^1$H-NMR spectrum (400 MHz, δ in ppm, DMSO-d6): for this compound, a 50%-50% mixture of tautomers is observed with: 3.84 (s, 3H); 6.40 (d, J=8.5 Hz, 1H); from 6.85 to 6.95 (m, 2H); 7.05 (d, J=2.5 Hz, 0.5H); 7.25 (t, J=7.5 Hz, 1H); 7.30 (d, J=2.5 Hz, 0.5H); 7.34 (t, J=7.5 Hz, 1H); from 7.44 to 7.53 (m, 2.5H); from 7.59 to 7.67 (m, 4.5H); 7.74 (d broad, J=8.0 Hz, 1H); 8.29 (d, J=5.0 Hz, 1H); 9.28 (d, J=8.5 Hz, 1H); 11.85 (m broad, 1H); 12.75 (s, 0.5H); 12.8 (s, 0.5H).

Example 229

Synthesis of [4-(5-hydroxy-5H-imidazo[4,5-c]pyridin-2-yl)-9H-fluoren-9-yl]amide of 1H-pyrrolo[2,3-b]pyridine-4-carboxylic acid In a 5 ml single-necked round-bottomed flask, dissolve 2 mg of trimethyl oxorhenium in 1 ml of dimethylformamide. Add 147 µl of 30% hydrogen peroxide and stir for 15 minutes at room temperature. Added, dropwise, to the yellow solution obtained is a solution of 160 mg of [4-(3H -imidazo[4,5-c]pyridin-2-yl)-9H-fluoren-9-yl]amide of 1H-pyrrolo[2,3-b]pyridine-4-carboxylic acid, obtained in Example 92, in 1 ml of dimethylformamide. After stirring for one hour at room temperature, the conversion rate reaches 50% and no longer changes. Evaporation of the solvent under reduced pressure gives an orange oil which is purified by flash chromatography on a silica column (gradient $CH_2Cl_2$/MeOH: from 100/0 to 70/30). We obtain 83 mg of [4-(5-hydroxy-5H-imidazo[4,5-c]pyridin-2-yl)-9H -fluoren-9-yl]amide of 1H-pyrrolo[2,3-b]pyridine-4-carboxylic acid, in the form of a pale yellow powder with the following characteristics:

Mass spectrum (ESI+): m/z=459 (MH+).

NMR spectrum (400 MHz, δ in ppm, DMSO-d6): 6.41 (d, J=8.5 Hz, 1H); 6.91 (m broad, 1H); 7.28 (t, J=7.5 Hz, 1H); 7.36 (t, J=7.5 Hz, 1H); 7.48 (t, J=5.0 Hz, 1H); 7.53 (t, J=7.5 Hz, 1H); 7.56 (d, J=8.0 Hz, 1H); 7.63 (m, 2H); 7.68 (m, 2H); 7.79 (d, J=7.5 Hz, 1H); 8.10 (dd, J=2.0 and 7.0 Hz, 1H); 8.29 (d, J=5.0 Hz, 1H); 8.70 (m broad, 1H); 9.33 (d, J=8.5 Hz, 1H); 11.9 (m broad, 1H); 13.5 (m very spread-out, 1H).

Example 230

Synthesis of 4-(5-hydroxy-1H-benzimidazol-2-yl)-9H-fluoren-9(R,S)-yl]amide of 1H-pyrrolo[2,3-b]pyridine-4-carboxylic acid Stage 1: In a 50 ml round-bottomed flask under argon, dissolve 1 g of 4-(5-methoxy-1H-benzimidazol-2-yl)-9H-fluoren-9-one, obtained in stage 2 of Example 228, in 15 ml of dichloromethane, cooled to 0° C., and add 7.7 ml of boron tribromide as a 1M solution in dichloromethane. After stirring for 20 hours, the reaction medium is poured into water, and the insoluble material is drained, washed with water and then dried. The crude product is purified by flash chromatography on silica gel (40-63 µm), eluting with a mixture of dichloromethane and methanol (98/2 then 95/5 by volume). After formation of a paste with diisopropyl ether, in this way we obtain 360 mg of 4-(5-hydroxy-1H-benzimidazol-2-yl)-9H-fluoren-9-one in the form of a yellow powder, which is used as it is in the following stage, with the following characteristics:

Mass spectrum (LC/MS/ES/+/−): m/z=312 (M+).

$^1$H-NMR spectrum (400 MHz, δ in ppm, DMSO-d6): for this compound, a 70%-30% mixture of tautomers is observed with: 6.77 (d broad, J=8.5 Hz, 1H); 6.90 (s broad, 0.7H); 7.07 (s broad, 0.3H); 7.39 (t, J=7.5 Hz, 1H); from 7.45 to 7.61 (m masked, 1H); 7.50 (t, J=7.5 Hz, 1H); 7.55 (t, J=7.5 Hz, 1H); 7.67 (d, J=8.0 Hz, 1H); 7.75 (m masked, 0.3H); 7.77 (d, J=8.0 Hz, 1H); 7.82 (d, J=8.0 Hz, 1H); 7.85 (m broad partially masked, 0.7H); 9.10 (s broad, 0.3H); 9.32 (s broad, 0.7H); 12.65 (s broad, 0.7H); 12.75 (s broad, 0.3H).

Stage 2: The procedure used in Example 5 is followed, but starting from 360 mg of 4-(5-hydroxy-1H-benzimidazol-2-yl)-9H-fluoren-9-one, obtained in the previous stage, of 240 mg of hydroxylamine hydrochloride and 470 mg of sodium acetate in 18 ml of ethanol, stirred for 20 hours at room temperature. After concentration of the solvent under reduced pressure, the residue is taken up successively with water, and then with toluene, brought to dryness. After formation of a paste with diisopropyl ether, in this way we obtain 358 mg of 4-(5-hydroxy-1H-benzimidazol-2-yl)-9H-fluoren-9-one oxime (Z,E) as a 50-50 mixture of Z and E isomers, in the form of a brown powder which is used as it is in the following stage, with the following characteristics:

Mass spectrum (LC/MS/ES/+/−): m/z=327 (M+).

Step 3: The procedure used in Example 216 is followed. In a 50 ml round-bottomed flask under an argon atmosphere, dissolve 355 mg of an equimolecular mixture of 4-(5-hydroxy-1H-benzimidazol-2-yl)-9H -fluoren-9-one oxime (Z,E), obtained in the previous stage, in a mixture of 2.5 ml of ethanol and 2.5 ml of water and 2.5 ml of acetic acid, at room temperature, add 283 mg of zinc in three stages, and, between each addition, stir for approximately one hour to two hours. Add Celite and filter. The filtrate is concentrated under pressure. The crude product is purified by flash chromatography on silica gel (40-63 µm), eluting with a mixture of dichloromethane and ammonia as a 7N solution in methanol (9/1 by volume). After formation of a paste with diisopropyl ether, in this way we obtain 232 mg of 4-(5-hydroxy-1H-benzimidazol-2-yl)-9H-fluorene-9(R,S) -amine, in the form of an off-white powder, which is used as it is in the following stage, with the following characteristics:

Mass spectrum (LC/MS/ES/+/−): m/z=313 (M+).

Stage 4: The procedure used in Example 14 is followed, but starting from 230 mg of 4-(5-hydroxy-1H-benzimidazol-2-yl)-9H-fluorene-9(R,S)-amine, obtained in the previous stage, 131 mg of 1H-pyrrolo[2,3-b]pyridine-4-carboxylic acid, 155 mg of 1-(3-dimethylaminopropyl)-3-ethylcarbodiimide hydrochloride (EDCI) and 49 mg of 1-hydroxybenzotriazole (HOBT) in 5 ml of dimethylformamide, for 20 hours at room temperature. Bring the dimethylformamide to dryness, add water and drain the precipitate that formed and then wash with water. The crude solid obtained is dried and then purified by flash chromatography on silica gel (40-63 µm), eluting with a mixture of dichloromethane and methanol (95/5 then 9/1 by volume). After formation of a paste with diisopropyl ether, in this way we obtain 220 mg of 4-(5-hydroxy-1H-benzimidazol-2-yl)-9H-fluoren-9(R,S)-yl]amide of 1H-pyrrolo-[2,3-b]pyridine-4-carboxylic acid, in the form of an off-white powder with the following characteristics:

Mass spectrum (LC/MS/ES+/−): m/z=457 (M+).

$^1$H-NMR spectrum (400 MHz, δ in ppm, DMSO-d6): for this compound, a 70%-30% mixture of tautomers is observed with: 6.39 (d, J=8.5 Hz, 1H); 6.75 (d broad, J=9.0 Hz, 0.7H); 6.80 (d broad, J=9.0 Hz, 0.3H); 6.90 (m broad partially masked, 0.7H); 6.91 (dd, J=2.0 and 3.5 Hz, 1H); 7.07 (m broad, 0.3H); 7.25 (t, J=7.5 Hz, 1H); 7.33 (t, J=7.5 Hz, 1H); 7.35 (m broad partially masked, 0.7H); 7.44 (m broad partially masked, 0.3H); 7.46 (d, J=5.0 Hz, 1H); 7.49 (t, J=7.5 Hz, 1H); 7.54 (d, J=8.0 Hz, 0.6H); from 7.58 to 7.66 (m, 3H); 7.72 (d broad, J=8.0 Hz, 1.4H); 8.29 (d, J=5.0 Hz, 1H); 9.05 (m broad, 0.3H); 9.26 (m broad partially masked, 0.7H); 9.27 (d, J=8.5 Hz, 1H); 11.85 (m broad, 1H); 12.5 (s broad, 0.7H); 12.6 (s broad, 0.3H).

Example 231

Synthesis of [4-(5-methylaminocarbonyl-1H-benzimidazol-2-yl)-9H-fluoren-9(R,S)-yl]amide of 1H-pyrrolo[2,3-b]pyridine-4-carboxylic acid The procedure used in Example 208 is followed, but starting from 200 mg of [4-(5-carboxy-1H-benzimidazol-2-yl)-9H-fluoren-9(R,S)-yl]amide of 1H-pyrrolo[2,3-b]pyridine-4-carboxylic acid, obtained in Example 206, 55 mg of methylamine hydrochloride, 321 mg of benzotriazol-1-yloxytris -pyrrolidinophosphonium hexafluorophosphate (PYBOP), 83 mg of 1-hydroxy-benzotriazole (HOBT) and 272 µl of N,N-diisopropylethylamine (DIPEA) in 2 ml of dimethylformamide, for 20 hours at room temperature. Bring the dimethylformamide to dryness, add water, drain the precipitate that forms and then wash with water and then with a 10% saturated solution of sodium hydrogen carbonate and, finally, with water. The crude solid obtained is dried and then purified by flash chromatography on silica gel (40-63 µm), eluting with a mixture of dichloromethane and methanol (95/5 then 9/1 by volume). After formation of a paste with diisopropyl ether, in this way we obtain 129 mg of [4-(5-methylaminocarbonyl-1H-benzimidazol-2-yl)-9H-fluoren-9 (R,S)-yl]amide of 1H-pyrrolo[2,3-b]pyridine-4-carboxylic acid, in the form of an off-white powder with the following characteristics:

Mass spectrum (LC/MS/ES/+/−): m/z=498 (M+).

$^1$H-NMR spectrum (300 MHz, δ in ppm, DMSO-d6): 2.84 (d, J=5.0 Hz, 3H); 6.41 (d, J=8.5 Hz, 1H); 6.91 (dd, J=2.0 and 3.5 Hz, 1H); 7.25 (t, J=7.5 Hz, 1H); 7.35 (t, J=7.5 Hz, 1H); 7.47 (d, J=5.0 Hz, 1H); 7.53 (t, J=7.5 Hz, 1H); from 7.57 to 7.77 (m, 5H); 7.77 (d, J=7.5 Hz, 1H); 7.82 (d broad, J=8.0 Hz, 1H); 8.21 (m spread-out, 1H); 8.30 (d, J=5.0 Hz, 1H); 8.46 (q broad, J=5.0 Hz, 1H); 9.28 (d, J=8.5 Hz, 1H); 11.85 (m broad, 1H); 13.2 (m spread-out, 1H).

Example 232

Synthesis of [4-(5-dimethylaminocarbonyl-1H-benzimidazol-2-yl)-9H-fluoren-9(R,S)-yl]amide of 1H-pyrrolo[2,3-b]pyridine-4-carboxylic acid The procedure used in Example 208 is followed, but starting from 200 mg of [4-(5-carboxy-1H-benzimidazol-2-yl)-9H-fluoren-9(R,S)-yl]amide of 1H-pyrrolo[2,3-b]pyridine-4-carboxylic acid, obtained in Example 206, 67 mg of dimethylamine hydrochloride, 321 mg of benzotriazol-1-yloxytris-pyrrolidinophosphonium hexafluorophosphate (PYBOP), 83 mg of 1-hydroxy-benzotriazole (HOBT) and 272 µl of N,N-diisopropylethylamine (DIPEA) in 2.5 ml of dimethylformamide, for 20 hours at room temperature. Bring the dimethylformamide to dryness, add water, drain the precipitate that forms and then wash with water and then with a 10% saturated solution of sodium hydrogen carbonate and, finally, with water. The crude solid obtained is dried and then purified by flash chromatography on silica gel (40-63 µm), eluting with a mixture of dichloromethane and methanol (95/5 then 9/1 by volume). After formation of a paste with diisopropyl ether, in this way we obtain 126 mg of [4-(5-dimethylaminocarbonyl-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Melting point (Köfler)=220° C.

Mass spectrum (EI/CI): m/z=512 (M+).

$^1$H-NMR spectrum (400 MHz, δ in ppm, DMSO-d6): 3.03 (s, 3H); 3.04 (s, 3H); 6.41 (d, J=8.5 Hz, 1H); 6.91 (dd, J=2.0 and 3.5 Hz, 1H); from 7.20 to 7.35 (m, 3H); 7.47 (d, J=5.0 Hz, 1H); 7.53 (t, J=7.5 Hz, 1H); from 7.56 to 7.67 (m, 4H); 7.68 (d broad, J=8.0 Hz, 1H); from 7.77 to 7.82 (m, 2H); 8.30 (d, J=5.0 Hz, 1H); 9.28 (d, J=8.5 Hz, 1H); 11.85 (m broad, 1H); 13.15 (m broad, 1H).

Example 233

Synthesis of 4-[5-(2-dimethylaminoethyl)aminocarbonyl-1H-benzimidazol-2-yl)-9H-fluoren-9(R,S)-yl] amide of 1H-pyrrolo[2,3-b]pyridine-4-carboxylic acid In a 10 ml round-bottomed flask, dissolve 200 mg of [4-(5-carboxy-1H-benzimidazol-2-yl)-9H-fluoren-9(R,S)-yl] amide of 1H-pyrrolo[2,3-b]pyridine-4-carboxylic acid, obtained in Example 206, in 2.5 ml of dimethylformamide, then add successively 100 µl of N,N-dimethylethylenediamine, 79 mg of 1-(3-dimethylaminopropyl)-3-ethylcarbodiimide hydrochloride (EDCI) and 28 mg of 1-hydroxybenzotriazole (HOBT), and then stir for 20 hours at room temperature. Bring the dimethylformamide to dryness, add water, and drain the precipitate that formed and then wash with water and then with a 10% saturated solution of sodium hydrogen carbonate and, finally, with water. The crude solid obtained is dried and then purified by flash chromatography on silica gel (40-63 µm), eluting with a mixture of dichloromethane and ammonia as a 7N solution in methanol (95/5 then 9/1 by volume). After formation of a paste with diisopropyl ether, in this way we obtain 103 mg of 4-[5-(2-dimethylaminoethyl)aminocarbonyl-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Melting point (Köfler)=>260° C.

Mass spectrum (LC/MS/ES+/−): m/z=555 (M+).

$^1$H-NMR spectrum (400 MHz, δ in ppm, DMSO-d6): 2.21 (s, 6H); 2.45 (t, J=6.5 Hz, 2H); 3.41 (q, J=6.5 Hz, 2H); 6.41 (d, J=8.5 Hz, 1H); 6.91 (dd, J=2.0 and 3.5 Hz, 1H); 7.25 (t, J=7.5 Hz, 1H); 7.35 (t, J=7.5 Hz, 1H); from 7.43 to 7.86 (m, 2H); 7.47 (d, J=5.0 Hz, 1H); 7.53 (t, J=7.5 Hz, 1H); 7.62 (m, 2H); 7.69 (d broad, J=8.0 Hz, 1H); 7.77 (d, J=7.5 Hz, 1H); 7.82 (d broad, J=8.0 Hz, 1H); 8.20 (m spread-out, 1H); 8.30 (d, J=5.0 Hz, 1H); 8.42 (t broad, J=6.5 Hz, 1H); 9.28 (d, J=8.5 Hz, 1H); 11.85 (m broad, 1H); 13.2 (m spread-out, 1H).

Example 234

Synthesis of [4-(4,5,6,7-tetrafluoro-1H-benzimidazol-2-yl)-9H-fluoren-9(R,S)-yl]amide of 1H-pyrrolo [2,3-b]pyridine-4-carboxylic acid Stage 1: The procedure used in stage 1 of Example 1 is followed, but starting from 16.7 ml of methanol, 22.98 ml of triethylamine and 20 g of 9H-fluoren-9-one-4-carboxylic acid chloride in 750 ml of dichloromethane. After stirring for 20 hours at room temperature, add 150 ml of water. The organic phase is decanted, washed with water and then with a saturated aqueous solution of sodium hydrogen carbonate, dried over magnesium sulphate and concentrated under reduced pressure. After formation of a paste with diisopropyl ether, in this way we obtain 18 g of methyl ester of fluoren-9-one-4-carboxylic acid, in the form of a yellow powder, which is used as it is in the following stage, with the following characteristics:

Mass spectrum (LC/MS/ES/+/−): m/z=238 (M+).

Stage 2: The procedure used in Example 5 is followed, but starting from 20 g of methyl ester of 9H-fluoren-9-one-4-carboxylic acid, obtained in the previous stage, 17.5 g of hydroxylamine hydrochloride and 34.45 g of sodium acetate, stirred for 20 hours at room temperature in 350 ml of ethanol. After concentration of the solvent under reduced pressure, the reaction medium is taken up in 1000 ml of ethyl acetate, washed with water and then with a saturated aqueous solution of sodium chloride, dried over magnesium sulphate and concentrated under reduced pressure. After formation of a paste with diisopropyl ether, in this way we obtain 22 g of 4-(methoxycarbonyl)-9H-fluoren-9-one oxime (Z,E), as a 50/50 mixture of Z and E isomers, in the form of a yellow powder which is used as it is in the following stage.

Stage 3: The procedure used in Example 6 is followed, but starting from 22 g of 4-(methoxycarbonyl)-9H-fluoren-9-one oxime (Z,E), obtained in the previous stage, and 5 g of Raney nickel in 900 ml of ethanol and 900 ml of tetrahydrofuran, for 6 hours at 60° C., under an initial hydrogen pressure of one bar. After filtration of the catalyst, concentration under reduced pressure and formation of a paste with diisopropyl ether, we obtain 20 g of the methyl ester of 9(R,S)-amino-9H-fluorene-4-carboxylic acid, in the form of a green solid which is used as it is in the following stage.

Stage 4: The procedure used in Example 14 is followed, but starting from 10 g of methyl ester of 9(R,S)-amino-9H-fluorene-4-carboxylic acid, obtained in the previous stage, 6.44 g of 1H-pyrrolo[2,3-b]pyridine-4-carboxylic acid, 8.37 g of 1-(3-dimethylaminopropyl)-3-ethylcarbodiimide hydrochloride (EDCI) and 5.9 g of 1-hydroxybenzotriazole (HOBT) in 150 ml of dimethylformamide, for 20 hours at room temperature. After purification by formation of a paste in diisopropyl ether, we obtain 12.4 g of methyl ester of 9(R,S)-[(1H-pyrrolo[2,3-b]pyridine-4-carbonyl)amino]-9H-fluorene-4-carboxylic acid, in the form of a beige powder with the following characteristics:

Mass spectrum (LC/MS/ES+/−): m/z=383 (M+).

NMR spectrum (400 MHz, δ in ppm, DMSO-d6): 3.99 (s, 3H); 6.33 (d, J=8.5 Hz, 1H); 6.88 (m broad, 1H); from 7.38 to 7.49 (m, 4H); 7.62 (m, 2H); 7.78 (m, 2H); 8.14 (d, J=7.5 Hz, 1H); 8.28 (d, J=5.0 Hz, 1H); 9.22 (d, J=8.5 Hz, 1H); 11.85 (m spread-out, 1H).

Stage 5: In a 100 ml three-necked flask under argon, reflux a suspension of 1 g of methyl ester of 9(R,S)-[(1H-pyrrolo[2,3-b]pyridine-4-carbonyl)amino]-9H-fluorene-4-carboxylic acid, obtained in the previous stage, in 50 ml of anhydrous tetrahydrofuran, and then add, dropwise, 7.825 ml of a 20% solution of diisopropylaluminium hydride (DIBAL-H) in toluene. After stirring for 15 minutes at reflux, add a further 2.6 ml of the above solution of DIBAL-H and maintain the reflux for a further 15 minutes. After cooling to room temperature, the reaction medium is run, dropwise, into 25 ml of a saturated aqueous solution of ammonium chloride, and then extracted 3 times with 25 ml of ethyl acetate. The combined organic phases are dried over magnesium sulphate and concentrated to dryness under reduced pressure. After purification by flash chromatography on silica gel (40-63 μm), eluting with a mixture of dichloromethane and methanol (97.5/2.5 by volume), and then formation of a paste with diisopropyl ether, in this way we obtain 200 mg of 9(R,S)-[(1H-pyrrolo[2,3-b]pyridine-4-carbonyl)amino]-9H-fluorene-4-methanol, in the form of a beige solid, which is used, with the following characteristics:

Mass spectrum (LC/MS/ES+/−): m/z=355 (M+).

Stage 6: In a 100 ml three-necked flask, add 440 mg of 2,2,6,6-tetramethyl-piperidine N-oxide (TEMPO) and 278.6 mg of ferrous chloride to a solution of 500 mg of 9(R,S)-[(1H-pyrrolo[2,3-b]pyridine-4-carbonyl)amino]-9H-fluorene-4-methanol, prepared in the previous stage, in 40 ml of dimethylformamide, and stir for 6 hours at room temperature, bubbling air slowly into the reaction medium. Then add a further 220 mg of TEMPO and 139.8 mg of ferrous chloride and maintain the stirring for a further 20 hours while bubbling air through. After dilution with 50 ml of water, bring to pH=2 by adding a 5M aqueous solution of hydrochloric acid and extract 3 times with ethyl acetate. The combined organic phases are washed with water, dried over magnesium sulphate and concentrated to dryness under reduced pressure. After purification by formation of a paste in diisopropyl ether, in this way we obtain 380 mg of [4-formyl-9H-fluoren-9(R,S)-yl]amide of 1H-pyrrolo[2,3-b]pyridine-4-carboxylic acid, in the form of a light-brown solid with the following characteristics:

Mass spectrum (LC/MS/ES+/−): m/z=353 (M+).

NMR spectrum (300 MHz, δ in ppm, DMSO-d6): 6.36 (d, J=8.5 Hz, 1H); 6.89 (dd, J=2.0 and 3.5 Hz, 1H); 7.44 (d, J=5.0 Hz, 1H); from 7.45 to 7.53 (m, 2H); from 7.56 to 7.70 (m, 3H); 7.89 (d broad, J=8.0 Hz, 1H); 8.02 (d, J=7.5 Hz, 1H); 8.29 (d broad, J=5.0 Hz, 1H); 8.61 (m, 1H); 9.23 (d, J=8.5 Hz, 1H); 10.6 (s, 1H); 11.85 (m spread-out, 1H).

Stage 7: In a 100 ml round-bottomed flask under argon, stir, for 20 hours at room temperature, a suspension of 100 mg of [4-formyl-9H-fluoren-9(R,S)-yl]-amide of 1H-pyrrolo[2,3-b]pyridine-4-carboxylic acid, obtained in the previous stage, 51 mg of 1,2-diamino-3,4,5,6-tetrafluorobenzene and 2.35 mg of ferric chloride in 6 ml of methanol and 2 ml of dimethylformamide. After concentration of the solvent under reduced pressure, the reaction medium is taken up in a mixture of water and dichloromethane. The organic phase is washed with water and then with a saturated solution of sodium chloride, dried over magnesium sulphate and concentrated to dryness under reduced pressure. After purification by flash chromatography on silica gel (40-63 μm), eluting with a mixture of dichloromethane and methanol (95/5 by volume), and then formation of a paste with diisopropyl ether, in this way we obtain 15 mg of [4-(4,5,6,7-tetrafluoro-1H-benzimidazol-2-yl)-9H-fluoren-9(R,S)-yl]amide of 1H-pyrrolo[2,3-b]pyridine-4-carboxylic acid, in the form of a brown powder with the following characteristics:

Mass spectrum (LC/MS/ES+/−): m/z=513 (M+).

$^1$H-NMR spectrum (400 MHz, δ in ppm, DMSO-d6): 6.41 (d, J=8.5 Hz, 1H); 6.91 (m broad, 1H); 7.27 (t, J=7.5 Hz, 1H); 7.36 (t, J=7.5 Hz, 1H); 7.46 (d, J=5.0 Hz, 1H); 7.51 (m broad partially masked, 1H); 7.53 (t, J=7.5 Hz, 1H); 7.62 (m, 2H); 7.70 (d broad, J=8.0 Hz, 1H); 7.79 (d, J=7.5 Hz, 1H); 8.30 (d, J=5.0 Hz, 1H); 9.29 (d, J=8.5 Hz, 1H); 11.85 (m broad, 1H); 14.2 (m spread-out, 1H).

Example 235

Synthesis of 4-[5-(3-methoxypropyl)aminocarbonyl-1H-benzimidazol-2-yl)-9H-fluoren-9(R,S)-yl]amide of 1H-pyrrolo[2,3-b]pyridine-4-carboxylic acid The procedure used in Example 233 is followed, but starting from 200 mg of [4-(5-carboxy-1H-benzimidazol-2-yl)-9H-fluoren-9(R,S)-yl]amide of 1H-pyrrolo[2,3-b]pyridine-4-carboxylic acid, obtained in Example 206, 84 μl of 3-methoxypropylamine, 79 mg of 1-(3-dimethylaminopropyl)-3-ethylcarbodiimide hydrochloride (EDCI) and 28 mg of 1-hydroxybenzotriazole (HOBT) in 2.5 ml of dimethylformamide for 20 hours at room temperature. Bring the dimethylformamide to dryness, add water and drain the precipitate that formed and then wash with water and then with a 10% saturated solution of sodium hydrogen carbonate and, finally, with water. The crude solid obtained is dried and then purified by flash chromatography on silica gel (40-63 μm), eluting with a mixture of dichloromethane and methanol (95/5 then 9/1 by volume). After formation of a paste with diisopropyl ether, in this way we obtain 153 mg of 4-[5-(3-methoxypropyl)aminocarbonyl-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Melting point (Köfler)=234-236° C.

Mass spectrum (LC/MS/ES+/−): m/z=556 (M+).

$^1$H-NMR spectrum (400 MHz, δ in ppm, DMSO-d6): 1.81 (m, 2H); 3.26 (s, 3H); 3.36 (q, J=6.5 Hz, 2H); 3.42 (t, J=6.5 Hz, 2H); 6.42 (d, J=8.5 Hz, 1H); 6.91 (dd, J=2.0 and 3.5 Hz, 1H); 7.23 (m spread-out partially masked, 1H); 7.25 (t, J=7.5 Hz, 1H); 7.35 (t, J=7.5 Hz, 1H); from 7.40 to 7.90 (m masked, 1H); 7.47 (d, J=5.0 Hz, 1H); 7.53 (t, J=7.5 Hz, 1H); 7.62 (m, 2H); 7.69 (d, J=7.5 Hz, 1H); 7.77 (d, J=7.5 Hz, 1H); 7.83 (d broad, J=7.5 Hz, 1H); 8.15 (m spread-out, 1H); 8.30 (d, J=5.0 Hz, 1H); 8.51 (t broad, J=6.5 Hz, 1H); 9.28 (d, J=8.5 Hz, 1H); 11.85 (m broad, 1H); 13.2 (m spread-out, 1H).

Example 236

Synthesis of 4-[5-(4-methylpiperazine-1-yl)carbonyl-1H-benzimidazol-2-yl)-9H-fluoren-9(R,S)-yl]amide of 1H-pyrrolo[2,3-b]pyridine-4-carboxylic acid The procedure used in Example 233 is followed, but starting from 200 mg of [4-(5-carboxy-1H-benzimidazol-2-yl)-

9H-fluoren-9(R,S)-yl]amide of 1H-pyrrolo[2,3-b]pyridine-4-carboxylic acid, obtained in Example 206, 50 µl of 1-methyl piperazine, 79 mg of 1-(3-dimethylaminopropyl)-3-ethylcarbodiimide hydrochloride (EDCI) and 28 mg of 1-hydroxybenzotriazole (HOBT) in 2.5 ml of dimethylformamide for 20 hours at room temperature. Bring the dimethylformamide to dryness, add water and drain the precipitate that formed and then wash with water, then with a 10% saturated solution of sodium hydrogen carbonate and, finally, with water. The crude solid obtained is dried and then purified by flash chromatography on silica gel (40-63 µm), eluting with a mixture of dichloromethane and ammonia in solution in methanol (95/5 then 9/1 by volume). After formation of a paste with diisopropyl ether, in this way we obtain 129 mg of 4-[5-(4-methylpiperazine-1-yl)carbonyl-1H-benzimidazol-2-yl)-9H-fluoren-9(R,S)-yl]amide of 1H-pyrrolo[2,3-b]pyridine-4-carboxylic acid, in the form of an off-white powder with the following characteristics:

Melting point (Köfler)=>260° C.
Mass spectrum (LC/MS/ES+/−): m/z=567 (M+).
$^1$H-NMR spectrum (400 MHz, δ in ppm, DMSO-d6): 2.22 (s, 3H); 2.36 (m broad, 4H); 3.56 (m broad, 4H); 6.41 (d, J=8.5 Hz, 1H); 6.91 (dd, J=2.0 and 3.5 Hz, 1H); 7.27 (t, J=7.5 Hz, 1H); 7.31 (m spread-out, partially masked, 1H); 7.35 (t, J=7.5 Hz, 1H); 7.47 (d, J=5.0 Hz, 1H); 7.53 (t, J=7.5 Hz, 1H); from 7.57 to 7.83 (m, 5H); 7.67 (d, J=8.0 Hz, 1H); 7.77 (d, J=7.5 Hz, 1H); 8.30 (d, J=5.0 Hz, 1H); 9.28 (d, J=8.5 Hz, 1H); 11.85 (m broad, 1H); 13.15 (m spread-out, 1H).

Example 237

Synthesis of [4-(6-dimethylsulphamoyl-1H-benzimidazol-2-yl)-9H-fluoren-9(R,S)-yl]amide of 1H-pyrrolo[2,3-b]pyridine-4-carboxylic acid In a microwave device (Biotage), heat, for 1 hour at 220° C., 20 mg of [4-formyl-9H-fluoren-9(R,S)-yl]amide of 1H-pyrrolo[2,3-b]pyridine-4-carboxylic acid, obtained in stage 6 of Example 234, and 13.4 mg of 4-N,N-dimethylsulphonamidobenzene-1,2-diamine in 1.5 ml of nitrobenzene. After a return to room temperature, add 2 ml of water and extract with 3 times 15 ml of ethyl acetate. The combined organic phases are concentrated to dryness under reduced pressure and the residue is purified by flash chromatography on silica gel (40-63 µm), eluting with a mixture of dichloromethane and ammonia at 7N in methanol (90/10 by volume). In this way, we obtain 2 mg of [4-(6-dimethylsulphamoyl-1H-benzimidazol-2-yl)-9H-fluoren-9(R,S)-yl]amide of 1H-pyrrolo[2,3-b]pyridine-4-carboxylic acid, in the form of an amber powder with the following characteristics:

Mass spectrum (LC/MS): m/z=549 (M+).

Example 238

Synthesis of 4-[5-(pyrrolidin-1-yl)carbonyl)-1H-benzimidazol-2-yl)-9H-fluoren-9(R,S)-yl]amide of 1H-pyrrolo[2,3-b]pyridine-4-carboxylic acid The procedure used in Example 233 is followed, but starting from 143 mg of [4-(5-carboxy-1H-benzimidazol-2-yl)-9H-fluoren-9(R,S)-yl]amide of 1H-pyrrolo[2,3-b]pyridine-4-carboxylic acid, obtained in Example 206, 27 µl of pyrrolidine, 56 mg of 1-(3-dimethylaminopropyl)-3-ethylcarbodiimide hydrochloride (EDCI) and 20 mg of 1-hydroxybenzotriazole (HOBT) in 1.5 ml of dimethylformamide for 20 hours at room temperature. Bring the dimethylformamide to dryness, add water and drain the precipitate that formed and then wash with water, then with a 10% saturated solution of sodium hydrogen carbonate and again with water. The crude solid obtained is dried and then purified by flash chromatography on silica gel (40-63 µm), eluting with a mixture of dichloromethane and methanol (95/5 then 9/1 by volume). After formation of a paste with diisopropyl ether, in this way we obtain 89.5 mg of 4-[5-(pyrrolidin-1-yl)carbonyl)-1H-benzimidazol-2-yl)-9H-fluoren-9(R,S)-yl]amide of 1H-pyrrolo[2,3-b]pyridine-4-carboxylic acid, in the form of a beige powder with the following characteristics:

Melting point (Kofler)=>260° C.
Mass spectrum (LC/MS/ES+/−): m/z=538 (M+).
$^1$H-NMR spectrum (400 MHz, δ in ppm, DMSO-d6): 1.88 (m broad, 4H); 3.52 (t broad, J=6.5 Hz, 4H); 6.41 (d, J=8.5 Hz, 1H); 6.91 (dd, J=2.0 and 3.5 Hz, 1H); 7.26 (t, J=7.5 Hz, 1H); 7.35 (t, J=7.5 Hz, 1H); 7.47 (d, J=5.0 Hz, 1H); 7.47 (m partially masked, 1H); 7.53 (t, J=7.5 Hz, 1H); from 7.58 to 7.95 (m, 5H); 7.68 (d broad, J=8.0 Hz, 1H); 7.77 (d, J=7.5 Hz, 1H); 8.30 (d, J=5.0 Hz, 1H); 9.28 (d, J=8.5 Hz, 1H); 11.85 (m broad, 1H); 13.1 (m spread-out, 1H).

Examples 239 and 240

Resolution of the enantiomers of the methyl ester of 2-{9(R,S)-[(1H-pyrrolo[2,3-b]pyridine-4-carbonyl)amino]-9H-fluoren-4-yl}-1H-benzimidazole-5-carboxylic acid By following the procedure used in Example 153, starting from 200 mg of methyl ester of 2-{9(R,S)-[(1H-pyrrolo[2,3-b]pyridine-4-carbonyl)amino]-9H-fluoren-4-yl}-1H-benzimidazole-5-carboxylic acid, obtained as in Example 205, but using a chiral column of Pirkle Whelk 01 SS type, eluting with a mixture of 50% n-heptane/50% EtOH/0.1% TEA and detecting the eluted products by UV spectroscopy at 254 nm, we obtain, by recovering the first fractions eluted and concentrating under reduced pressure, 63.4 mg of dextrorotatory enantiomer of 2-{9(R,S)-[(1H-pyrrolo[2,3-b]pyridine-4-carbonyl)amino]-9H-fluoren-4-yl}-1H-benzimidazole-5-carboxylic acid, in the form of an amorphous pale yellow solid with the following characteristics:

αD20=+168.8+/−2.2° (c=0.5; DMSO).

By recovering the second fractions eluted and concentrating under reduced pressure, we obtain 78.9 mg of levorotatory enantiomer of 2-{9(R,S)-[(1H-pyrrolo[2,3-b]pyridine-4-carbonyl)amino]-9H-fluoren-4-yl}-1H-benzimidazole-5-carboxylic acid, containing approximately 1% of dextrorotatory enantiomer, in the form of an amorphous pale yellow solid with the following characteristics:

αD20=−155.75+/−2.1° (c=0.5; DMSO).

Example 241

Synthesis of {{4-{5-[2-(pyrrolidin-1-yl)ethylaminocarbonyl]-1H-benzimidazol-2-yl}-9H-fluoren-9(R,S)-yl}}amide of 1H-pyrrolo[2,3-b]pyridine-4-carboxylic acid Stage 1: In a 50 ml round-bottomed flask under argon, dissolve 1 g of [4-(5-methoxycarbonyl-1H-benzimidazol-2-yl)-9H-fluoren-9-one, obtained as in stage 2 of Example 205, in 15 ml of methanol, and then add 5.9 ml of a 1.2M aqueous solution of lithium hydroxide and reflux for 24 hours. Bring to dryness under reduced pressure, add water, cool to 10° C., and then acidify to pH 4-5 with a 1M aqueous solution of hydrochloric acid. The crude product is filtered, washed with water and then dried. The solid obtained is made into a paste with diisopropyl ether, filtered and rinsed. In this way, we obtain 919 mg of 4-(5-carboxy-1H-benzimidazol-2-yl)-9H-fluoren-9-one, in the form of a yellow powder, which is used as it is in the following stage with the following characteristics:

Mass spectrum (LC/MS/ES/+/−): m/z=340 (M+).

Stage 2: The procedure used in Example 234 is followed, but starting from 380 mg of [4-(5-carboxy-1H-benzimidazol-2-yl)-9H-fluoren-9-one, obtained in the previous stage, 140 mg of N-(2-aminoethyl)pyrrolidine, 214 mg of 1-(3-dimethylaminopropyl)-3-ethylcarbodiimide hydrochloride (EDCI) and 75 mg of 1-hydroxybenzotriazole (HOBT) in 4 ml of dimethylformamide for 20 hours at room temperature. After the crude product has been made into a paste with diisopropyl ether, filtered and rinsed, in this way we obtain 472 mg of 4-{5-[2-(pyrrolidin-1-yl)ethylaminocarbonyl]-1H-benzimidazol-2-yl}-9H-fluoren-9-one, in the form of a yellow powder, which is used as it is in the following stage with the following characteristics:

Mass spectrum (LC/MS/ES+/−): m/z=436 (M+).

Stage 3: The procedure used in Example 5 is followed, but starting from 380 mg of 4-{5-[2-(pyrrolidin-1-yl)ethylaminocarbonyl]-1H-benzimidazol-2-yl}-9H-fluoren-9-one, obtained in the previous stage, 225 mg of hydroxylamine hydrochloride and 442 mg of sodium acetate in 6 ml of ethanol, stirred for 20 h at room temperature. After purification by flash chromatography on silica gel (40-63 μm), eluting with a mixture of dichloromethane and ammonia as a 7N solution in methanol (95/5 then 9/1 by volume), and then formation of a paste with diisopropyl ether, filter and rinse. In this way, we obtain 303 mg of 4-{5-[2-(pyrrolidin-1-yl)ethylaminocarbonyl]-1H-benzimidazol-2-yl}-9H-fluoren-9-one oxime (Z,E), in the form of an off-white solid, which is used as it is in the following stage, with the following characteristics:

Mass spectrum (LC/MS/ES/+/−): m/z=451 (M+).

Stage 4: The procedure used in Example 216 is followed. In a 20 ml round-bottomed flask under an argon atmosphere, dissolve 303 mg of 4-{5-[2-(pyrrolidin-1-yl)ethylaminocarbonyl]-1H-benzimidazol-2-yl}-9H-fluoren-9-one oxime (Z,E), obtained in the previous stage, in a mixture of 1.5 ml of ethanol and 1.5 ml of water and 1.5 ml of acetic acid, at room temperature. Add 175 mg of zinc in three stages, and, between each addition, stir for approximately one hour to two hours. Add Celite and filter. The filtrate is concentrated under reduced pressure. After purification by flash chromatography on silica gel (40-63 μm), eluting with a mixture of dichloromethane and ammonia as a 7N solution in methanol (9/1 by volume) and then formation of a paste with diisopropyl ether, in this way we obtain 257 mg of 4-{5-[2-(pyrrolidin-1-yl)ethylaminocarbonyl]-1H-benzimidazol-2-yl}-9H-fluorene-9(R,S)-amine, in the form of a beige solid, which is used as it is in the following stage with the following characteristics:

Mass spectrum (EI/CI): m/z=437 (M+).

Stage 5: The procedure used in Example 14 is followed, but starting from 257 mg of 4-{5-[2-(pyrrolidin-1-yl)ethylaminocarbonyl]-1H-benzimidazol-2-yl}-9H-fluorene-9(R,S)-amine, obtained in the previous stage, 95 mg of 1H-pyrrolo[2,3-b]pyridine-4-carboxylic acid, 112 mg of 1-(3-dimethylaminopropyl)-3-ethylcarbodiimide hydrochloride (EDCI) and 40 mg of 1-hydroxybenzotriazole (HOBT) in 2.5 ml of dimethylformamide, for 20 hours at room temperature. After purification by flash chromatography on silica gel (40-63 μm), eluting with a mixture of dichloromethane and ammonia as a 7N solution in methanol (95/5 then 9/1 by volume), and formation of a paste with diisopropyl ether, in this way we obtain 196 mg of {{4-{5-[2-(pyrrolidin-1-yl)ethylaminocarbonyl]-1H-benzimidazol-2-yl}-9H-fluoren-9 (R,S)-yl}}amide of 1H-pyrrolo[2,3-b]pyridine-4-carboxylic acid, in the form of a pale yellow solid with the following characteristics:

Mass spectrum (LC/MS/ES+/−): m/z=581 (M+).

$^1$H-NMR spectrum (400 MHz, δ in ppm, DMSO-d6): 1.69 (m, 4H); 2.61 (t, J=7.0 Hz, 2H); 3.31 (m masked, 4H); 3.43 (m, 2H); 6.41 (d, J=8.5 Hz, 1H); 6.91 (dd, J=2.0 and 3.5 Hz, 1H); 7.25 (t, J=7.5 Hz, 1H); 7.35 (t, J=7.5 Hz, 1H); 7.47 (d, J=5.0 Hz, 1H); from 7.50 to 7.89 (m, 4H); 7.53 (t, J=7.5 Hz, 1H); 7.69 (d, J=8.0 Hz, 1H); 7.78 (d, J=7.5 Hz, 1H); 7.83 (d broad, J=8.0 Hz, 1H); 8.19 (m spread-out, 1H); 8.30 (d, J=5.0 Hz, 1H); 8.47 (t broad, J=6.0 Hz, 1H); 9.28 (d, J=8.5 Hz, 1H); 11.85 (m broad, 1H); 13.2 (m spread-out, 1H).

Example 242

Synthesis of {4-[5-fluoro-6-(4-methylperhydro-1,4-diazepin-1-yl)-1H-benzimidazol-2-yl]-9H-fluoren-9 (R,S)-yl}amide of 1H-pyrrolo[2,3-b]-pyridine-4-carboxylic acid Stage 1: The procedure used in stage 1 of Example 1 is followed, but starting from 2.86 g of 4-fluoro-5-(4-methylperhydro-1,4-diazepin-1-yl)benzene-1,2-diamine, which can be prepared according to J. Het. Chem. 2005, 42(1), 67-71, 2.81 ml of triethylamine and 2.427 g of 9H-fluoren-9-one-4-carboxylic acid chloride in 50 ml of dichloromethane for 20 hours at room temperature. After purification by flash chromatography on silica gel (40-63 μm), eluting with a mixture of dichloromethane and methanol (95/5 by volume), then formation of a paste with diisopropyl ether, in this way we obtain 950 mg of [2-amino-5-fluoro-4-(4-methylperhydro-1,4-diazepin-1-yl)phenyl]amide of 9-oxo-9H-fluorene-4-carboxylic acid, in the form of an orange powder, which is used as it is in the following stage, with the following characteristics:

Mass spectrum (LC/MS/ES/+/−): m/z=444 (M+).

Stage 2: The procedure used in Example 68 is followed. In a 100 ml round-bottomed flask under an argon atmosphere, reflux, for 6 hours, a suspension of 950 mg of [2-amino-5-fluoro-4-(4-methylperhydro-1,4-diazepin-1-yl)phenyl]-amide of 9-oxo-9H-fluorene-4-carboxylic acid, obtained in the previous stage, in 15 ml of acetic acid. After purification by formation of a paste with diisopropyl ether, in this way we obtain 950 mg of 4-[5-fluoro-6-(4-methyl-perhydro-1,4-diazepin-1-yl)-1H-benzimidazol-2-yl]-9H-fluoren-9-one, in the form of an orange powder, which is used as it is in the following stage, with the following characteristics:

Mass spectrum (LCMS): m/z=426 (M+).

Stage 3: The procedure used in Example 5 is followed, but starting from 950 mg of 4-[5-fluoro-6-(4-methylperhydro-1,4-diazepin-1-yl)-1H-benzimidazol-2-yl]-9H-fluoren-9-one, obtained in the previous stage, 464 mg of hydroxylamine hydrochloride and 914 mg of sodium acetate in 45 ml of ethanol, stirred for 20 h at room temperature. After concentration of the solvent under reduced pressure, the residue is taken up successively with water, filtered, washed with water, rinsed with diisopropyl ether and redissolved in toluene. After concentration to dryness under reduced pressure, in this way we obtain 950 mg of 4-[5-fluoro-6-(4-methylperhydro-1,4-diazepin-1-yl)-1H-benzimidazol-2-yl]-9H-fluoren-9-one oxime (Z,E), as a 50-50 mixture of Z and E isomers, in the form of a brown powder which is used as it is in the following stage.

Mass spectrum (LCMS): m/z=441 (M+).

Stage 4: The procedure used in Example 6 is followed, starting from 950 mg of 4-[5-fluoro-6-(4-methylperhydro-1, 4-diazepin-1-yl)-1H-benzimidazol-2-yl]-9H-fluoren-9-one oxime (Z,E), obtained in the previous stage, and 135 mg of Raney nickel in 20 ml of ethanol and 20 ml of tetrahydrofuran for 16 hours at 60° C. under an initial hydrogen pressure of one bar. After filtration of the catalyst, concentration to dryness under reduced pressure, and then purification by formation of a paste with diisopropyl ether, in this way we obtain 700 mg of 4-[5-fluoro-6-(4-methylperhydro-1,4-diazepin-1-yl)-1H-benzimidazol-2-yl]-9H-fluoren-9(R,S)-ylamine, in the form of an orange powder which is used as it is in the following stage.

Mass spectrum (LCMS): m/z=427 (M+).

Stage 5: The procedure used in Example 14 is followed, but starting from 700 mg of 4-[5-fluoro-6-(4-methylperhydro-1,4-diazepin-1-yl)-1H-benzimidazol-2-yl]-9H-fluoren-9(R,S)-ylamine, obtained in the previous stage, 162 mg of 1H-pyrrolo-[2,3-b]pyridine-4-carboxylic acid, 211 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. After purification by flash chromatography on silica gel (40-63 μm), eluting with a mixture of dichloromethane and 7N ammoniacal methanol (95/5 by volume), and then formation of a paste with methanol, in this way we obtain 255 mg of {4-[5-fluoro-6-(4-methylperhydro -1,4-diazepin-1-yl)-1H-benzimidazol-2-yl]-9H-fluoren-9(R,S)-yl}amide of 1H -pyrrolo[2,3-b]-pyridine-4-carboxylic acid, in the form of a beige powder with the following characteristics:

Mass spectrum (LC/MS/ES+/−): m/z=571 (M+).

$^1$H-NMR spectrum (300 MHz, δ in ppm, DMSO-d6): 1.96 (m, 2H); 2.32 (s, 3H); 2.63 (m, 2H); 2.73 (m, 2H); 3.36 (t broad, J=5.5 Hz, 4H); 6.40 (d, J=8.5 Hz, 1H); 6.90 (d broad, J=3.5 Hz, 1H); 7.05 (m spread-out, 1H); from 7.20 to 7.80 (m masked, 1H); 7.26 (t, J=7.5 Hz, 1H); 7.34 (t, J=7.5 Hz, 1H); 7.46 (d, J=5.0 Hz, 1H); 7.49 (t, J=7.5 Hz, 1H); from 7.57 to 7.68 (m, 4H); 7.72 (d broad, J=8.0 Hz, 1H); 8.29 (d, J=5.0 Hz, 1H); 9.26 (d, J=8.5 Hz, 1H); 11.85 (m broad, 1H); 12.7 (m spread-out, 1H).

Examples 243 and 244

Synthesis of 2-bromo-5-(3H-imidazo[4,5-c]pyridin-2-yl)-9H-fluoren-9-one and of 2,7-dibromo-5-(3H-imidazo[4,5-c]pyridin-2-yl)-fluoren-9-one Stage 1: In a 100 ml three-necked round-bottomed flask, equipped with mechanical stirring, stir 4.48 g of 9-fluorenone-4-carboxylic acid in suspension in 40 ml of trifluoroacetic acid and 12 ml of concentrated sulphuric acid. To this dark reaction mixture, add 5.33 g of N-bromosuccinimide over a period of 9 h. The conversion rate of the starting product is followed by LC/MS, and the reaction is stopped when it platforms at 75%. The yellow precipitate that formed is filtered over sintered glass, washed with 3 times 20 ml of trifluoroacetic acid and 6 times 50 ml of water, and then dried in an oven at 50° C. under a strong vacuum. We obtained 6.6 g of a yellow powder, composed of a 55/45 mixture of 2-bromo-9H-fluoren-9-one-4-carboxylic acid and 2,7-dibromo-9H-fluoren-9-one-4-carboxylic acid, which is used as it is in the following stage.

Stage 2: In a 10 ml round-bottomed flask, place 150 mg of the mixture obtained in stage 1 in 2 ml of dichloromethane to which 50 μl of dimethylformamide have been added. Add 70 mg of oxalyl chloride and stir the reaction mixture at room temperature for 30 minutes. After dilution with 10 ml of dichloromethane, the solution obtained is added dropwise (over 20 min and under argon, to a suspension of 61 mg of 3,4-diaminopyridine and of 102 mg of triethylamine in 2 ml of dichloromethane. The precipitate obtained is filtered off and washed with 3 times 20 ml of dichloromethane so as to give 110 mg of a 65/35 mixture of (3-aminopyridin-4-yl) amide of 7-bromo-9-oxo-9H-fluorene-4-carboxylic acid and (3-aminopyridin-4-yl)amide of 2,7-dibromo-9-oxo-9H-fluorene-4-carboxylic acid, in the form of a yellow powder.

Stage 3: A suspension of 80 mg of the mixture, obtained in stage 2, in 2 ml of acetic acid is refluxed for 45 minutes. 30 ml of water are added to the reaction medium which is then brought to pH=9 by adding a 1N aqueous solution of sodium hydroxide. The yellow precipitate that formed is filtered off, washed with 3 times 20 ml of water and dried in an oven at 50° C. under a vacuum for 4 hours. The yellow powder obtained is purified by flash chromatography on silica gel, eluting with a gradient of mixtures of dichloromethane and methanol (from 100/0 to 90/10 by volume) to give:

–29 mg of 2-bromo-5-(3H-imidazo[4,5-c]pyridin-2-yl)-9H-fluoren-9-one (Example 243), in the form of a yellow powder with the following characteristics:

Mass spectra (EI): m/z=376 (M+).

NMR spectrum (300 MHz, δ in ppm, DMSO-d6): 7.62 (t, J=7.5 Hz, 1H); 7.69 (d broad, J=5.5 Hz, 1H); 7.72 (dd partially masked, J=2.0 and 8.5 Hz, 1H); from 7.79 to 7.86 (m, 3H); 7.95 (d broad, J=7.5 Hz, 1H); 8.39 (d, J=5.5 Hz, 1H); 9.05 (s broad, 1H); 13.5 (m very spread-out, 1H).

and 14 mg of 2,7-dibromo-5-(3H-imidazo[4,5-c]pyridin-2-yl)-9H-fluoren-9-one (Example 244), in the form of a yellow powder with the following characteristics:

Mass spectrum (EI): m/z=454 (M+).

Example 245

Synthesis of [4-(6-dimethylamino-1H-benzimidazol-2-yl)-9H -fluoren-9(R,S)-yl]amide of 1H-pyrrolo[2,3-b]pyridine-4-carboxylic acid In a 20 ml single-necked flask, introduce successively, under an argon atmosphere, 23 mg of N4,N4-dimethylbenzene-1,2,4-triamine, which can be obtained by catalytic hydrogenation of N4,N4-dimethyl-2-nitrobenzene-1,4-diamine in the presence of 10% palladium-on-charcoal under an initial hydrogen pressure of 5 bar at 20° C., 53 mg of (4-formyl-9H -fluoren-9(R,S)-yl)amide of 1H-pyrrolo[2,3-b] pyridine-4-carboxylic acid, prepared as in stage 6 of Example 234, and 24 mg of ferric chloride and 2 ml of dimethylformamide. After stirring for 3 h at 20° C., concentrate the solution under reduced pressure, and then take up the residue obtained in 4 ml of water. After draining of the insoluble material formed on a porous plate, washing with 2 ml of ethyl acetate and air-drying, in this way we obtain 41 mg of [4-(6-dimethylamino-1H-benzimidazol-2-yl)-9H-fluoren-9(R,S)-yl]amide of 1H-pyrrolo[2,3-b]-pyridine-4-carboxylic acid, in the form of a violet powder with the following characteristics:

Mass spectrum (E/I): m/z=487 (M+).

$^1$H-NMR spectrum (400 MHz, δ in ppm, DMSO): 3.08 (s broad, 6H); 6.41 (d, J=8.5 Hz, 1H); 6.89 (m broad, 1H); from 6.95 to 7.34 (m spread-out, 3H); 7.31 (t, J=7.5 Hz, 1H); 7.41 (t, J=7.5 Hz, 1H); 7.47 (d, J=5.0 Hz, 1H); 7.60 (t, J=7.5 Hz, 1H); 7.63 (d, J=3.0 Hz, 1H); 7.68 (d, J=7.5 Hz, 1H); 7.73 (d, J=8.5 Hz, 1H); 7.77 (d, J=7.5 Hz, 1H); 7.89 (d, J=7.5 Hz, 1H); 8.31 (d, J=5.0 Hz, 1H); 9.34 (d, J=8.5 Hz, 1H); 11.9 (m broad, 1H); 14.8 (m spread-out, 1H).

Example 246

Synthesis of {4-[6-(4-methylpiperazin-1-yl)-1H-benzimidazol-2-yl]-9H-fluoren-9(R,S)-yl}amide of 1H-pyrrolo[2,3-b]pyridine-4-carboxylic acid Stage 1: The procedure used in stage 1 of Example 1 is followed, but starting from 2.06 g of 4-(4-methylpiperazin- 1-yl)benzene-1,2-diamine, 2.85 ml of triethylamine and 2.43 g of 9H-fluoren-9-one-4-carboxylic acid chloride in 50 ml of dichloromethane, for 20 hours at room temperature. After purification by flash chromatography on silica gel (40-63 µm), eluting with a mixture of dichloromethane and methanol (95/5 by volume), and then formation of a paste with diisopropyl ether, in this way we obtain 4 g of [2-amino-4-(4-methylpiperazin-1-yl)phenyl]amide of 9-oxo-9H-fluorene-4-carboxylic acid, in the form of an orange powder, which is used as it is in the following stage, with the following characteristics:

Mass spectrum (LC/MS/ES/+/−): m/z=412 (M+).

Stage 2: The procedure used in Example 68 is followed. In a 250 ml round-bottomed flask under an argon atmosphere, reflux, for 6 hours, a suspension of 4 g of [2-amino-4-(4-methylpiperazin-1-yl)phenyl]amide of 9-oxo-9H-fluorene-4-carboxylic acid, obtained in the previous stage, in 64 ml of acetic acid. After purification by formation of a paste with diisopropyl ether, in this way we obtained 2.5 g of 4-[6-(4-methylpiperazin-1-yl)-1H-benzimidazol-2-yl]-9H-fluoren-9-one, in the form of an orange powder, which is used as it is in the following stage, with the following characteristics:

Mass spectrum (LCMS): m/z=394 (M+).

Stage 3: The procedure used in Example 5 is followed, but starting from 2.5 g of 4-[6-(4-methylpiperazin-1-yl)-1H-benzimidazol-2-yl]-9H-fluoren-9-one, obtained in the previous stage, 1.32 g of hydroxylamine hydrochloride and 2.6 g of sodium acetate in 130 ml of ethanol, stirred at 20 hours at room temperature. After purification by formation of a paste with diisopropyl ether, in this way we obtained 1.5 g of 4-[6-(4-methylpiperazin-1-yl)-1H-benzimidazol-2-yl]-9H-fluoren-9-one oxime (Z,E), as a 50-50 mixture of Z and E isomers, in the form of a brown powder, which is used as it is in the following stage, with the following characteristics:

Mass spectrum (LCMS): m/z=409 (M+).

Stage 4: The procedure used in Example 6 is followed, but starting from 1.5 g of 4-[6-(4-methylpiperazin-1-yl)-1H-benzimidazol-2-yl]-9H-fluoren-9-one oxime (Z,E), obtained in the previous stage, and 229 mg of Raney nickel in 35 ml of ethanol and 35 ml of tetrahydrofuran for 48 hours at 60° C. under an initial hydrogen pressure of one bar. After filtration of the catalyst, concentration to dryness under reduced pressure and purification by formation of a paste in diisopropyl ether, in this way we obtained 1.3 g of 4-[6-(4-methylpiperazin-1-yl)-1H-benzimidazol-2-yl]-9H-fluoren-9(R,S)-ylamine, in the form of an orange powder, which is used as it is in the following stage, with the following characteristics:

Mass spectrum (LCMS): m/z=427 (M+).

Stage 5: The procedure used in Example 14 is followed, but starting from 416 mg of 4-[6-(4-methylpiperazin-1-yl)-1H-benzimidazol-2-yl]-9H-fluoren-9(R,S)-ylamine, obtained in the previous stage, 162 mg of 1H-pyrrolo-[2,3-b]pyridine-4-carboxylic acid, 211 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. After purification by flash chromatography on silica gel (40-63 µm), eluting with a mixture of dichloromethane and 7N ammoniacal methanol (97.5/2.5 by volume), and then formation of a paste with diisopropyl ether, in this way we obtained 250 mg of {4-[6-(4-methylpiperazin-1-yl)-1H-benzimidazol-2-yl]-9H-fluoren-9(R,S)-yl}amide of 1H-pyrrolo[2,3-b]pyridine-4-carboxylic acid, in the form of a beige powder with the following characteristics:

Mass spectrum (LC/MS/ES+/−): m/z=539 (M+).

$^1$H-NMR spectrum (400 MHz, δ in ppm, DMSO-d6): for this compound, a 50%-50% mixture of tautomers is observed with: 2.25 (s, 3H); 2.51 (m partially masked, 4H); 3.15 (m, 4H); 6.40 (d, J=8.5 Hz, 1H); 6.91 (d, J=3.5 Hz, 1H); from 6.93 to 7.10 (m spread-out, 1.5H); from 7.15 to 7.70 (m spread-out partially masked, 1.5H); 7.25 (t, J=7.5 Hz, 1H); 7.33 (t, J=7.5 Hz, 1H); 7.47 (d, J=5.0 Hz, 1H); 7.49 (t partially masked, J=7.5 Hz, 1H); from 7.57 to 7.64 (m, 3H); 7.67 (d, J=8.5 Hz, 1H); 7.72 (d, J=7.5 Hz, 1H); 8.29 (d, J=5.0 Hz, 1H); 9.27 (d, J=8.5 Hz, 1H); 11.85 (m broad, 1H); 12.6 (m spread-out, 0.5H); 12.65 (m spread-out, 0.5H).

Example 247

[[6-(Methyl-4(5)(R,S)-imidazolin-2-yl)-1H-benzimidazol-2-yl]-9H-fluoren-9(R,S)-yl]amide of 1H-pyrrolo[2,3-b]pyridine-4-carboxylic acid Stirred, at room temperature under argon, a mixture of 94 mg of (4-formyl-9H-fluoren-9(R,S)-yl)amide of 1H-pyrrolo[2,3-b]pyridine-4-carboxylic acid, prepared as in stage 6 of Example 234, 60 mg of 2-(3,4-diaminophenyl)-4(5)(R,S)-methyl-2-imidazoline hydrochloride, which can be prepared according to patent DE 2,804,835, and 43 mg of ferric trichloride in 3 ml of dry DMF. After 50 hours, evaporate the reaction medium to dryness and purify the residue by flash chromatography on silica gel, eluting with a mixture of methanol and dichloromethane (10/90 by volume). In this way, we obtain 105 mg of [[6-(methyl-4(5)(R,S)-imidazolin-2-yl)-1H -benzimidazol-2-yl]-9H-fluoren-9(R,S)-yl]amide of 1H-pyrrolo[2,3-b]pyridine-4-carboxylic acid, in the form of a beige foam with the following characteristics:

TLC (SiO$_2$) Rf=0.3 (methanol-dichloromethane 20:80 by volume).

NMR spectrum (400 MHz, δ in ppm, DMSO-d6): 1.41 (d, J=6.5 Hz, 3H); 3.62 (dd, J=8.0 and 11.0 Hz, 1H); 4.16 (t, J=11.0 Hz, 1H); 4.50 (m, 1H); 6.41 (d, J=8.5 Hz, 1H); 6.90 (dd, J=2.0 and 3.5 Hz, 1H); 7.24 (t, J=7.5 Hz, 1H); 7.36 (t, J=7.5 Hz, 1H); from 7.43 to 7.68 (m masked, 1H); 7.46 (d, J=5.0 Hz, 1H); 7.55 (t, J=7.5 Hz, 1H); from 7.60 to 7.66 (m, 2H); 7.72 (d, J=7.5 Hz, 1H); 7.81 (d, J=7.5 Hz, 1H); from 7.85 to 7.98 (m spread-out, 2H); 8.30 (d, J=5.0 Hz, 1H); 8.46 (m spread-out, 1H); 9.29 (d, J=8.5 Hz, 1H); 10.6 (m spread-out, 2H); 11.9 (m broad, 1H); 13.6 (m spread-out, 1H).

Example 248

Synthesis of {{4-{5-[(3-dimethylaminopropyl)aminocarbonyl]-1H-benzimidazol-2-yl}-9H-fluoren-9(R,S)-yl}}amide of 1H -pyrrolo[2,3-b]-pyridine-4-carboxylic acid Stage 1: The procedure used in Example 233 is followed, but starting from 400 mg of [4-(5-carboxy-1H-benzimidazol-2-yl)-9H-fluoren-9-one, obtained in stage 1 of Example 241, 220 µl of N,N-dimethyl-1,3-propanediamine, 225 mg of 1-(3-dimethylaminopropyl)-3-ethylcarbodiimide hydrochloride (EDCI) and 79 mg of 1-hydroxybenzotriazole (HOBT) in 4 ml of dimethylformamide, for 20 hours at room temperature. After purification by flash chromatography on silica gel (40-63 µm), eluting with a mixture of dichloromethane and ammonia as a 7N solution in methanol (95/5 then 9/1 by volume), and then formation of a paste with diisopropyl ether, in this way we obtain 273 mg of 4-{5-[(3-dimethylaminopropyl)aminocarbonyl]-1H-benzimidazol-2-yl}-9H-fluoren-9-one, in the form of a yellow solid, which is used as it is in the following stage, with the following characteristics:

Mass spectrum (LC/MS/ES+/−): m/z=424 (M+).

Stage 2: The procedure used in Example 5 is followed, starting from 273 mg of 4-[5-(3-dimethylaminopropylaminocarbonyl)-1H-benzimidazol-2-yl]-9H-fluoren-9-one, obtained in the previous stage, 134 mg of hydroxylamine hydrochloride and 264 mg of sodium acetate in 10 ml of ethanol, stirred for 20 h at room temperature. After concentration of the solvent under reduced pressure, the residue is poured into water containing a few ml of ammonia as a 7N solution in methanol, and then extracted with ethyl acetate. The organic phase is dried over magnesium sulphate and brought to dryness under reduced pressure. The crude product is made into a paste with diisopropyl ether, filtered and rinsed. In this way, we obtain 229 mg of 4-{5-[(3-dimethylaminopropyl)aminocarbonyl]-1H-benzimidazol-2-yl}-9H-fluoren-9-one oxime (Z,E), in the form of a pale yellow solid, which is used as it is in the following stage, with the following characteristics:

Mass spectrum (LC/MS/ES/+/−): m/z=439 (M+).

Stage 3: The procedure used in Example 216 is followed. In a 10 ml round-bottomed flask under an argon atmosphere, dissolve 229 mg of 4-{5-[(3-dimethylaminopropyl)aminocarbonyl]-1H-benzimidazol-2-yl}-9H-fluoren-9-one oxime (Z,E), obtained in the previous stage, in a mixture of 1.2 ml of ethanol, 1.2 ml of water and 1.2 ml of acetic acid. At room temperature, add 136 mg of zinc in three stages. Between each addition, stir for approximately one hour to two hours. Add Celite and filter. The filtrate is concentrated under pressure. The crude product is purified by flash chromatography on silica gel (40-63 μm), eluting with a mixture of dichloromethane and ammonia as a 7N solution in methanol (9/1 by volume). After formation of the paste with diisopropyl ether, in this way we obtain 150 mg of 4-{5-[(3-dimethylaminopropyl)aminocarbonyl]-1H-benzimidazol-2-yl}-9H-fluorene-9(R,S)-amine, in the form of an off-white powder, which is used as it is in the following stage, with the following characteristics:

Mass spectrum (EI/CI): m/z=425 (M+).

Stage 4: The procedure used in Example 14 is followed, but starting from 150 mg of 4-{5-[(3-dimethylamino)propylaminocarbonyl]-1H-benzimidazol-2-yl}-9H-fluorene-9(R,S)-amine, obtained in the previous stage, 57 mg of 1H-pyrrolo[2,3-b]pyridine-4-carboxylic acid, 68 mg of 1-(3-dimethylamino-propyl)-3-ethylcarbodiimide hydrochloride (EDCI) and 24 mg of 1-hydroxybenzotriazole (HOBT) in 2.5 ml of dimethylformamide, for 20 hours at room temperature. After purification by flash chromatography on silica gel (40-63 μm), eluting with a mixture of dichloromethane and ammonia as a 7N solution in methanol (9/1 then 85/15 by volume), and then formation of a paste with diisopropyl ether, in this way we obtain 32 mg of {{4-{5-[(3-dimethylaminopropyl)aminocarbonyl]-1H-benzimidazol-2-yl}-9H-fluoren-9(R,S)-yl}}amide of 1H-pyrrolo[2,3-b]pyridine-4-carboxylic acid, in the form of an off-white powder with the following characteristics:

Mass spectrum (LC/MS/ES+/−): m/z=569 (M+).

$^1$H-NMR spectrum (400 MHz, δ in ppm, DMSO-d6): 1.70 (m, 2H); 2.16 (s, 6H); 2.30 (t, J=7.0 Hz, 2H); 3.32 (m partially masked, 2H); 6.41 (d, J=8.5 Hz, 1H); 6.91 (dd, J=2.0 and 3.5 Hz, 1H); 7.25 (t, J=7.5 Hz, 1H); 7.35 (t, J=7.5 Hz, 1H); from 7.42 to 7.88 (m masked, 1H); 7.47 (d, J=5.0 Hz, 1H); 7.53 (t, J=7.5 Hz, 1H); 7.62 (m, 2H); 7.69 (d, J=7.5 Hz, 1H); 7.77 (d, J=7.5 Hz, 1H); 7.81 (m spread-out, 1H); from 8.05 to 8.35 (m spread-out, 1H); 8.30 (d, J=5.0 Hz, 1H); 8.55 (m spread-out, 1H); 9.28 (d, J=8.5 Hz, 1H); 11.85 (m broad, 1H); 13.2 (m spread-out, 1H).

Example 249

Synthesis of {4-[5-fluoro-6-(4-methyl-piperazin-1-yl)-1H-benzimidazol-2-yl]-9H-fluoren-9(R,S)-yl}amide of 1H-pyrrolo[2,3-b]pyridine-4-carboxylic acid Stage 1: The procedure used in stage 1 of Example 1 is followed, but starting from 2.69 g of 4-fluoro-5-(4-methylpiperazin-1-yl)benzene-1,2-diamine, which can be prepared according to J. Het. Chem. 2005, 42(1), 67-71, 2.82 ml of triethylamine and 2.43 g of 9H-fluoren-9-one-4-carboxylic acid chloride in 50 ml of dichloromethane for 20 hours at room temperature. After purification by flash chromatography on silica gel (40-63 μm), eluting with a mixture of dichloromethane and methanol (95/5 by volume), and then formation of a paste with diisopropyl ether, in this way we obtain 1 g of [2-amino-4-fluoro-5-(4-methyl piperazin-1-yl)phenyl]amide of 9-oxo-9H-fluorene-4-carboxylic acid, in the form of an orange powder, which is used as it is in the following stage, with the following characteristics:

Mass spectrum (LC/MS/ES/+/−): m/z=430 (M+).

We also obtain 1 g of [2-amino-5-fluoro-4-(4-methylpiperazin-1-yl)-phenyl]amide of 9-oxo-9H-fluorene-4-carboxylic acid, in the form of an orange powder, which is used as it is in the following stage, with the following characteristics:

Mass spectrum (LC/MS/ES/+/−): m/z=430 (M+).

Stage 2: The procedure used in Example 68 is followed. In a 250 ml round-bottomed flask under an argon atmosphere, reflux, for 6 hours, a suspension of 1 g of [2-amino-5-fluoro-4-(4-methylpiperazin-1-yl)phenyl]amide of 9-oxo-9H-fluorene-4-carboxylic acid and of 1 g of [2-amino-4-fluoro-5-(4-methyl piperazin-1-yl)phenyl]amide of 9-oxo-9H-fluorene-4-carboxylic acid, obtained in the previous stage, in 30 ml of acetic acid. After purification by a formation of a paste with diisopropyl ether, in this way we obtain 1.9 g of 4-[5-fluoro-6-(4-methylpiperazin-1-yl)-1H-benzimidazol-2-yl]-9H-fluoren-9-one, in the form of an orange powder, which is used as it is in the following stage, with the following characteristics:

Mass spectrum (LCMS): m/z=412 (M+).

Stage 3: The procedure used in Example 5 is followed, but starting from 1.9 g of 4-[5-fluoro-6-(4-methylpiperazin-1-yl)-1H-benzimidazol-2-yl]-9H-fluoren-9-one, obtained in the previous stage, 960 mg of hydroxylamine hydrochloride and 1.89 g of sodium acetate in 95 ml of ethanol, stirred for 20 h at room temperature. After purification by a formation of a paste with diisopropyl ether, in this way we obtained 1.95 g of 4-[5-fluoro-6-(4-methylpiperazin-1-yl)-1H-benzimidazol-2-yl]-9H-fluoren-9-one oxime (Z,E), as a 50-50 mixture of Z and E isomers, in the form of an orange powder which is used as it is in the following stage.

Mass spectrum (LCMS): m/z=427 (M+).

Stage 4: The procedure used in Example 6 is followed, starting from 1.95 g of 4-[5-fluoro-6-(4-methylpiperazin-1-yl)-1H-benzimidazol-2-yl]-9H-fluoren-9-one oxime (Z,E), obtained in the previous stage, and 285 mg of Raney nickel in 40 ml of ethanol and 40 ml of tetrahydrofuran for 16 hours at 60° C. under an initial hydrogen pressure of one bar. After filtration of the catalyst, concentration to dryness under reduced pressure and purification by formation of a paste with diisopropyl ether, in this way we obtain 1.7 g of 4-[5-fluoro-6-(4-methylpiperazin-1-yl)-1H-benzimidazol-2-yl]-9H-fluoren-9(R,S)-ylamine, in the form of an orange powder, which is used as it is in the following stage, with the following characteristics:

Mass spectrum (LCMS): m/z=413 (M+).

This compound contains approximately 50% of an N-acetylated analogue that cannot be separated at this stage.

Stage 5: The procedure used in Example 14 is followed, but starting from 689 mg of 4-[5-fluoro-6-(4-methylpiperazin-1-yl)-1H-benzimidazol-2-yl]-9H-fluoren-9(R,S)-ylamine, obtained in the previous stage, as a 50% mixture with an N-acetylated analogue, 162 mg of 1H-pyrrolo[2,3-b]pyridine-4-carboxylic acid, 211 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. After purification by flash chromatography on silica gel (40-63 µm), eluting with a mixture of dichloromethane and 7N ammoniacal methanol (97.5/2.5 by volume), and then formation of a paste with diisopropyl ether, in this way we obtain 175 mg of {4-[5-fluoro-6-(4-methyl piperazin-1-yl)-1H -benzimidazol-2-yl]-9H-fluoren-9(R,S)-yl}amide of 1H-pyrrolo[2,3-b]pyridine-4-carboxylic acid, in the form of a beige powder with the following characteristics:

Mass spectrum (LC/MS/ES+/−): m/z=557 (M+).

$^1$H-NMR spectrum (400 MHz, δ in ppm, DMSO-d6): 2.26 (s, 3H); 2.54 (m partially masked, 4H); 3.06 (m, 4H); 6.40 (d, J=8.5 Hz, 1H); 6.91 (d, J=3.5 Hz, 1H); from 7.10 to 7.80 (m masked, 2H); 7.26 (t, J=7.5 Hz, 1H); 7.34 (t, J=7.5 Hz, 1H); 7.46 (d, J=5.0 Hz, 1H); 7.50 (t, J=7.5 Hz, 1H); from 7.59 to 7.66 (m, 4H); 7.73 (d, J=7.5 Hz, 1H); 8.29 (d, J=5.0 Hz, 1H); 9.26 (d, J=8.5 Hz, 1H); 11.9 (m broad, 1H); 12.85 (m spread-out, 1H).

Example 250

Synthesis of N-{4-[5-fluoro-6-(4-methylpiperazin-1-yl)-1H-benzimidazol-2-yl]-9H-fluoren-9(R,S)-yl}acetamide During the purification by flash chromatography of the product of stage 5 of Example 249, we isolate a side product. After formation of a paste with diisopropyl ether, in this way we obtain 135 mg of N-{4-[5-fluoro-6-(4-methylpiperazin-1-yl)-1H-benzimidazol-2-yl]-9H-fluoren-9(R,S)-yl}acetamide, in the form of a beige powder with the following characteristics:

Mass spectrum (LC/MS/ES+/−): m/z=455 (M+).

Example 251

Synthesis of {{4-{5-[(3-dimethylaminopropyl)carbonyloxy]-1H-benzimidazol-2-yl}-9H-fluoren-9(R,S)-yl}}amide of 1H-pyrrolo[2,3-b]pyridine-4-carboxylic acid Stage 1: The procedure used in Example 233 is followed, but starting from 500 mg of 4-(5-carboxy-1H-benzimidazol-2-yl)-9H-fluoren-9-one, obtained in stage 1 of Example 241, 261 µl of 3-dimethylaminopropanol, 280 mg of 1-(3-dimethylaminopropyl)-3-ethylcarbodiimide hydrochloride (EDCI), 50 mg of N,N-dimethylaminopyridine (DMAP) in a mixture of 4 ml of dichloromethane, 2 ml of tetrahydrofuran and 1 ml of dimethylformamide, for 20 hours at room temperature. After purification by flash chromatography on silica gel (40-63 µm), eluting with a mixture of dichloromethane and methanol (9/1 by volume) and then dichloromethane and ammonia as a 7N solution in methanol (9/1 by volume), in this way we obtain 582 mg of 4-{5-[(3-dimethylaminopropyl)carbonyloxy]-1H-benzimidazol-2-yl}-9H-fluoren-9-one, in the form of a yellow resin, which is used as it is in the following stage, with the following characteristics:

Mass spectrum (LC/MS/ES+/−): m/z=425 (M+).

Stage 2: The procedure used in Example 5 is followed, but starting from 582 mg of 4-{5-[(3-dimethylaminopropyl)carbonyloxy]-1H-benzimidazol-2-yl}-9H-fluoren-9-one, obtained in the previous stage, 283 mg of hydroxylamine hydrochloride and 561 mg of sodium acetate in 30 ml of ethanol, stirred for 20 h at room temperature. After formation of a paste with diisopropyl ether, in this way we obtain 468 mg of 4-{5-[(3-dimethylaminopropyl)carbonyloxy]-1H-benzimidazol-2-yl}-9H-fluoren-9-one oxime (Z,E), in the form of a pale yellow solid, which is used as it is in the following stage, with the following characteristics:

Mass spectrum (LC/MS/ES/+/−): m/z=440 (M+).

Stage 3: The procedure used in Example 216 is followed. In a 20 ml round-bottomed flask under an argon atmosphere, dissolve 468 mg of 4-{5-[(3-dimethylaminopropyl)carbonyloxy]-1H-benzimidazol-2-yl}-9H-fluoren-9-one oxime (Z,E), obtained in the previous stage, in a mixture of 2.5 ml of ethanol, 2.5 ml of water and 2.5 ml acetic acid, at room temperature. Add 278 mg of zinc in three stages. Between each addition, stir for approximately one hour to two hours. Add Celite 545 and filter. The filtrate is concentrated under pressure. After purification by flash chromatography on silica gel (40-63 µm), eluting with a mixture of dichloromethane and ammonia as a 7N solution in methanol (9/1 by volume), and then formation of a paste with diisopropyl ether, in this way we obtain 327 mg of 4-{5-[(3-dimethylaminopropyl)carbonyloxy]-1H-benzimidazol-2-yl}-9H-fluorene-9(R,S)-amine, in the form of an off-white solid, which is used as it is in the following stage, with the following characteristics:

Mass spectrum (LC/MS/ES+/−): m/z=426 (M+).

Stage 4: The procedure used in Example 14 is followed, but starting from 327 mg of 4-{5-[(3-dimethylaminopropyl)carbonyloxy]-1H-benzimidazol-2-yl}-9H-fluorene-9(R,S)-amine, obtained in the previous stage, 124 mg of 1H-pyrrolo[2,3-b]pyridine-4-carboxylic acid, 147 mg of 1-(3-dimethylamino-propyl)-3-ethylcarbodiimide hydrochloride (EDCI) and 52 mg of 1-hydroxybenzotriazole (HOBT) in 3.5 ml of dimethylformamide, for 20 hours at room temperature. After purification by flash chromatography on silica gel (40-63 µm), eluting with a mixture of dichloromethane and ammonia as a 7N solution in methanol (95/5 then 9/1 by volume), and then formation of a paste with diisopropyl ether, in this way we obtain 258 mg of {{4-{5-[(3-dimethylaminopropyl)carbonyloxy]-1H-benzimidazol-2-yl}-9H-fluoren-9 (R,S)-yl}}amide of 1H-pyrrolo[2,3-b]pyridine-4-carboxylic acid, in the form of an off-white solid with the following characteristics:

Mass spectrum (LC/MS/ES+/−): m/z=570 (M+).

$^1$H-NMR spectrum (400 MHz, δ in ppm, DMSO-d6): 1.90 (m, 2H); 2.17 (s, 6H); 2.39 (t, J=6.5 Hz, 2H); 4.35 (t, J=6.5 Hz, 2H); 6.42 (d, J=8.5 Hz, 1H); 6.91 (m broad, 1H); 7.26 (t, J=7.5 Hz, 1H); 7.35 (t, J=7.5 Hz, 1H); 7.47 (d, J=5.0 Hz, 1H); 7.53 (t, J=7.5 Hz, 1H); from 7.57 to 7.64 (m, 3H); 7.70 (d, J=7.5 Hz, 1H); 7.75 (m spread-out, 1H); 7.78 (d, J=7.5 Hz, 1H); 7.93 (d, J=8.5 Hz, 1H); 8.28 (m spread-out, 1H); 8.30 (d, J=5.0 Hz, 1H); 9.28 (d, J=8.5 Hz, 1H); 11.85 (m broad, 1H); 13.3 (m spread-out, 1H).

Example 252

Synthesis of [4-(6-nitro-1H-benzimidazol-2-yl)-9H-fluoren-9(R,S)-yl]amide of 1H-pyrrolo[2,3-b]pyridine-4-carboxylic acid In a 20 ml single-necked flask, introduced successively, under an argon atmosphere, 23 mg of 4-nitrobenzene-1,2-diamine, 53 mg of (4-formyl-9H-fluoren-9-yl)amide of 1H-pyrrolo[2,3-b]pyridine-4-carboxylic acid, prepared as in stage 6 of Example 234, 24 mg of ferric chloride and 2 ml of dimethylformamide. After stirring for 16 h at 20° C., concentrate the solution under reduced pressure and then take up the residue obtained in 5 ml of water. After draining of the insoluble material formed on a porous plate, washing with 4 times 2 ml of water and drying at 40° C. under reduced pressure, we obtain 72 mg of [4-(6-nitro-1H-benzimidazol-2-yl)-9H-fluoren-9(R,S)-yl]amide of 1H-pyrrolo[2,3-b]pyridine-4-carboxylic acid, in the form of a violet powder with the following characteristics:

Mass spectrum (E/I): m/z=486 (M+).

$^1$H-NMR spectrum (300 MHz, δ in ppm, DMSO): for this compound, a 70%-30% mixture of rotamers is observed with: 6.41 (d, J=8.5 Hz, 1H); 6.91 (s broad, 1H); from 7.00 to 8.00 (m spread-out masked, 1H); 7.27 (t, J=7.5 Hz, 1H); 7.37 (t, J=7.5 Hz, 1H); 7.47 (d, J=5.0 Hz, 1H); 7.56 (t, J=7.5 Hz, 1H); 7.58 (d broad, J=8.5 Hz, 1H); 7.63 (m, 2H); 7.72 (d, J=7.5 Hz, 1H); 7.81 (d, J=7.5 Hz, 1H); 8.22 (m broad, 1H); 8.30 (d, J=5.0 Hz, 1H); 8.45 (m broad, 0.3H); 8.68 (m broad, 0.7H); 9.29 (d, J=8.5 Hz, 1H); 11.86 (m broad, 1H); 13.7 (m spread-out, 1H).

Example 253

Synthesis of 4-(6-methyl-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, but starting from 5 g of 1,2-diamino-4-methylbenzene, 12 ml of triethylamine and 10 g of fluoren-4-one-9-carboxylic acid chloride in 300 ml of dichloromethane. After stirring for 20 hours at room temperature, the reaction mixture is washed with water, dried over magnesium sulphate, and concentrated to dryness under reduced pressure. The residue is purified by flash chromatography on silica gel (40-63 μm), eluting with a mixture of dichloromethane and methanol (95/5 by volume). In this way, we obtain 11.5 g of (2-amino-4-methylphenyl)-amide of 9-oxo-9H-fluorene-4-carboxylic acid in the form of an orange solid, which is used as it is in the following stage, with the following characteristic:

Mass spectrum (EI): m/z=328 (M+).

Stage 2: The procedure used in Example 68 is followed. In a 500 ml round-bottomed flask under an argon atmosphere, heat, at 110° C. for 6 hours, a solution of 11.5 g of (2-amino-4-methylphenyl)amide of 9-oxo-9H-fluorene-4-carboxylic acid, obtained in the previous stage, in 300 ml of acetic acid. After cooling, bring to dryness under reduced pressure. The crude solid obtained is purified by flash chromatography on silica gel (40-63 μm), eluting with a mixture of dichloromethane and methanol (99/1 by volume). In this way, we obtain 5.3 g of 4-(6-methyl-1H-benzimidazol-2-yl)-9H-fluoren-9-one, in the form of a yellow powder, which is used as it is in the following stage, with the following characteristics:

Mass spectrum (EI): m/z=310 (M+).

Stage 3: The procedure used in Example 5 is followed, but starting from 1 g of 4-(6-methyl-1H-benzimidazol-2-yl)-9H-fluoren-9-one, obtained in the previous stage, 672 mg of hydroxylamine hydrochloride and 1.3 g sodium acetate in 45 ml of ethanol, stirred for 20 h at room temperature. After concentration of the solvent under reduced pressure, the residue is taken up successively with water, filtered and rinsed with isopropyl ether. In this way, we obtain 1 g (95%) of 4-(6-methyl-1H-benzimidazol-2-yl)-9H-fluoren-9-one oxime (Z,E), as a 50-50 mixture of Z and E isomers, in the form of a beige solid, which is used as it is in the following stage, with the following characteristics:

Mass spectrum (EI): m/z=325 (M+).

Stage 4: The procedure used in Example 6 is followed. In a 100 ml autoclave, dissolve 1 g of 4-(6-methyl-1H-benzimidazol-2-yl)-9H-fluoren -9-one oxime (Z,E), obtained in the previous stage, in a mixture of 40 ml of ethanol and 40 ml of tetrahydrofuran, add a spatula of Raney activated nickel and then subject to an initial hydrogen pressure of 1 bar and heat the autoclave at 60° C. for 3 hours. After cooling, the volume of hydrogen absorbed is 142 ml. After filtration of the catalyst over Celite, the filtrate is concentrated under reduced pressure and then taken up in petroleum ether and filtered. In this way, we obtain 720 mg of 4-(6-methyl-1H-benzimidazol-2-yl)-9H-fluorene-9(R,S)-amine, in the form of a beige solid, which is used as it is in the following stage, with the following characteristic:

Mass spectrum (LC/MS): m/z=311 (M+).

Stage 5: The procedure used in Example 14 is followed, but starting from 370 mg of 4-(6-methyl-1H-benzimidazol-2-yl)-9H-fluorene-9(R,S)-amine, obtained in the previous stage, 162 mg of 1H-pyrrolo[2,3-b]pyridine-4-carboxylic acid, 210 mg of 1-(3-dimethylaminopropyl)-3-ethylcarbodiimide hydrochloride (EDCI) and 148 mg of 1-hydroxybenzotriazole (HOBT) in 7 ml of dimethylformamide, for 20 hours at room temperature. Bring the dimethylformamide to dryness, add water and drain the precipitate that formed and then wash with water, then with a 10% saturated solution of sodium hydrogen carbonate and, finally, with water. The crude solid obtained is dried and then purified by flash chromatography on silica gel (40-63 μm), eluting with a mixture of dichloromethane and methanol (95/5 by volume). In this way, we obtain 290 mg of 4-(6-methyl-1H-benzimidazol-2-yl)-9H-fluoren-9(R,S)-yl]amide of 1H-pyrrolo[2,3-b]pyridine-4-carboxylic acid, in the form of a beige solid with the following characteristics:

Mass spectrum (LC/MS): m/z=455 (M+).

$^1$H-NMR spectrum (400 MHz, δ in ppm, DMSO-d6): for this compound, a 50%-50% mixture of rotamers is observed with: from 2.47 to 2.51 (s masked, 3H); 6.41 (d, J=8.5 Hz, 1H); 6.91 (dd, J=1.5 and 3.5 Hz, 1H); 7.10 (m, 1H); 7.24 (t, J=7.5 Hz, 1H); from 7.30 to 7.37 (m, 2H); from 7.43 to 7.67 (m, 7H); 7.74 (d, J=7.5 Hz, 1H); 8.29 (d, J=5.0 Hz, 1H); 9.26 (d, J=8.5 Hz, 1H); 11.85 (m broad, 1H); 12.7 (m broad, 0.5H); 12.8 (m broad, 0.5H).

Example 254

Synthesis of 5-(1H-benzimidazol-2-yl)-2-bromo-9H-fluoren-9-one

Stage 1: In a 100 ml three-necked round-bottomed flask, equipped with mechanical stirring, stir 4.48 g of 9H-fluoren-9-one-4-carboxylic acid in suspension in 40 ml of trifluoroacetic acid and 12 ml of concentrated sulphuric acid. To this dark reaction mixture, add 5.33 g of N-bromosuccinimide over a period of 9 h. The yellow precipitate that formed is filtered over sintered glass, washed with 3 times 20 ml of trifluoroacetic acid and 6 times 50 ml of water, and then dried in an oven at 50° C. under a strong vacuum. We obtain 6.6 g of a yellow powder, composed of a 55/45 mixture of 2-bromo-9-oxo-9H-fluorene-4-carboxylic acid and 2,7-dibromo-9-oxo-9H-fluorenecarboxylic acid, used as it is in the following stage.

Stage 2: In a 250 ml round-bottomed flask, stir 3.80 g of the mixture obtained in stage 1 in 100 ml of dichloromethane to which 1 ml of dimethylformamide has been added. Add 1.93 g of oxalyl chloride and stir the reaction mixture at ambient temperature for 30 minutes. The yellow solution obtained is added, under argon and dropwise over 20 min, to a solution of 1.78 g of ortho-phenylenediamine and 3.12 g of triethylamine in 100 ml of dichloromethane. The precipitate that formed is filtered off and washed with twice 50 ml of dicholoromethane and 50 ml of water, to give, after drying at 50° C. in an oven under vacuum, 4.90 g of a 60/40 mixture of 2-aminobenzoylamide of 7-bromo-9-oxo-9H-fluorene-4-carboxylic acid and 2-aminobenzoylamide of 2,7-dibromo-9-oxo-9H-fluorene-4-carboxylic acid, in the form of a yellow powder which is used as it is in the following stage.

Stage 3: A suspension of 4.30 g of the mixture obtained in stage 2 in 200 ml of acetic acid is refluxed for 1 hour 30 minutes. Evaporation of the acetic acid under reduced pressure gives a yellow paste which is taken up in 250 ml of water. The pH of the supernatant is brought to 9 by adding a 5N aqueous solution of sodium hydroxide. The yellow precipitate obtained is filtered over sintered glass, washed with water and dried at 50° C. in an oven under vacuum. After recrystallization from 100 ml of dimethylformamide, the product being isolated by filtration at a temperature of 80° C., in this way we obtain 1.57 g of 5-(1H-benzimidazol-2-yl)-2-bromo-9H-fluoren-9-one, in the form of yellow crystals with the following characteristics:

Mass spectrum (EI): m/z=375 (M+).

NMR spectrum (400 MHz, δ in ppm, DMSO-d6): 7.30 (m, 2H); 7.61 (t, J=7.5 Hz, 1H); 7.69 (m, 2H); 7.73 (dd, J=2.0 and 8.0 Hz, 1H); 7.80 (d, J=2.0 Hz, 1H); 7.81 (d broad, J=7.5 Hz, 1H); 7.90 (d, J=8.0 Hz, 1H); 7.92 (d broad, J=7.5 Hz, 1H); 13.0 (m spread-out, 1H).

Example 255

Synthesis of {{4-{5-[(3-hydroxypropyl)aminocarbonyl]-1H-benzimidazol-2-yl}-9H-fluoren-9(R,S)-yl}}amide of 1H-pyrrolo[2,3-b]pyridine-4-carboxylic acid In a 30 ml round-bottomed flask under argon, dissolve 300 mg of [4-(5-methoxycarbonyl-1H-benzimidazol-2-yl)-9H-fluoren-9(R,S)-yl]amide of 1H-pyrrolo[2,3-b]pyridine-4-carboxylic acid, obtained in Example 205, in 5 ml of 3-aminopropanol, and then heat at 170° C. for 2 h 30. The reaction medium is poured into water containing a few ml of ammonia as a 7N solution in sodium chloride methanol, the mixture is extracted with ethyl acetate, and the organic phase is then washed with a saturated solution of sodium chloride, dried over magnesium sulphate and brought to dryness under reduced pressure. The crude solid obtained is purified by flash chromatography on silica gel (40-63 μm), eluting with a mixture of dichloromethane and methanol (95/5 then 9/1 by volume). After formation of a paste with diisopropyl ether, in this way we obtain 38 mg of {{4-{5-[(3-hydroxypropyl)aminocarbonyl]-1H-benzimidazol-2-yl}-9H-fluoren-9(R,S)-yl}}amide of 1H-pyrrolo[2,3-b]pyridine-4-carboxylic acid, in the form of an off-white powder with the following characteristics:

Melting point (Kofler)>260° C.

Mass spectrum (LC/MS/ES+/−): m/z=542 (M+).

$^1$H-NMR spectrum (400 MHz, δ in ppm, DMSO-d6): 1.73 (m, 2H); 3.38 (q, J=6.5 Hz, 2H); 3.50 (m, 2H); 4.49 (t, J=5.5 Hz, 1H); 6.41 (d, J=8.5 Hz, 1H); 6.91 (dd, J=1.5 and 3.5 Hz, 1H); 7.25 (t, J=7.5 Hz, 1H); 7.35 (t, J=7.5 Hz, 1H); 7.47 (d, J=5.0 Hz, 1H); from 7.49 to 7.71 (m masked, 1H); 7.53 (t, J=7.5 Hz, 1H); 7.62 (m, 3H); 7.69 (d, J=7.5 Hz, 1H); 7.78 (d, J=7.5 Hz, 1H); 7.82 (m broad, 1H); from 8.00 to 8.39 (m spread-out, 1H); 8.30 (d, J=5.0 Hz, 1H); 8.48 (t broad, J=6.5 Hz, 1H); 9.29 (d, J=8.5 Hz, 1H); 11.85 (m broad, 1H); 13.15 (m spread-out, 1H).

Example 256

Synthesis of 4-[5-aminomethyl-1H-benzimidazol-2-yl]-9H-fluoren-9(R,S)-yl}amide of 1H-pyrrolo[2,3-b]pyridine-4-carboxylic acid In a 67 ml autoclave, dissolve 425 mg of [4-(5-cyano-1H-benzimidazol-2-yl)-9H-fluoren-9(R,S)-yl]amide of 1H-pyrrolo[2,3-b]pyridine-4-carboxylic acid, obtained in Example 216, in a mixture of 15 ml of ethanol and 15 ml of tetrahydrofuran, add a spatula of Raney activated nickel and then subject to an initial hydrogen pressure of 1 bar and heat the autoclave at 600 for 10 hours. After cooling, the volume of hydrogen absorbed is 69 ml. After filtration of the catalyst over Celite, the filtrate is concentrated under reduced pressure, and the crude solid obtained is purified by flash chromatography on silica gel (40-63 μm), eluting with a mixture of dichloromethane and ammonia as a 7N solution in methanol (95/5 then 9/1 by volume). After treatment with diisopropyl ether, in this way we obtain 220 mg of 4-[5-aminomethyl-1H-benzimidazol-2-yl]-9H-fluoren-9(R,S)-yl}amide of 1H-pyrrolo[2,3-b]pyridine-4-carboxylic acid, in the form of a white solid with the following characteristics:

Melting point (Kofler)=>260° C.

Mass spectrum (LC/MS/ES+/−): m/z=470 (M+).

$^1$H-NMR spectrum (400 MHz, δ in ppm, DMSO-d6): 3.93 (s broad, 2H); 6.41 (d, J=8.5 Hz, 1H); 6.91 (dd, J=1.5 and 3.5 Hz, 1H); 7.25 (t, J=7.5 Hz, 1H); 7.31 (m masked, 1H); 7.35 (t, J=7.5 Hz, 1H); from 7.42 to 7.57 (m masked, 1H); 7.47 (d, J=5.0 Hz, 1H); 7.52 (t, J=7.5 Hz, 1H); from 7.58 to 7.78 (m, H); from 7.70 to 7.81 (m, 2H); 8.30 (d, J=5.0 Hz, 1H); 9.28 (d, J=8.5 Hz, 1H); 11.85 (m broad, 1H); 12.85 (m broad, 1H).

Examples 257 and 258

Resolution of the enantiomers of 4-[5-cyano-1H-benzimidazol-2-yl]-9H-fluoren-9(R,S)-yl}amide of 1H-pyrrolo[2,3-b]pyridine-4-carboxylic acid By following the procedure used in Example 153, starting from 422 mg of [5-cyano-1H-benzimidazol-2-yl]-9H-fluoren-9(R,S)-yl}amide of 1H-pyrrolo-[2,3-b]pyridine-4-carboxylic acid, obtained as in Example 216, but using a chiral column of Chiralcel OJ20 μm type, 25 cm long and 5 cm in diameter, eluting with a supercritical mobile phase composed of carbon dioxide, ethanol and trifluoroacetic acid (75/25/0.1) at a flow rate of 150 ml/nm and under a pressure of 124 bar, and detecting the eluted products by UV spectroscopy at 254 nm, we obtain, by recovering the first fractions eluted and concentrating under reduced pressure, 205 mg of dextrorotatory enantiomer of 4-[5-cyano-1H-benzimidazol-2-yl]-9H-fluoren-9(R,S)-yl}amide of 1H-pyrrolo[2,3-b]-pyridine-4-carboxylic acid, in the form of an amorphous white solid with the following characteristics:

αD20=+157+/−2.3° (c=0.468; DMSO).

By recovering the second fractions eluted and concentrating under reduced pressure, we obtain 206 mg of levorotary enantiomer of 4-[5-cyano-1H -benzimidazol-2-yl]-9H-fluoren-9(R,S)-yl}amide of 1H-pyrrolo[2,3-b]pyridine-4-carboxylic acid, containing approximately 1.2% of dextrorotatory enantiomer, in the form of an amorphous white solid with the following characteristics:

αD20=−156.7+/−2.2° (c=0.56; DMSO).

Example 259

Synthesis of [4-(3H-imidazo[4,5-c]pyridin-2-yl)-9H-fluoren-9(R,S)-yl]amide of 7H-pyrrolo[2,3-d]pyrimidine-4-carboxylic acid Stage 1: In a 1 l three-necked flask, introduce, with stirring, 11.8 g of 4-chloro-7H-pyrrolo[2,3-d]pyrimidine and 137 ml of toluene, then 16.11 g of 4-methyl-benzenesulphonyl chloride and 5.2 g of tetra-n-butylammonium hydrogen sulphate, then run in, dropwise, 275 ml of an aqueous solution containing 30.7 g of sodium hydroxide. After 30 minutes at room temperature, add 200 ml of ethyl acetate and 200 ml of water. The organic phase is decanted, dried over magnesium sulphate, and concentrated under reduced pressure. After purification by flash chromatography on silica gel, eluting with dichloromethane, we obtain 22.6 g of 4-chloro-7-(4-methylbenzenesulphonyl)-7H-pyrrolo[2,3-d]pyrimidine, in the form of a white solid with the following characteristics:

Mass spectrum (E/I): m/z=307 (M+).

Stage 2: In an autoclave, introduce successively 1 g of 4-chloro-7-(4-methylbenzenesulphonyl)-7H-pyrrolo[2,3-d]pyrimidine, obtained in the previous stage, 0.18 g of 1,1'-bis(diphenylphosphino)ferrocene, 0.073 g of palladium(II) acetate, 0.53 g of sodium acetate and 20 ml of ethanol. Stir for 24 hours at 100° C. under a carbon monoxide pressure of 20 bar. After evaporation of the solvent and flash chromatography on silica gel, eluting with a mixture of ethyl acetate and dichloromethane (95/5 by volume), we obtain 0.78 g of ethyl ester of 7-(4-methylbenzenesulphonyl)-7H-pyrrolo[2,3-d]-pyrimidine-4-carboxylic acid, in the form of a white solid with the following characteristics:

Mass spectrum (E/I): m/z=345 (M+).

Stage 3: Dissolve 0.16 g of ethyl ester of 7-(4-methylbenzenesulphonyl)-7H-pyrrolo[2,3-d]pyrimidine-4-carboxylic acid, obtained in the previous stage, in 10 ml of tetrahydrofuran; then run in 1.38 ml of a molar solution of tetra-n-butylammonium fluoride in tetrahydrofuran, at 20° C. over 20 minutes. After 2 h at 20° C., take up the reaction medium with 10 ml of water and 20 ml of ethyl acetate. After decanting, washing the organic phase with water, drying over magnesium sulphate and concentrating to dryness under reduced pressure, we obtain 70 mg of ethyl ester of 7H-pyrrolo[2,3-d]pyrimidine-4-carboxylic acid, in the form of a whitish solid with the following characteristics:

Mass spectrum (E/I): m/z=191 (M+).

NMR spectrum (400 MHz, δ in ppm, DMSO-d6): 1.40 (t, J=7.5 Hz, 3H); 4.44 (q, J=7.5 Hz, 2H); 6.89 (d, J=3.5 Hz, 1H); 7.80 (d, J=3.5 Hz, 1H); 8.90 (s, 1H); 12.5 (m spread-out, 1H).

Stage 4: In a 100 ml three-necked flask, dissolve 100 mg of 4-(1H-imidazo[4,5-c]pyridin-2-yl)-9H-fluoren-9(R,S)-ylamine, obtained in Example 6, and 64 mg of ethyl ester of 7H-pyrrolo[2,3-d]pyrimidine-4-carboxylic acid, obtained in the previous stage, in 10 ml of tetrahydrofuran; then run in, dropwise, 6 ml of a 2.0M solution of trimethylaluminium in toluene and stir at 20° C. for 5 hours. The reaction medium is taken up with 50 ml of water and 50 ml of ethyl acetate. After decanting, washing the organic phase with water, drying over magnesium sulphate and concentrating at 30° C. under reduced pressure, we obtain 133 mg of a residue which is resuspended in 5 ml of ethyl acetate. The precipitate that formed is drained, washed twice with 2 ml of ethyl acetate and dried, and in this way we obtain 93 mg of [4-(3H-imidazo[4,5-c]pyridin-2-yl)-9H-fluoren-9(R,S)-yl]amide of 7H-pyrrolo[2,3-d]-pyrimidine-4-carboxylic acid, in the form of a greyish powder with the following characteristics:

Melting point (Kofler)=260° C.

Mass spectrum (E/I): m/z=443 (M+).

$^1$H-NMR spectrum (300 MHz, 6 ppm, DMSO): 6.27 (d, J=8.5 Hz, 1H); 7.10 (d, J=3.5 Hz, 1H); 7.25 (t, J=7.5 Hz, 1H); 7.31 (t broad, J=7.5 Hz, 1H); 7.50 (t, J=7.5 Hz, 1H); 7.51 (m masked, 1H); 7.56 (d, J=7.5 Hz, 1H); 7.67 (m masked, 1H); 7.68 (d, J=7.5 Hz, 1H); 7.73 (d, J=7.5 Hz, 1H); 7.78 (d, J=3.5 Hz, 1H); 8.40 (d, J=5.0 Hz, 1H); 8.83 (s, 1H); 9.04 (s, 1H); 9.51 (d, J=8.5 Hz, 1H); 12.4 (m broad, 1H); 13.4 (m spread-out, 1H).

Example 260

Synthesis of the methyl ester of 2-{9-[(Z,E)-hydroxyimino]-9H-fluoren-4-yl}-1H-imidazo[4,5-c]pyridine-6-carboxylic acid Stage 1: In a 500 ml round-bottomed flask under an argon atmosphere, reflux, for 24 hours, a suspension of 3 g of 4-amino-5-nitropyridine-2-carboxylic acid monohydrate in 300 ml of methanol in the presence of 6 ml of 98% concentrated sulphuric acid. After cooling, bring to dryness under reduced pressure. Pick up the residue in 200 ml of water, cool in an ice bath, and neutralize to pH=8 with a saturated aqueous solution of sodium hydrogen carbonate. The precipitate that formed is filtered off, washed with water, and rinsed with diisopropyl ether. In this way, we obtain 2.5 g of the methyl ester of 4-amino-5-nitropyridine-2-carboxylic acid, in the form of a beige powder, which is used as it is in the following stage, with the following characteristics:

Mass spectrum (LC/MS/ES/+/−): m/z=197 (M+).

Stage 2: In an autoclave, dissolve 2.5 g of methyl ester of 4-amino-5-nitropyridine-2-carboxylic acid, obtained in the previous stage, in 300 ml of ethanol and stir in the presence of 179 mg of 10% palladium-on-charcoal for 6 hours at 60° C. under an initial hydrogen pressure of one bar. After filtration of the catalyst, concentration of the filtrate under reduced pressure and formation of a paste with diisopropyl ether, in this way we obtain 2.1 g of the methyl ester of 4,5-diaminopyridine-2-carboxylic acid, in the form of a beige powder, which is used as it is in the following stage, with the following characteristics:

Mass spectrum (LC/MS/ES/+/−): m/z=167 (M+).

Stage 3: The procedure used in stage 1 in Example 1 is followed, but starting from 2.1 g of the methyl ester of 4,5-diaminopyridine-2-carboxylic acid, 3.55 ml of triethylamine and 3.05 g of fluoren-9-one-4-carboxylic acid chloride in 50 ml of dichloromethane for 20 hours at room temperature. After purification by flash chromatography on silica gel (40-63 µm), eluting with a mixture of dichloromethane and methanol (95/5 by volume), and then formation of a paste with diisopropyl ether, in this way we obtain 2.5 g of the methyl ester of 5-amino-4-[(9-oxo-9H-fluoren-4-yl)carboxamido]pyridine-2-carboxylic acid, in the form of an orange powder, which is used as it is in the following stage, with the following characteristics:

Mass spectrum (LC/MS/ES/+/−): m/z=373 (M+).

Stage 4: The procedure used in Example 68 is followed. In a 250 ml round-bottomed flask under an argon atmosphere, reflux, for 30 hours, a suspension of 2.5 g of the methyl ester of 5-amino-4-[(9-oxo-9H-fluoren-4-yl)carboxamido]pyridine-2-carboxylic acid, obtained in the previous stage, in 44 ml of acetic acid. After cooling, bring to dryness under reduced pressure. Take up the residue with water, and neutralize to pH=8 by adding a saturated aqueous solution of sodium hydrogen carbonate. The precipitate that formed is filtered off, washed with water, and rinsed with diisopropyl ether. The crude product is recrystallized from a mixture of dichloromethane and methanol (7/3 by volume). We obtain 1.5 g of methyl ester of 2-(9-oxo-9H-fluoren-4-yl)-1H-imidazo[4,5-c]pyridine-6-carboxylic acid, in the form of a yellow powder, which is used as it is in the following stage, with the following characteristics:

Mass spectrum (LCMS): m/z=355 (M+).

Stage 5: The procedure used in Example 5 is followed, but starting from 1.35 g of methyl ester of 2-(9-oxo-9H-fluoren-4-yl)-1H-imidazo[4,5-c]pyridine-6-carboxylic acid, obtained in the previous stage, 792 mg of hydroxylamine hydrochloride and 1.55 g of sodium acetate in 80 ml of ethanol, stirred for 20 h at room temperature. After purification by flash chromatography on silica gel (40-63 µm), eluting with a mixture of dichloromethane and methanol (95/5 by volume), and then formation of a paste with diisopropyl ether, in this way we obtain 950 mg of methyl ester of 2-{9-[(Z,E)-hydroxyimino]-9H -fluoren-4-yl}-1H-imidazo[4,5-c]pyridine-6-carboxylic acid, as a 50-50 mixture of Z and E isomers, in the form of a beige powder with the following characteristics:

Mass spectrum (LCMS): m/z=370 (M+).

NMR spectrum (400 MHz, δ in ppm, DMSO-d6): for this compound, a 50%-50% mixture of Z and E isomers is observed with: 3.92 (s, 3H); 7.24 (m, 1H); from 7.31 to 7.36 (m, 1H); 7.40 (t, J=7.5 Hz, 0.5H); 7.49 (d, J=7.5 Hz, 0.5H); 7.54 (t, J=7.5 Hz, 0.5H); 7.60 (t, J=7.5 Hz, 0.5H); 7.72 (d, J=7.5 Hz, 0.5H); 7.76 (d, J=7.5 Hz, 0.5H); 7.78 (d, J=7.5 Hz, 0.5H); 7.96 (d, J=7.5 Hz, 0.5H); 8.36 (s broad, 1H); 8.44 (d, J=7.5 Hz, 0.5H); 8.64 (d, J=7.5 Hz, 0.5H); 9.11 (s broad, 1H); 12.78 (s, 0.5H); 12.82 (s, 0.5H); 13.8 (m spread-out, 1H).

Example 261

4-(6-Amino-1H-benzimidazol-2-yl)-9H-fluoren-9(R,S)-yl]amide of 1H-pyrrolo[2,3-b]pyridine-4-carboxylic acid In a hydrogenation autoclave, introduce successively 3 mg of 10% palladium-on-charcoal, 20 mg of [4-(6-nitro-1H-benzimidazol-2-yl)-9H-fluoren-9(R,S)-yl]amide of 1H-pyrrolo[2,3-b]pyridine-4-carboxylic acid, obtained as in Example 252, and 10 ml of ethyl alcohol. Stir for 18 hours at 15° C. under an initial hydrogen pressure of 1 bar. After filtration of the catalyst, and then concentration to dryness under reduced pressure, we obtained, after drying in an oven at 40° C., 15 mg of [4-(6-amino-1H-benzimidazol-2-yl)-9H-fluoren-9(R,S)-yl]amide of 1H-pyrrolo[2,3-b]pyridine-4-carboxylic acid, in the form of a beige solid with the following characteristics:

Mass spectrum (E/I): m/z=456 (M+).

¹H-NMR spectrum (300 MHz, δ in ppm, DMSO): 6.27 (d, J=8.5 Hz, 1H); 7.10 (d, J=3.5 Hz, 1H); 7.25 (t, J=7.5 Hz, 1H); 7.31 (t broad, J=7.5 Hz, 1H); 7.50 (t, J=7.5 Hz, 1H); 7.51 (m masked, 1H); 7.56 (d, J=7.5 Hz, 1H); 7.67 (m masked, 1H); 7.68 (d, J=7.5 Hz, 1H); 7.73 (d, J=7.5 Hz, 1H); 7.78 (d, J=3.5 Hz, 1H); 8.40 (d, J=5.0 Hz, 1H); 8.83 (s, 1H); 9.04 (s, 1H); 9.51 (d, J=8.5 Hz, 1H); 12.4 (m broad, 1H); 13.4 (m spread-out, 1H).

Example 262

Synthesis of [5-(1H-benzimidazol-2-yl)-2-bromo-9H-fluoren-9(R,S)-yl]amide of 1H-pyrrolo[2,3-b]pyridine-4-carboxylic acid Stage 1: The procedure used in Example 5 is followed, but starting from 5-(1H-benzimidazol-2-yl)-2-bromo-9H-fluoren-9-one, obtained as in Example 254, 285 mg of hydroxylamine hydrochloride and 560 mg of sodium acetate, at reflux for 14 hours in 30 ml of ethanol. The yellow powder, obtained after evaporation of the solvent under reduced pressure, is taken up in 80 ml of water, filtered, washed with twice 50 ml of water, and dried at 50° C. in an oven under vacuum, and in this way we obtained 530 mg of 5-(1H-benzimidazol-2-yl)-2-bromo-9H-fluoren-9-one oxime, as a 50/50 mixture of Z and E isomers, in the form of an off-white powder which is used as it is in the following stage.

Stage 2: Place 500 mg of 5-(1H-benzimidazol-2-yl)-2-bromo-9H-fluoren-9-one oxime (Z,E) in suspension in a mixture of 3.5 ml of water, 7 ml of ethanol and 3.5 ml of acetic acid. Add 335 mg of powdered zinc and stir at room temperature for 19 hours. The insoluble residues are filtered over sintered glass and rinsed with ethanol. Evaporation of the solvent under reduced pressure is a colourless foam which is taken up in suspension in 100 ml of water. The pH of the supernatant is then brought to 9 by the addition of a 1N aqueous solution of sodium hydroxide, and the persisting precipitate is filtered off, and washed with 3 times 50 ml of water and twice 100 ml of isopropyl ether. After drying at 50° C. in an oven under vacuum, in this way we obtain 1.08 g of 5-(1H-benzimidazol-2-yl)-2-bromo-9H-fluorene-9(R,S)-amine, in the form of a white powder which is used as it is in the following stage.

Stage 3: The procedure used in Example 14 is followed, but starting from 500 mg of 5-(1H-benzimidazol-2-yl)-2-bromo-9H-fluorene-9(R,S)-amine, obtained in the previous stage, 237 mg of 1H-pyrrolo[2,3-b]pyridine-4-carboxylic acid, 280 mg of 1-(3-dimethylaminopropyl)-3-ethylcarbodiimide hydrochloride (EDCI) and 203 mg of hydroxybenzotriazole hydrate (HOBT) in 10 ml of dimethylformamide for 1 h 30. After purification by flash chromatography on a silica column, eluting with a gradient of mixture of dichloromethane and methanol (from 100/0 to 90/10 by volume), in this way we obtain 169 mg of [5-(1H-benzimidazol-2-yl)-2-bromo-9H -fluoren-9(R,S)-yl]amide of 1H-pyrrolo[2,3-b]pyridine-4-carboxylic acid, in the form of an off-white powder with the following characteristics:

Mass spectrum (ESI): m/z=520 (MH+).

NMR spectrum (400 MHz, δ in ppm, DMSO-d6): 6.40 (d, J=8.5 Hz, 1H); 6.91 (dd, J=1.5 and 3.5 Hz, 1H); 7.29 (m broad, 2H); 7.48 (d, J=5.0 Hz, 1H); 7.49 (m masked, 1H); 7.55 (t, J=7.5 Hz, 1H); 7.60 (m spread-out, 1H); 7.63 (t, J=3.5 Hz, 1H); 7.71 (d, J=7.5 Hz, 1H); from 7.72 to 7.80 (m, 4H); 8.30 (d, J=5.0 Hz, 1H); 9.34 (d, J=8.5 Hz, 1H); 11.9 (m broad, 1H); 12.95 (m broad, 1H).

Examples 263 and 264

Resolution of the enantiomers of 4-[5-fluoro-1H-benzimidazol-2-yl]-9H-fluoren-9(R,S)-yl}amide of 1H-pyrrolo[2,3-b]pyridine-4-carboxylic acid By following the procedure used in Example 153, starting from 2.65 g of 4-[5-fluoro-1H-benzimidazol-2-yl]-9H-fluoren-9(R,S)-yl}amide of 1H-pyrrolo-[2,3-b]pyridine-4-carboxylic acid, obtained as in Example 188, but using a chiral column of Chiralcel OJ20 µm type, 35 cm long and 5 cm in diameter, eluting with a supercritical mobile phase composed of carbon dioxide and methanol (70/30) at a flow rate of 250 ml/min and under a pressure of 120 bar, as 16 successive injections and detecting the eluted products by UV spectroscopy at 254 nm, we obtain, by recovering the first fractions eluted and concentrating under reduced pressure, 1.15 g of dextrorotatory enantiomer of 4-[5-fluoro-1H-benzimidazol-2-yl]-9H-fluoren-9(R,S)-yl}amide of 1H-pyrrolo[2,3-b]pyridine-4-carboxylic acid, in the form of an amorphous white solid with the following characteristics:

$\alpha D20$=+146.2+/−1.9° (c=0.51; methanol).

By recovering the second fractions eluted and concentrating under reduced pressure, we obtain 1.01 g of levorotatory enantiomer of 4-[5-fluoro-1H-benzimidazol-2-yl]-9H-fluoren-9(R,S)-yl}amide of 1H-pyrrolo[2,3-b]pyridine-4-carboxylic acid, in the form of an amorphous white solid with the following characteristics:

αD20=−159.3+/−2.1° (c=0.48; methanol).

Example 265

Synthesis of the methyl ester of 2-{9(R,S)-[(1H-pyrrolo[2,3-b]pyridine-4-carbonyl)amino]-9H-fluoren-4-yl}-1H-imidazo[4,5-c]pyridine-6-carboxylic acid Stage 1: The procedure used in Example 6 is followed, starting from 800 mg of the methyl ester of 2-{9-[(Z,E)-hydroxyimino]-9H-fluoren-4-yl}-1H-imidazo[4,5-c]pyridine-6-carboxylic acid, obtained in Example 260, and 135 mg of Raney nickel in 21 ml of ethanol and 21 ml of tetrahydrofuran for 8 hours at 60° C. under an initial hydrogen pressure of one bar. After filtration of the catalyst, concentration of the filtrate under reduced pressure and purification by formation of a paste in diisopropyl ether, in this way we obtain 700 mg of the methyl ester of 2-(9(R,S)-amino-9H-fluoren-4-yl)-1H-imidazo[4,5-c]pyridine-6-carboxylic acid, in the form of an orange powder, which is used as it is in the following stage, with the following characteristics:

Mass spectrum (LCMS): m/z=356 (M+).

Stage 2: The procedure used in Example 14 is followed, but starting from 700 mg of the methyl ester of 2-(9(R,S)-amino-9H-fluoren-4-yl)-1H-imidazo[4,5-c]pyridine-6-carboxylic acid obtained in the previous stage, 319 mg of 1H-pyrrolo-[2,3-b]pyridine-4-carboxylic acid, 414 mg of 1-(3-dimethylaminopropyl)-3-ethylcarbodiimide hydrochloride (EDCI) and 292 mg of 1-hydroxybenzotriazole (HOBT) in 14 ml of dimethylformamide, for 20 hours at room temperature. After purification by flash chromatography on silica gel (40-63 μm), eluting with a mixture of dichloromethane and methanol (95/5 by volume) and formation of a paste in diisopropyl ether, we obtain 650 mg of beige solid which contains a mixture of methyl ester and of ethyl ester of the expected product. After an additional chromatography on a Kromasil C8 20 μm column, 35 cm in length and 8 cm in diameter, eluting with a phase of a mixture of aqueous ammonium acetate buffer (pH=4.9) and acetonitrile (65/35) at a flow rate of 70 ml/min, and detecting the eluted product by UV spectroscopy at 254 nm, we obtain 87 mg of methyl ester of 2-{9(R,S)-[(1H-pyrrolo[2,3-b]pyridine-4-carbonyl)amino]-9H-fluoren-4-yl}-1H-imidazo[4,5-c]pyridine-6-carboxylic acid, in the form of a white solid with the following characteristics:

Mass spectrum (LC/MS/ES+/−): m/z=500 (M+).

$^1$H-NMR spectrum (400 MHz, δ in ppm, DMSO-d6): 3.88 (s, 3H); 6.39 (d, J=8.5 Hz, 1H); 6.91 (s, 1H); 7.23 (t, J=7.5 Hz, 1H); 7.31 (t, J=7.5 Hz, 1H); from 7.36 to 7.51 (m, 2H); 7.59 (d, J=7.5 Hz, 1H); 7.62 (s, 1H); 7.69 (d, J=7.5 Hz, 1H); 7.81 (d, J=7.5 Hz, 1H); 8.01 (m spread-out, 1H); 8.28 (s, 1H); 8.29 (d, J=5.0 Hz, 1H); 8.94 (s, 1H); 9.26 (d, J=8.5 Hz, 1H); 11.85 (m broad, 1H); 12.9 (m broad, 1H).

Example 266

Synthesis of [5-(1H-benzimidazol-2-yl)-2-cyano-9H-fluoren-9(R,S)-yl]amide of 1H-pyrrolo[2,3-b]pyridine-4-carboxylic acid Stage 1: A suspension of 250 mg of 5-(1H-benzimidazol-2-yl)-2-bromo-9H-fluoren-9-one, obtained in stage 3 of Example 254, and 179 mg of copper cyanide in 15 ml of N-methylpyrrolidinone is stirred in a sealed tube at 220° C. under microwaves for 50 minutes. The reaction mixture is poured over 250 ml of ice. After stirring for 15 minutes at room temperature, the green precipitate that formed is filtered off, washed with 3 times 50 ml of water and then dried at 50° C. in an oven under vacuum. The green powder thus obtained is taken up in 50 ml of dimethylformamide and the suspension is refluxed for 30 minutes. The insoluble residues are filtered under hot conditions and washed with 50 ml of boiling dimethylformamide. Evaporation of the filtrate gives 210 mg of an orange-coloured powder which is taken up in 50 ml of a mixture of dichloromethane and methanol (90/10 by volume). The suspension is refluxed for 30 minutes. The persisting precipitate is filtered off, and washed with twice 25 ml of dichloromethane and of isopropyl ether. In this way, we obtain 140 mg of 5-(1H-benzimidazol-2-yl)-9-oxo-9H-fluorene-2-carbonitrile, in the form of a yellow powder which is used without any other purification.

Stage 2: Stir 136 mg of 5-(1H-benzimidazol-2-yl)-9-oxo-9H-fluorene-2-carbonitrile, obtained in the previous stage, in suspension in 3 ml of N-methylpyrrolidinone and add 88 mg of hydroxylamine hydrochloride and 173 mg of sodium acetate. The mixture is heated at 60° C. for 1 hour 30 minutes. The light-yellow solution obtained is poured into 100 ml of ice-cold water. The yellow precipitate that formed is filtered off, washed with water and then dried at 50° C. in an oven under vacuum for 18 hours. In this way, we obtain 83 mg of a yellow powder, the LC/MS analysis of which shows the presence of approximately 30% of 5-(1H-benzimidazol-2-yl)-9 (Z,E)-oximino-9H-fluorene-2-carbonitrile, and which is used, without purification, in the following stage.

Stage 3: The mixture obtained in the previous stage is dissolved in a mixture of 2 ml of ethanol, 1 ml of water and 1 ml of acetic acid. Add 58 mg of powdered zinc and the reaction mixture is stirred at room temperature for 1 hour 30 minutes. The excess zinc is filtered over Celite and washed with ethanol. Evaporation of the filtrate under reduced pressure gives a white powder which is taken up in 50 ml of a saturated aqueous solution of sodium hydrogen carbonate and 50 ml of a mixture of dichloromethane and methanol (90/10 by volume). The insoluble material is filtered off, and the aqueous phase of the filtrate is extracted with 3 times 50 ml of a mixture of dichloromethane and methanol (90/10 by volume). The organic phases are combined, dried over magnesium sulphate and evaporated to dryness under reduced pressure. In this way, we obtain 33 mg of a white powder which is used as it is in the following stage.

Stage 4: The powder obtained in the previous stage is dissolved in 3 ml of dimethylformamide, then add successively 16 mg of 1H-pyrrolo[2,3-b]-pyridine-4-carboxylic acid, 13 mg of hydroxybenzotriazole hydrate (HOBT) and 19 mg of 1-(3-dimethylaminopropyl)-3-ethylcarbodiimide hydrochloride (EDCI). The reaction mixture is stirred for 17 hours at room temperature. Evaporation of the solvent under reduced pressure is a yellow oil which is purified by flash chromatography on silica gel, eluting with a gradient of mixtures of dichloromethane and methanol (from 100/0 to 90/10 by volume). In this way, we obtain 19 mg of [5-(1H-benzimidazol-2-yl)-2-cyano-9H-fluoren-9(R,S)-yl]amide of 1H-pyrrolo[2,3-b]pyridine-4-carboxylic acid, in the form of a light-beige powder with the following characteristic:

Mass spectrum (ESI+): m/z=467 (MH+).

Example 267

Synthesis of (3-diethylaminopropyl)amide of 2-{9 (R,S)-[(1H -pyrrolo[2,3-b]pyridine-4-carbonyl) amino]-9H-fluoren-4-yl}-1H -benzimidazole-5-carboxylic acid Stage 1: Dissolve 500 mg of 4-(5-carboxy-1H-benzimidazol-2-yl)-fluoren-9-one, obtained as in stage 1 of Example 241, in 10 ml of dimethylformamide. Add successively 191 mg of 3-diethylaminopropylamine, 225 mg of hydroxybenzotriazole hydrate (HOBT) and 281 mg of 1-(3-dimethylaminopropyl)-3-ethylcarbodiimide hydrochloride (EDCI). The solution obtained is stirred for 17 hours at room temperature. The yellow paste obtained after evaporation of the solvent under reduced pressure is taken up in a mixture of 50 ml of water and 50 ml of a saturated aqueous solution of sodium hydrogen carbonate and extracted with 4 times 100 ml of a solution composed of 90 ml of dichloromethane and 10 ml of 7N ammonical methanol. The combined organic phases are dried over magnesium sulphate. The yellow oil obtained after evaporation of the solvent under reduced pressure is purified by flash chromatography on silica gel, eluting with a gradient of dichloromethane a 7N solution of ammonia in methanol (from 100/0 to 90/10 by volume). We obtain 457 mg of (3-diethylaminopropyl)amide of 2-(9-oxo-9H-fluoren-4-yl)-1H-benzimidazole-5-carboxylic acid, in the form of a yellow powder which is used as it is in the following stage.

Stage 2: Dissolve 340 mg of (3-diethylaminopropyl)amide of 2-(9-oxo-9H-fluoren-4-yl)-1H-benzimidazole-5-carboxylic acid, obtained in the previous stage, in 20 ml of ethanol. 308 mg of sodium acetate and 156 mg of hydroxylamine hydrochloride are added to the yellow solution obtained. The suspension is stirred for 17 h at room temperature. The ethanol is evaporated off under reduced pressure and white powder obtained is taken up in 100 ml of water and then extracted with 3 times 100 ml of a solution composed of 90 ml of dichloromethane and 10 ml of 7N ammoniacal methanol. The combined organic phases are then dried over magnesium sulphate. After evaporation of the solvate under reduced pressure, we obtain 346 mg of (3-diethylaminopropyl)amide of 2-{9(Z,E)-[hydroxyimino]-9H-fluoren-4-yl}-1H-benzimidazole-5-carboxylic acid, as a 50/50 mixture of Z and E isomers, in the form of an off-white powder.

Stage 3: Dissolve 333 mg of (3-diethylaminopropyl)amide of 2-{9(Z,E)-[hydroxyimino]-9H-fluoren-4-yl}-1H-benzimidazole-5-carboxylic acid, obtained in the previous stage, in a mixture of 2 ml of water, 4 ml of ethanol and 1.9 ml of acetic acid. 186 mg of powdered zinc are added to the colourless solution obtained. The suspension is stirred for 2 hours at room temperature. The pinkish oil obtained after evaporation of the solvent under reduced pressure is solubilized in 90 ml of dichloromethane and 10 ml of 7N ammoniacal methanol. This solution is washed with 100 ml of a saturated aqueous solution of sodium hydrogen carbonate. The aqueous phase is separated and reextracted with twice 100 ml of a solution composed of 90 ml of dichloromethane and 10 ml of 7N ammoniacal methanol. The organic phases are combined and dried over magnesium sulphate. After evaporation of the solvent under reduced pressure, we obtain 330 mg of (3-diethylaminopropyl)-amide of 2-(9(R,S)-amino-9H-fluoren-4-yl)-1H-benzimidazole-5-carboxylic acid, in the form of a slightly bluish powder which is used as it is in the following stage.

Stage 4: Dissolve 330 mg of (3-diethylaminopropyl)amide of 2-(9(R,S)-amino-9H-fluoren-4-yl)-1H-benzimidazole-5-carboxylic acid, obtained in the previous stage, in 6 ml of dimethylformamide. Add 118 mg of 1H-pyrrolo[2,3-b]pyridine-4-carboxylic acid, 56 mg of hydroxybenzotriazole hydrate (HOBT) and 139 mg of 1-(3-dimethylaminopropyl)-3-ethylcarbodiimide hydrochloride (EDCI). The yellow solution obtained is stirred at room temperature for 1 hour 30 minutes. The yellow gum obtained after evaporation of the solvent under reduced pressure is taken up in a mixture of 100 ml of a saturated aqueous solution of sodium hydrogen carbonate, 90 ml of dichloromethane and 10 ml of 7N ammoniacal methanol. The precipitate that formed is filtered off and washed with water and then with dichloromethane and with methanol, to give, after drying for 16 hours at 50° C. in an oven under vacuum, 112 mg of (3-diethylaminopropyl)amide of 2-{9(R,S)-[(1H-pyrrolo[2,3-b]pyridine-4-carbonyl)amino]-9H-fluoren-4-yl}-1H-benzimidazole-5-carboxylic acid, in the form of a white powder with the following characteristics:

Mass spectrum (ESI+): m/z=598 (MH+).
$^1$H-NMR spectrum (400 MHz, δ in ppm DMSO-d6): 3.93 (s, 3H); 6.40 (d, J=8.5 Hz, 1H); 6.91 (dd, J=1.5 and 3.5 Hz, 1H); 7.23 (m masked, 1H); 7.25 (t, J=7.5 Hz, 1H); 7.34 (t, J=7.5 Hz, 1H); 7.46 (d, J=5.0 Hz, 1H); 7.50 (t, J=7.5 Hz, 1H); 7.57 (m spread-out, 1H); 7.62 (m, 4H); 7.74 (d, J=7.5 Hz, 1H); 8.30 (d, J=5.0 Hz, 1H); 9.27 (d, J=8.5 Hz, 1H); 11.85 (m broad, 1H); 12.9 (m broad, 1H).

Example 268

Synthesis of [4-(6-fluoro-5-methoxy-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 1 is followed, starting from 1 g of 4-fluoro-5-methoxy-2-nitrophenylamine, which can be prepared according to Chem Pharm Bull 37(6), 1517-1523, 1989, in 20 ml of dichloromethane and 10 ml of tetrahydrofuran, 1.5 ml of triethylamine and 1.3 g of fluoren-4-one-9-carboxylic acid chloride, for 20 hours at room temperature and then 5 hours at reflux and, finally, 72 hours at room temperature. After purification by formation of a paste with diisopropyl ether, in this way we obtain 700 mg of (4-fluoro-5-methoxy-2-nitrophenyl)amide of 9-oxo-9H-fluorene-4-carboxylic acid, in the form of a yellow powder which is used as it is in the following stage, with the following characteristics:
Mass spectrum (LC/MS): m/z=392 (M+).

Stage 2: In a 100 ml round-bottomed flask under an argon atmosphere, heat, at 90° C. for 4 hours, a solution of 700 mg of (4-fluoro-5-methoxy-2-nitrophenyl)amide of 9-oxo-9H-fluorene-4-carboxylic acid, obtained in the previous stage, and 300 mg of iron, in a mixture of 45 ml of ethanol, 5 ml of water and 70 µl of a 37% aqueous solution of hydrochloric acid. After cooling, adjust to pH=9 by adding a saturated aqueous solution of sodium carbonate, filter the insoluble material, which is washed with a saturated aqueous solution of sodium hydrogen carbonate and then with water, and bring to dryness under reduced pressure. The aqueous phases are extracted twice with ethyl acetate. The organic phases are washed with water, dried over magnesium sulphate and brought to dryness under reduced pressure. After purification by formation of a paste with diisopropyl ether, we obtain 200 mg of (2-amino-4-fluoro-5-methoxyphenyl)amide of 9-oxo-9H-fluorene-4-carboxylic acid, in the form of a yellow powder, which is used as it is in the following stage, with the following characteristics:
Mass spectrum (EI): m/z=362 (M+).

Stage 3: The procedure used in Example 68 is followed. In a 25 ml round-bottomed flask under an argon atmosphere, heat, at 140° C. for 1 hour, a solution of 200 mg of (2-amino-4-fluoro-5-methoxyphenyl)amide of 9-oxo-9H-fluorene-4-carboxylic acid, obtained in the previous stage, in 9 ml of acetic acid. After cooling, bring to dryness under reduced pressure. After purification by formation of a paste with diisopropyl ether, we obtain 170 mg of 4-(5-fluoro-6-methoxy-1H-benzimidazol-2-yl)-9H-fluoren-9-one, in the form of a pale yellow powder, which is used as it is in the following stage, with the following characteristics:
Mass spectrum (EI): m/z=344 (M+).

Stage 4: The procedure used in Example 5 is followed, starting from 170 mg of 4-(5-fluoro-6-methoxy-1H-benzimidazol-2-yl)-9H-fluoren-9-one, obtained in the previous stage, 103 mg of hydroxylamine hydrochloride and 203 mg of sodium acetate in 3 ml of ethanol, stir for 20 hours at room temperature. After concentration of the solvent under reduced pressure, the residue is taken up successively with water, then with toluene, and brought to dryness. In this way, we obtain 141 mg of 4-(5-fluoro-6-methoxy-1H-benzimidazol-2-yl)-9H-fluoren-9-one oxime (Z,E), as a 50-50 mixture of Z and E isomers, in the form of a beige powder, which is used as it is in the following stage, with the following characteristics:

Mass spectrum (EI/CI): m/z=359 (M+).

Stage 5: The procedure used in stage 4 of Example 216 is followed. In a 30 ml round-bottomed flask under an argon atmosphere, dissolve 140 mg of equimolecular mixture of 4-(5-fluoro-6-methoxy-1H-benzimidazol-2-yl)-9H-fluoren-9-one oxime (Z,E), obtained in the previous stage, in a mixture of 0.7 ml of ethanol, 0.7 ml of water and 0.7 ml of acetic acid. At room temperature, add 100 mg of zinc, in three stages, and, between each addition, stir for approximately one hour to two hours. After purification by flash chromatography on silica gel (40-63 µm), eluting with a mixture of dichloromethane and ammonia as a 7N solution in methanol (95/5 by volume), in this way we obtain 127 mg of 4-(5-fluoro-6-methoxy-1H-benzimidazol-2-yl)-9H-fluorene-9(R,S)-amine, in the form of a beige resin which is used as it is in the following stage, with the following characteristics:

Mass spectrum (LC/MS): m/z=345 (M+).

Stage 6: The procedure used in Example 14 is followed. In a 10 ml round-bottomed flask, dissolve 127 mg of 4-(5-fluoro-6-methoxy-1H-benzimidazol-2-yl)-9H-fluorene-9(R,S)-amine, obtained in the previous stage, 60 mg of 1H-pyrrolo[2,3-b]pyridine-4-carboxylic acid, 70 mg of 1-(3-dimethylamino-propyl)-3-ethylcarbodiimide hydrochloride (EDCI) and 25 mg of 1-hydroxybenzotriazole (HOBT), in 2 ml of dimethylformamide for 20 hours at room temperature. After purification by flash chromatography on silica gel (40-63 µm), eluting with a mixture of dichloromethane and methanol (98/2 then 95/5 by volume), and then formation of a paste with diisopropyl ether, in this way we obtain 95.5 mg of [4-(5-fluoro-6-methoxy-1H-benzimidazol-2-yl)-9H-fluoren-9(R,S)-yl]amide of 1H-pyrrolo[2,3-b]pyridine-4-carboxylic acid, in the form of a beige powder with the following characteristics:

Melting point (Kofler)=200-210° C. (sticky).
Mass spectrum (LC/MS): m/z=489 (M+).

Example 269

Synthesis of [4-(6-fluoro-5-hydroxy-1H-benzimidazol-2-yl)-9H-fluoren-9(R,S)-yl]amide of 1H-pyrrolo[2,3-b]pyridine-4-carboxylic acid Stage 1: The procedure used in stage 1 of Example 230 is followed. In a 50 ml round-bottomed flask under argon, dissolve 1.07 g of 4-(5-fluoro-6-methoxy-1H-benzimidazol-2-yl)-9H-fluoren-9-one, obtained in stage 3 of Example 268, in 20 ml of dichloromethane, cooled to 0° C. and add 7.8 ml of a molar solution of boron tribromide in dichloromethane. After stirring for 20 hours, the reaction mixture is poured into water, and the insoluble material is drained, washed with water and then dried. After purification by formation of a paste with diisopropyl ether, in this way we obtain 914 mg of 4-(5-fluoro-6-hydroxy-1H-benzimidazol-2-yl)-9H-fluoren-9-one, in the form of a brown powder, which is used as it is in the following stage, with the following characteristics:

Mass spectrum (LC/MS/ES/+/−): m/z=330 (M+).

Stage 2: The procedure used in Example 5 is followed, but starting from 914 mg of 4-(5-fluoro-6-hydroxy-1H-benzimidazol-2-yl)-9H-fluoren-9-one, obtained in the previous stage, 580 mg of hydroxylamine hydrochloride and 1.1 g of sodium acetate in 17 ml of ethanol, stirred for 20 h at room temperature. After concentration of the solvent under reduced pressure, the residue is taken up successively with water, then with toluene, and brought to dryness. After purification by flash chromatography on silica gel (40-63 µm), eluting with a mixture of dichloromethane and methanol (95/5 then 9/1 by volume), and then formation of a paste with diisopropyl ether, in this way we obtain 667 mg of 4-(5-fluoro-6-hydroxy-1H-benzimidazol-2-yl)-9H-fluoren-9-one oxime (Z,E), as a 50-50 mixture of Z and E isomers, in the form of a beige powder, which is used as it is in the following stage, with the following characteristics:

Mass spectrum (EI/CI): m/z=345 (M+).

Stage 3: The procedure used in stage 4 of Example 216 is followed. In a 30 ml round-bottomed flask under an argon atmosphere, dissolve 667 mg of equimolecular mixture of 4-(5-fluoro-6-hydroxy-1H-benzimidazol-2-yl)-9H-fluoren-9-one oxime (Z,E), obtained in the previous stage, in a mixture of 3.5 ml of ethanol and 3.5 ml of water and 3.5 ml of acetic acid; at room temperature, add 500 mg of zinc in three stages. Between each addition, stir for approximately one hour to two hours. After purification by flash chromatography on silica gel (40-63 µm), eluting with a mixture of dichloromethane and ammonia as a 7N solution in methanol (9/1 then 85/15 by volume), in this way we obtain 456 mg of 4-(5-fluoro-6-hydroxy-1H-benzimidazol-2-yl)-9H-fluorene-9(R,S)-amine, in the form of a beige powder, which is used as it is in the following stage, with the following characteristics:

Mass spectrum (LC/MS): m/z=331 (M+).

Stage 4: The procedure used in Example 14 is followed, but starting from 450 mg of 4-(5-fluoro-6-hydroxy-1H-benzimidazol-2-yl)-9H-fluorene-9(R,S)-amine, obtained in the previous stage, 220 mg of 1H-pyrrolo[2,3-b]pyridine-4-carboxylic acid, 260 mg of 1-(3-dimethylaminopropyl)-3-ethylcarbodiimide hydrochloride (EDCI) and 92 mg of 1-hydroxybenzotriazole (HOBT) in 7 ml of dimethylformamide, for 20 hours at room temperature. After purification by flash chromatography on silica gel (40-63 µm), eluting with a mixture of dichloromethane and 7N ammonia in methanol (95/5 then 9/1 by volume), and then formation of a paste with diisopropyl ether, in this way we obtain 492 mg of [4-(5-fluoro-6-hydroxy-1H-benzimidazol-2-yl)-9H-fluoren-9(R,S)-yl]amide of 1H-pyrrolo[2,3-b]pyridine-4-carboxylic acid, in the form of a white powder with the following characteristics:

Melting point (Kofler)=>260° C.
Mass spectrum (LC/MS): m/z=475 (M+).

Example 270

Synthesis of {4-[5-fluoro-6-(3-methoxypropoxy)-1H-benzimidazol-2-yl]-9H-fluoren-9(R,S)-yl}amide of 1H-pyrrolo[2,3-b]pyridine-4-carboxylic acid Stage 1: In a 250 ml three-necked flask under an argon atmosphere, 1 g of 3-methoxy-1-propanol in 20 ml of tetrahydrofuran are cooled to 0° C. using an ice bath and then 450 mg of sodium hydride at 50% in liquid petroleum jelly are introduced in fractions. After stirring for 15 minutes at 0° C., add, over 5 minutes, a solution of 1.5 g of 4,5-difluoro-2-nitroaniline in 20 ml of tetrahydrofuran and then heat in the region of 70° C. for 1 hour 30 minutes. The reaction mixture is poured into 200 ml of water, and extracted with three times 50 ml of ethyl acetate. The combined organic phases are dried over magnesium sulphate and brought to dryness under reduced pressure. After purification by flash chromatography on silica gel (15-20 µm), eluting with a mixture of cyclohexane and ethyl acetate (80/20 by volume), in this way we obtain 1 g of 4-fluoro-5-(3-methoxypropoxy)-2-nitrophenylamine, in the form of a red solid, which is used as it is in the following stage, with the following characteristic:

Mass spectrum (LCMS): m/z=244 (M+).

Stage 2: In a 25 ml autoclave, dissolve 330 mg of 4-fluoro-5-(3-methoxypropoxy)-2-nitrophenylamine, obtained in the previous stage, in 20 ml of ethanol, add 40 mg of 10% palladium-on-charcoal and then subject to an initial hydrogen pressure of 1 bar at 20° C. for 16 hours. After cooling, the volume of hydrogen absorbed is 91 ml. After filtration of the catalyst and then concentration to dryness under reduced pressure, we obtain 290 mg of 4-fluoro-5-(3-methoxypropoxy)benzene-1,2-diamine, in the form of a viscous black oil, which is used as it is in the following stage, with the following characteristic:

Mass spectrum (EI): m/z=214 (M+).

Stage 3: Stir, at room temperature under argon, a mixture of 100 mg of (4-formyl-9H-fluoren-9(R,S)-yl)amide of 1H-pyrrolo[2,3-b]pyridine-4-carboxylic acid, prepared as in Example 234, 60 mg of 4-fluoro-5-(3-methoxypropoxy)-benzene-1,2-diamine, prepared in the previous stage, and 46 mg of ferric trichloride in 5 ml of anhydrous DMF. After 48 hours, evaporate the reaction medium to dryness and purify the residue by flash chromatography on silica gel (20-40 µm), eluting with a mixture of methanol and dichloromethane (10/90 by volume). In this way, we obtain 58 mg of {4-[5-fluoro-6-(3-methoxypropoxy)-1H-benzimidazol-2-yl]-9H-fluoren-9(R,S)-yl}amide of 1H-pyrrolo[2,3-b]pyridine-4-carboxylic acid, in the form of an orange solid with the following characteristics:

Melting point (Kofler): >260° C.
Mass spectrum (EI): m/z=547 (M+).

Example 271

{4-[6-(3-dimethylaminopropoxy)-5-fluoro-1H-benzimidazol-2-yl]-9H-fluoren-9(R,S)-yl}amide of 1H-pyrrolo[2,3-b]pyridine-4-carboxylic acid Stage 1: In a 250 ml three-necked flask under an argon atmosphere, 5.3 g of 3-dimethylamino-1-propanol, in solution in 100 ml of tetrahydrofuran, are cooled to 0° C. using an ice bath and then introduce 2.3 g of sodium hydride at 50% in liquid petroleum jelly. After stirring for 1 hour at 0° C., rapidly add a solution of 3 g of 4,5-difluoro-2-nitroaniline in 100 ml of tetrahydrofuran and then heat in the region of 70° C. for 1 hour. The reaction mixture is poured into 100 ml of water and extracted with three times 100 ml of ethyl acetate. The organic phase is dried over magnesium sulphate and brought to dryness under reduced pressure. The solid obtained is washed with pentane, filtered, and dried under a hood. In this way, we obtain 3.5 g of 5-(3-dimethylaminopropoxy)-4-fluoro-2-nitrophenylamine, in the form of a yellow solid with the following characteristics:

Melting point (Kofler): 128° C.
Mass spectrum (LCMS): m/z=257 (M+).

Stage 2: In a 25 ml autoclave, dissolve 350 mg of 5-(3-dimethylaminopropoxy)-4-fluoro-2-nitrophenylamine, obtained in the previous stage, in 20 ml of ethanol, add 40 mg of 10% palladium-on-charcoal and then subject to an initial hydrogen pressure of 1 bar at 20° C. for 16 hours. After cooling, the volume of hydrogen absorbed is 123 ml. After filtration of the catalyst and then concentration to dryness under reduced pressure, we obtain 280 mg of 4-(3-dimethylaminopropoxy)-5-fluorobenzene-1,2-diamine, in the form of a viscous black oil, which is used as it is in the following stage, with the following characteristic:

Mass spectrum (EI): m/z=227 (M+).

Stage 3: Stir, at room temperature under argon, a mixture of 100 mg of (4-formyl-9H-fluoren-9(R,S)-yl)amide of 1H-pyrrolo[2,3-b]pyridine-4-carboxylic acid, prepared as in Example 234, 65 mg of 4-(3-dimethylaminopropoxy)-5-fluorobenzene-1,2-diamine, prepared in the previous stage, and 46 mg of ferric trichloride in 5 ml of anhydrous dimethylformamide. After 48 hours, evaporate the reaction medium to dryness and then purify the residue by flash chromatography on silica gel (20-40 µm), eluting with a mixture of dichloromethane and ammonia as a 7N solution in methanol (95/5 then 9/1 by volume). In this way, we obtain 42 mg of {4-[6-(3-dimethylaminopropoxy)-5-fluoro-1H-benzimidazol-2-yl]-9H-fluoren-9(R,S)-yl}amide 1H-pyrrolo[2,3-b]-pyridine-4-carboxylic acid, in the form of a yellow solid with the following characteristics:

Melting point (Kofler): 226° C.
Mass spectrum (EI): m/z=560 (M+).

Example 272

Pharmaceutical Composition

Tablets were prepared according to the following formulation:

| | |
|---|---|
| Product of Example 87 | 0.2 g |
| Excipients for a finished tablet of | 1 g |
| (excipients in detail: lactose, talc, starch, magnesium stearate). | |

Example 273

Pharmaceutical Composition

Tablets were prepared according to the following formulation:

| | |
|---|---|
| Product of Example 92 | 0.2 g |
| Excipients for a finished tablet of | 1 g |
| (excipients in detail: lactose, talc, starch, magnesium stearate). | |

Biological tests for biological characterization of the products of the invention:

The inorganic phosphate released during hydrolysis of ATP by the ATPase activity of Hsp82 is quantified by the Malachite Green method. In the presence of this reagent, there is formation of the inorganic phosphate-molybdate-malachite green complex, which absorbs at a wavelength of 620 nm.

The products to be evaluated are incubated in a reaction volume of 30 µl, in the presence of 1 µM Hsp82 and 250 µM of substrate (ATP) in a buffer composed of 50 mM Hepes-NaOH (pH 7.5), 1 mM DTT, 5 mM MgCl$_2$ and 50 mM KCl at 37° C. for 60 min. In parallel, a range of inorganic phosphate from 1 to 40 µM is made up in the same buffer. The ATPase activity is then detected by adding 60 µl of Biomol Green reagent (Tebu). After incubation for 20 min at room temperature, the absorbance of the various wells is measured using a microplate reader at 620 nm. The concentration of inorganic phosphate in each specimen is then calculated from the calibration curve. The ATPase activity of Hsp82 is expressed as concentration of inorganic phosphate produced in 60 min. The effect of the various products tested is expressed as percentage inhibition of ATPase activity.

In the above test, the compound A000187458 has a 50% inhibitory concentration ($IC_{50}$) equal to 2.5 µM The formation of ADP due to the ATPase activity of Hsp82 was utilized for developing another method of evaluating the enzymatic activity of this enzyme by application of an enzyme coupling system employing pyruvate kinase (PK) and lactate dehydrogenase (LDH). In this spectrophotometric method of the kinetic type, the PK catalyses the formation of ATP and of pyruvate starting from phosphoenol-pyruvate (PEP) and the ADP produced by HSP82. The pyruvate that formed, an LDH substrate, is then converted to lactate in the presence of NADH. In this case, the decrease in the concentration of NADH, measured by the decrease in absorbance at wavelength of 340 nm, is proportional to the concentration of ADP produced by HSP82.

The products tested are incubated in a reaction volume of 100 µl of buffer composed of 100 mM Hepes-NaOH (pH 7.5), 5 mM $MgCl_2$, 1 mM DTT, 150 mM KCl, 0.3 mM NADH, 2.5 mM PEP and 250 µM ATP. This mixture is preincubated at 37° C. for 30 min before adding 3.77 units of LDH and 3.77 units of PK. The reaction is started by adding the product to be evaluated, in variable concentrations, and of Hsp82, at a concentration of 1 µM. The enzymatic activity of Hsp82 is then measured continuously in a microplate reader at 37° C., at wavelength of 340 nm. The initial reaction rate is found by measuring the slope of the tangent at the origin of the recorded curve. The enzymatic activity is expressed as µM of ADP formed per minute. The effect of the various products tested is expressed as percentage of inhibition of ATPase activity, using the following codes:

A: $IC_{50} < 1$ µM
B: $1$ µM $< IC_{50} < 10$ µM
C: $10$ µM $< IC_{50} < 100$ µM

Table of results

| Ex | Structure | Hsp82 ATPase $IC_{50}$ µM |
|---|---|---|
| 1 | 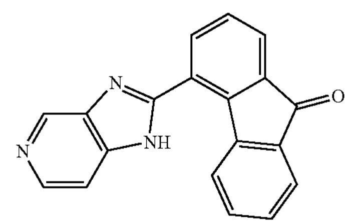 | B |
| 2 | 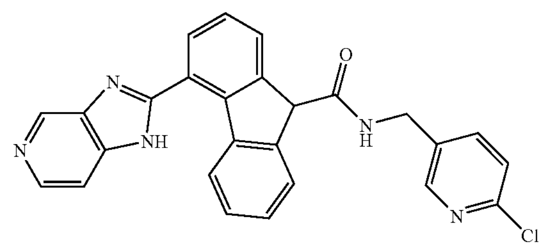 | C |
| 3 | 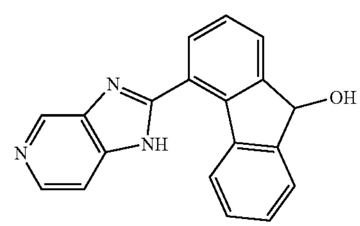 | C |
| 4 | 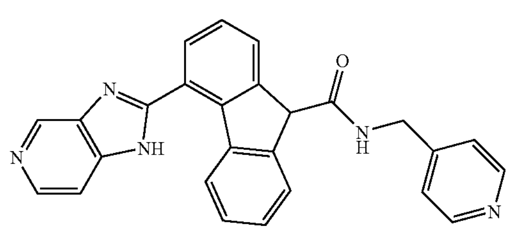 | C |

-continued

Table of results

| Ex | Structure | Hsp82 ATPase IC$_{50}$ µM |
|---|---|---|
| 5 | 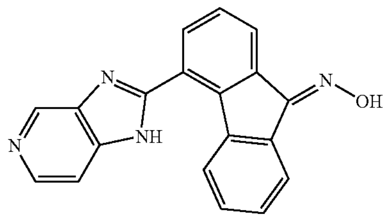 | B |
| 6 | 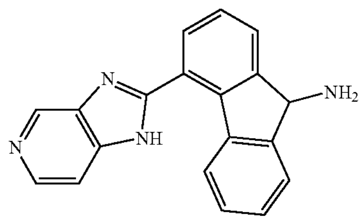 | C |
| 7 | 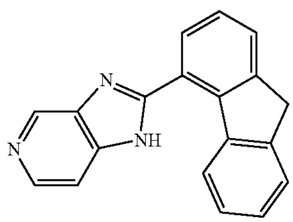 | C |
| 8 | 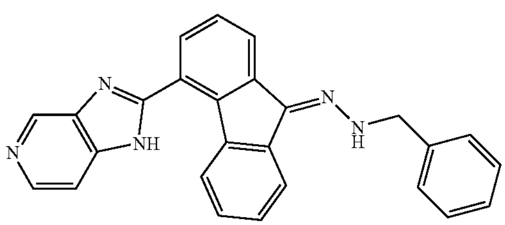 | B |
| 9 | 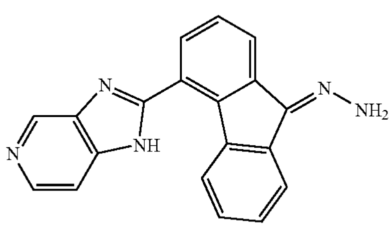 | B |
| 10 | 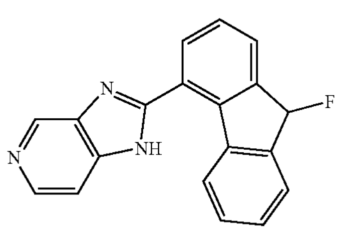 | B |

-continued

Table of results

| Ex | Structure | Hsp82 ATPase IC$_{50}$ μM |
|---|---|---|
| 11 | (structure) 2 HCl | B |
| 12 | (structure) | C |
| 13 | (structure) | C |
| 14 | (structure) | A |
| 14A | (structure) dextrorotatory enantiomer | A |
| 14B | (structure) levorotatory enantiomer | C |

-continued
Table of results
| Ex | Structure | Hsp82 ATPase IC$_{50}$ µM |
|---|---|---|
| 15 | 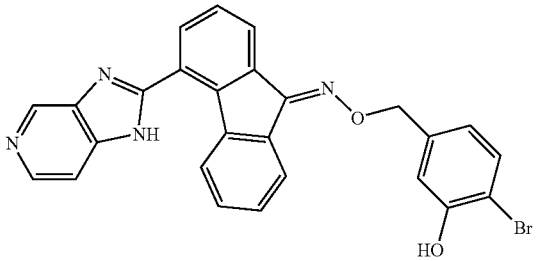 | B |
| 16 | 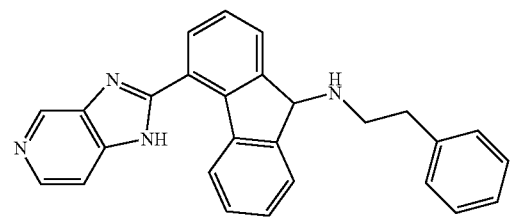 | C |
| 17 | 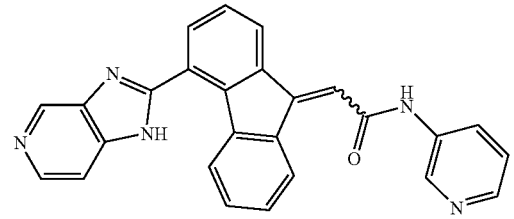 | B |
| 18 | 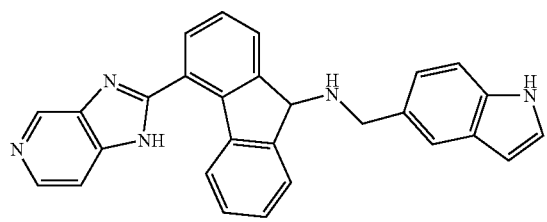 | C |
| 19 | 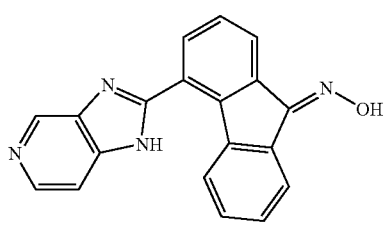 | B |
| 20 | 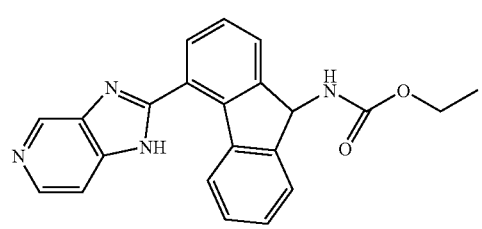 | B |

-continued

Table of results

| Ex | Structure | Hsp82 ATPase IC$_{50}$ μM |
|---|---|---|
| 21 | 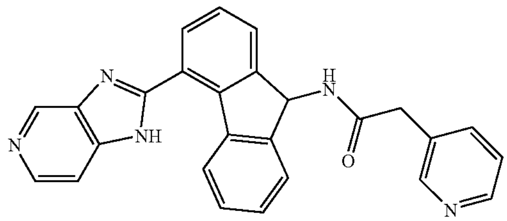 | B |
| 22 | 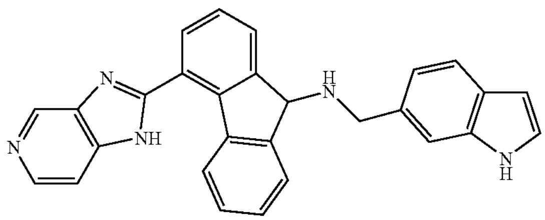 | C |
| 23 | 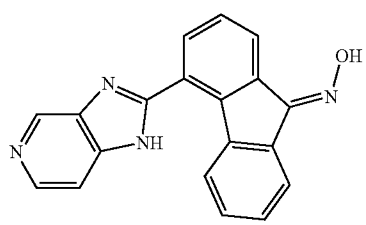 | A |
| 24 | 1 TFA | B |
| 25 | 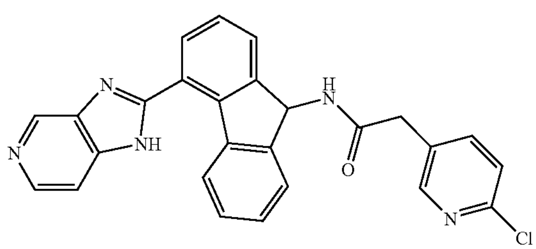 | B |
| 26 | TFA | B |

-continued

Table of results

| Ex | Structure | Hsp82 ATPase IC$_{50}$ μM |
|---|---|---|
| 27 | 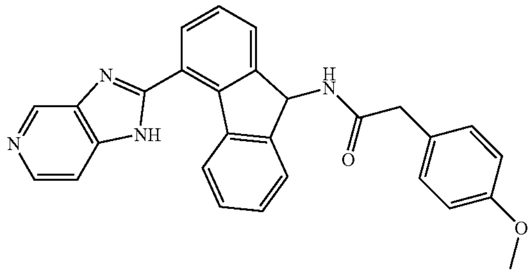 | B |
| 28 | (TFA salt) | C |
| 29 | (HCl salt) | C |
| 30 | (TFA salt) | C |
| 31 | 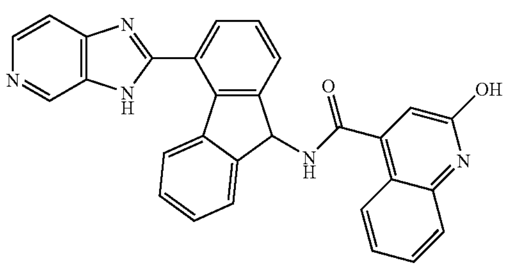 | B |
| 32 | 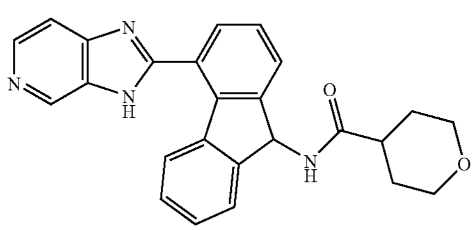 | C |

-continued
Table of results
| Ex | Structure | Hsp82 ATPase IC$_{50}$ μM |
|---|---|---|
| 33 | 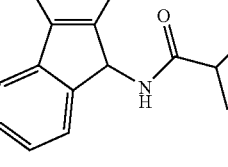 | B |
| 34 | 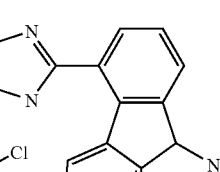 | B |
| 35 | 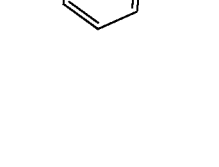 | C |
| 36 | 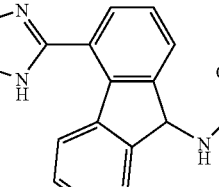 | B |
| 37 | 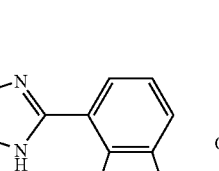 | B |

-continued

Table of results

| Ex | Structure | Hsp82 ATPase IC$_{50}$ μM |
|---|---|---|
| 38 | 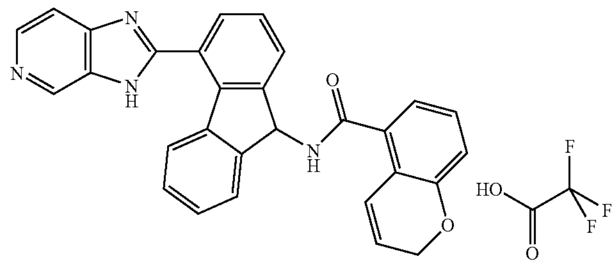 | B |
| 39 | 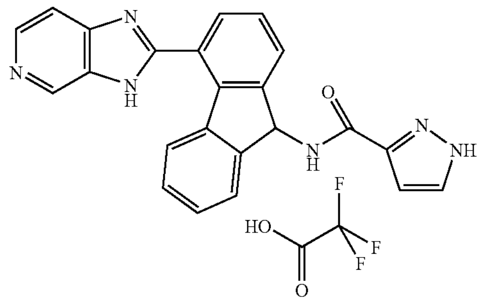 | B |
| 40 | 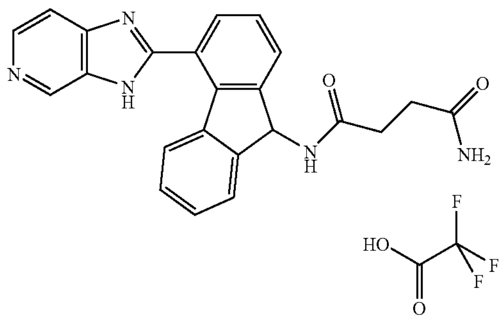 | B |
| 41 | 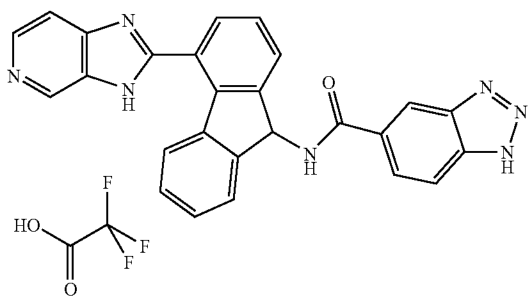 | A |
| 42 | 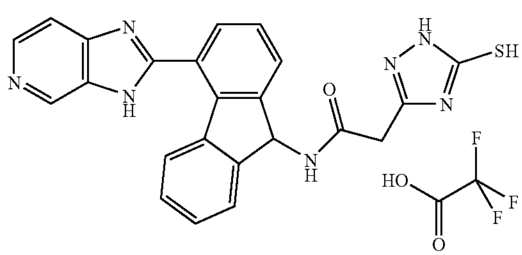 | B |

-continued

Table of results

| Ex | Structure | Hsp82 ATPase IC$_{50}$ μM |
|---|---|---|
| 43 | 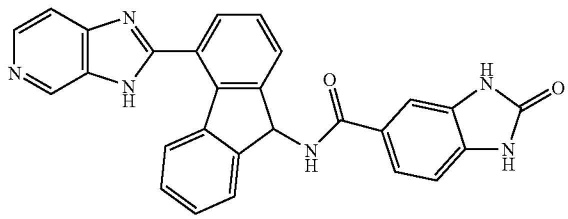 | C |
| 44 | 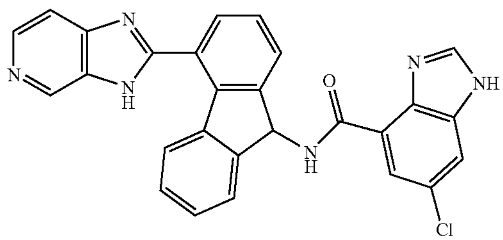 | B |
| 45 | 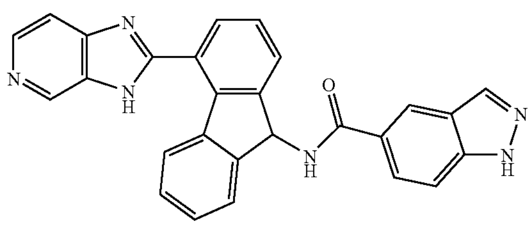 | B |
| 46 | 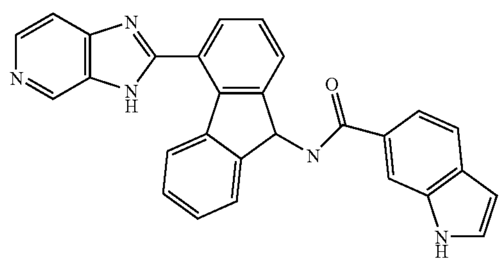 | B |
| 47 | 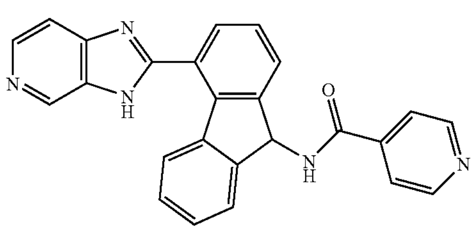 | A |
| 48 | 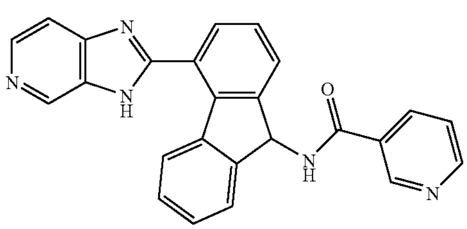 | B |

-continued

Table of results

| Ex | Structure | Hsp82 ATPase IC$_{50}$ μM |
|---|---|---|
| 49 | 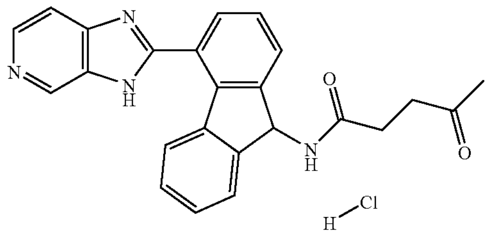 | C |
| 50 | 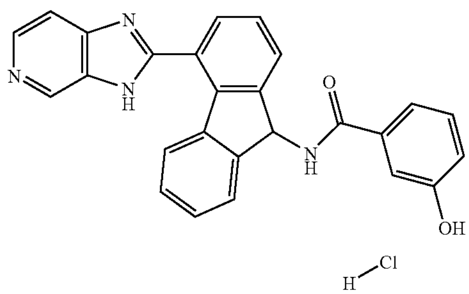 | B |
| 51 | 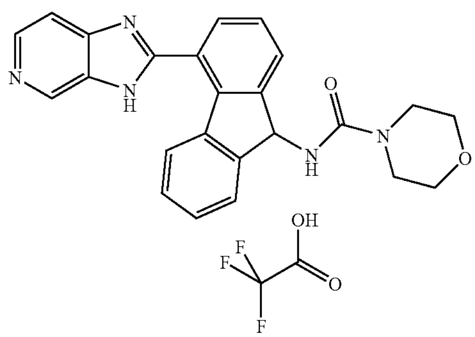 | B |
| 52 | 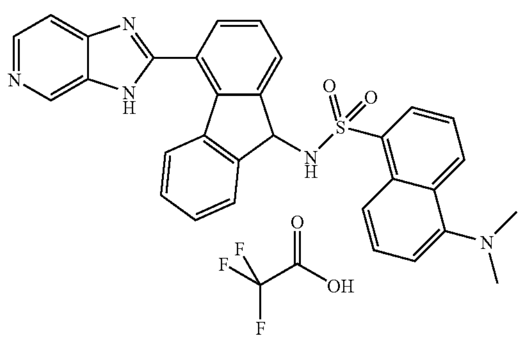 | C |
| 53 | 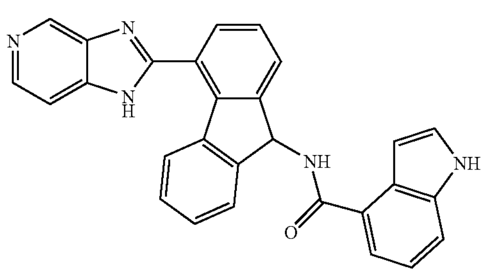 | B |

-continued

Table of results

| Ex | Structure | Hsp82 ATPase IC$_{50}$ μM |
|---|---|---|
| 54 | 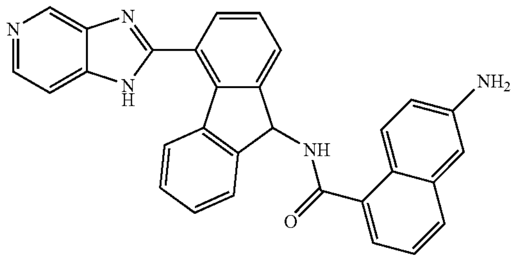 | B |
| 55 | 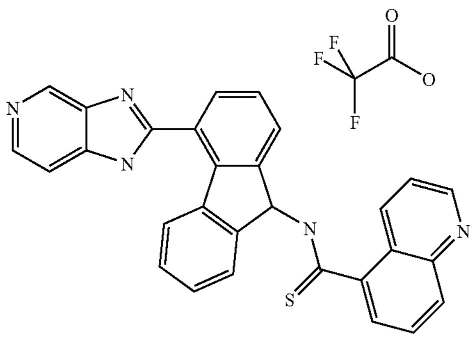 | A |
| 56 | 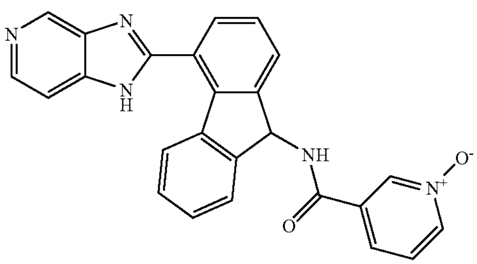 | B |
| 57 | 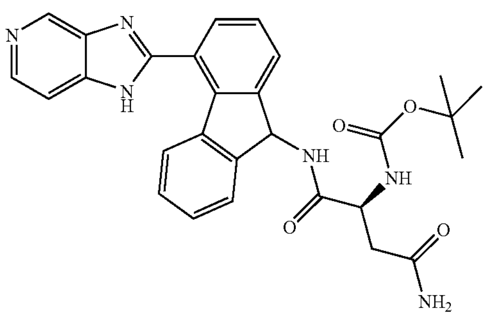 | B |
| 58 | 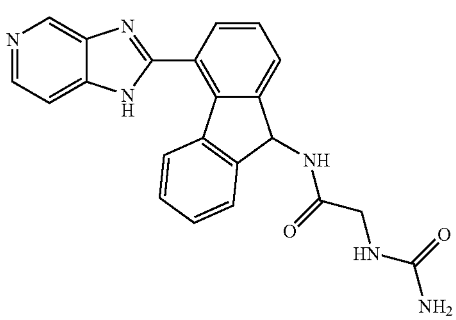 | B |

-continued

Table of results

| Ex | Structure | Hsp82 ATPase IC$_{50}$ μM |
|---|---|---|
| 59 | 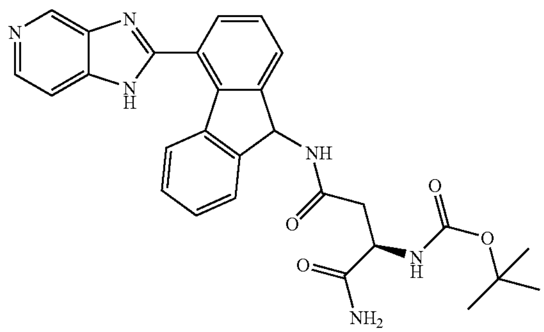 | B |
| 60 | 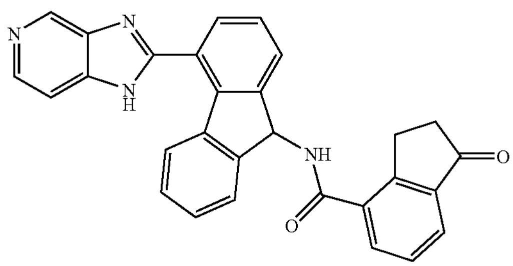 | B |
| 61 | 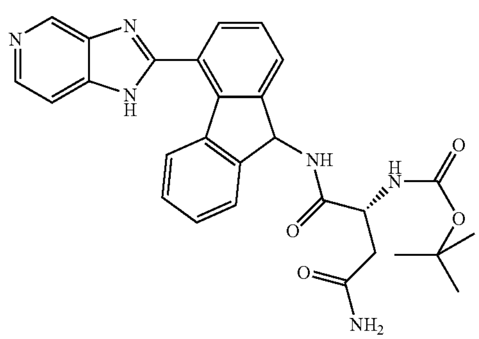 | B |
| 62 | 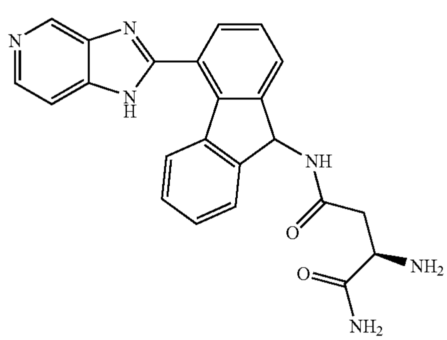 | B |

-continued
Table of results
| Ex | Structure | Hsp82 ATPase IC$_{50}$ μM |
|---|---|---|
| 63 | 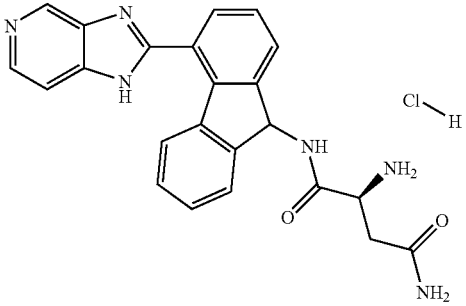 | B |
| 64 | 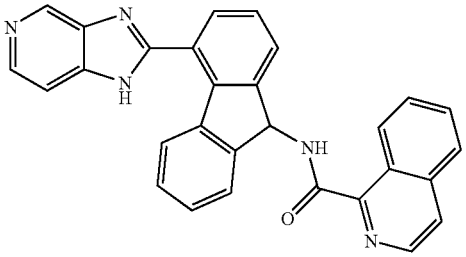 | C |
| 65 | 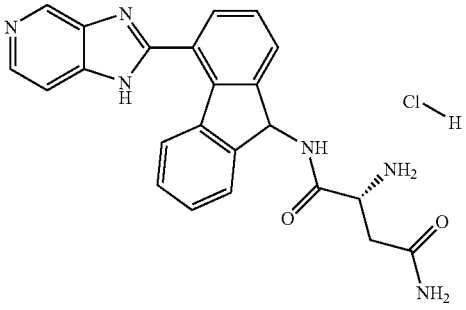 | B |
| 66 | 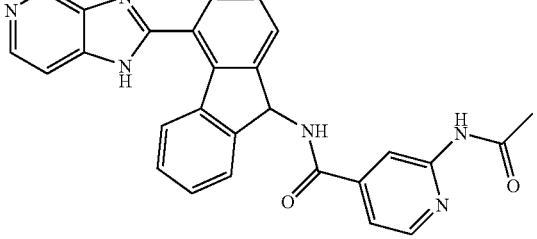 | A |
| 67 | 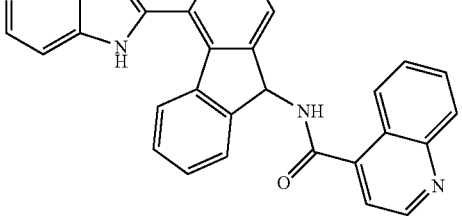 | A |

-continued

Table of results

| Ex | Structure | Hsp82 ATPase IC$_{50}$ μM |
|---|---|---|
| 68 | 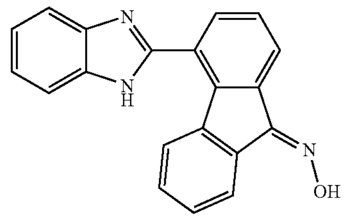 | C |
| 69 | 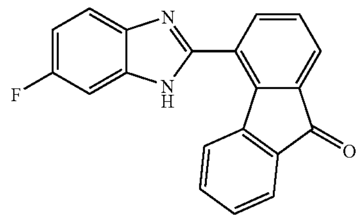 | C |
| 70 | 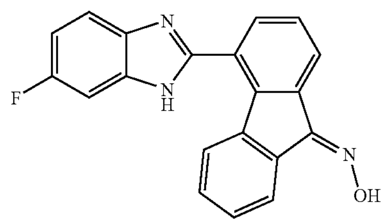 | B |
| 71 | 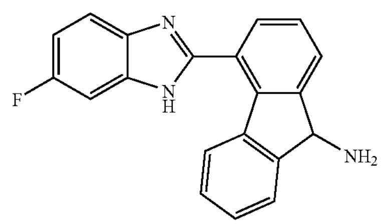 | C |
| 72 | 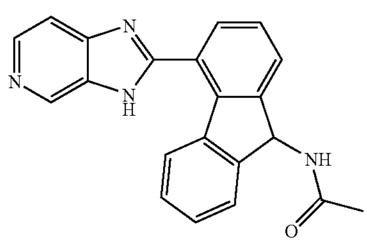 | B |
| 73 | 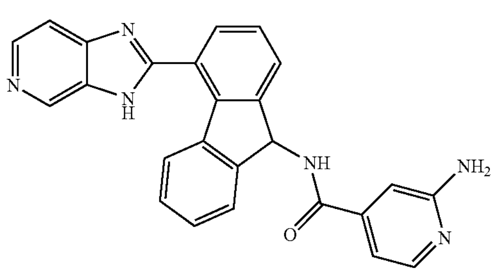 | A |

-continued

Table of results

| Ex | Structure | Hsp82 ATPase IC$_{50}$ μM |
|---|---|---|
| 74 | 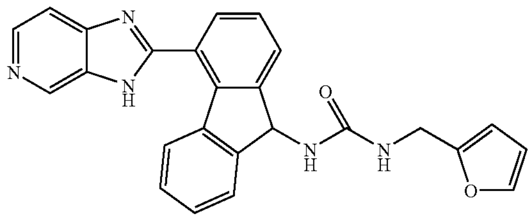 | C |
| 75 | 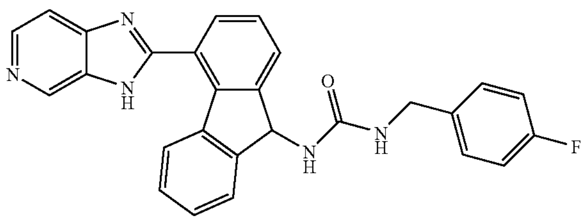 | C |
| 76 | 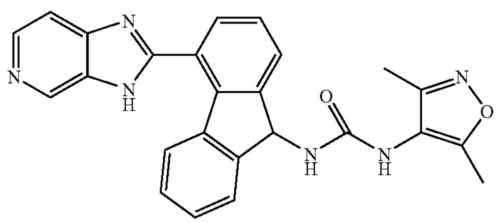 | C |
| 77 | 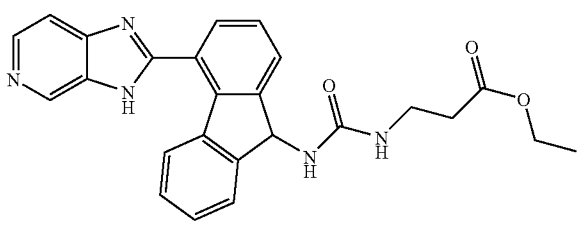 | B |
| 78 | 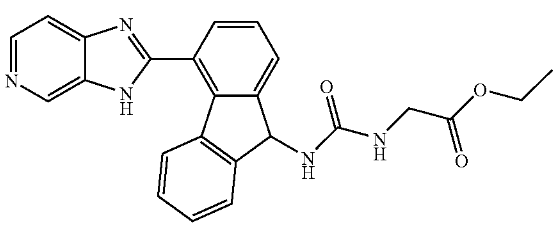 | C |
| 79 | 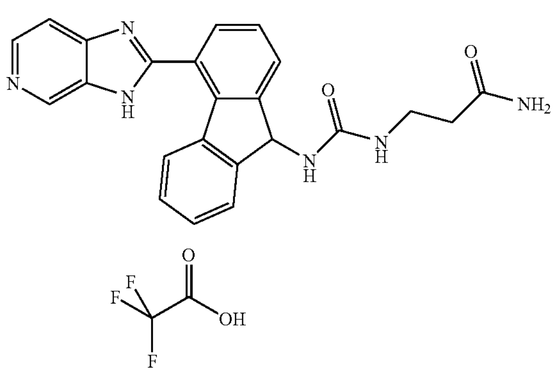 | C |

-continued

Table of results

| Ex | Structure | Hsp82 ATPase IC$_{50}$ μM |
|---|---|---|
| 80 | 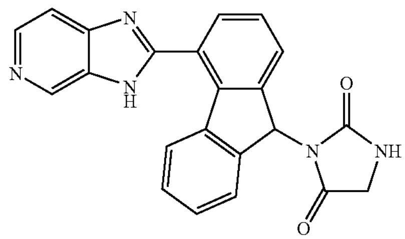 | C |
| 81 | 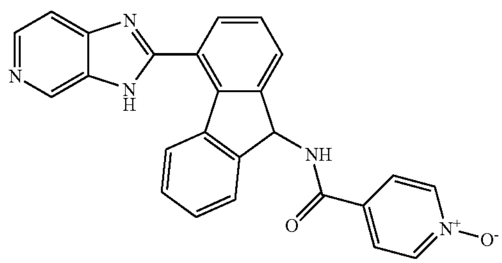 | B |
| 82 | 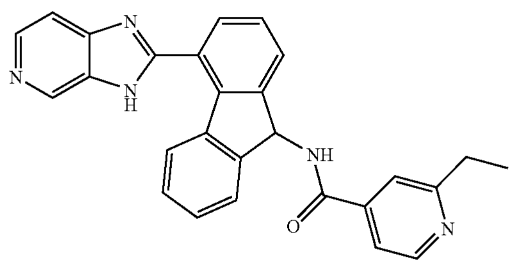 | A |
| 83 | 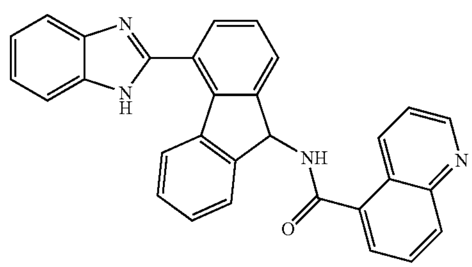 | C |
| 84 | 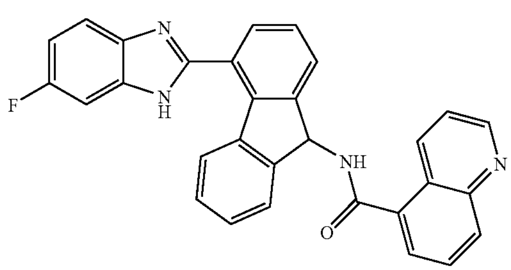 | B |

-continued

Table of results

| Ex | Structure | Hsp82 ATPase IC$_{50}$ μM |
|---|---|---|
| 85 | 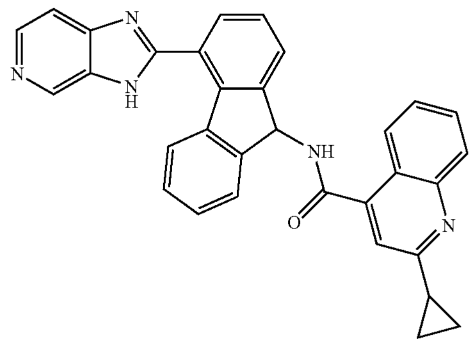 | B |
| 86 | 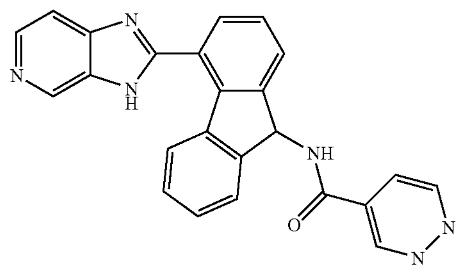 | B |
| 87 | 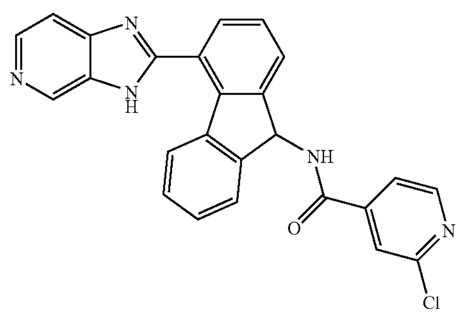 | B |
| 88 | 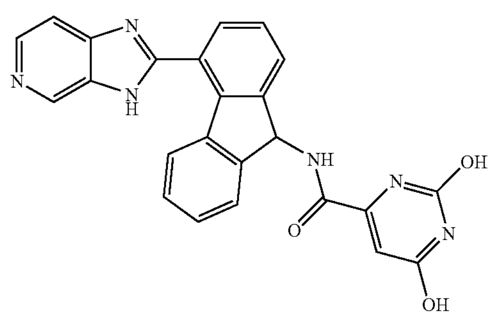 | B |
| 89 | 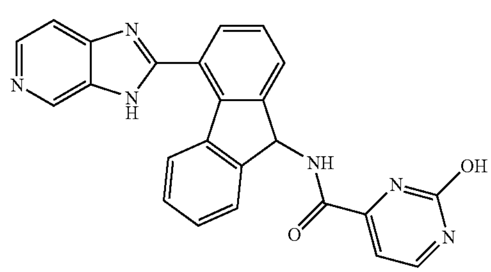 | B |

-continued

Table of results

| Ex | Structure | Hsp82 ATPase IC$_{50}$ μM |
|---|---|---|
| 90 | 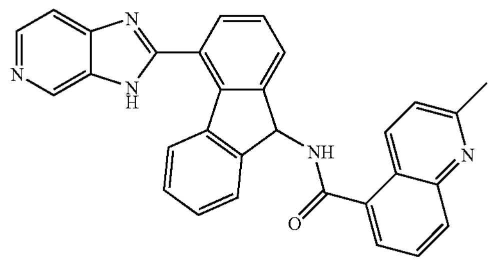 | B |
| 91 | 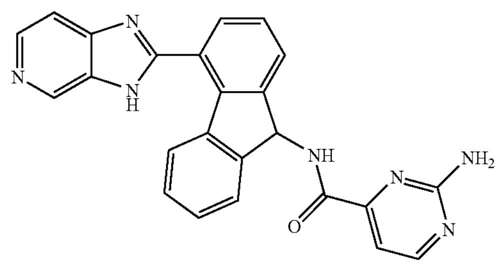 | A |
| 92 | 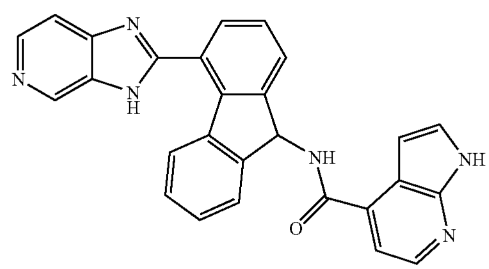 | A |
| 93 | 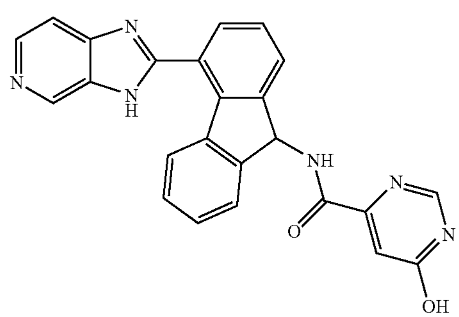 | B |
| 94 | 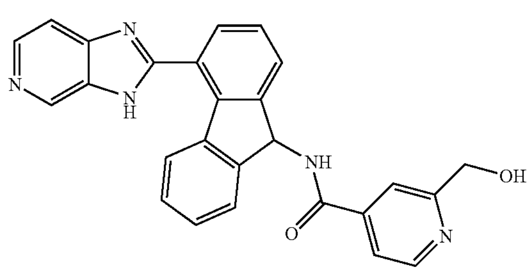 | B |

-continued

Table of results

| Ex | Structure | Hsp82 ATPase IC$_{50}$ μM |
|---|---|---|
| 95 | 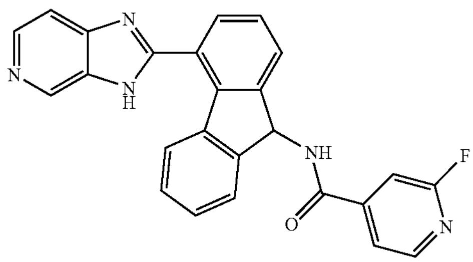 | B |
| 96 | 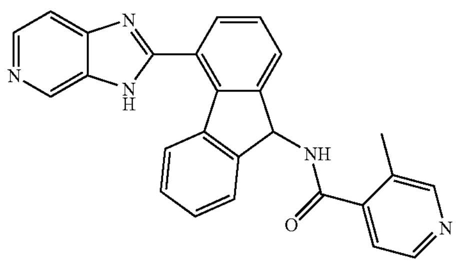 | B |
| 97 | 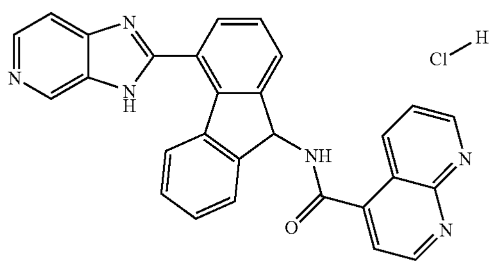 | B |
| 98 | 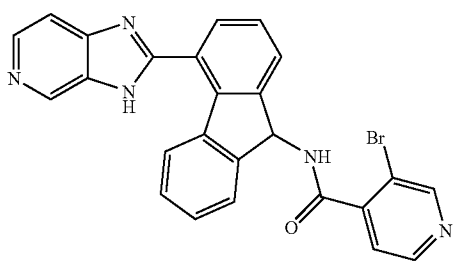 | B |
| 99 | 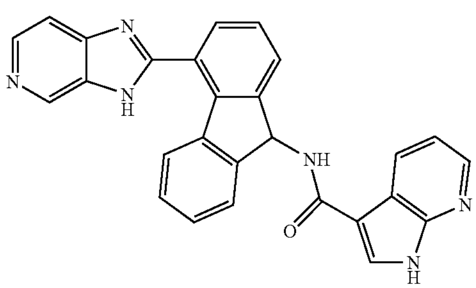 | A |

-continued

Table of results

| Ex | Structure | Hsp82 ATPase IC$_{50}$ μM |
|---|---|---|
| 100 | 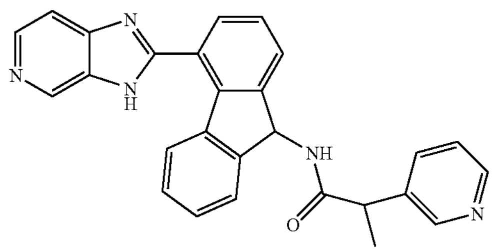 | C |
| 101 | 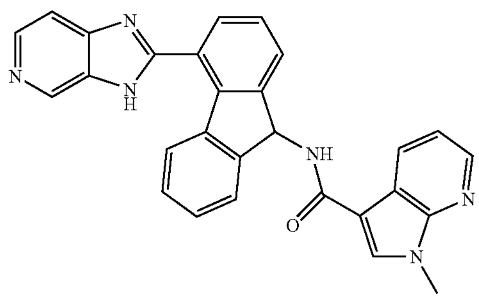 | B |
| 102 | 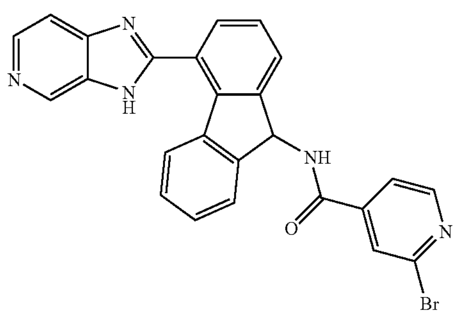 | A |
| 103 | 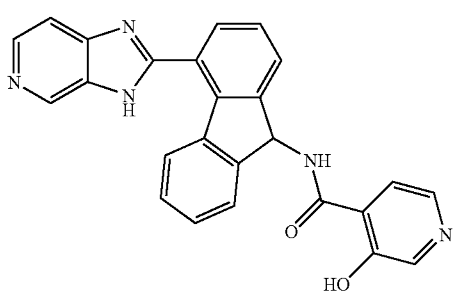 | A |
| 104 | 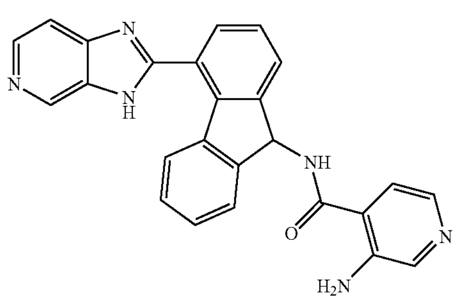 | A |

-continued

Table of results

| Ex | Structure | Hsp82 ATPase IC$_{50}$ μM |
|---|---|---|
| 105 | 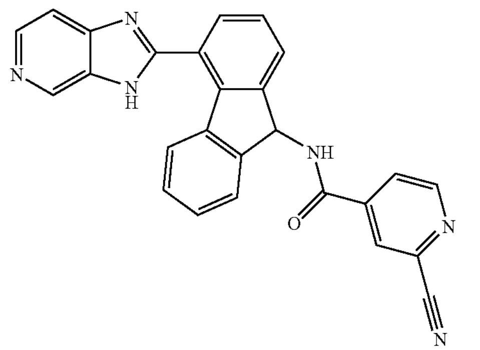 | B |
| 106 | 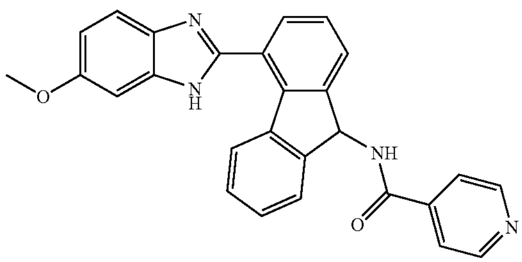 | B |
| 107 | 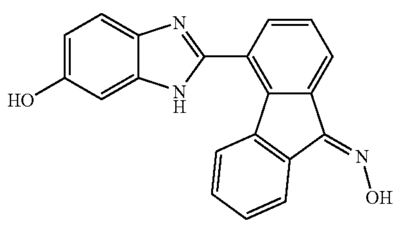 | C |
| 108 | 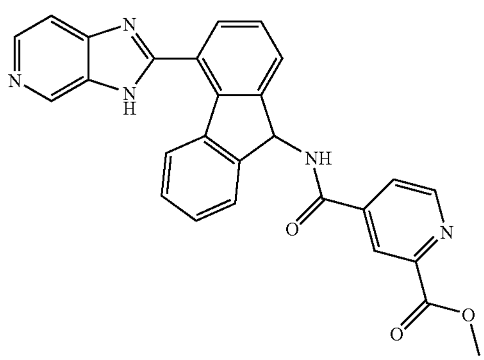 | A |

-continued

Table of results

| Ex | Structure | Hsp82 ATPase IC$_{50}$ μM |
|---|---|---|
| 109 | 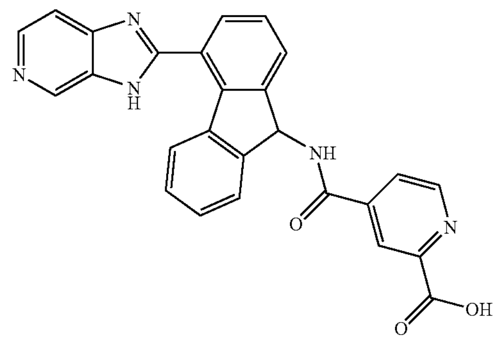 | C |
| 110 | 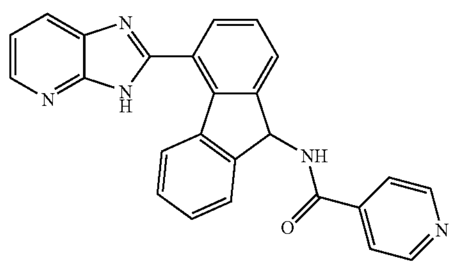 | C |
| 111 | 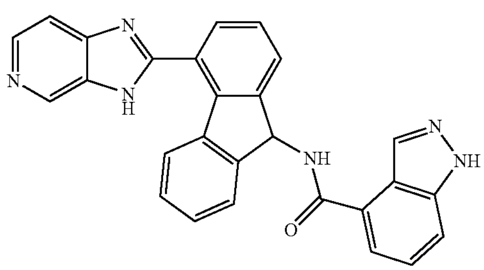 | A |
| 112 | 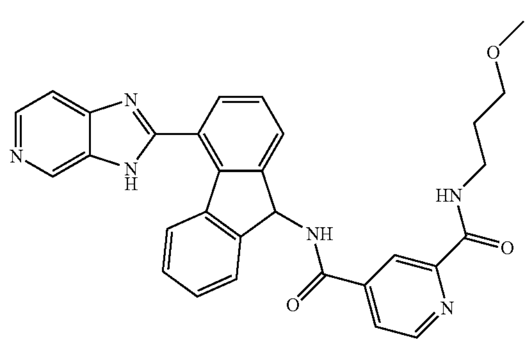 | B |

| Ex | Structure | Hsp82 ATPase IC$_{50}$ μM |
|---|---|---|
| 113 | 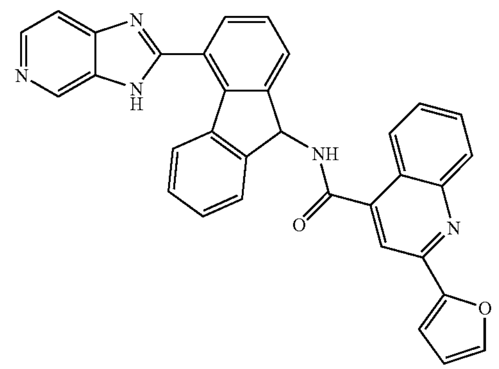 | B |
| 114 | 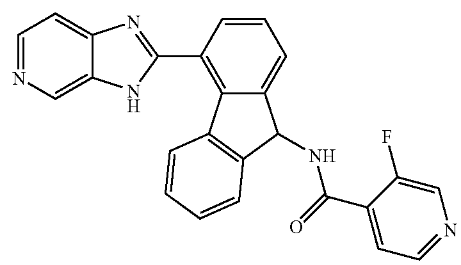 | B |
| 115 | 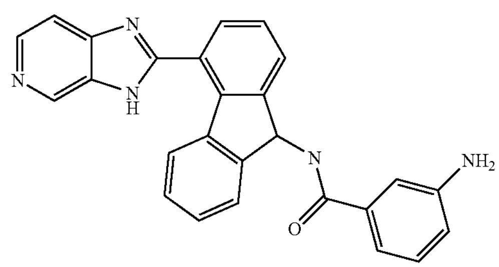 | C |
| 116 | 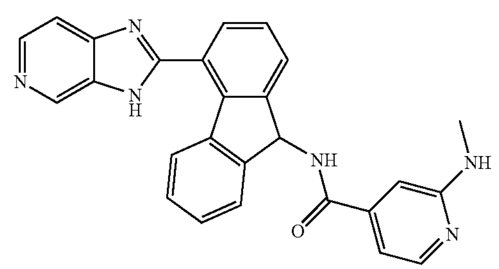 | B |
| 117 | 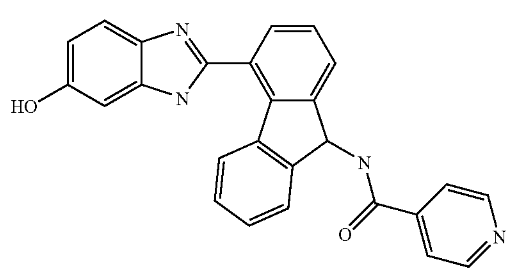 | B |

-continued

Table of results

| Ex | Structure | Hsp82 ATPase IC$_{50}$ μM |
|---|---|---|
| 118 | 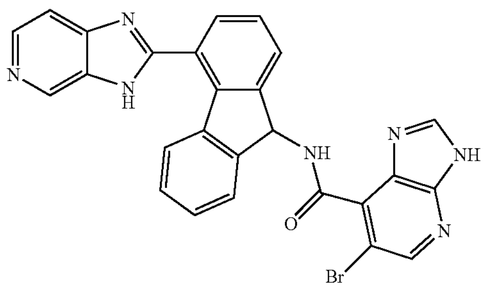 | A |
| 119 | 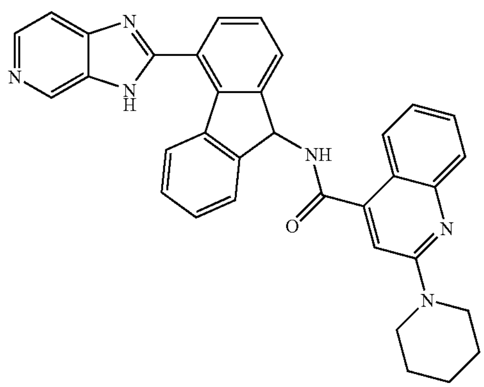 | B |
| 120 | 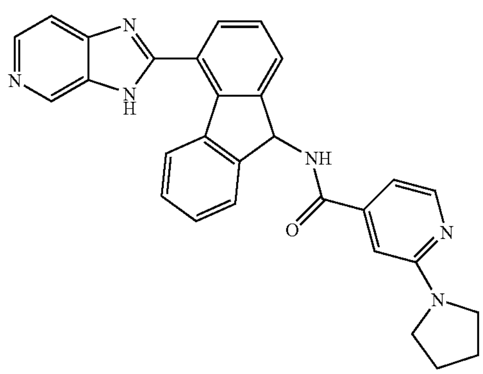 | B |
| 121 | 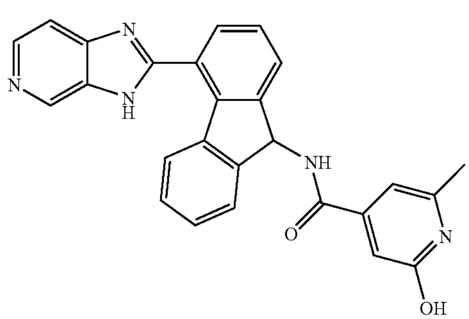 | B |

-continued

Table of results

| Ex | Structure | Hsp82 ATPase IC$_{50}$ μM |
|---|---|---|
| 122 | 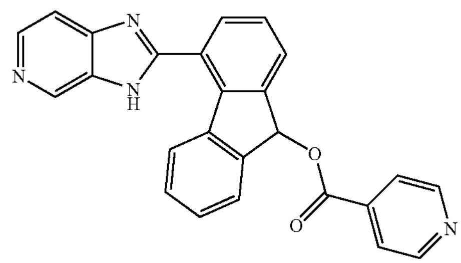 | A |
| 123 | 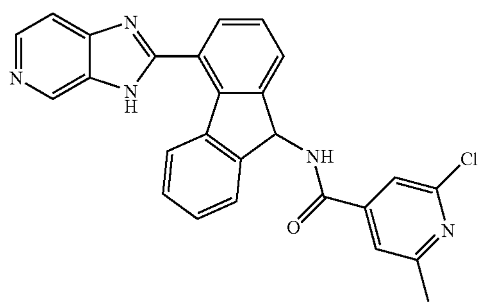 | B |
| 124 | 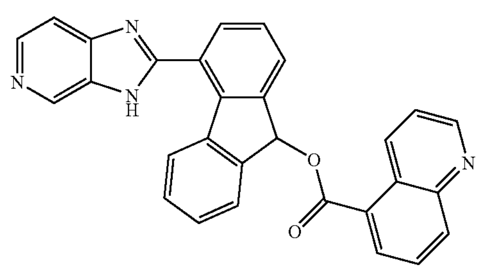 | B |
| 125 | 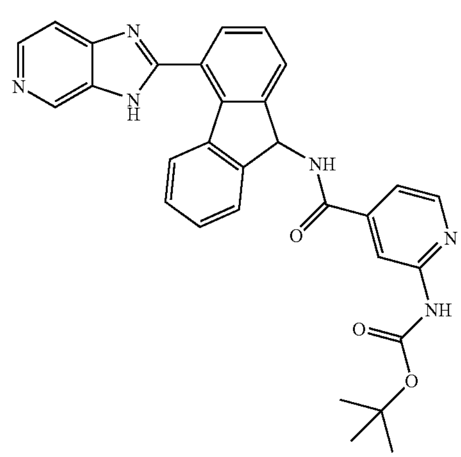 | A |

| Ex | Structure | Hsp82 ATPase IC$_{50}$ μM |
|---|---|---|
| 126 | 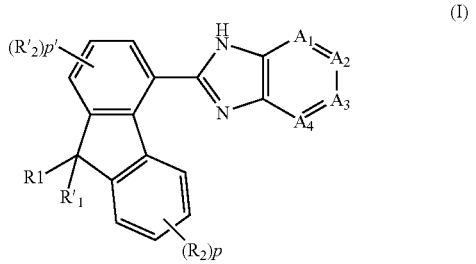 | B |

What is claimed is:

1. A compound of formula (I)

(I)

wherein:

A$_1$, A$_2$, A$_3$ and A4, which may be identical or different, represent CRa or N or NRb, where Rb represents alkyl, alkoxy or OH;

R1 and R'$_1$ are such that:

either

R1 and R'$_1$, which may be identical or different, are such that one of R1 and R'$_1$ represents a hydrogen or halogen atom or a radical selected from C$_1$C$_3$-alkyl, C$_1$C$_3$-alkoxy, alkyl-OH, CF$_3$, cyano, carboxy and carboxamido;

and the other one of R1 and R'$_1$ is selected from the group consisting of H; halogen; CF$_3$; hydroxyl; mercapto; nitro; amino; NH—OH; NH—CO—H; NH—CO—OH, NH—CO-Oalkyl, NH—CO—NH$_2$; carboxy; CN; CO—NH$_2$; X—(CH$_2$)$_m$-alkyl; X—(CH$_2$)$_m$-cycloalkyl; X—(CH$_2$)$_m$-heterocycloalkyl; X—(CH$_2$)$_m$-aryl and X—(CH$_2$)$_m$-heteroaryl; wherein X is a single bond, CH$_2$, CH=CH, CH$_2$—O, CH$_2$—NH, CH$_2$—C(O), CH$_2$—C(O)—O, CH$_2$—C(O)—NH, CH$_2$—NH—(CO), CH$_2$—NH—S(O), CH$_2$—NH—S(O)$_2$, O, S, NH, O—C(O), C(O)—NH, —NH—C(O), —NH—C(O)—C(O)—, —NH—C(O)—NH—; NH—CS, NH—S(O) or NH—S(O)$_2$, —NH—CO—CH$_2$—O— —NH—CO—CH$_2$—S—CH$_2$—CO—NH—, —NH—CO—(CH$_2$)$_2$—SO$_2$—, or —NH—CO—CH$_2$—N(CH$_3$)—CO—; m=0, 1 or 2; and wherein all the alkyl, cycloalkyl, heterocycloalkyl, aryl and heteroaryl radicals are optionally substituted; the cycloalkyl radical contains from 3 to 10 ring members; the aryl radical contains from 6 to 10 ring members; and the heterocycloalkyl and heteroaryl radicals, optionally substituted, contain from 4 to 10 ring members including 1 to 4 heteroatoms selected from O, S, N and NR$_3$ where R$_3$ represents H or alkyl, itself optionally substituted;

or

R$_1$ and R'$_1$ form, together with the carbon atom to which they are bound, an =O; =S; =N—OH; =N—NH$_2$; =N—NH—CO—NH$_2$, =CH—OH; =Y$_1$—(CH$_2$)$_m$-aryl or =Y$_1$—(CH$_2$)$_m$-heteroaryl radical, in which Y$_1$ represents CH, CH—CO—, CH—CO—NH, N, N—O or N—NH—; wherein m=0, 1 or 2; and wherein the aryl radical, optionally substituted, contains from 6 to 10 ring members; and wherein the heteroaryl radical, optionally substituted, contains from 4 to 10 ring members including 1 to 4 heteroatoms selected from O, S, N and NR$_3$ where R$_3$ represents H or alkyl, itself optionally substituted;

or

R1 and R'$_1$ form, together with the carbon atom to which they are bound, a partially saturated ring made up of 4 to 6 ring members and optionally containing from 1 to 3 heteroatoms selected from O, S, N and NR$_4$ where R$_4$ represents H or alkyl, itself optionally substituted;

R$_2$ and R'$_2$, which may be identical or different, are selected independently from the group consisting of H, halogen, CF$_3$, nitro, cyano, alkyl, hydroxy, mercapto, amino, alkylamino, dialkylamino, alkoxy, alkylthio, free carboxy or carboxy esterified with an alkyl radical, carboxamide, CO—NH(alkyl) and CO—N(alkyl)$_2$, wherein all the alkyl, alkoxy and alkylthio radicals are optionally substituted;

p and p', which may be identical or different, represent the integers 1 to 4 and 1 to 3, respectively;

Ra is selected from the group consisting of H; halogen; CF$_3$; hydroxy; OCF$_3$; SO$_2$—NH$_2$; SO$_2$—NH(alk), SO$_2$—N(alk)$_2$; mercapto; nitro; amino; NH(alk); N(alk)$_2$; NH—OH; NH—CO—H; NH—CO—NH$_2$; free carboxy or carboxy esterified with an alkyl radical, itself optionally substituted; CN; CO—NH$_2$; Y—(CH$_2$) n-alkyl; Y—(CH$_2$)$_n$-cycloalkyl, Y—(CH$_2$)$_n$-heterocycloalkyl, Y—(CH$_2$)$_n$-aryl and Y—(CH$_2$)$_n$-heteroaryl; wherein Y represents a single bond, O, S, NH, O—C(O), C(O)—NH, —C(O)N(CH₃)—; CO; NH—C(O), NH—S(O) or NH—S(O)₂ and wherein n=0, 1, 2 or 3; wherein the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or NR₃ where R₃ represents H or alkyl, itself optionally substituted; and wherein all the alkyl, alkoxy, alkylthio, cycloalkyl, heterocycloalkyl, aryl and heteroaryl radicals of the substituents of the compounds of formula (I) are optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

2. A compound according to claim 1 wherein:

A₁, A₂, A₃ and A4, which may be identical or different, represent CRa or N or NRb, where Rb represents CH₃ or OH;

Ra is selected from the group consisting of H; halogen; CF₃; hydroxy; OCF₃; SO₂—NH₂; SO₂—NHCH₃, SO₂—N(CH₃)₂; mercapto; nitro; amino; NH(CH₃); N(CH₃)₂; NH—OH; NH—CO—H; NH—CO—NH₂; free carboxy or carboxy esterified with an alkyl radical, itself optionally substituted; CO₂—CH₃; CO₂—(CH₂)₃N(CH₃)₂; CN; CO—NH₂; Y—(CH₂)ₙ-alkyl; Y—(CH₂)ₙ-cycloalkyl, Y—(CH₂)ₙ-heterocycloalkyl, Y—(CH₂)ₙ-aryl and Y—(CH₂)ₙ-heteroaryl, wherein Y represents a single bond, O, —C(O)—NH—, —C(O)N(CH₃)—; or CO; and n=0, 1, 2, or 3; and wherein the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or NR₃ where R₃ represents H or alkyl, itself optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

3. A compound of formula (I)

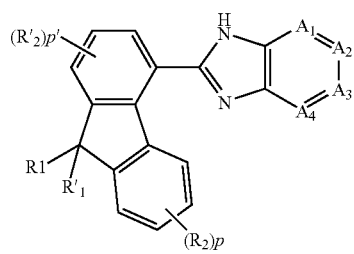

(I)

wherein:

A₁, A₂, A₃ and A4, which may be identical or different, represent CRa or N;

R1 and R'₁ are such that:

either

R1 and R'₁, which may be identical or different, are such that one of R1 and R'₁ represents a hydrogen or halogen atom or a radical selected from C₁C₃-alkyl, C₁C₃-alkoxy, alkyl-OH, CF₃, cyano, carboxy and carboxamido; and the other one of R1 and R'₁ is selected from the group consisting of H; halogen; CF₃; hydroxyl; mercapto; nitro; amino; NH—OH; NH—CO—H; NH—CO—OH, NH—CO-Oalkyl, NH—CO—NH₂; carboxy; CN; CO—NH₂; X—(CH₂)ₘ-alkyl; X—(CH₂)ₘ-cycloalkyl; X—(CH₂)ₘ-heterocycloalkyl; X—(CH₂)ₘ-aryl and X—(CH₂)ₘ-heteroaryl; wherein X is a single bond, CH₂, CH=CH, CH₂—O, CH₂—NH, CH₂—C(O), CH₂—C(O)—O, CH₂—C(O)—NH, CH₂—NH—(CO), CH₂—NH—S(O), CH₂—NH—S(O)₂, O, S, NH, O—C(O), C(O)—NH, —NH—C(O), —NH—C(O)—C(O)—, —NH—C(O)—NH—; NH—CS, NH—S(O) or NH—S(O)₂; m=0, 1 or 2; and wherein all the alkyl, cycloalkyl, heterocycloalkyl, aryl and heteroaryl radicals are optionally substituted; the cycloalkyl radical contains from 3 to 10 ring members; the aryl radical contains from 6 to 10 ring members; and the heterocycloalkyl and heteroaryl radicals, optionally substituted, contain from 4 to 10 ring members including 1 to 4 heteroatoms selected from O, S, N or NR₃ where R₃ represents H or alkyl, itself optionally substituted;

or R1 and R'₁ form, together with the carbon atom to which they are bound, an =O; =S; =N—OH; =N—NH₂; =N—NH—CO—NH₂, =CH—OH; =Y₁—(CH₂)ₘ-aryl or =Y₁—(CH₂)ₘ-heteroaryl radical, in which Y₁ represents CH, CH—CO—, CH—CO—NH, N, N—O or N—NH—; wherein m=0, 1 or 2; and wherein the aryl radical, optionally substituted, contains from 6 to 10 ring members; and wherein the heteroaryl radical, optionally substituted, contains from 4 to 10 ring members including 1 to 4 heteroatoms selected from O, S, N and NR₃ where R₃ represents H or alkyl, itself optionally substituted;

or

R1 and R'₁ form, together with the carbon atom to which they are bound, a partially saturated ring made up of 4 to 6 ring members and optionally containing from 1 to 3 heteroatoms selected from O, S, N or NR₄ where R₄ represents H or alkyl, itself optionally substituted;

R₂ and R'₂, which may be identical or different, are selected independently from the group consisting of H, halogen, CF₃, nitro, cyano, alkyl, hydroxy, mercapto, amino, alkylamino, dialkylamino, alkoxy, alkylthio, free or esterified carboxy, carboxamide, CO—NH(alkyl) and CON(alkyl)₂;

p and p', which may be identical or different, represent the integers 1 to 4 and 1 to 3, respectively;

Ra is selected from the group consisting of H; halogen; CF₃; hydroxy; mercapto; nitro; amino; NH—OH; NH—CO—H; NH—CO—NH₂; carboxy; CN; CO—NH₂; Y—(CH₂)ₙ-alkyl; Y—(CH₂)ₙ-cycloalkyl, Y—(CH₂)ₙ-heterocycloalkyl, Y—(CH₂)ₙ-aryl and Y—(CH₂)ₙ-heteroaryl, wherein Y represents O, S, NH, O—C(O), C(O)—NH, NH—C(O), NH—S(O) or NH—S(O)₂, and wherein n=0, 1, 2, or 3; and wherein the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or $NR_3$ where $R_3$ represents H or alkyl, itself optionally substituted; and wherein all the alkyl, alkoxy, alkylthio, cycloalkyl, heterocycloalkyl, aryl and heteroaryl radicals of the substituents of the compounds of formula (I) are optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

4. A compound according to claim 1 wherein:

$A_1$, $A_2$, $A_3$ and A4, which may be identical or different, represent CRa or N;

Ra is selected from the group consisting of H; halogen; hydroxy; mercapto; amino; $Y$—$(CH_2)_n$-alkyl; $Y$—$(CH_2)_n$-cycloalkyl, $Y$—$(CH_2)_n$-heterocycloalkyl, $Y$—$(CH_2)_n$-aryl or $Y$—$(CH_2)_n$-heteroaryl; wherein Y represents O, and wherein n=0, 1, 2, or 3; and wherein all the alkyl, cycloalkyl, heterocycloalkyl, aryl and heteroaryl radicals are optionally substituted and the heterocycloalkyl and heteroaryl radicals contain from 4 to 10 ring members including 1 to 4 heteroatoms selected from O, S, N or $NR_3$ where $R_3$ represents H or alkyl, itself optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

5. A compound according to claim 1 wherein:

$A_1$, $A_2$, $A_3$ and A4, which may be identical or different, represent CRa or N; and Ra is selected from the group consisting of H; halogen; hydroxy; $Y$—$(CH_2)_n$-alkyl; $Y$—$(CH_2)_n$-cycloalkyl, $Y$—$(CH_2)_n$-heterocycloalkyl, $Y$—$(CH_2)_n$-aryl and $Y$—$(CH_2)_n$-heteroaryl, wherein Y represents O, and wherein n=2 or 3; and wherein all the alkyl, cycloalkyl, heterocycloalkyl, aryl and heteroaryl radicals are optionally substituted, and the heterocycloalkyl and heteroaryl radicals contain from 4 to 10 ring members including 1 to 4 heteroatoms selected from O, S, N or $NR_3$ where $R_3$ represents H or alkyl, itself optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

6. A compound according to claim 1 wherein:

$A_1$, $A_2$, $A_3$ and A4 are such that either all four of $A_1$, $A_2$, $A_3$ and $A_4$ represent CRa;

or one of them represents CRa and the other three, which may be identical or different, represent N or CRa, where Ra represents H; halogen; hydroxy or alkoxy;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

7. A compound according to claim 1 wherein:

$R_2$ and $R'_2$, which may be identical or different, are selected independently from the group consisting of H, halogen, methyl, ethyl, amino, methoxy, $CH_2$—$NH_2$, $CH_2$—NHalk, $CH_2$—$N(alk)_2$, $CH_2$—OH and $CH_2$—Oalk; and p and p', which may be identical or different, represent the integers 1 to 4 and 1 to 3, respectively;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

8. A compound according to claim 1 wherein:

$R_2$ and $R_2'$, which may be identical or different, are selected independently from the group consisting of H, halogen, methyl, ethyl, amino, and methoxy: and p and p', which may be identical or different, represent the integers 1 to 4 and 1 to 3, respectively;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

9. A compound according to claim 1 wherein:

$R_2$ and $R_2'$, which may be identical or different, are selected independently from the group consisting of H and methyl; and p and p', which may be identical or different, represent the integers 1 to 4 and 1 to 3, respectively;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

10. A compound according to claim 1 wherein:

R1 and $R'_1$ are such that:

either

R1 and $R'_1$, which may be identical or different, are such that one of R1 and $R'_1$ represents a hydrogen atom;

and the other one of R1 and $R'_1$ is selected from the group consisting of H; halogen; hydroxyl; amino; NH—CO—H; NH—CO—OH, NH—CO-Oalkyl, NH—CO—$NH_2$; carboxy; CO—$NH_2$; X—$(CH_2)_m$-alkyl; X—$(CH_2)_m$-cycloalkyl; X—$(CH_2)_m$-heterocycloalkyl; X—$(CH_2)_m$-aryl and X—$(CH_2)_m$-heteroaryl, wherein X is a single bond, $CH_2$, CH=CH, $CH_2$—C(O), NH, O—C(O), C(O)—NH, —NH—C(O), —NH—C(O)—C(O)—, —NH—C(O)—NH—; NH—CS, NH—S(O) or NH—$S(O)_2$, wherein m=0; and wherein all the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members including 1 to 4 heteroatoms selected from O, S, N and $NR_3$ where $R_3$ represents H or alkyl, itself optionally substituted;

or

R1 and $R'_1$ form, together with the carbon atom to which they are bound, an =O; =S; =N—OH; =N—$NH_2$; =N—NH—CO—$NH_2$, =CH—OH; =$Y_1$—$(CH_2)_m$-aryl or =$Y_1$—$(CH_2)_m$-heteroaryl radical, in which $Y_1$ represents CH, CH—CO—, CH—CO—NH, N, N—O or N—NH—; wherein m=0, 1 or 2 and wherein the aryl radical, optionally substituted, contains from 6 to 10 ring members; and wherein the heteroaryl radical, optionally substituted, contains from 4 to 10 ring members including 1 to 4 heteroatoms selected from O, S, N and NR$_3$ where R$_3$ represents H or alkyl, itself optionally substituted;

or

R$_1$ and R$_1$' form, together with the carbon atom to which they are bound, a partially saturated heterocycle made up of 5 to 6 ring members and containing from 1 to 3 heteroatoms selected from O, S, N or NR$_4$ where R$_4$ represents H or alkyl, itself optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

11. A compound of formula I

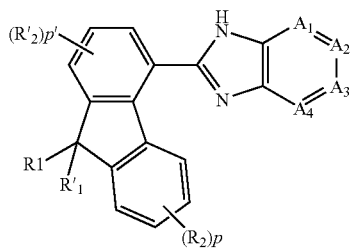

wherein:

A$_1$, A$_2$, A$_3$ and A4, which may be identical or different, represent CRa or N or NRb where Rb represents CH$_3$ or OH;

Ra is selected from the group consisting of H; CH$_3$; CH$_2$—NH$_2$; halogen; CF$_3$; hydroxy; OCF$_3$; SO$_2$—NH$_2$; SO$_2$—N(CH$_3$)$_2$; mercapto; nitro; amino; NH(CH$_3$); N(CH$_3$)$_2$; NH—OH; NH—CO—H; NH—CO—NH$_2$; free carboxy or carboxy esterified with an alkyl radical, itself optionally substituted; CO$_2$—CH$_3$; CO$_2$—(CH$_2$)$_3$—N(CH$_3$)$_2$; CN; CO—NH$_2$; CO—N(CH$_3$)$_2$; CO—CH$_3$, CO—(CH$_2$)$_3$—O—CH$_3$); morpholinyl; piperazinyl-CH$_3$; imidazolinyl-CH$_3$; diazepin-CH$_3$; —CO-piperazinyl-CH$_3$; —CO-pyrrolidinyl; Y—(CH$_2$)$_n$-alkyl; Y—(CH$_2$)$_n$-cycloalkyl, Y—(CH$_2$)$_n$-heterocycloalkyl, Y—(CH$_2$)$_n$-aryl and Y—(CH$_2$)$_n$-heteroaryl, where Y represents a single bond, =O, —C(O)—NH—, —C(O)N(CH$_3$)—; or CO; wherein n=0, 1, 2 or 3; and wherein the alkyl, cycloalkyl, heterocycloalkyl, aryl and heteroaryl radicals are optionally substituted, the cycloalkyl radical contains from 3 to 10 ring members, the aryl radical contains from 6 to 10 ring members, and the heterocycloalkyl and heteroaryl radicals, optionally substituted, contain from 4 to 10 ring members, including 1 to 4 heteroatoms selected from O, S, N or NR$_3$ where R$_3$ represents H or alkyl, itself optionally substituted;

R1 and R'$_1$ are such that:

either one of R1 and R'$_1$ represents a hydrogen atom, and the other one of R$_1$ and R$_1$' is selected from the group consisting of X—(CH$_2$)$_m$-heterocycloalkyl, X—(CH$_2$)$_m$-aryl and X—(CH$_2$)$_m$-heteroaryl, where X represents —O—C(O), —NH—C(O), NH—CS, —NH—CO—CH$_2$—O—; —NH—CO—CH$_2$—S—CH$_2$—CO—NH—; —NH—CO—(CH$_2$)$_2$—SO$_2$—; —NH—CO—CH$_2$—N(CH$_3$)—CO—; where m=0;

or

R1 and R'$_1$ form, together with the carbon atom to which they are bound an =N—OH or =N—NH$_2$ radical;

R$_2$ and R$_{12}$, which may be identical or different, are selected independently from the group consisting of H, halogen, methyl, ethyl, amino, methoxy, CH$_2$—NH$_2$, CH$_2$—NHalk, CH$_2$—N(alk)$_2$, CH$_2$—OH and CH$_2$—Oalk; and p and p', which may be identical or different, represent the integers 1 to 4 and 1 to 3, respectively; and wherein all the alkyl, alkoxy, alkylthio, cycloalkyl, heterocycloalkyl, aryl and heteroaryl radicals of the substituents of the compounds of formula (I) are optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

12. A compound according to claim 11 wherein R1 represents a hydrogen atom and R'$_1$ represents X—(CH$_2$)$_m$-heteroaryl;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

13. A compound according to claim 1 wherein:

R$_1$ and R$_1$' are such that:

either one of R1 and R'$_1$ represents a hydrogen atom and the other one of R1 and R'$_1$ is selected from the group consisting of X —(CH$_2$)$_m$-heterocycloalkyl, X—(CH$_2$)$_m$-aryl and X—(CH$_2$)$_m$-heteroaryl, where X represents —O—C(O), —NH—C(O) or NH—CS, and m represents 0;

or

R1 and R'$_1$ form, together with the carbon atom to which they are bound, a radical =N—OH or =N—NH$_2$; and wherein the heterocycloalkyl, aryl and heteroaryl radicals are optionally substituted;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

14. A compound according to claim 13 wherein:

R$_1$ and R'$_1$ are such that:

one of R1 and R'$_1$ represents a hydrogen atom and the other one of R1 and R'$_1$ is X—(CH$_2$)$_m$-heteroaryl, where X represents —O —C(O), —NH—C(O) or NH—CS, and m represents 0;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

15. A compound according to claim 1 which is 4-(3H-imidazo[4,5-c]pyridin-2-yl)-9H-fluoren-9-one oxime (Z, E);

N-[4-(1H-imidazo[4,5-c]pyridin-2-yl)-9H-fluoren-9-ylidene]-hydrazine, 60/40 mixture of E and Z isomers;

[4-(3H-imidazo[4,5-c]pyridin-2-yl)-9H-fluoren-9(R,S)-yl]amide of quinoline-5-carboxylic acid;
dextrorotatory enantiomer of [4-(3H-imidazo[4,5-c]pyridin-2-yl)-9H-fluoren -9(R,S)-yl]amide of quinoline-5-carboxylic acid;
4-(3H-imidazo[4,5-c]pyridin-2-yl)-9H-fluoren-9-one oxime (E);
trifluoroacetate of [4-(3H-imidazo[4,5-c]pyridin-2-yl)-9H-fluoren-9(R,S)-yl]amide of 1H-pyrazole-4-carboxylic acid;
trifluoroacetate of N-[4-(3H-imidazo[4,5-c]pyridin-2-yl)-9H-fluoren-9(R,S)-yl]-succinamide;
trifluoroacetate of [4-(3H-imidazo[4,5-c]pyridin-2-yl)-9H-fluoren-9(R,S)-yl]amide of 1H-benzotriazole-5-carboxylic acid;
[4-(3H-imidazo[4,5-c]pyridin-2-yl)-9H-fluoren-9(R,S)-yl]amide of 1H-indazole -5-carboxylic acid;
[4-(3H-imidazo[4,5-c]pyridin-2-yl)-9H-fluoren-9(R,S)-yl]amide of 1H-indole-6-carboxylic acid;
N-[4-(3H-imidazo[4,5-c]pyridin-2-yl)-9H-fluoren-9(R,S)-yl]-isonicotinamide;
[4-(3H-imidazo[4,5-c]pyridin-2-yl)-9H-fluoren-9(R,S)-yl]amide of 1H-indole-4-carboxylic acid;
trifluoroacetate of [4-(3H-imidazo[4,5-c]pyridin-2-yl)-9H-fluoren-9(R,S)-yl]amide of quinoline-5-carbothioic acid;
2-acetylamino-N-[4-(3H-imidazo[4,5-c]pyridin-2-yl)-9H-fluoren-9(R,S)-yl]-iso-nicotinamide;
[4-(3H-imidazo[4,5-c]pyridin-2-yl)-9H-fluoren-9(R,S)-yl]amide of quinoline-4-carboxylic acid;
2-amino-N-[4-(3H-imidazo[4,5-c]pyridin-2-yl)-9H-fluoren-9(R,S)-yl]-iso-nicotinamide;
2-ethyl-N-[4-(3H-imidazo[4,5-c]pyridin-2-yl)-9H-fluoren-9(R,S)-yl]-iso-nicotinamide;
[4-(6-fluoro-1H-benzimidazol-2-yl)-9H-fluoren-9(R,S)-yl]amide of quinoline-5-carboxylic acid;
2-chloro-N-[4-(3H-imidazo[4,5-c]pyridin-2-yl)-9H-fluoren-9(R,S)-yl]-iso-nicotinamide;
[4-(3H-imidazo[4,5-c]pyridin-2-yl)-9H-fluoren-9(R,S)-yl]amide of 2-amino-pyrimidine -4-carboxylic acid;
[4-(3H-imidazo[4,5-c]pyridin-2-yl)-9H-fluoren-9(R,S)-yl]amide of 1H-pyrrolo[2,3-b]pyridine-4-carboxylic acid;
2-hydroxymethyl-N-[4-(3H-imidazo[4,5-c]pyridin-2-yl)-9H-fluoren-9(R,S)-yl]-isonicotinamide;
N-[4-(3H-imidazo[4,5-c]pyridin-2-yl)-9H-fluoren-9(R,S)-yl]-3-methyl-iso-nicotinamide;
hydrochloride of [4-(3H-imidazo[4,5-c]pyridin-2-yl)-9H-fluoren-9(R,S)-yl]amide of 1,8-naphthyridine-4-carboxylic acid;
[4-(3H-imidazo[4,5-c]pyridin-2-yl)-9H-fluoren-9(R,S)-yl]amide of 1H-pyrrolo[2,3-b]pyridine-3-carboxylic acid;
[4-(3H-imidazo[4,5-c]pyridin-2-yl)-9H-fluoren-9(R,S)-yl]amide of 1-methyl-1H-pyrrolo[2,3-b]pyridine-3-carboxylic acid;
2-bromo-N-[4-(3H-imidazo[4,5-c]pyridin-2-yl)-9H-fluoren-9(R,S)-yl]-iso-nicotinamide;
3-hydroxy-N-[4-(3H-imidazo[4,5-c]pyridin-2-yl)-9H-fluoren-9(R,S)-yl]-isonicotinamide;
3-amino-N-[4-(3H-imidazo[4,5-c]pyridin-2-yl)-9H-fluoren-9(R,S)-yl]-iso-nicotinamide;
methyl ester of 4-[4-(3H-imidazo[4,5-c]pyridin-2-yl)-9H-fluoren-9(R,S)-ylcarbamoyl]-pyridine-2-carboxylic acid;
[4-(3H-imidazo[4,5-c]pyridin-2-yl)-9H-fluoren-9(R,S)-yl]amide of 1H-indazole -4-carboxylic acid;
N-[4-(3H-imidazo[4,5-c]pyridin-2-yl)-9H-fluoren-9(R,S)-yl]-2-methylamino-isonicotinamide;
N-[4-(6-hydroxy-1H-benzimidazol-2-yl)-9H-fluoren-9 (R,S)-yl]-isonicotinamide;
[4-(3H-imidazo[4,5-c]pyridin-2-yl)-9H-fluoren-9(R,S)-yl]amide of 6-bromo-3H-imidazo[4,5-b]pyridine-7-carboxylic acid;
4-(3H-imidazo[4,5-c]pyridin-2-yl)-9H-fluoren-9(R,S)-yl ester of isonicotinic acid;
N-[4-(3H-imidazo[4,5-c]pyridin-2-yl)-9H-fluoren-9(R,S)-yl]amide of 2-tert-butoxycarbonylamino-isonicotinic acid;
N-[4-(3H-imidazo[4,5-c]pyridin-2-yl)-9H-fluoren-9(R,S)-yl]amide of 3-chloro-6-methoxy-quinoline-4-carboxylic acid;
N-[4-(3H-imidazo[4,5-c]pyridin-2-yl)-9H-fluoren-9(R,S)-yl]amide of 3-hydroxy-quinoline -4-carboxylic acid;
N-[4-(3H-imidazo[4,5-c]pyridin-2-yl)-9H-fluoren-9(R,S)-yl]amide of 2-amino-5-chloro-pyrimidine-4-carboxylic acid;
[4-(3H-imidazo[4,5-c]pyridin-2-yl)-9H-fluoren-9(R,S)-yl]amide of 3-bromo-1H-pyrrolo[2,3-b]pyridine-4-carboxylic acid;
dextrorotatory enantiomer of [4-(3H-imidazo[4,5-c]pyridin-2-yl)-9H-fluoren-9(R,S)-yl]amide of 1H-pyrrolo[2,3-b]pyridine-4-carboxylic acid;
N-[4-(3H-imidazo[4,5-c]pyridin-2-yl)-9H-fluoren-9(R,S)-yl]amide of 9H-purine -6-carboxylic acid;
N-[4-(3H-imidazo[4,5-c]pyridin-2-yl)-9H-fluoren-9(R,S)-yl]amide of 2-amino-6-methyl-pyrimidine-4-carboxylic acid;
[4-(3H-imidazo[4,5-c]pyridin-2-yl)-9H-fluoren-9(R,S)-yl]amide of 5-amino-3H -1,2,3-triazole-4-carboxylic acid;
N-[4-(3H-imidazo[4,5-c]pyridin-2-yl)-9H-fluoren-9(R,S)-yl]amide of 6-methyl-2-methylamino-pyrimidine-4-carboxylic acid;
N-[4-(3H-imidazo[4,5-c]pyridin-2-yl)-9H-fluoren-9(R,S)-yl]amide of 6-methoxy-quinoline-4-carboxylic acid;
3,5-dihydroxy-N-[4-(3H-imidazo[4,5-c]pyridin-2-yl)-9H-fluoren-9(R,S)-yl]-benzamide;
N-[4-(3H-imidazo[4,5-c]pyridin-2-yl)-9H-fluoren-9(R,S)-yl]amide of pyrimidine -4-carboxylic acid;
4-hydroxy-N-[4-(3H-imidazo[4,5-c]pyridin-2-yl)-9H-fluoren-9(R,S)-yl]-benzamide;
2,4-dihydroxy-N-[4-(3H-imidazo[4,5-c]pyridin-2-yl)-9H-fluoren-9(R,S)-yl]-benzamide;
[4-(5-cyano-6-fluoro-1H-benzimidazol-2-yl)-9H-fluoren-9(R,S)-yl]amide of 1H-pyrrolo[2,3-b]pyridine-4-carboxylic acid;
4-(1H-benzimidazol-2-yl)-9H-fluoren-9(R,S)-yl]amide of 2-amino-5-chloro-pyrimidine -4-carboxylic acid;
[4-(5-fluoro-1H-benzimidazol-2-yl)-9H-fluoren-9(R,S)-yl]amide of 2-amino-5-chloro-pyrimidine-4-carboxylic acid;
[4-(5-fluoro-1H-benzimidazol-2-yl)-9H-fluoren-9(R,S)-yl]amide of 1H-pyrrolo[2,3-b]pyridine-4-carboxylic acid;
[4-(3H-imidazo[4,5-c]pyridin-2-yl)-9H-fluoren-9(R,S)-yl]amide of 2,3-dimethyl-quinoxaline-5-carboxylic acid;
[4-(3H-imidazo[4,5-c]pyridin-2-yl)-9H-fluoren-9(R,S)-yl]amide of 3-amino-1H-pyrazole-4-carboxylic acid;
dextrorotatory enantiomer of N-[4-(3H-imidazo[4,5-c]pyridin-2-yl)-9H-fluoren -9(R,S)-yl]amide of 2-amino-5-chloro-pyrimidine-4-carboxylic acid;

levorotatory enantiomer of N-[4-(3H-imidazo[4,5-c]pyridin-2-yl)-9H-fluoren-9(R,S)-yl]amide of 2-amino-5-chloro-pyrimidine-4-carboxylic acid;

[4-(3H-imidazo[4,5-c]pyridin-2-yl)-9H-fluoren-9(R,S)-yl]amide of 3-methyl-quinoxaline -5-carboxylic acid;

[4-(3H-imidazo[4,5-c]pyridin-2-yl)-9H-fluoren-9(R,S)-yl]amide of quinoxaline-5-carboxylic acid;

[4-(9H-purine-8-yl)-9H-fluoren-9(R,S)-yl]amide of 1H-pyrrolo[2,3-b]pyridine-4-carboxylic acid;

[4-(1H-benzimidazol-2-yl)-9H-fluoren-9(R,S)-yl]amide of 1H-pyrrolo[2,3-b]-pyridine-4-carboxylic acid;

[4-(5-trifluoromethyl-1H-benzimidazol-2-yl)-9H-fluoren-9(R,S)-yl]amide of 1H-pyrrolo[2,3-b]pyridine-4-carboxylic acid;

[4-(5-methoxycarbonyl-1H-benzimidazol-2-yl)-9H-fluoren-9(R,S)-yl]amide of 1H-pyrrolo[2,3-b]pyridine-4-carboxylic acid;

[4-(5-carboxy-1H-benzimidazol-2-yl)-9H-fluoren-9(R,S)-yl]amide of 1H-pyrrolo[2,3-b]pyridine-4-carboxylic acid;

[4-(4-methyl-1H-benzimidazol-2-yl)-9H-fluoren-9(R,S)-yl]amide of 1H-pyrrolo[2,3-b]pyridine-4-carboxylic acid;

[4-(5-carboxamido-1H-benzimidazol-2-yl)-9H-fluoren-9(R,S)-yl]amide of 1H-pyrrolo[2,3-b]pyridine-4-carboxylic acid;

[4-(6-sulphamoyl-1H-benzimidazol-2-yl)-9H-fluoren-9(R,S)-yl]amide of 1H-pyrrolo[2,3-b]pyridine-4-carboxylic acid;

[4-(5-trifluoromethoxy-1H-benzimidazol-2-yl)-9H-fluoren-9(R,S)-yl]amide of 1H-pyrrolo[2,3-b]pyridine-4-carboxylic acid;

[4-(5-cyano-1H-benzimidazol-2-yl)-9H-fluoren-9(R,S)-yl]amide of 1H-pyrrolo[2,3-b]pyridine-4-carboxylic acid;

D diastereoisomer of [4-(3H-imidazo[4,5-c]pyridin-2-yl)-9H-fluoren-9(R,S)-yl]amide of 2-(3-acetyl-2,2-dimethyl-cyclobutan-1-yl)acetic acid;

[4-(6-chloro-1H-benzimidazol-2-yl)-9H-fluoren-9(R,S)-yl]amide of 1H-pyrrolo[2,3-b]pyridine-4-carboxylic acid;

[4-(5-fluoro-6-morpholino-1H-benzimidazole-2-yl)-9H-fluoren-9(R,S)-yl]amide of 1H-pyrrolo[2,3-b]pyridine-4-carboxylic acid;

[4-(6-chloro-5-fluoro-1H-benzimidazole-2-yl)-9H-fluoren-9(R,S)-yl]amide of 1H-pyrrolo[2,3-b]pyridine-4-carboxylic acid;

[4-(4,5,6,7-tetrahydro-1H-benzimidazol-2-yl)-9H-fluoren-9(R,S)-yl]amide of 1H-pyrrolo[2,3-b]pyridine-4-carboxylic acid;

[2-amino-5-(1H-benzimidazol-2-yl)-9H-fluoren-9(R,S)-yl]amide of 1H-pyrrolo[2,3-b]pyridine-4-carboxylic acid;

[4-(5-hydroxy-5H-imidazo[4,5-c]pyridin-2-yl)-9H-fluoren-9(R,S)-yl]amide of 1H-pyrrolo[2,3-b]pyridine-4-carboxylic acid;

[4-(5-hydroxy-1H-benzimidazole-2-yl)-9H-fluoren-9(R,S)-yl]amide of 1H-pyrrolo[2,3-b]pyridine-4-carboxylic acid;

[4-(5-methylaminocarbonyl-1H-benzimidazol-2-yl)-9H-fluoren-9(R,S)-yl]amide of 1H-pyrrolo[2,3-b]pyridine-4-carboxylic acid;

[4-(5-dimethylaminocarbonyl-1H-benzimidazol-2-yl)-9H-fluoren-9(R,S)-yl]amide of 1H-pyrrolo[2,3-b]pyridine-4-carboxylic acid;

[4-5-(2-dimethylamino-ethyl)aminocarbonyl-1H-benzimidazol-2-yl)-9H-fluoren-9(R,S)-yl]amide of 1H-pyrrolo[2,3-b]pyridine-4-carboxylic acid;

[4-(4,5,6,7-tetrafluoro-1H-benzimidazol-2-yl)-9H-fluoren-9(R,S)-yl]amide of 1H-pyrrolo[2,3-b]pyridine-4-carboxylic acid;

4-[5-(3-methoxypropyl)aminocarbonyl-1H-benzimidazol-2-yl)-9H-fluoren-9(R,S)-yl]amide of 1H-pyrrolo[2,3-b]pyridine-4-carboxylic acid;

4-[5-(4-methyl-piperazine-1-yl)carbonyl-1H-benzimidazol-2-yl)-9H-fluoren-9(R,S)-yl]amide of 1H-pyrrolo[2,3-b]pyridine-4-carboxylic acid;

[4-(6-dimethylsulphamoyl-1H-benzimidazol-2-yl)-9H-fluoren-9(R,S)-yl]amide of 1H-pyrrolo[2,3-b]pyridine-4-carboxylic acid;

[4-[5-(pyrrolidin-1-yl)carbonyl)-1H-benzimidazol-2-yl)-9H-fluoren-9(R,S)-yl]amide of 1H-pyrrolo[2,3-b]pyridine-4-carboxylic acid;

dextrorotatory enantiomer of 2-{9(R,S)-[(1H-pyrrolo[2,3-b]pyridine-4-carbonyl)-amino]-9H-fluoren-4-yl}-1H-benzimidazole-5-carboxylic acid;

{{4-{5-[2-(pyrrolidin-1-yl)ethylaminocarbonyl]-1H-benzimidazole-2-yl}-9H-fluoren-9(R,S)-yl}}amide of 1H-pyrrolo[2,3-b]pyridine-4-carboxylic acid;

[4-(6-dimethylamino-1H-benzimidazol-2-yl)-9H-fluoren-9(R,S)-yl]amide of 1H-pyrrolo[2,3-b]pyridine-4-carboxylic acid;

{4-[6-(4-methyl-piperazin-1-yl)-1H-benzimidazol-2-yl]-9H-fluoren-9(R,S)-yl}-amide of 1H-pyrrolo[2,3-b]pyridine-4-carboxylic acid;

[[6-(methyl-4(5)-imidazolin-2-yl)-1H-benzimidazol-2-yl]-9H-fluoren-9(R,S)-yl]amide of 1H-pyrrolo[2,3-b]pyridine-4-carboxylic acid;

{{4-{5-[(3-dimethylamino-propyl)aminocarbonyl]-1H-benzimidazol-2-yl}-9H-fluoren-9(R,S)-yl}}-amide of 1H-pyrrolo[2,3-b]pyridine-4-carboxylic acid;

{4-[5-fluoro-6-(4-methyl-piperazin-1-yl)-1H-benzimidazol-2-yl]-9H-fluoren-9(R,S)-yl}-amide of 1H-pyrrolo[2,3-b]pyridine-4-carboxylic acid;

{{4-{5-[(3-dimethylamino-propyl)carbonyloxy]-1H-benzimidazol-2-yl}-9H-fluoren-9(R,S)-yl}}-amide of 1H-pyrrolo[2,3-b]pyridine-4-carboxylic acid;

[4-(6-amino-1H-benzimidazol-2-yl)-9H-fluoren-9-(R,S)yl]amide of 1H-pyrrolo[2,3-b]pyridine-4-carboxylic acid;

[4-(6-methyl-1H-benzimidazol-2-yl)-9H-fluoren-9(R,S)-yl]amide of 1H-pyrrolo[2,3-b]pyridine-4-carboxylic acid;

{{4-{5-[(3-hydroxy-propyl)aminocarbonyl]-1H-benzimidazole-2-yl}-9H-fluoren-9(R,S)-yl}}-amide of 1H-pyrrolo[2,3-b]pyridine-4-carboxylic acid;

dextrorotatory enantiomer of {4-[5-cyano-1H-benzimidazol-2-yl]-9H-fluoren-9(R,S)-yl}-amide of 1H-pyrrolo[2,3-b]pyridine-4-carboxylic acid;

[4-(3H-imidazo[4,5-c]pyridin-2-yl)-9H-fluoren-9(R,S)-yl]amide of 7H-pyrrolo[2,3-d]pyrimidine-4-carboxylic acid;

[4-(6-amino-1H-benzimidazol-2-yl)-9H-fluoren-9(R,S)-yl]amide of 1H-pyrrolo[2,3-b]pyridine-4-carboxylic acid;

dextrorotatory enantiomer of {4-[5-fluoro-1H-benzimidazol-2-yl]-9H-fluoren-9(R,S)-yl}-amide of 1H-pyrrolo[2,3-b]pyridine-4-carboxylic acid;

methyl ester of 2-{9(R,S)-[(1H-pyrrolo[2,3-b]pyridine-4-carbonyl)-amino]-9H-fluoren-4-yl}-1H-imidazo[4,5-c]pyridine-6-carboxylic acid;

[4-(6-fluoro-5-methoxy-1H-benzimidazol-2-yl)-9H-fluoren-9(R,S)-yl]amide of 1H-pyrrolo[2,3-b]pyridine-4-carboxylic acid;

[4-(6-fluoro-5-hydroxy-1H-benzimidazol-2-yl)-9H-fluoren-9(R,S)-yl]amide of 1H-pyrrolo[2,3-b]pyridine-4-carboxylic acid;

{4-[5-fluoro-6-(3-methoxy-propoxy)-1H-benzimidazol-2-yl]-9H-fluoren-9(R,S)-yl}-amide of 1H-pyrrolo[2,3-b]pyridine-4-carboxylic acid; or {4-[6-(3-dimethylamino-propoxy)-5-fluoro-1H-benzimidazol-2-yl]-9H-fluoren-9(R,S)-yl}-amide of 1H-pyrrolo[2,3-b]pyridine-4-carboxylic acid;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

16. A compound according to claim 1 which is:

4-(3H-imidazo[4,5-c]pyridin-2-yl)-fluoren-9-one oxime (Z, E);

N-[4-(1H-imidazo[4,5-c]pyridin-2-yl)-fluoren-9-ylidene]-hydrazine, 60/40 mixture of E and Z isomers;

[4-(3H-imidazo[4,5-c]pyridin-2-yl)-9H-fluoren-9(R,S)-yl]amide of quinoline-5-carboxylic acid;

dextrorotatory enantiomer of [4-(3H-imidazo[4,5-c]pyridin-2-yl)-9H-fluoren-9(R,S)-yl]amide of quinoline-5-carboxylic acid;

4-(3H-imidazo[4,5-c]pyridin-2-yl)-fluoren-9-one oxime (E);

trifluoroacetate of [4-(3H-imidazo[4,5-c]pyridin-2-yl)-9H-fluoren-9(R,S)-yl]amide of 1H-pyrazole-4-carboxylic acid;

trifluoroacetate of N-[4-(3H-imidazo[4,5-c]pyridin-2-yl)-9H-fluoren-9(R,S)-yl]-succinamide;

trifluoroacetate of [4-(3H-imidazo[4,5-c]pyridin-2-yl)-9H-fluoren-9(R,S)-yl]amide of 1H-benzotriazole-5-carboxylic acid;

[4-(3H-imidazo[4,5-c]pyridin-2-yl)-9H-fluoren-9(R,S)-yl]amide of 1H-indazole -5-carboxylic acid;

[4-(3H-imidazo[4,5-c]pyridin-2-yl)-9H-fluoren-9(R,S)-yl]amide of 1H-indole-6-carboxylic acid;

N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9(R,S)-yl]amide of 1H-indole-4-carboxylic acid;

trifluoroacetate of [4-(3H-imidazo[4,5-c]pyridin-2-yl)-9H-fluoren-9(R,S)-yl]amide of quinoline-5-carbothioic acid;

2-acetylamino-N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9(R,S)-yl]amide of quinoline-4-carboxylic acid;

2-amino-N-[4-(3H-imidazo[4,5-c]pyridin-2-yl)-9H-fluoren-9(R,S)-yl]-isonicotinamide;

2-ethyl-N-[4-(3H-imidazo[4,5-c]pyridin-2-yl)-9H-fluoren-9(R,S)-yl]-isonicotinamide;

[4-(6-fluoro-1H-benzimidazol-2-yl)-9H-fluoren-9(R,S)-yl]amide of quinoline-5-carboxylic acid;

2-chloro-N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9-yl] amide of 2-amino-pyrimidine-4-carboxylic acid;

[4-(3H-imidazo[4,5-c]pyridin-2-yl)-9H-fluoren-9(R,S)-yl]amide of 1H-pyrrolo[2,3-b]pyridine-4-carboxylic acid;

2-hydroxymethyl-N-[4-(3H-imidazo[4,5-c]pyridin-2-yl)-9H-fluoren-9(R,S)-yl]-isonicotinamide;

N-[4-(3H-imidazo[4,5-c]pyridin-2-yl)-9H-fluoren-9(R,S)-yl]-3-methyl-isonicotinamide;

hydrochloride of [4-(3H-imidazo[4,5-c]pyridin-2-yl)-9H-fluoren(R,S)-9-yl]amide of 1,8-naphthyridine-4-carboxylic acid;

[4-(3H-imidazo[4,5-c]pyridin-2-yl)-9H-fluoren(R,S)-9-yl]amide of 1H-pyrrolo[2,3-b]pyridine-3-carboxylic acid;

[4-(3H-imidazo[4,5-c]pyridin-2-yl)-9H-fluoren(R,S)-9-yl]amide of 1-methyl-1H-pyrrolo[2,3-b]pyridine-3-carboxylic acid;

2-bromo-N-[4-(3H-imidazo[4,5-c]pyridin-2-yl)-9H-fluoren-9(R,S)-yl]-isonicotinamide;

3-hydroxy-N-[4-(3H-imidazo[4,5-c]pyridin-2-yl)-9H-fluoren-9(R,S)-yl]-isonicotinamide;

3-amino-N-[4-(3H-imidazo[4,5-c]pyridin-2-yl)-9H-fluoren-9(R,S)-yl]-isonicotinamide;

methyl ester of 4-[4-(3H-imidazo[4,5-c]pyridin-2-yl)-9H-fluoren-9(R,S)-ylcarbamoyl]-pyridine-2-carboxylic acid;

[4-(3H-imidazo[4,5-c]pyridin-2-yl)-9H-fluoren(R,S)-9-yl]amide of 1H-indazole-4-carboxylic acid;

N-[4-(3H-imidazo[4,5-c]pyridin-2-yl)-9H-fluoren-9(R,S)-yl]-2-methylamino-isonicotinamide;

N-[4-(6-hydroxy-1H-benzimidazol-2-yl)-9H-fluoren-9(R,S)-yl]-isonicotinamide;

[4-(3H-imidazo[4,5-c]pyridin-2-yl)-9H-fluoren-9(R,S)-yl]amide of 6-bromo-3H-imidazo[4,5-b]pyridine-7-carboxylic acid;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

17. A compound according to claim 1 which is

[4-(3H-imidazo[4,5-c]pyridin-2-yl)-9H-fluoren-9(R,S)-yl]amide of quinoline-5-carboxylic acid;

dextrorotatory enantiomer of [4-(3H-imidazo[4,5-c]pyridin-2-yl)-9H-fluoren-9(R,S)-yl]amide of quinoline-5-carboxylic acid;

4-(3H-imidazo[4,5-c]pyridin-2-yl)-fluoren-9-one oxime (E);

trifluoroacetate of [4-(3H-imidazo[4,5-c]pyridin-2-yl)-9H-fluoren-9(R,S)-yl]amide of 1H-benzotriazole-5-carboxylic acid;

N-[4-(3H-imidazo[4,5-c]pyridin-2-yl)-9H-fluoren-9(R,S)-yl]-isonicotinamide;

trifluoroacetate of [4-(3H-imidazo[4,5-c]pyridin-2-yl)-9H-fluoren-9(R,S)-yl]amide of quinoline-5-carbothioic acid;

2-acetylamino-N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9(R,S)-yl]amide of quinoline-4-carboxylic acid;

2-amino-N-[4-(3H-imidazo[4,5-c]pyridin-2-yl)-9H-fluoren-9(R,S)-yl]-isonicotinamide;

2-ethyl-N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9-yl] amide of 2-amino-pyrimidine-4-carboxylic acid;

[4-(3H-imidazo[4,5-c]pyridin-2-yl)-9H-fluoren-9(R,S)-yl]amide of 1H-pyrrolo[2,3-b]pyridine-4-carboxylic acid;

[4-(3H-imidazo[4,5-c]pyridin-2-yl)-9H-fluoren(R,S)-9-yl]amide of 1H-pyrrolo[2,3-b]pyridine-3-carboxylic acid;

2-bromo-N-[4-(3H-imidazo[4,5-c]pyridin-2-yl)-9H-fluoren-9(R,S)-yl]-isonicotinamide;

3-hydroxy-N-[4-(3H-imidazo[4,5-c]pyridin-2-yl)-9H-fluoren-9(R,S)-yl]-isonicotinamide;

3-amino-N-[4-(3H-imidazo[4,5-c]pyridin-2-yl)-9H-fluoren-9(R,S)-yl]-isonicotinamide;

methyl ester of 4-[4-(3H-imidazo[4,5-c]pyridin-2-yl)-9H-fluoren-9(R,S)-ylcarbamoyl]-pyridine-2-carboxylic acid;

[4-(3H-imidazo[4,5-c]pyridin-2-yl)-9H-fluoren(R,S)-9-yl]amide of 1H-indazole-4-carboxylic acid;

[4-(3H-imidazo[4,5-c]pyridin-2-yl)-9H-fluoren-9(R,S)-yl]amide of 6-bromo-3H-imidazo[4,5-b]pyridine-7-carboxylic acid; or 4-(3H-imidazo[4,5-c]pyridin-2-yl)-9H-fluoren-9-yl ester of isonicotinic acid;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

18. A compound according to claim 1 which is:

[4-(3H-imidazo[4,5-c]pyridin-2-yl)-9H-fluoren-9(R,S)-yl]amide of quinoline-5-carboxylic acid;

N-[4-(3H-imidazo[4,5-c]pyridin-2-yl)-9H-fluoren-9(R,S)-yl]-isonicotinamide;

2-amino-N-[4-(3H-imidazo[4,5-c]pyridin-2-yl)-9H-fluoren-9(R,S)-yl]-isonicotinamide;

2-ethyl-N-[4-(3H-imidazo[4,5-c]pyridin-2-yl)-9H-fluoren-9(R,S)-yl]-isonicotinamide;

[4-(3H-imidazo[4,5-c]pyridin-2-yl)-9H-fluoren-9-yl] amide of 2-amino-pyrimidine-4-carboxylic acid;

[4-(3H-imidazo[4,5-c]pyridin-2-yl)-9H-fluoren-9(R,S)-yl]amide of 1H-pyrrolo[2,3-b]pyridine-4-carboxylic acid;

[4-(3H-imidazo[4,5-c]pyridin-2-yl)-9H-fluoren(R,S)-9-yl]amide of 1H-pyrrolo[2,3-b]pyridine-3-carboxylic acid;

3-amino-N-[4-(3H-imidazo[4,5-c]pyridin-2-yl)-9H-fluoren-9(R,S)-yl]-isonicotinamide; or

[4-(3H-imidazo[4,5-c]pyridin-2-yl)-9H-fluoren-9(R,S)-yl]amide of 6-bromo-3H-imidazo[4,5-b]pyridine-7-carboxylic acid;

or a tautomer, isomer, racemate, enantiomer, or diastereomer of such compound, or an inorganic or organic acid addition salt, or an inorganic or organic base addition salt of such compound, tautomer, isomer, racemate, enantiomer or diastereomer.

19. A pharmaceutical composition comprising a pharmaceutically effective amount of a compound according to claim 1 and a pharmaceutically acceptable excipient.

\* \* \* \* \*